US012516348B2

(12) United States Patent
Giese et al.

(10) Patent No.: US 12,516,348 B2
(45) Date of Patent: Jan. 6, 2026

(54) RECOMBINANT NUCLEIC ACID CONSTRUCT

(71) Applicant: PANTHERNA THERAPEUTICS GmbH, Hennigsdorf (DE)

(72) Inventors: Klaus Giese, Berlin (DE); Oliver Keil, Berlin (DE); Jörg Kaufmann, Berlin (DE)

(73) Assignee: PANTHERNA THERAPEUTICS GmbH, Hennigsdorf (DE)

( * ) Notice: Subject to any disclaimer, the term of this patent is extended or adjusted under 35 U.S.C. 154(b) by 1070 days.

(21) Appl. No.: 17/173,109

(22) Filed: Feb. 10, 2021

(65) Prior Publication Data

US 2021/0261980 A1 Aug. 26, 2021

Related U.S. Application Data

(63) Continuation of application No. PCT/EP2019/071173, filed on Aug. 7, 2019.

(30) Foreign Application Priority Data

Aug. 10, 2018 (EP) .................................... 18188489
Sep. 12, 2018 (EP) .................................... 18194023
Dec. 28, 2018 (EP) .................................... 18248243

(51) Int. Cl.
*C12N 15/85* (2006.01)
*A61K 9/00* (2006.01)
*A61K 9/51* (2006.01)

(52) U.S. Cl.
CPC ............ *C12N 15/85* (2013.01); *A61K 9/0019* (2013.01); *A61K 9/5123* (2013.01); *C12N 2830/50* (2013.01); *C12N 2840/203* (2013.01)

(58) Field of Classification Search
None
See application file for complete search history.

(56) References Cited

U.S. PATENT DOCUMENTS

2005/0266488 A1 12/2005 Coste et al.

FOREIGN PATENT DOCUMENTS

| | | | |
|---|---|---|---|
| JP | 2002-524036 | A | 8/2002 |
| JP | 2002-537843 | A | 11/2002 |
| JP | 2010-519172 | A | 6/2010 |
| JP | 2012-529906 | A | 11/2012 |
| RU | 2016131391 | A | 2/2018 |
| WO | 00/06759 | A2 | 2/2000 |
| WO | 00/53785 | A2 | 9/2000 |
| WO | 2007/096882 | A2 | 8/2007 |
| WO | 2010/146584 | A1 | 12/2010 |
| WO | 2016/091391 | A1 | 6/2016 |
| WO | 2017/201332 | A1 | 11/2017 |
| WO | 2018/115525 | A1 | 6/2018 |

OTHER PUBLICATIONS

Leppek, et al. (2018) "Functional 5' UTR mRNA structures in eukaryotic translation regulation and how to find them", Nature Reviews, 19: 158-74.*

Zhao, et al. (2011) "Toward a Systematic Understanding of mRNA 3' Untranslated Regions", Proceedings of the American Thoracic Society, 8(2): 163-66.*

Haller, et al. (2010) "Therapeutic efficacy of a DNA vaccine targeting the endothelial tip cell antigen delta-like ligand 4 in mammary carcinoma", Oncogene, 29: 4276-86.*

Thebaud, et al. (2005) "Vascular Endothelial Growth Factor Gene Therapy Increases Survival, Promotes Lung Angiogenesis, and Prevent Alveolar Damage in Hyperoxia-Induced Lung Injury", Circulation, 112(16): 2477-86.*

Japanese Notice of Reasons for Refusal with English language translation in corresponding Japanese Application No. 2021-531184, Jun. 19, 2023, 17 pages.

Japanese Search Report and English language machine translation in corresponding JP Application No. 2021-531184, Jun. 16, 2023, 24 pages.

Rubtsova, M. et al., "Distinctive Properties of the 5'-Untranslated Region of Human Hsp70 mRNA", Journal of Biological Chemistry, vol. 278(25), Jun. 2003, pp. 22350-22356.

Dvir, S., et al., "Deciphering the rules by which 5'-UTR sequences affect protein expression in yeast", Proceedings of the National Academy of Sciences, vol. 10(30), pp. E2792-E2801 (2013).

Reamon-Buettner, S., et al., "Mutations in the 3'-untranslated region of GATA4 as molecular hotspots for congenital heart disease (CHD)", Bmc Medical Genetics, vol. 8(38), 12 pages (2007).

English translation of Search Report cited in corresponding Russian Application No. 2021105796, dated Dec. 9, 2021, 2 pages.

English translation of Office Action issued Dec. 9, 2021 in corresponding Russian Application No. 2021105796, 6 pages.

English translation of Office Action issued Jun. 8, 2022 in corresponding Russian Application No. 2021105796, 9 pages.

International Search Report and Written Opinion in corresponding PCT Application No. PCT/EP2019/071173, dated Sep. 24, 2019, 9 pages.

European Search Report in corresponding EP Application No. 18188489, dated Dec. 21, 2018, 5 pages.

English translation of Singer, M., et al., "Genes and Genomes", University Science Books, 1.3 Structure of Proteins, 4 pages (1991).

(Continued)

*Primary Examiner* — Robert M Kelly
(74) *Attorney, Agent, or Firm* — Edell, Shapiro & Finnan, LLC

(57) ABSTRACT

The present invention is related to a recombinant nucleic acid construct comprising in 5'→3' direction
a 5' UTR,
a coding region coding for an effector molecule, and
a 3' UTR,
wherein 5' UTR is selected from the group comprising a 5' UTR of a gene or a derivative thereof having a nucleotide identity of at least 85%, wherein the gene is selected from the group consisting of MCP-1, RPL12s.c., Ang-2, HSP70, H3.3., Galectin-9, GADD34, EDN1, HSP70m5, E-selectin, ICAM-1, IL-6 and vWF.

17 Claims, 124 Drawing Sheets

Specification includes a Sequence Listing.

(56) References Cited

OTHER PUBLICATIONS

Notification of Second Office Action with English language translation issued in corresponding Chinese Patent Application No. 201980053544.5, dated Jan. 24, 2025, 19 pages.
Zhang, F. et al., “Relationship between 5'UTR and Gene Expression”, Technology, Economy and the Marketplace, No. 3, pp. 13-16 (2011).
Yu, S. et al., Role of 3'UTR in the Regulation of Gene Expression, China Animal Husbandry & Veterinary Medicine, vol. 43(11), pp. 2907-2913 (2016).
Notice of Deficiencies issued in corresponding Israeli Patent Application No. 280157, dated Dec. 19, 2024, 5 pages.

* cited by examiner

5'-Primers

| Construct | 5'UTR | Sequence |
|---|---|---|
| PAN01-PAN03 | Ang-1 | 5' TAATACGACT CACTATAGGG CCCTAAGCCA TCAGCAAT 3' |
| PAN04-PAN06 | Ang-2 | 5' TAATACGACT CACTATAGGA AAGTGATTGA TTCGGATA 3' |
| PAN07 | Galectin-9 | 5' TAATACGACT CACTATAGGT CCCCATTGAA TAACAGCC 3' |
| PAN08 | HSP70 | 5' TAATACGACT CACTATAGGA TAAAAGCCCA GGGGCAAG 3' |
| PAN09 | H3.3. | 5' TAATACGACT CACTATAGGG TCAGCCATCT TTCAATTG 3' |
| PAN10 | RPL12s.c. | 5' TAATACGACT CACTATAGGC ATATCTTCAT TCTTCACT 3' |
| PAN11 | GADD34 | 5' TAATACGACT CACTATAGGA TAAAAGCCTA GTGGCCAT 3' |
| PAN12 | MCP-1 | 5' TAATACGACT CACTATAGGG AGGAACCGAG AGGCTGAG 3' |
| PAN13 | EDN1 | 5' TAATACGACT CACTATAGGG GAGCTGTTTA CCCCCACT 3' |
| PAN28 | Ang-2 | 5' TAATACGACT CACTATAGGA AAGTGATTGA TTCGGATA 3' |

Fig. 7A

3'-Primers

| Construct | 3'UTR | |
|---|---|---|
| PAN01-PAN03 | Ang-1 | 5' (100xT)-TTTTTTTTTT TTTTTTTTTT TTGCACAAAT ATTACTTTC 3' |
| PAN04-PAN06 | vWF | 5' (100xT)-TTTTTTTTTT TTTTTTTTTT GCCTTTTGCA AGATAAGAG 3' |
| PAN07 | vWF | 5' (100xT)-TTTTTTTTTT TTTTTTTTTT GCCTTTTGCA AGATAAGAG 3' |
| PAN08 | HSP70 | 5' (100xT)-TTTTTTTTTT TTTTTTTTTT GAATTTTAAA GTTTATTTA 3' |
| PAN09 | H3.3. | 5' (100xT)-TTTTTTTTTT TTTTTTTTTT ATAGTTTAAT GTATTTTAA 3' |
| PAN10 | RPL12s.c. | 5' (100xT)-TTTTTTTTTT TTTTTTTTTT TTAACTACAT CTAAACCCA 3' |
| PAN11 | GADD34 | 5' (100xT)-TTTTTTTTTT TTTTTTTTTT TCGCTACAAA TCAAAAGGC 3' |
| PAN12 | MCP-1 | 5' (100xT)-TTTTTTTTTT TTTTTTTTTT TGTACAAAAA TATATTTAT 3' |
| PAN13 | EDN1 | 5' (100xT)-TTTTTTTTTT TTTTTTTTTT TTTACAGTAA GGAAAAAAAT ATTT 3' |
| PAN28 | Ang-2 | 5' (100xT)-TTTTTTTTTT TTTTTTTTTT GCCTTTTGCA AGATAAGAG 3' |

Fig. 7B 0.1μg 0.5μg

Homo sapiens C-C motif chemokine ligand 2 (CCL2), mRNA (MCP-1) <NM_002982.3>

5'-UTR:

gaggaaccgagaggctgagactaacccagaaacatccaattctcaaactgaagctcgcactctcgcctccagc

Fig. 15A sig_peptide:

nt:

atgaaagtctctgccgcccttctgtgcctgctgctcatagcagccaccttcattccccaagggctcgct aa:

MKVSAALLCLLLIAATFIPQGLA

Fig. 15B

3’-UTR:

acactcactccacaacccaagaatctgcagctaacttattttcccctagctttccccagacaccctgttttattttattataatgaattttgtttgttgatgtgaaacattatgccttaagta
atgttaattcttatttaagttattgatgttttaagtttatctttcatggtactagtgtttttagatacagagacttggggaaattgcttttcctcttgaaccacagttctacccctgggatgtt
ttgagggtctttgcaagaatcattaatacaaagaatttttttaacattccaatgcattgctaaaatattattgtggaaatgaatattttgtaactattacaccaaataaatatatttttgta
ca

Fig. 15C

Spinacia oleracea 50S ribosomal protein L12, chloroplastic (LOC110782793), mRNA (RPL12s.c.) (predicted) <XM_021987044.1>

5’-UTR:

catatcttcattcttcactctttccccccccccccttatcctcctatctaatcctctcatctctctcctcctcttcctccaacaacaactaaca

Fig. 16A ttttgagtaattttcaattttgtttttgtttttgtttttgttgttgggagttgttgtaatttggtaaatgttggggtcactaaaatcttttgttgcaattttagcaccttttttattagatatataaaa
ttgggtttagatgtagttaa

Fig. 16B

Homo sapiens angiopoietin 2 (ANGPT2; Ang-2), transcript variant 1, mRNA <NM_001147.2>

5’-UTR:

aaagtgattgattcggatactgacactgtaggatctggggagagaggaacaaaggaccgtgaaagctgctctgtaaaagctgacacagccctcccaagtgagcaggactgttcttcc
cactgcaatctgacagtttactgcatgcctggagagaacacagcagtaaaaaccaggtttgctactggaaaaagaggaaagagaagactttcattgacggacccagccatggcagc
gtagcagccctgcgttttagacggcagcagctcgggactctggacgtgtgtttgccctcaagtttgctaagctgctggtttattactgaagaaaga

Fig. 17A sig_peptide:

nt:

atgtggcagattgttttctttactctgagctgtgatcttgtcttggccgcagcc aa:

MWQIVFFTLSCDLVLAAA

Fig. 17B

3'-UTR:

acatcccagtccacctgaggaactgtctcgaactattttcaaagacttaagcccagtgcactgaaagtcacggctgcgcactgtgtcctcttccaccacagagggcgtgtgctcggtgc
tgacgggacccacatgctccagattagagcctgtaaactttatcacttaaacttgcatcacttaacggaccaaagcaagaccctaaacatccataattgtgattagacagaacaccta
tgcaaagatgaacccgaggctgagaatcagactgacagtttacagacgctgctgtcacaaccaagaatgttatgtgcaagtttatcagtaaataactggaaaacagaacacttatgt
tatacaatacagatcatcttggaactgcattcttctgagcactgtttatacactgtgtaaatacccatatgtcctgaattcaccatcactatcacaattaaaaggaagaaaaaaactctc
taagccataaaaagacatattcagggatattctgagaaggggttactagaagtttaatatttggaaaaacagttagtgcatttttactccatctcttaggtgctttaaatttttatttcaa
aaacagcgtatttacatttatgttgacagcttagttataagttaatgctcaaatacgtatttcaaatttatatggtagaaacttccagaatctctgaaattatcaacagaaacgtgccatt
ttagtttatatgcagaccgtactatttttttctgcctgattgttaaatatgaaggtatttttagtaattaaatataacttattaggggatatgcctatgtttaacttttatgataatatttacaa
ttttataatttgtttccaaaagacctaattgtgccttgtgataaggaaacttcttacttttaatgatgaggaaaattatacatttcattctatgacaaagaaactttactatcttctcactatt
ctaaaacagaggtctgttttctttcctagtaagatatatttttatagaactagactacaatttaatttctggttgagaaaagccttctatttaagaaatttacaaagctatatgtctcaaga
ttcacccttaaatttacttaaggaaaaaaataattgacactagtaagttttttatgtcaatcagcaaactgaaaaaaaaaaaagggtttcaaagtgcaaaaacaaaatctgatgttc
ataatatatttaaatatttaccaaaaatttgagaacacagggctgggcgcagtggctcacacctataatcccagtacattggtaggcaaggtgggcagatcacctgaggtcaggagtt
caagaccagcctggacaacatggtgaaaccctgtctctactaaataatacaaaaattagccaggcgtgctggcgggcacctgtaatcccagctactcgggaggctgaggcagggag
aattgcttgcaccagggaggtagaggttgcagtgagccaagatcgcaccactgcactccagccggggcaacagagcaagactccatctcaaaaaaaaaaaaaaaaaaagaaaga
aaagaaaatttgagaacacagctttatactcgggactacaaaaccataaactcctggagttttaactccttttgaaattttcatagtacaattaatactaatgaacatttgtgtaaagct
ttataatttaaaggcaatttctcatatattcttttctgaatcatttgcaaggaagttcagagtccagtctgtaactagcatctactatatgtctgtcttcaccttacagtgttctaccattatt
ttttctttattccatttcaaaatctaatttattttaccccaacttctccccaccacttgacgtagttttagaacacacaggtgttgctacatatttggagtcaatgatggactctggcaaagt
caaggctctgttttatttccaccaaggtgcacttttccaacaactatttaactagttaagaacctccctatcttagaactgtatctactttatatttaagaaggttttatgaattcaacaacg
gtatcatggccttgtatcaagttgaaaaacaactgaaaataagaaaatttcacagcctcgaaagacaacaacaagtttctaggatatctcaatgacaagagtgatggatacttaggt

Fig. 17C (cont.)

agggaaacgctaatgcaggaaaaactggcaacaacacaatttatatcaattctctttgtaggcaggtgataaaaaattcaaggacaaatctcattatgtcattgtgcatcatatataat
ctcttatgagcgagaatgggggaatttgtgtttttactttacacttcaattccttacacggtatttcaaacaaacagttttgctgagaggagcttttgtctctccttaagaaaatgtttata
aagctgaaaggaaatcaaacagtaatcttaaaaatgaaaacaaaacaacccaacaacctagataactacagtgatcagggagcacagttcaactccttgttatgttttagtcatatg
gcctactcaaacagctaaataacaacaccagtggcagataaaaatcaccatttatctttcagctattaatcttttgaatgaataaactgtgacaaacaaattaacatttttgaacatga
aaggcaacttctgcacaatcctgtatccaagcaaactttaaattatccacttaattattacttaatcttaaaaaaaattagaacccagaacttttcaatgaagcatttgaaagttgaagt
ggaatttaggaaagccataaaaatataaatactgttatcacagcaccagcaagccataatctttatacctatcagttctatttctattaacagtaaaaacattaagcaagatataagac
tacctgcccaagaattcagtctttttcatttttgtttttctcagttctgaggatgttaatcgtcaaattttctttggactgcattcctcactactttttgcacaatggtctcacgttctcacattt
gttctcgcgaataaattgataaaaggtgttaagttctgtgaatgtctttttaattatgggcataattgtgcttgactggataaaaacttaagtccacccttatgtttataataatttcttgag
aacagcaaactgcatttaccatcgtaaaacaacatctgacttacgggagctgcagggaagtggtgagacagttcgaacggctcctcagaaatccagtgacccaattctaaagaccat
agcacctgcaagtgacacaacaagcagatttattatacatttattagccttagcaggcaataaaccaagaatcactttgaagacacagcaaaaagtgatacactccgcagatctgaa
atagatgtgttctcagacaacaaagtcccttcagaatcttcatgttgcataaatgttatgaatattaataaaaagttgattgagaaaaa

Fig. 17C

Homo sapiens interleukin 6 (IL6), transcript variant 1, mRNA <NM_000600.4>

5'-UTR:

gtctcaatattagagtctcaacccccaataaatataggactggagatgtctgaggctcattctgccctcgagcccaccgggaacgaaagagaagctctatctcccctccaggagcccagct

Fig. 18A sig_peptide:

nt:

atgaactccttctccacaagcgccttcggtccagttgccttctccctggggctgctcctggtgttgcctgctgccttccctgcccca aa:

MNSFSTSAFGPVAFSLGLLLVLPAAFPAP

Fig. 18B catgggcacctcagattgttgttgttaatgggcattccttcttctggtcagaaacctgtccactgggcacagaacttatgttgttctctatggagaactaaaagtatgagcgttaggacac
tattttaattatttttaatttattaatatttaaatatgtgaagctgagttaatttatgtaagtcatatttatatttttaagaagtaccacttgaaacattttatgtattagttttgaaataataa
t
tatttatataatgtataaatggtttttataccaataaatggcattttaaaaaattcagcaa

Fig. 18C

Homo sapiens von Willebrand factor (VWF), mRNA <NM_000552.4>

5′-UTR:

gtggcagctcacagctattgtggtgggaaagggagggtggttggtggatgtcacagcttgggctttatctcccccagcagtggggactccacagcccctgggctacataacagcaaga
cagtccggagctgtagcagacctgattgagcctttgcagcagctgagagcatggcctagggtgggcggcaccattgtccagcagctgagtttcccagggaccttggagatagccgca
gccctcatttgcaggggaag

Fig. 19A atgattcctgccagatttgccggggtgctgcttgctctggccctcattttgccagggaccctttgt aa:

MIPARFAGVLLALALILPGTLC

Fig. 19B

3′-UTR:

ggctgctgcagctgcatgggtgcctgctgctgcctgccttggcctgatggccaggccagagtgctgccagtcctctgcatgttctgctcttgtgcccttctgagcccacaataaaggctg
agctcttatcttgcaaaaggc

Fig. 19C

Homo sapiens heat shock protein family A (Hsp70) member 1A (HSPA1A), mRNA <NM_005345.5>

5'-UTR:

ataaaagcccaggggcaagcggtccggataacggctagcctgaggagctgctgcgacagtccactacctttttcgagagtgactcccgttgtcccaaggcttcccagagcgaacctgt
gcggctgcaggcaccggcgcgtcgagtttccggcgtccggaaggaccgagctcttctcgcggatccagtgttccgtttccagcccccaatctcagagcggagccgacagagagcagg
gaaccggc

Fig. 20A

3'-UTR:

gggcctttccaagattgctgtttttgttttggagcttcaagactttgcatttcctagtatttctgtttgtcagttctcaatttcctgtgtttgcaatgttgaaatttttggtgaagtactgaact
tgctttttttccggtttctacatgcagagatgaatttatactgccatcttacgactatttcttctttttaatacacttaactcaggccatttttaagttggttacttcaaagtaaataaacttt
aaaattc

Fig. 20B

Homo sapiens heat shock protein family A (Hsp70) member 5 (HSPA5), mRNA <NM_005347.4>

5'-UTR:

gggctgggggagggtatataagccgagtaggcgacggtgaggtcgacgccggccaagacagcacagacagattgacctattggggtgtttcgcgagtgtgagagggaagcgccgc
ggcctgtatttctagacctgcccttcgcctggttcgtggcgccttgtgaccccgggcccctgccgcctgcaagtcggaaattgcgctgtgctcctgtgctacggcctgtggctggactgcc
tgctgctgcccaactggctggcaag

Fig. 21A sig_peptide:

nt:

atgaagctctccctggtggccgcgatgctgctgctgctcagcgcggcgcgggcc aa:

MKLSLVAAMLLLLSAARA

Fig. 21B

3'-UTR:

acactgatctgctagtgctgtaatattgtaaatactggactcaggaacttttgttaggaaaaaattgaaagaacttaagtctcgaatgtaattggaatcttcacctcagagtggagttga
aactgctatagcctaagcggctgtttactgcttttcattagcagttgctcacatgtctttgggtgggggggagaagaagaattggccatcttaaaaagcgggtaaaaaacctgggttag
ggtgtgtgttcaccttcaaaatgttctatttaacaactgggtcatgtgcatctggtgtaggaagtttttctaccataagtgacaccaataaatgtttgttatttacactggtctaatgtttg
tgagaagcttctaattagatcaattacttattttaggaaatttaagactagatactcgtgtgtggggtgaggggagggagtatttggtatgttgggataaggaaacacttctatttaatg
cttccagggatttttttttttttttaaccctcctgggcccaagtgatccttccacctcagtctcccagctaattgagaccacaggcttgttaccaccatgctcggcttttgcattaatctaa
gaaaaggggagagaagttaatccacatctttactcaggcaaggggcatttcacagtgcccaagagtggggttttcttgaacatacttggtttcctatttccccttatctttctaaaactgc
ctttctggtggctttttttaaaattattactaatgatgcttttatagctgcttggattctctgagaaatgatggggagtgagtgatcactggtattaactttatacacttggatttcatttgta
actttaggatgtaaaggtatattgtgaaccctagctgtgtcagaatctccatccctgaaatttctcattagtggtactggggtgggatcttggatggtgacattgaaactacactaaatcc
cctcactatgaatgggttgttaaaggcaatggtttgtgtcaaaactggtttaggattacttagattgtgttcctgaagaaaagagtccaggtaaatggtatgatcaataaaggacaggc
tggtgctaacataaaatccaatattgtaatcctagcactttgggaggccaaggcgggtggatcacaaggtcaagagatagagaccatctttgccaacatggtgaaactccatctctac
tgaaaatacaaaaattagctgggcgtggtagtgcaagctgaaggctgaggcaggagaatcactcgaacccgggaggcagaggttgcagtgagccgagatcacaccactgtactcc
agcccggcactccagcctggcgacaagagtgagactccacctcaaaaaaaaaaaaaagaatccaatactgcccaaggataggtattttatagatgggcaactggctgaaaggttaa
ttctctagggctagtagaactggatcccaacaccaaactcttaattagacctaggcctcagctgcactgcccgaaaagcatttgggcagaccctgagcagaatactggtctcaggcca
agcccaatacagccattaaagatgacctacagtgctgtgtaccctggggcaatagggttaaatggtagttagcaactagggctagtcttcccttacctcaaaggctctcactaccgtgg
accacctagtctgtaactctttctgaggagctgttactgaatattaaaaagatagacttcaactatg

Fig. 21C

Homo sapiens H3 histone family member 3A (H3F3A), mRNA (H3.3) <NM_002107.4>

5′-UTR:

gtcagccatctttcaattgtgttcgcagccgccgccgcgccgccgtcgctctccaacgccagcgccgcctctcgctcgccgagctccagccgaaggagaagggggtaagtaaggag
gtctctgtacc

Fig. 22A

3′-UTR:

gaatccactatgatgggaaacatttcattctcaaaaaaaaaaaaaaaaatttctcttcttcctgttattggtagttctgaacgttagatattttttttccatggggtcaaaaggtacctaa
gtatatgattgcgagtggaaaaataggggacagaaatcaggtattggcagtttttccattttcatttgtgtgtgaatttttaatataaatgcggagacgtaaagcattaatgcaagttaa
aatgtttcagtgaacaagtttcagcggttcaactttataataattataaataaacctgttaaatttttctggacaatgccagcatttggatttttttaaaacaagtaaatttcttattgatgg
caactaaatggtgtttgtagcatttttatcatacagtagattccatccattcactatacttttctaactgagttgtcctacatgcaagtacatgtttttaatgttgtctgtcttctgtgctgttc
ctgtaagtttgctattaaaatacattaaactat

Fig. 22B

Homo sapiens galectin-9 (LGALS9), transcript variant 1, mRNA <NM_009587.2>

5'-UTR:

tccccattgaataacagccaagttgctttggtttctatttctttgttaagtcgttccctctacaaaggacttcctagtgggtgtgaaaggcagcggtggccacagaggcggcggagag

Fig. 23A

3'-UTR:

gcggcttcctggccctggggccgggggctggggtgtggggcagtctgggtcctctcatcatccccacttcccaggcccagcctttccaaccctgcctgggatctgggctttaatgcagag
gccatgtccttgtctggtcctgcttctggctacagccaccctggaacggagaaggcagctgacggggattgccttcctcagccgcagcagcacctggggctccagctgctggaatccta
ccatcccaggaggcaggcacagccagggagaggggaggagtgggcagtgaagatgaagccccatgctcagtcccctcccatcccccacgcagctccaccccagtcccaagccacc
agctgtctgctcctggtgggaggtggcctcctcagcccctcctctctgacctttaacctcactctcaccttgcaccgtgcaccaacccttcacccctcctggaaagcaggcctgatggctt
cccactggcctccaccacctgaccagagtgttctcttcagaggactggctcctttcccagtgtccttaaaataaagaaatgaaaatgcttgttggcacattca

Fig. 23B

PAN01

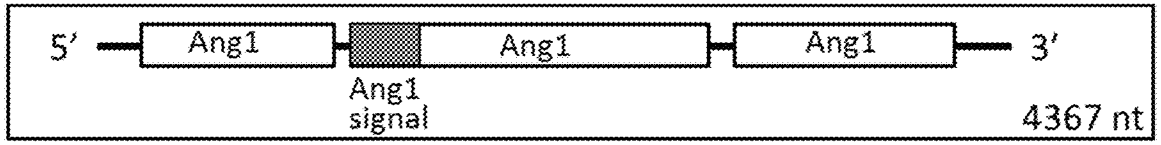

Fig. 24A

PAN01 gccctaagccatcagcaatccttagtataggggcacactcatgcattcctgtcaagtcatcttgtgaaaggctgcctgcttccagcttggcttggatgtgcaaccttaataaaactcact
gaggtctgggagaaaatagcagatctgcagcagatagggtagaggaaagggtctagaatatgtacacgcagctgactcaggcaggctccatgctgaacggtcacacagagaggaa
acaataaatctcagctactatgcaataaatatctcaagttttaacgaagaaaaacatcattgcagtgaaataaaaaattttaaattttagaacaaagctaacaaatggctagttttct
atgattcttcttcaaacgctttctttgagggggaaagagtcaaacaaacaagcagttttacctgaaataaagaactagttttagaggtcagaagaaaggagcaagttttgcgagaggc
acggaaggagtgtgctggcagtacaatgacagttttcctttcctttgctttcctcgctgccattctgactcacatagggtgcagcaatcagcgccgaagtccagaaaacagtgggagaa
gatataaccggattcaacatgggcaatgtgcctacactttcattcttccagaacacgatggcaactgtcgtgagagtacgacagaccagtacaacacaaacgctctgcagagagatg
ctccacacgtggaaccggatttctcttcccagaaacttcaacatctggaacatgtgatggaaaattatactcagtggctgcaaaaacttgagaattacattgtggaaaacatgaagtc
ggagatggcccagatacagcagaatgcagttcagaaccacacggctaccatgctggagataggaaccagcctcctctctcagactgcagagcagaccagaaagctgacagatgttg
agacccaggtactaaatcaaacttctcgacttgagatacagctgctggagaattcattatccacctacaagctagagaagcaacttcttcaacagacaaatgaaatcttgaagatcca
tgaaaaaaacagtttattagaacataaaatcttagaaatggaaggaaaacacaaggaagagttggacaccttaaaggaagagaaagagaaccttcaaggcttggttactcgtcaa
acatatataatccaggagctggaaaagcaattaaacagagctaccaccaacaacagtgtccttcagaagcagcaactggagctgatggacacagtccacaaccttgtcaatctttgc
actaaagaaggtgttttactaaagggaggaaaaagagaggaagagaaaccatttagagactgtgcagatgtatatcaagctggttttaataaaagtggaatctacactatttatatt

Fig 24B aataatatgccagaacccaaaaaggtgttttgcaatatggatgtcaatgggggaggttggactgtaatacaacatcgtgaagatggaagtctagatttccaaagaggctggaagga
atataaaatgggttttggaaatccctccggtgaatattggctggggaatgagtttatttttgccattaccagtcagaggcagtacatgctaagaattgagttaatggactgggaaggga
accgagcctattcacagtatgacagattccacataggaaatgaaaagcaaaactataggttgtatttaaaaggtcacactgggacagcaggaaaacagagcagcctgatcttacac
ggtgctgatttcagcactaaagatgctgataatgacaactgtatgtgcaaatgtgccctcatgttaacaggaggatggtggtttgatgcttgtggcccctccaatctaaatggaatgttc
tatactgcgggacaaaaccatggaaaactgaatgggataaagtggcactacttcaaagggcccagttactccttacgttccacaactatgatgattcgacctttagatttttgaaagcg
caatgtcagaagcgattatgaaagcaacaaagaaatccggagaagctgccaggtgagaaactgtttgaaaacttcagaagcaaacaatattgtctcccttccagcaataagtggta
gttatgtgaagtcaccaaggttcttgaccgtgaatctggagccgtttgagttcacaagagtctctacttggggtgacagtgctcacgtggctcgactatagaaaactccactgactgtcg
ggctttaaaaagggaagaaactgctgagcttgctgtgcttcaaactactactggaccttattttggaactatggtagccagatgataaatatggttaatttcatgtaaaacagaaaaaa
agagtgaaaaagagaatatacatgaagaatagaaacaagcctgccataatcctttggaaaagatgtattataccagtgaaaaggtgttatatctatgcaaacctactaacaaattat
actgttgcacaattttgataaaaatttagaacagcattgtcctctgagttggttaaatgttaatggatttcagaagcctaattccagtatcatacttactagttgatttctgcttacccatct
tcaaatgaaaattccatttttgtaagccataatgaactgtagtacatggacaataagtgtgtggtagaaacaaactccattactctgatttttgatacagttttcagaaaaagaaatga
acataatcaagtaaggatgtatgtggtgaaaacttaccacccccatactatggttttcatttactctaaaaactgattgaatgatatataaatatatttatagcctgagtaaagttaaaa
gaatgtaaaatatatcatcaagttcttaaaataatatacatgcatttaatatttcctttgatattatacaggaaagcaatattttggagtatgttaagttgaagtaaaagcaagtactctg
gagcagttcattttacagtatctacttgcatgtgtatacatacatgtaacttcattattttaaaaatatttttagaactccaatactcaccctgttatgtcttgctaatttaaattttgctaatt
aactgaaacatgcttaccagattcacactgttccagtgtctataaaagaaacactttgaagtctataaaaaataaaataattataaatatcattgtacatagcatgtttatatctgcaaa
aaacctaatagctaattaatctggaatatgcaacattgtccttaattgatgcaaataacacaaatgctcaaagaaatctactatatcccttaatgaaatacatcattcttcatatatttct
ccttcagtccattcccttaggcaatttttaatttttaaaaattattatcaggggagaaaaattggcaaaactattatatgtaagggaaatatatacaaaaagaaaattaatcatagtcac
ctgactaagaaattctgactgctagttgccataaataactcaatggaaatattcctatgggataatgtattttaagtgaattttggggtgcttgaagttactgcattattttatcaagaa
gtcttctctgcctgtaagtgtccaaggttatgacagtaaacagtttttattaaaacatgagtcactatgggatgagaaaattgaaataaagctactgggcctcctctcataaaagagac

Fig. 24b (cont.)

agttgttggcaaggtagcaataccagtttcaaacttggtgacttgatccactatgccttaatggtttcctccatttgagaaaataaagctattcacattgttaagaaaaatactttttaaa
gtttaccatcaagtctttttatatttatgtgtctgtattctacccctttttgccttacaagtgatatttgcaggtattataccatttttctattcttggtggcttcttcatagcaggtaagcctct
ccttctaaaaacttctcaactgttttcatttaagggaaagaaaatgagtattttgtccttttgtgttcctacagacactttcttaaaccagtttttggataaagaatactatttccaaactca
tattacaaaaacaaaataaaataataaaaaaagaaagcatgatatttactgttttgttgtctgggtttgagaaatgaaatattgtttccaattatttataataaatcagtataaaatgtt
ttatgattgttatgtgtattatgtaatacgtacatgtttatggcaatttaacatgtgtattcttttaattgtttcagaataggataattaggtattcgaattttgtctttaaaattcatgtggttt
ctatgcaaagttcttcatatcatcacaacattatttgatttaaataaaattgaaagtaatatttgtgcaa

Fig. 24B (continued

PAN03

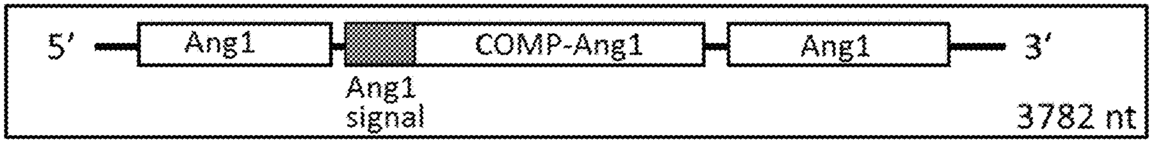

Fig. 25A

PAN03 gccctaagccatcagcaatccttagtataggggcacactcatgcattcctgtcaagtcatcttgtgaaaggctgcctgcttccagcttggcttggatgtgcaaccttaataaaactcact
gaggtctgggagaaaatagcagatctgcagcagatagggtagaggaaagggtctagaatatgtacacgcagctgactcaggcaggctccatgctgaacggtcacacagagaggaa
acaataaatctcagctactatgcaataaatatctcaagttttaacgaagaaaaacatcattgcagtgaaataaaaaattttaaattttagaacaaagctaacaaatggctagttttct
atgattcttcttcaaacgctttctttgagggggaaagagtcaaacaaacaagcagttttacctgaaataaagaactagttttagaggtcagaagaaaggagcaagttttgcgagaggc
acggaaggagtgtgctggcagtacaatgacagttttcctttcctttgctttcctcgctgccattctgactgggatcttagacctagccccacagatgcttcgagaactccaggagactaa
tgcggcgctgcaagacgtgagagagctcttgcgacagcaggtcaaggagatcaccttcctgaagaatacggtgatggaatgtgacgcttgcggaggctcccttgtcaatctttgcact
aaagaaggtgttttactaaagggaggaaaaagagaggaagagaaaccatttagagactgtgcagatgtatatcaagctggttttaataaaagtggaatctacactatttatattaat
aatatgccagaacccaaaaaggtgttttgcaatatggatgtcaatgggggaggttggactgtaatacaacatcgtgaagatggaagtctagatttccaaagaggctggaaggaatat
aaaatgggttttggaaatccctccggtgaatattggctggggaatgagtttatttttgccattaccagtcagaggcagtacatgctaagaattgagttaatggactgggaagggaaccg
agcctattcacagtatgacagattccacataggaaatgaaaagcaaaactataggttgtatttaaaaggtcacactgggacagcaggaaaacagagcagcctgatcttacacggtg
ctgatttcagcactaaagatgctgataatgacaactgtatgtgcaaatgtgccctcatgttaacaggaggatggtggtttgatgcttgtggcccctccaatctaaatggaatgttctata
ctgcgggacaaaaccatggaaaactgaatgggataaagtggcactacttcaaagggcccagttactccttacgttccacaactatgatgattcgacctttagatttttgaaagcgcaat
gtcagaagcgattatgaaagcaacaaagaaatccggagaagctgccaggtgagaaactgtttgaaaacttcagaagcaaacaatattgtctcccttccagcaataagtggtagttat
gtgaagtcaccaaggttcttgaccgtgaatctggagccgtttgagttcacaagagtctctacttggggtgacagtgctcacgtggctcgactatagaaaactccactgactgtcgggctt

Fig. 25B taaaaagggaagaaactgctgagcttgctgtgcttcaaactactactggaccttattttggaactatggtagccagatgataaatatggttaatttcatgtaaaacagaaaaaaagag
tgaaaaagagaatatacatgaagaatagaaacaagcctgccataatcctttggaaaagatgtattataccagtgaaaaggtgttatatctatgcaaacctactaacaaattatactgt
tgcacaattttgataaaaatttagaacagcattgtcctctgagttggttaaatgttaatggatttcagaagcctaattccagtatcatacttactagttgatttctgcttacccatcttcaa
atgaaaattccatttttgtaagccataatgaactgtagtacatggacaataagtgtgtggtagaaacaaactccattactctgatttttgatacagttttcagaaaaagaaatgaacat
aatcaagtaaggatgtatgtggtgaaaacttaccacccccatactatggttttcatttactctaaaaactgattgaatgatatataaatatatttatagcctgagtaaagttaaaagaat
gtaaaatatatcatcaagttcttaaaataatatacatgcatttaatatttcctttgatattatacaggaaagcaatattttggagtatgttaagttgaagtaaaagcaagtactctggagc
agttcattttacagtatctacttgcatgtgtatacatacatgtaacttcattattttaaaaatatttttagaactccaatactcaccctgttatgtcttgctaatttaaattttgctaattaact
gaaacatgcttaccagattcacactgttccagtgtctataaaagaaacactttgaagtctataaaaaataaaataattataaatatcattgtacatagcatgtttatatctgcaaaaaa
cctaatagctaattaatctggaatatgcaacattgtccttaattgatgcaaataacacaaatgctcaaagaaatctactatatcccttaatgaaatacatcattcttcatatatttctcctt
cagtccattcccttaggcaatttttaatttttaaaaattattatcaggggagaaaaattggcaaaactattatatgtaagggaaatatatacaaaaagaaaattaatcatagtcacctg
actaagaaattctgactgctagttgccataaataactcaatggaaatattcctatgggataatgtattttaagtgaatttttggggtgcttgaagttactgcattattttatcaagaagtct
tctctgcctgtaagtgtccaaggttatgacagtaaacagtttttattaaaacatgagtcactatgggatgagaaaattgaaataaagctactgggcctcctctcataaaagagacagtt
gttggcaaggtagcaataccagtttcaaacttggtgacttgatccactatgccttaatggtttcctccatttgagaaaataaagctattcacattgttaagaaaaatactttttaaagttt
accatcaagtctttttatatttatgtgtctgtattctaccccttttgccttacaagtgatatttgcaggtattataccatttttctattcttggtggcttcttcatagcaggtaagcctctcctt
ctaaaaacttctcaactgttttcatttaagggaaagaaaatgagtattttgtccttttgtgttcctacagacactttcttaaaccagtttttggataaagaatactatttccaaactcatatt
acaaaaacaaaataaaataataaaaaaagaaagcatgatatttactgttttgttgtctgggtttgagaaatgaaatattgtttccaattatttataataaatcagtataaaatgttttat
gattgttatgtgtattatgtaatacgtacatgtttatggcaatttaacatgtgtattcttttaattgtttcagaataggataattaggtattcgaattttgtctttaaaattcatgtggtttcta
tgcaaagttcttcatatcatcacaacattatttgatttaaataaaattgaaagtaatatttgtgcaa Fig. 25B (continued)

PAN04

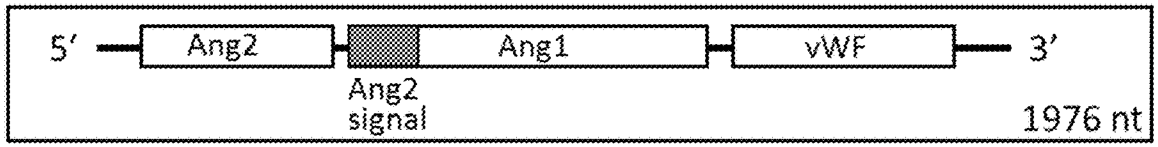

Fig. 26A

PAN04 aaagtgattgattcggatactgacactgtaggatctggggagagaggaacaaaggaccgtgaaagctgctctgtaaaagctgacacagccctcccaagtgagcaggactgttcttcc
cactgcaatctgacagtttactgcatgcctggagagaacacagcagtaaaaaccaggtttgctactggaaaaagaggaaagagaagactttcattgacggacccagccatggcagc
gtagcagccctgcgttttagacggcagcagctcgggactctggacgtgtgtttgccctcaagtttgctaagctgctggtttattactgaagaaagaatgtggcagattgttttctttactct
gagctgtgatcttgtcttggccgcagcccacatagggtgcagcaatcagcgccgaagtccagaaaacagtgggagaagatataaccggattcaacatgggcaatgtgcctacacttt
cattcttccagaacacgatggcaactgtcgtgagagtacgacagaccagtacaacacaaacgctctgcagagagatgctccacacgtggaaccggatttctcttcccagaaacttca
acatctggaacatgtgatggaaaattatactcagtggctgcaaaaacttgagaattacattgtggaaaacatgaagtcggagatggcccagatacagcagaatgcagttcagaacc
acacggctaccatgctggagataggaaccagcctcctctctcagactgcagagcagaccagaaagctgacagatgttgagacccaggtactaaatcaaacttctcgacttgagatac
agctgctggagaattcattatccacctacaagctagagaagcaacttcttcaacagacaaatgaaatcttgaagatccatgaaaaaaacagtttattagaacataaaatcttagaaat
ggaaggaaaacacaaggaagagttggacaccttaaaggaagagaaagagaaccttcaaggcttggttactcgtcaaacatatataatccaggagctggaaaagcaattaaacag
agctaccaccaacaacagtgtccttcagaagcagcaactggagctgatggacacagtccacaaccttgtcaatctttgcactaaagaaggtgttttactaaagggaggaaaaagag
aggaagagaaaccatttagagactgtgcagatgtatatcaagctggttttaataaaagtggaatctacactatttatattaataatatgccagaacccaaaaaggtgttttgcaatatg
gatgtcaatgggggaggttggactgtaatacaacatcgtgaagatggaagtctagatttccaaagaggctggaaggaatataaaatgggttttggaaatccctccggtgaatattgg
ctggggaatgagtttatttttgccattaccagtcagaggcagtacatgctaagaattgagttaatggactgggaagggaaccgagcctattcacagtatgacagattccacataggaa
atgaaaagcaaaactataggttgtatttaaaaggtcacactgggacagcaggaaaacagagcagcctgatcttacacggtgctgatttcagcactaaagatgctgataatgacaact
gtatgtgcaaatgtgccctcatgttaacaggaggatggtggtttgatgcttgtggcccctccaatctaaatggaatgttctatactgcgggacaaaaccatggaaaactgaatgggata
aagtggcactacttcaaagggcccagttactccttacgttccacaactatgatgattcgacctttagatttttgaggctgctgcagctgcatgggtgcctgctgctgcctgccttggcctg
atggccaggccagagtgctgccagtcctctgcatgttctgctcttgtgcccttctgagcccacaataaaggctgagctcttatcttgcaaaaggc

Fig. 26B

PAN06

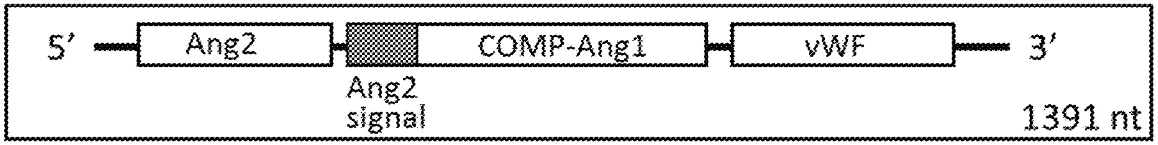

Fig. 27A

PAN06 aaagtgattgattcggatactgacactgtaggatctggggagagaggaacaaaggaccgtgaaagctgctctgtaaaagctgacacagccctcccaagtgagcaggactgttcttcc
cactgcaatctgacagtttactgcatgcctggagagaacacagcagtaaaaaccaggtttgctactggaaaaagaggaaagagaagactttcattgacggacccagccatggcagc
gtagcagccctgcgttttagacggcagcagctcgggactctggacgtgtgtttgccctcaagtttgctaagctgctggtttattactgaagaaagaatgtggcagattgttttctttactct
gagctgtgatcttgtcttggccgcagccgggatcttagacctagccccacagatgcttcgagaactccaggagactaatgcggcgctgcaagacgtgagagagctcttgcgacagca
ggtcaaggagatcaccttcctgaagaatacggtgatggaatgtgacgcttgcggaggctcccttgtcaatctttgcactaaagaaggtgttttactaaagggaggaaaaagagagga
agagaaaccatttagagactgtgcagatgtatatcaagctggttttaataaaagtggaatctacactatttatattaataatatgccagaacccaaaaaggtgttttgcaatatggatg
tcaatgggggaggttggactgtaatacaacatcgtgaagatggaagtctagatttccaaagaggctggaaggaatataaaatgggttttggaaatccctccggtgaatattggctgg
ggaatgagtttatttttgccattaccagtcagaggcagtacatgctaagaattgagttaatggactgggaagggaaccgagcctattcacagtatgacagattccacataggaaatga
aaagcaaaactataggttgtatttaaaaggtcacactgggacagcaggaaaacagagcagcctgatcttacacggtgctgatttcagcactaaagatgctgataatgacaactgtat
gtgcaaatgtgccctcatgttaacaggaggatggtggtttgatgcttgtggcccctccaatctaaatggaatgttctatactgcgggacaaaaccatggaaaactgaatgggataaag
tggcactacttcaaagggcccagttactccttacgttccacaactatgatgattcgacctttagatttttgaggctgctgcagctgcatgggtgcctgctgctgcctgccttggcctgatgg
ccaggccagagtgctgccagtcctctgcatgttctgctcttgtgcccttctgagcccacaataaaggctgagctcttatcttgcaaaaggc

Fig. 27B

PAN36

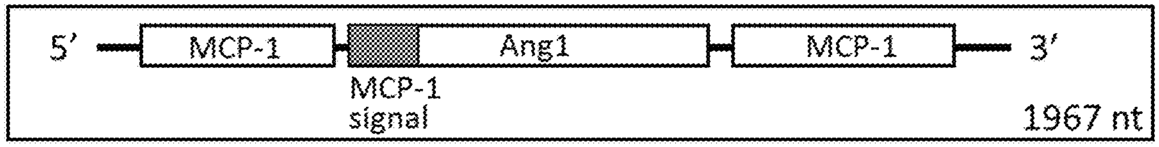

Fig. 28A

PAN36 gaggaaccgagaggctgagactaacccagaaacatccaattctcaaactgaagctcgcactctcgcctccagcatgaaagtctctgccgcccttctgtgcctgctgctcatagcagcc
accttcattccccaagggctcgctcacatagggtgcagcaatcagcgccgaagtccagaaaacagtgggagaagatataaccggattcaacatgggcaatgtgcctacactttcatt
cttccagaacacgatggcaactgtcgtgagagtacgacagaccagtacaacacaaacgctctgcagagagatgctccacacgtggaaccggatttctcttcccagaaacttcaacat
ctggaacatgtgatggaaaattatactcagtggctgcaaaaacttgagaattacattgtggaaaacatgaagtcggagatggcccagatacagcagaatgcagttcagaaccacac
ggctaccatgctggagataggaaccagcctcctctctcagactgcagagcagaccagaaagctgacagatgttgagacccaggtactaaatcaaacttctcgacttgagatacagct
gctggagaattcattatccacctacaagctagagaagcaacttcttcaacagacaaatgaaatcttgaagatccatgaaaaaaacagtttattagaacataaaatcttagaaatgga
aggaaaacacaaggaagagttggacaccttaaaggaagagaaagagaaccttcaaggcttggttactcgtcaaacatatataatccaggagctggaaaagcaattaaacagagct
accaccaacaacagtgtccttcagaagcagcaactggagctgatggacacagtccacaaccttgtcaatctttgcactaaagaaggtgttttactaaagggaggaaaaagagagga
agagaaaccatttagagactgtgcagatgtatatcaagctggttttaataaaagtggaatctacactatttatattaataatatgccagaacccaaaaaggtgttttgcaatatggatg
tcaatgggggaggttggactgtaatacaacatcgtgaagatggaagtctagatttccaaagaggctggaaggaatataaaatgggttttggaaatccctccggtgaatattggctgg
ggaatgagtttatttttgccattaccagtcagaggcagtacatgctaagaattgagttaatggactgggaagggaaccgagcctattcacagtatgacagattccacataggaaatga
aaagcaaaactataggttgtatttaaaaggtcacactgggacagcaggaaaacagagcagcctgatcttacacggtgctgatttcagcactaaagatgctgataatgacaactgtat
gtgcaaatgtgccctcatgttaacaggaggatggtggtttgatgcttgtggcccctccaatctaaatggaatgttctatactgcgggacaaaaccatggaaaactgaatgggataaag

Fig. 28B tggcactacttcaaagggcccagttactccttacgttccacaactatgatgattcgacctttagatttttgaacactcactccacaacccaagaatctgcagctaacttattttcccctag
ctttccccagacaccctgttttattttattataatgaattttgtttgttgatgtgaaacattatgccttaagtaatgttaattcttatttaagttattgatgttttaagtttatctttcatggtact
agtgtttttagatacagagacttggggaaattgcttttcctcttgaaccacagttctacccctgggatgttttgagggtctttgcaagaatcattaatacaaagaatttttttaacattcc
aatgcattgctaaaatattattgtggaaatgaatattttgtaactattacaccaaataaatatattttgtaca Fig. 28B (continued)

PAN37

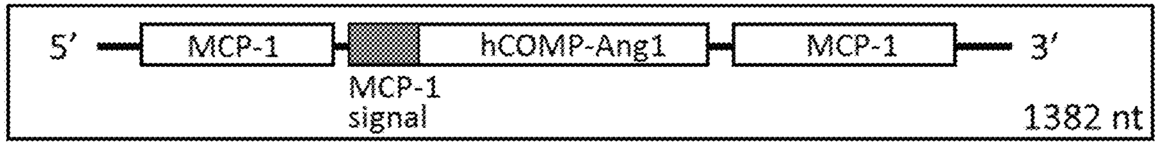

Fig. 29A

PAN37 gaggaaccgagaggctgagactaacccagaaacatccaattctcaaactgaagctcgcactctcgcctccagcatgaaagtctctgccgcccttctgtgcctgctgctcatagcagcc
accttcattccccaagggctcgctgggatcttagacttgggcccgcagatgcttcgggaactgcaggaaaccaacgcggcgctgcaggacgtgcgggagctgctgcggcagcaggtc
agggagatcacgttcctgaaaaacacggtgatggagtgtgacgcgtgcggaggctcccttgtcaatctttgcactaaagaaggtgttttactaaagggaggaaaaagagaggaaga
gaaaccatttagagactgtgcagatgtatatcaagctggttttaataaaagtggaatctacactatttatattaataatatgccagaacccaaaaaggtgttttgcaatatggatgtca
atgggggaggttggactgtaatacaacatcgtgaagatggaagtctagatttccaaagaggctggaaggaatataaaatgggttttggaaatccctccggtgaatattggctgggga
atgagtttatttttgccattaccagtcagaggcagtacatgctaagaattgagttaatggactgggaagggaaccgagcctattcacagtatgacagattccacataggaaatgaaaa
gcaaaactataggttgtatttaaaaggtcacactgggacagcaggaaaacagagcagcctgatcttacacggtgctgatttcagcactaaagatgctgataatgacaactgtatgtgc
aaatgtgccctcatgttaacaggaggatggtggtttgatgcttgtggcccctccaatctaaatggaatgttctatactgcgggacaaaaccatggaaaactgaatgggataaagtggc
actacttcaaagggcccagttactccttacgttccacaactatgatgattcgacctttagatttttgaacactcactccacaacccaagaatctgcagctaacttattttcccctagctttc
cccagacaccctgttttattttattataatgaattttgtttgttgatgtgaaacattatgccttaagtaatgttaattcttatttaagttattgatgttttaagtttatctttcatggtactagtg
tttttagatacagagacttggggaaattgcttttcctcttgaaccacagttctacccctgggatgttttgagggtctttgcaagaatcattaatacaaagaatttttttaacattccaatg
cattgctaaaatattattgtggaaatgaatattttgtaactattacaccaaataaatatattttgtaca

Fig. 29B

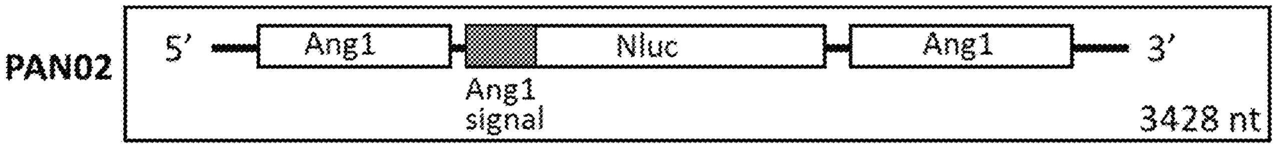

Figure 30A

PAN02 gccctaagccatcagcaatccttagtataggggcacactcatgcattcctgtcaagtcatcttgtgaaaggctgcctgcttccagcttggcttggatgtgcaaccttaataaaactcact
gaggtctgggagaaaatagcagatctgcagcagatagggtagaggaaagggtctagaatatgtacacgcagctgactcaggcaggctccatgctgaacggtcacacagagaggaa
acaataaatctcagctactatgcaataaatatctcaagttttaacgaagaaaaacatcattgcagtgaaataaaaaattttaaattttagaacaaagctaacaaatggctagttttct
atgattcttcttcaaacgctttctttgagggggaaagagtcaaacaaacaagcagttttacctgaaataaagaactagttttagaggtcagaagaaaggagcaagttttgcgagaggc
acggaaggagtgtgctggcagtacaatgacagttttcctttcctttgctttcctcgctgccattctgactgtcttcacactcgaagatttcgttggggactggcgacagacagccggctac
aacctggaccaagtccttgaacagggaggtgtgtccagtttgtttcagaatctcggggtgtccgtaactccgatccaaaggattgtcctgagcggtgaaaatgggctgaagatcgaca
tccatgtcatcatcccgtatgaaggtctgagcggcgaccaaatgggccagatcgaaaaaatttttaaggtggtgtaccctgtggatgatcatcactttaaggtgatcctgcactatggc
acactggtaatcgacggggttacgccgaacatgatcgactatttcggacggccgtatgaaggcatcgccgtgttcgacggcaaaaagatcactgtaacagggaccctgtggaacggc
aacaaaattatcgacgagcgcctgatcaaccccgacggctccctgctgttccgagtaaccatcaacggagtgaccggctggcggctgtgcgaacgcattctggcgtaaaagcgcaat
gtcagaagcgattatgaaagcaacaaagaaatccggagaagctgccaggtgagaaactgtttgaaaacttcagaagcaaacaatattgtctcccttccagcaataagtggtagttat
gtgaagtcaccaaggttcttgaccgtgaatctggagccgtttgagttcacaagagtctctacttggggtgacagtgctcacgtggctcgactatagaaaactccactgactgtcgggctt
taaaaagggaagaaactgctgagcttgctgtgcttcaaactactactggaccttattttggaactatggtagccagatgataaatatggttaatttcatgtaaaacagaaaaaaagag
tgaaaaagagaatatacatgaagaatagaaacaagcctgccataatcctttggaaaagatgtattataccagtgaaaaggtgttatatctatgcaaacctactaacaaattatactgt
tgcacaattttgataaaaatttagaacagcattgtcctctgagttggttaaatgttaatggatttcagaagcctaattccagtatcatacttactagttgatttctgcttacccatcttcaa

Fig. 30B atgaaaattccatttttgtaagccataatgaactgtagtacatggacaataagtgtgtggtagaaacaaactccattactctgatttttgatacagttttcagaaaaagaaatgaacat
aatcaagtaaggatgtatgtggtgaaaacttaccacccccatactatggttttcatttactctaaaaactgattgaatgatatataaatatatttatagcctgagtaaagttaaaagaat
gtaaaatatatcatcaagttcttaaaataatatacatgcatttaatatttcctttgatattatacaggaaagcaatattttggagtatgttaagttgaagtaaaagcaagtactctggagc
agttcattttacagtatctacttgcatgtgtatacatacatgtaacttcattattttaaaaatatttttagaactccaatactcaccctgttatgtcttgctaatttaaattttgctaattaact
gaaacatgcttaccagattcacactgttccagtgtctataaaagaaacactttgaagtctataaaaaataaaataattataaatatcattgtacatagcatgtttatatctgcaaaaaa
cctaatagctaattaatctggaatatgcaacattgtccttaattgatgcaaataacacaaatgctcaaagaaatctactatatcccttaatgaaatacatcattcttcatatatttctcctt
cagtccattcccttaggcaatttttaatttttaaaaattattatcaggggagaaaaattggcaaaactattatatgtaagggaaatatatacaaaaagaaaattaatcatagtcacctg
actaagaaattctgactgctagttgccataaataactcaatggaaatattcctatgggataatgtattttaagtgaatttttggggtgcttgaagttactgcattattttatcaagaagtct
tctctgcctgtaagtgtccaaggttatgacagtaaacagtttttattaaaacatgagtcactatgggatgagaaaattgaaataaagctactgggcctcctctcataaaagagacagtt
gttggcaaggtagcaataccagtttcaaacttggtgacttgatccactatgccttaatggtttcctccatttgagaaaataaagctattcacattgttaagaaaaatactttttaaagttt
accatcaagtctttttttatatttatgtgtctgtattctacccctttttgccttacaagtgatatttgcaggtattataccatttttctattcttggtggcttcttcatagcaggtaagcctctcctt
ctaaaaacttctcaactgttttcatttaagggaaagaaaatgagtattttgtccttttgtgttcctacagacactttcttaaaccagtttttggataaagaatactatttccaaactcatatt
acaaaaacaaaataaaataataaaaaaagaaagcatgatatttactgttttgttgtctgggtttgagaaatgaaatattgtttccaattatttataataaatcagtataaaatgttttat
gattgttatgtgtattatgtaatacgtacatgtttatggcaatttaacatgtgtattcttttaattgtttcagaataggataattaggtattcgaattttgtctttaaaattcatgtggtttcta
tgcaaagttcttcatatcatcacaacattatttgatttaaataaaattgaaagtaatatttgtgcaa

Fig. 30 B (continued)

PAN05

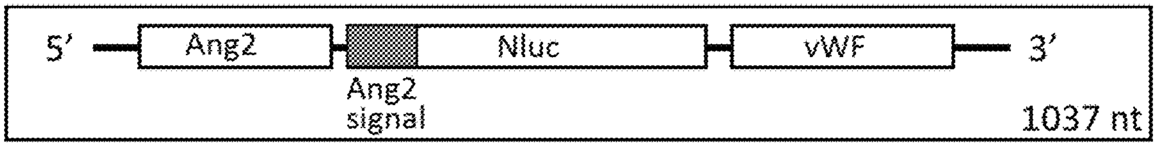

Fig. 31A

PAN05 aaagtgattgattcggatactgacactgtaggatctggggagagaggaacaaaggaccgtgaaagctgctctgtaaaagctgacacagccctcccaagtgagcaggactgttcttcc
cactgcaatctgacagtttactgcatgcctggagagaacacagcagtaaaaaccaggtttgctactggaaaaagaggaaagagaagactttcattgacggacccagccatggcagc
gtagcagccctgcgttttagacggcagcagctcgggactctggacgtgtgtttgccctcaagtttgctaagctgctggtttattactgaagaaagaatgtggcagattgttttctttactct
gagctgtgatcttgtcttggccgcagccgtcttcacactcgaagatttcgttggggactggcgacagacagccggctacaacctggaccaagtccttgaacagggaggtgtgtccagtt
tgtttcagaatctcggggtgtccgtaactccgatccaaaggattgtcctgagcggtgaaaatgggctgaagatcgacatccatgtcatcatcccgtatgaaggtctgagcggcgacca
aatgggccagatcgaaaaaatttttaaggtggtgtaccctgtggatgatcatcactttaaggtgatcctgcactatggcacactggtaatcgacggggttacgccgaacatgatcgact
atttcggacggccgtatgaaggcatcgccgtgttcgacggcaaaaagatcactgtaacagggaccctgtggaacggcaacaaaattatcgacgagcgcctgatcaaccccgacggc
tccctgctgttccgagtaaccatcaacggagtgaccggctggcggctgtgcgaacgcattctggcgtaaggctgctgcagctgcatgggtgcctgctgctgcctgccttggcctgatgg
ccaggccagagtgctgccagtcctctgcatgttctgctcttgtgcccttctgagcccacaataaaggctgagctcttatcttgcaaaaggc

Fig. 31B

PAN07

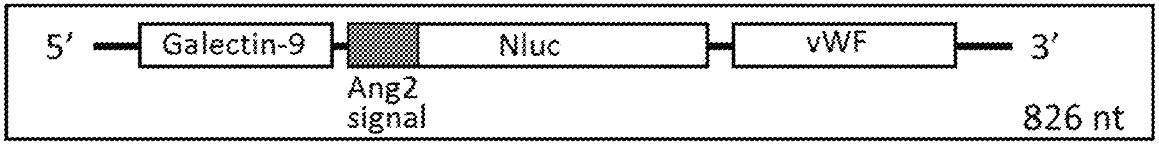

Fig. 32A

PAN07 tccccattgaataacagccaagttgctttggtttctatttctttgttaagtcgttccctctacaaaggacttcctagtgggtgtgaaaggcagcggtggccacagaggcggcggagagat
gtggcagattgttttctttactctgagctgtgatcttgtcttggccgcagccgtcttcacactcgaagatttcgttggggactggcgacagacagccggctacaacctggaccaagtcctt
gaacagggaggtgtgtccagtttgtttcagaatctcggggtgtccgtaactccgatccaaaggattgtcctgagcggtgaaaatgggctgaagatcgacatccatgtcatcatcccgta
tgaaggtctgagcggcgaccaaatgggccagatcgaaaaaatttttaaggtggtgtaccctgtggatgatcatcactttaaggtgatcctgcactatggcacactggtaatcgacggg
gttacgccgaacatgatcgactatttcggacggccgtatgaaggcatcgccgtgttcgacggcaaaaagatcactgtaacagggaccctgtggaacggcaacaaaattatcgacga
gcgcctgatcaaccccgacggctccctgctgttccgagtaaccatcaacggagtgaccggctggcggctgtgcgaacgcattctggcgtaaggctgctgcagctgcatgggtgcctgc
tgctgcctgccttggcctgatggccaggccagagtgctgccagtcctctgcatgttctgctcttgtgcccttctgagcccacaataaaggctgagctcttatcttgcaaaaggc

Fig. 32B

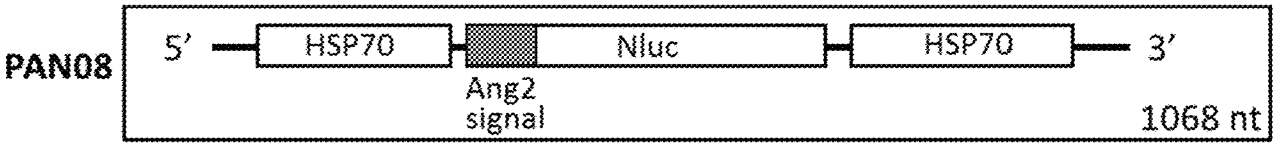

Fig. 33A

PAN08 ataaaagcccaggggcaagcggtccggataacggctagcctgaggagctgctgcgacagtccactacctttttcgagagtgactcccgttgtcccaaggcttcccagagcgaacctgt
gcggctgcaggcaccggcgcgtcgagtttccggcgtccggaaggaccgagctcttctcgcgaatccagtgttccgtttccagcccccaatctcagagcggagccgacagagagcagg
gaaccggcatgtggcagattgttttctttactctgagctgtgatcttgtcttggccgcagccgtcttcacactcgaagatttcgttggggactggcgacagacagccggctacaacctgg
accaagtccttgaacagggaggtgtgtccagtttgtttcagaatctcggggtgtccgtaactccgatccaaaggattgtcctgagcggtgaaaatgggctgaagatcgacatccatgtc
atcatcccgtatgaaggtctgagcggcgaccaaatgggccagatcgaaaaaatttttaaggtggtgtaccctgtggatgatcatcactttaaggtgatcctgcactatggcacactggt
aatcgacggggttacgccgaacatgatcgactatttcggacggccgtatgaaggcatcgccgtgttcgacggcaaaaagatcactgtaacagggaccctgtggaacggcaacaaaa
ttatcgacgagcgcctgatcaaccccgacggctccctgctgttccgagtaaccatcaacggagtgaccggctggcggctgtgcgaacgcattctggcgtaagggcctttccaagattg
ctgtttttgttttggagcttcaagactttgcatttcctagtatttctgtttgtcagttctcaatttcctgtgtttgcaatgttgaaatttttggtgaagtactgaacttgctttttttccggtttct
acatgcagagatgaatttatactgccatcttacgactatttcttctttttaatacacttaactcaggccatttttaagttggttacttcaaagtaaataaactttaaaattc

Fig. 33B

PAN09

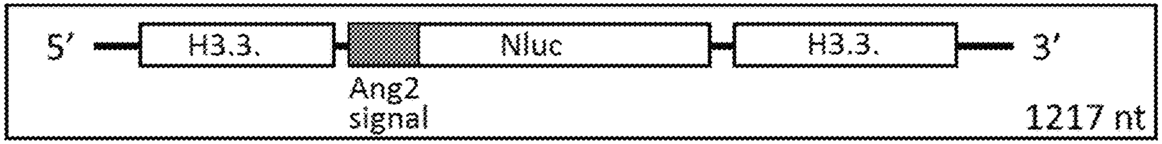

FIG. 34A

PAN09 gtcagccatctttcaattgtgttcgcagccgccgccgcgccgccgtcgctctccaacgccagcgccgcctctcgctcgccgagctccagccgaaggagaagggggggtaagtaaggag
gtctctgtaccatgtggcagattgttttctttactctgagctgtgatcttgtcttggccgcagccgtcttcacactcgaagatttcgttggggactggcgacagacagccggctacaacct
ggaccaagtccttgaacagggaggtgtgtccagtttgtttcagaatctcggggtgtccgtaactccgatccaaaggattgtcctgagcggtgaaaatgggctgaagatcgacatccat
gtcatcatcccgtatgaaggtctgagcggcgaccaaatgggccagatcgaaaaaatttttaaggtggtgtaccctgtggatgatcatcactttaaggtgatcctgcactatggcacact
ggtaatcgacggggttacgccgaacatgatcgactatttcggacggccgtatgaaggcatcgccgtgttcgacggcaaaaagatcactgtaacagggaccctgtggaacggcaaca
aaattatcgacgagcgcctgatcaaccccgacggctccctgctgttccgagtaaccatcaacggagtgaccggctggcggctgtgcgaacgcattctggcgtaagaatccactatgat
gggaaacatttcattctcaaaaaaaaaaaaaaaaatttctcttcttcctgttattggtagttctgaacgttagatattttttttccatggggtcaaaaggtacctaagtatatgattgcga
gtggaaaaataggggacagaaatcaggtattggcagtttttccattttcatttgtgtgtgaatttttaatataaatgcggagacgtaaagcattaatgcaagttaaaatgtttcagtgaa
caagtttcagcggttcaactttataataattataaataaacctgttaaatttttctggacaatgccagcatttggattttttaaaacaagtaaatttcttattgatggcaactaaatggtg
tttgtagcatttttatcatacagtagattccatccattcactatacttttctaactgagttgtcctacatgcaagtacatgtttttaatgttgtctgtcttctgtgctgttcctgtaagtttgcta
ttaaaatacattaaactat

Fig. 34B

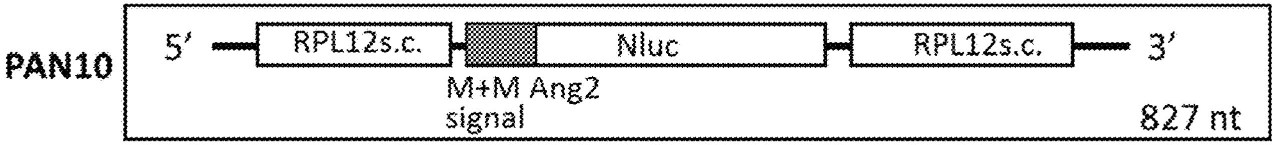

Fig. 35A

PAN10

Catatcttcattcttcactctttcccccccccccttatcctcctatctaatcctctcatctctctcctcctcttcctccaacaacaactaacaatggcagcaactacaacaatggcacagat
tgttttctttactctgagctgtgatcttgtcttggccgcagccgtcttcacactcgaagatttcgttggggactggcgacagacagccggctacaacctggaccaagtccttgaacaggg
aggtgtgtccagtttgtttcagaatctcggggtgtccgtaactccgatccaaaggattgtcctgagcggtgaaaatgggctgaagatcgacatccatgtcatcatcccgtatgaaggtct
gagcggcgaccaaatgggccagatcgaaaaaatttttaaggtggtgtaccctgtggatgatcatcactttaaggtgatcctgcactatggcacactggtaatcgacggggttacgccg
aacatgatcgactatttcggacggccgtatgaaggcatcgccgtgttcgacggcaaaaagatcactgtaacagggaccctgtggaacggcaacaaaattatcgacgagcgcctgatc
aaccccgacggctccctgctgttccgagtaaccatcaacggagtgaccggctggcggctgtgcgaacgcattctggcgtaattttgagtaattttcaattttgtttttgtttttgtttttgtt
gttgggagttgttgtaatttggtaaatgttggggtcactaaaatcttttgttgcaattttagcacctttttattagatatataaaattgggtttagatgtagttaa

Fig. 35B

PAN11

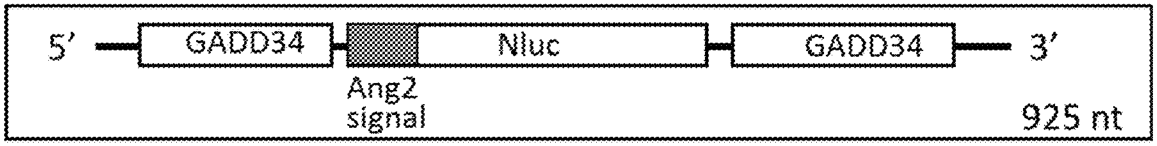

Fig. 36A

PAN11 ataaaagcctagtggccattgtgttcgttgctcttatcggttcccatcccagttgttgatcttatgcaagacgctgcacgaccccgcgcccgcttgtcgccacggcacttgaggcagccg
gagatactctgagttactcggagcccgacgcctgagggtgagatgaacgcgctggcctccctaaccgtccggacctgtgatcgcttctggcagaccgaaccggcgctcctgcccccgg
ggtgacgcgcagctcccagccgcccagacacatgtggcagattgttttctttactctgagctgtgatcttgtcttggccgcagccgtcttcacactcgaagatttcgttggggactggcga
cagacagccggctacaacctggaccaagtccttgaacagggaggtgtgtccagtttgtttcagaatctcggggtgtccgtaactccgatccaaaggattgtcctgagcggtgaaaatg
ggctgaagatcgacatccatgtcatcatcccgtatgaaggtctgagcggcgaccaaatgggccagatcgaaaaaatttttaaggtggtgtaccctgtggatgatcatcactttaaggt
gatcctgcactatggcacactggtaatcgacggggttacgccgaacatgatcgactatttcggacggccgtatgaaggcatcgccgtgttcgacggcaaaaagatcactgtaacagg
gaccctgtggaacggcaacaaaattatcgacgagcgcctgatcaaccccgacggctccctgctgttccgagtaaccatcaacggagtgaccggctggcggctgtgcgaacgcattct
ggcgtaagaccaactggtttgcctataatttattaactatttatttttctaagtgtgggtttatataaggaataaagccttttgatttgtagcga

Fig. 36B

PAN12

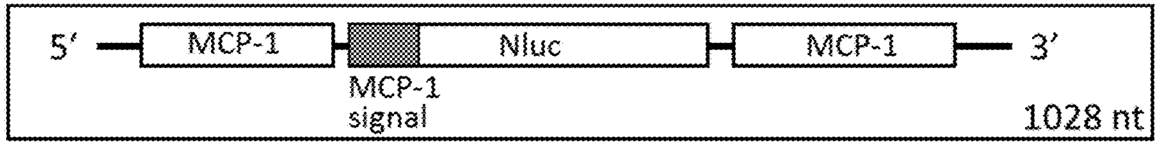

Fig. 37A

PAN12 gaggaaccgagaggctgagactaacccagaaacatccaattctcaaactgaagctcgcactctcgcctccagcatgaaagtctctgccgcccttctgtgcctgctgctcatagcagcc
accttcattccccaagggctcgctgtcttcacactcgaagatttcgttggggactggcgacagacagccggctacaacctggaccaagtccttgaacagggaggtgtgtccagtttgtt
tcagaatctcggggtgtccgtaactccgatccaaaggattgtcctgagcggtgaaaatgggctgaagatcgacatccatgtcatcatcccgtatgaaggtctgagcggcgaccaaatg
ggccagatcgaaaaaatttttaaggtggtgtaccctgtggatgatcatcactttaaggtgatcctgcactatggcacactggtaatcgacggggttacgccgaacatgatcgactattt
cggacggccgtatgaaggcatcgccgtgttcgacggcaaaaagatcactgtaacagggaccctgtggaacggcaacaaaattatcgacgagcgcctgatcaaccccgacggctccc
tgctgttccgagtaaccatcaacggagtgaccggctggcggctgtgcgaacgcattctggcgtaaacactcactccacaacccaagaatctgcagctaacttattttcccctagctttcc
ccagacaccctgttttattttattataatgaattttgtttgttgatgtgaaacattatgccttaagtaatgttaattcttatttaagttattgatgttttaagtttatctttcatggtactagtgtt
ttttagatacagagacttggggaaattgcttttcctcttgaaccacagttctacccctgggatgttttgagggtctttgcaagaatcattaatacaaagaatttttttaacattccaatgc
attgctaaaatattattgtggaaatgaatattttgtaactattacaccaaataaatatattttgtaca

Fig. 37B

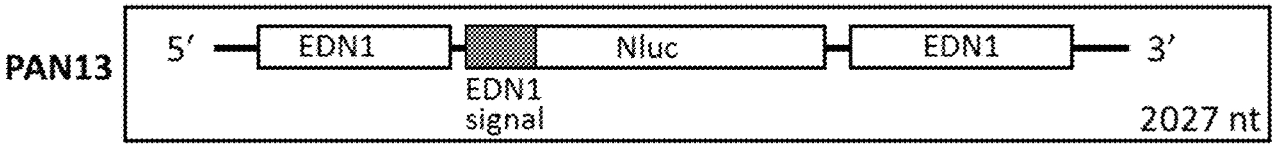

Fig. 38A

PAN13 ggagctgtttacccccactctaataggggttcaatataaaaagccggcagagagctgtccaagtcagacgcgcctctgcatctgcgccaggcgaacgggtcctgcgcctcctgcagtc
ccagctctccaccgccgcgtgcgcctgcagacgctccgctcgctgccttctctcctggcaggcgctgccttttctccccgttaaaagggcacttgggctgaaggatcgctttgagatctg
aggaacccgcagcgctttgagggacctgaagctgtttttcttcgttttcctttgggttcagtttgaacgggaggtttttgatcccttttttcagaatggattatttgctcatgattttctctct
gctgtttgtggcttgccaaggagtcttcacactcgaagatttcgttggggactggcgacagacagccggctacaacctggaccaagtccttgaacagggaggtgtgtccagtttgtttc
agaatctcggggtgtccgtaactccgatccaaaggattgtcctgagcggtgaaaatgggctgaagatcgacatccatgtcatcatcccgtatgaaggtctgagcggcgaccaaatgg
gccagatcgaaaaaatttttaaggtggtgtaccctgtggatgatcatcactttaaggtgatcctgcactatggcacactggtaatcgacggggttacgccgaacatgatcgactatttc
ggacggccgtatgaaggcatcgccgtgttcgacggcaaaaagatcactgtaacagggaccctgtggaacggcaacaaaattatcgacgagcgcctgatcaaccccgacggctccct
gctgttccgagtaaccatcaacggagtgaccggctggcggctgtgcgaacgcattctggcgtaacagaccttcggggcctgtctgaagccatagcctccacggagagccctgtggccg
actctgcactctccaccctggctgggatcagagcaggagcatcctctgctggttcctgactggcaaaggaccagcgtcctcgttcaaaacattccaagaaaggttaaggagttccccc
aaccatcttcactggcttccatcagtggtaactgctttggtctcttctttcatctggggatgacaatggacctctcagcagaaacacacagtcacattcgaattcgggtggcatcctccgg
agagagagagaggaaggagattccacacaggggtggagtttctgacgaaggtcctaagggagtgtttgtgtctgactcaggcgcctggcacatttcagggagaaactccaaagtcc
acacaaagattttctaaggaatgcacaaattgaaaacacactcaaaagacaaacatgcaagtaaagaaaaaaaaaagaaagacttttgtttaaatttgtaaaatgcaaaactgaat
gaaactgttactaccataaatcaggatatgtttcatgaatatgagtctacctcacctatattgcactctggcagaagtatttcccacatttaattattgcctccccaaactcttcccacccc
tgctgccccttcctccatcccccatactaaatcctagcctcgtagaagtctggtctaatgtgtcagcagtagatataatattttcatggtaatctactagctctgatccataagaaaaaaa
agatcattaaatcaggagattccctgtccttgatttttggagacacaatggtatagggttgtttatgaaatatattgaaaagtaagtgtttgttacgctttaaagcagtaaaattattttcc
tttatataaccggctaatgaaagaggttggattgaattttgatgtacttatttttttatagatatttatattcaaacaatttattccttatatttaccatgttaaatatctgtttgggcaggcc
atattggtctatgtatttttaaaatatgtatttctaaatgaaattgagaacatgctttgttttgcctgtcaaggtaatgactttagaaaataaatattttttccttactgtaaa

Fig. 38B

PAN28

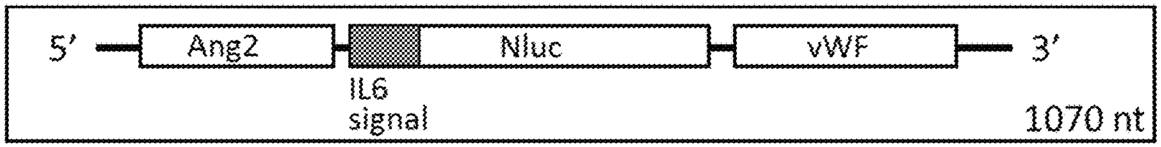

Fig. 39A

PAN28 aaagtgattgattcggatactgacactgtaggatctggggagagaggaacaaaggaccgtgaaagctgctctgtaaaagctgacacagccctcccaagtgagcaggactgttcttcc
cactgcaatctgacagtttactgcatgcctggagagaacacagcagtaaaaaccaggtttgctactggaaaaagaggaaagagaagactttcattgacggacccagccatggcagc
gtagcagccctgcgttttagacggcagcagctcgggactctggacgtgtgtttgccctcaagtttgctaagctgctggtttattactgaagaaagaatgaactccttctccacaagcgcc
ttcggtccagttgccttctccctgggcctgctcctggtgttgcctgctgccttccctgccccagtcttcacactcgaagatttcgttggggactggcgacagacagccggctacaacctgg
accaagtccttgaacagggaggtgtgtccagtttgtttcagaatctcggggtgtccgtaactccgatccaaaggattgtcctgagcggtgaaaatgggctgaagatcgacatccatgtc
atcatcccgtatgaaggtctgagcggcgaccaaatgggccagatcgaaaaaatttttaaggtggtgtaccctgtggatgatcatcactttaaggtgatcctgcactatggcacactggt
aatcgacggggttacgccgaacatgatcgactatttcggacggccgtatgaaggcatcgccgtgttcgacggcaaaaagatcactgtaacagggaccctgtggaacggcaacaaaa
ttatcgacgagcgcctgatcaaccccgacggctccctgctgttccgagtaaccatcaacggagtgaccggctggcggctgtgcgaacgcattctggcgtaaggctgctgcagctgcat
gggtgcctgctgctgcctgccttggcctgatggccaggccagagtgctgccagtcctctgcatgttctgctcttgtgcccttctgagcccacaataaaggctgagctcttatcttgcaaaa
ggc

Fig. 39B

PAN29

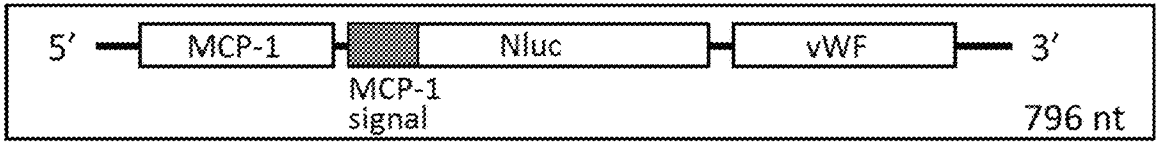

Fig. 40A

PAN29 gaggaaccgagaggctgagactaacccagaaacatccaattctcaaactgaagctcgcactctcgcctccagcatgaaagtctctgccgcccttctgtgcctgctgctcatagcagcc
accttcattccccaagggctcgctgtcttcacactcgaagatttcgttggggactggcgacagacagccggctacaacctggaccaagtccttgaacagggaggtgtgtccagtttgtt
tcagaatctcggggtgtccgtaactccgatccaaaggattgtcctgagcggtgaaaatgggctgaagatcgacatccatgtcatcatcccgtatgaaggtctgagcggcgaccaaatg
ggccagatcgaaaaaatttttaaggtggtgtaccctgtggatgatcatcactttaaggtgatcctgcactatggcacactggtaatcgacggggttacgccgaacatgatcgactattt
cggacggccgtatgaaggcatcgccgtgttcgacggcaaaaagatcactgtaacagggaccctgtggaacggcaacaaaattatcgacgagcgcctgatcaaccccgacggctccc
tgctgttccgagtaaccatcaacggagtgaccggctggcggctgtgcgaacgcattctggcgtaaggctgctgcagctgcatgggtgcctgctgctgcctgccttggcctgatggccag
gccagagtgctgccagtcctctgcatgttctgctcttgtgcccttctgagcccacaataaaggctgagctcttatcttgcaaaaggc

Fig. 40B

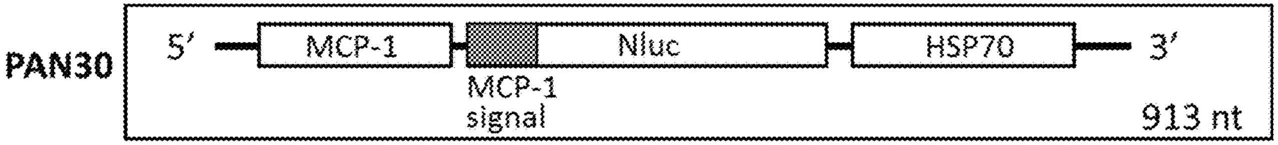

Fig. 41A

PAN30 gaggaaccgagaggctgagactaacccagaaacatccaattctcaaactgaagctcgcactctcgcctccagcatgaaagtctctgccgcccttctgtgcctgctgctcatagcagcc
accttcattccccaagggctcgctgtcttcacactcgaagatttcgttggggactggcgacagacagccggctacaacctggaccaagtccttgaacagggaggtgtgtccagtttgtt
tcagaatctcggggtgtccgtaactccgatccaaaggattgtcctgagcggtgaaaatgggctgaagatcgacatccatgtcatcatcccgtatgaaggtctgagcggcgaccaaatg
ggccagatcgaaaaaatttttaaggtggtgtaccctgtggatgatcatcactttaaggtgatcctgcactatggcacactggtaatcgacggggttacgccgaacatgatcgactattt
cggacggccgtatgaaggcatcgccgtgttcgacggcaaaaagatcactgtaacagggaccctgtggaacggcaacaaaattatcgacgagcgcctgatcaaccccgacggctccc
tgctgttccgagtaaccatcaacggagtgaccggctggcggctgtgcgaacgcattctggcgtaagggcctttccaagattgctgtttttgttttggagcttcaagactttgcatttccta
gtatttctgtttgtcagttctcaatttcctgtgtttgcaatgttgaaatttttttggtgaagtactgaacttgcttttttttccggtttctacatgcagagatgaatttatactgccatcttacgact
atttcttctttttaatacacttaactcaggccattttttaagttggttacttcaaagtaaataaactttaaaattc

Fig. 41B

PAN31

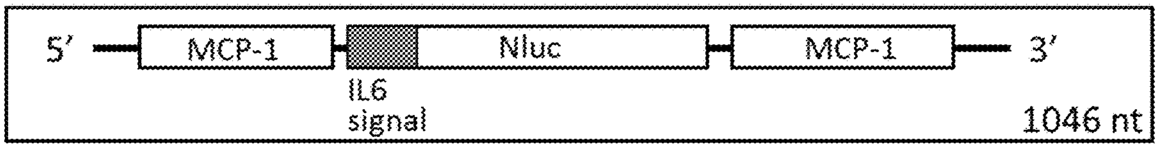

Fig. 42A

PAN31 gaggaaccgagaggctgagactaacccagaaacatccaattctcaaactgaagctcgcactctcgcctccagcatgaactccttctccacaagcgccttcggtccagttgccttctccc
tgggcctgctcctggtgttgcctgctgccttccctgccccagtcttcacactcgaagatttcgttggggactggcgacagacagccggctacaacctggaccaagtccttgaacaggga
ggtgtgtccagtttgtttcagaatctcggggtgtccgtaactccgatccaaaggattgtcctgagcggtgaaaatgggctgaagatcgacatccatgtcatcatcccgtatgaaggtctg
agcggcgaccaaatgggccagatcgaaaaaatttttaaggtggtgtaccctgtggatgatcatcactttaaggtgatcctgcactatggcacactggtaatcgacggggttacgccga
acatgatcgactatttcggacggccgtatgaaggcatcgccgtgttcgacggcaaaaagatcactgtaacagggaccctgtggaacggcaacaaaattatcgacgagcgcctgatca
accccgacggctccctgctgttccgagtaaccatcaacggagtgaccggctggcggctgtgcgaacgcattctggcgtaaacactcactccacaacccaagaatctgcagctaactta
ttttcccctagctttccccagacaccctgttttattttattataatgaattttgtttgttgatgtgaaacattatgccttaagtaatgttaattcttatttaagttattgatgttttaagtttatct
ttcatggtactagtgtttttagatacagagacttggggaaattgcttttcctcttgaaccacagttctacccctgggatgttttgagggtctttgcaagaatcattaatacaaagaattttt
tttaacattccaatgcattgctaaaatattattgtggaaatgaatattttgtaactattacaccaaataaatatattttgtaca

Fig. 42B

PAN32

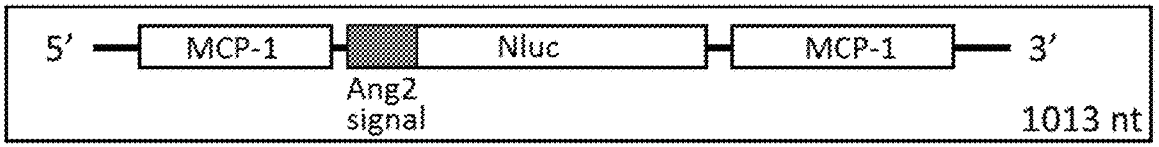

Fig. 43A

PAN32 gaggaaccgagaggctgagactaacccagaaacatccaattctcaaactgaagctcgcactctcgcctccagcatgtggcagattgttttctttactctgagctgtgatcttgtcttggc
cgcagccgtcttcacactcgaagatttcgttggggactggcgacagacagccggctacaacctggaccaagtccttgaacagggaggtgtgtccagtttgtttcagaatctcggggtgt
ccgtaactccgatccaaaggattgtcctgagcggtgaaaatgggctgaagatcgacatccatgtcatcatcccgtatgaaggtctgagcggcgaccaaatgggccagatcgaaaaa
atttttaaggtggtgtaccctgtggatgatcatcactttaaggtgatcctgcactatggcacactggtaatcgacggggttacgccgaacatgatcgactatttcggacggccgtatgaa
ggcatcgccgtgttcgacggcaaaaagatcactgtaacagggaccctgtggaacggcaacaaaattatcgacgagcgcctgatcaaccccgacggctccctgctgttccgagtaacc
atcaacggagtgaccggctggcggctgtgcgaacgcattctggcgtaaacactcactccacaacccaagaatctgcagctaacttattttcccctagctttccccagacaccctgtttta
ttttattataatgaattttgtttgttgatgtgaaacattatgccttaagtaatgttaattcttatttaagttattgatgttttaagtttatctttcatggtactagtgtttttagatacagagac
ttggggaaattgcttttcctcttgaaccacagttctacccctgggatgttttgagggtctttgcaagaatcattaatacaaagaatttttttaacattccaatgcattgctaaaatattatt
gtggaaatgaatattttgtaactattacaccaaataaatatatttttgtaca

Fig. 43B

PAN33

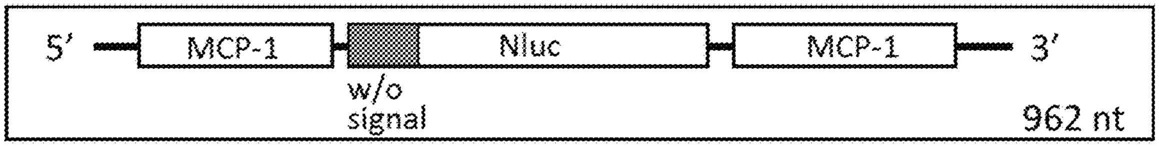

Fig. 44A

PAN33 gaggaaccgagaggctgagactaacccagaaacatccaattctcaaactgaagctcgcactctcgcctccagcatggtcttcacactcgaagatttcgttggggactggcgacagac
agccggctacaacctggaccaagtccttgaacagggaggtgtgtccagtttgtttcagaatctcggggtgtccgtaactccgatccaaaggattgtcctgagcggtgaaaatgggctg
aagatcgacatccatgtcatcatcccgtatgaaggtctgagcggcgaccaaatgggccagatcgaaaaaatttttaaggtggtgtaccctgtggatgatcatcactttaaggtgatcct
gcactatggcacactggtaatcgacggggttacgccgaacatgatcgactatttcggacggccgtatgaaggcatcgccgtgttcgacggcaaaaagatcactgtaacagggaccct
gtggaacggcaacaaaattatcgacgagcgcctgatcaaccccgacggctccctgctgttccgagtaaccatcaacggagtgaccggctggcggctgtgcgaacgcattctggcgta
aacactcactccacaacccaagaatctgcagctaacttattttcccctagctttccccagacaccctgttttattttattataatgaattttgtttgttgatgtgaaacattatgccttaagt
aatgttaattcttatttaagttattgatgttttaagtttatctttcatggtactagtgtttttttagatacagagacttggggaaattgcttttcctcttgaaccacagttctacccctgggatgt
tttgagggtctttgcaagaatcattaatacaaagaattttttttaacattccaatgcattgctaaaatattattgtggaaatgaatattttgtaactattacaccaaataaatatatttttgt
aca

Fig. 44B

PAN34

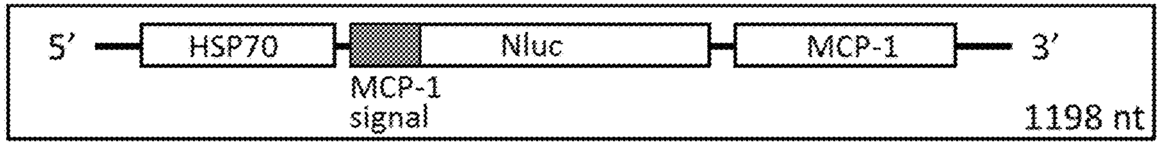

Fig. 45A

PAN34 ataaaagcccaggggcaagcggtccggataacggctagcctgaggagctgctgcgacagtccactaccttttcgagagtgactcccgttgtcccaaggcttcccagagcgaacctgt
gcggctgcaggcaccggcgcgtcgagtttccggcgtccggaaggaccgagctcttctcgcgaatccagtgttccgtttccagcccccaatctcagagcggagccgacagagagcagg
gaaccggcatgaaagtctctgccgcccttctgtgcctgctgctcatagcagccaccttcattccccaagggctcgctgtcttcacactcgaagatttcgttggggactggcgacagacag
ccggctacaacctggaccaagtccttgaacagggaggtgtgtccagtttgtttcagaatctcggggtgtccgtaactccgatccaaaggattgtcctgagcggtgaaaatgggctgaa
gatcgacatccatgtcatcatcccgtatgaaggtctgagcggcgaccaaatgggccagatcgaaaaaatttttaaggtggtgtaccctgtggatgatcatcactttaaggtgatcctgc
actatggcacactggtaatcgacggggttacgccgaacatgatcgactatttcggacggccgtatgaaggcatcgccgtgttcgacggcaaaaagatcactgtaacagggaccctgt
ggaacggcaacaaaattatcgacgagcgcctgatcaaccccgacggctccctgctgttccgagtaaccatcaacggagtgaccggctggcggctgtgcgaacgcattctggcgtaaa
cactcactccacaacccaagaatctgcagctaacttattttcccctagctttccccagacaccctgttttattttattataatgaattttgtttgttgatgtgaaacattatgccttaagtaat
gttaattcttatttaagttattgatgttttaagtttatctttcatggtactagtgtttttagatacagagacttggggaaattgcttttcctcttgaaccacagttctacccctgggatgtttt
gagggtctttgcaagaatcattaatacaaagaatttttttaacattccaatgcattgctaaaatattattgtggaaatgaatattttgtaactattacaccaaataaatatatttttgtac
a

Fig. 45B

PAN35

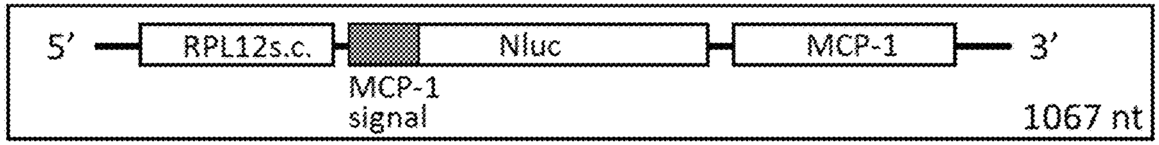

Fig. 46A

PAN35 catatcttcattcttcactctttccccccccccccttatcctcctatctaatcctctcatctctctcctcctcttcctccaacaacaactaacaatggcagcaactacaacaatgaaagtctct
gccgcccttctgtgcctgctgctcatagcagccaccttcattccccaagggctcgctgtcttcacactcgaagatttcgttggggactggcgacagacagccggctacaacctggacca
agtccttgaacagggaggtgtgtccagtttgtttcagaatctcggggtgtccgtaactccgatccaaaggattgtcctgagcggtgaaaatgggctgaagatcgacatccatgtcatca
tcccgtatgaaggtctgagcggcgaccaaatgggccagatcgaaaaaatttttaaggtggtgtaccctgtggatgatcatcactttaaggtgatcctgcactatggcacactggtaatc
gacggggttacgccgaacatgatcgactatttcggacggccgtatgaaggcatcgccgtgttcgacggcaaaaagatcactgtaacagggaccctgtggaacggcaacaaaattat
cgacgagcgcctgatcaaccccgacggctccctgctgttccgagtaaccatcaacggagtgaccggctggcggctgtgcgaacgcattctggcgtaaacactcactccacaacccaa
gaatctgcagctaacttattttcccctagctttccccagacaccctgttttattttattataatgaattttgtttgttgatgtgaaacattatgccttaagtaatgttaattcttatttaagttat
tgatgttttaagtttatctttcatggtactagtgtttttttagatacagagacttggggaaattgcttttcctcttgaaccacagttctacccctgggatgttttgagggtctttgcaagaatca
ttaatacaaagaatttttttaacattccaatgcattgctaaaatattattgtggaaatgaatattttgtaactattacaccaaataaatatatttttgtaca

Fig. 46B

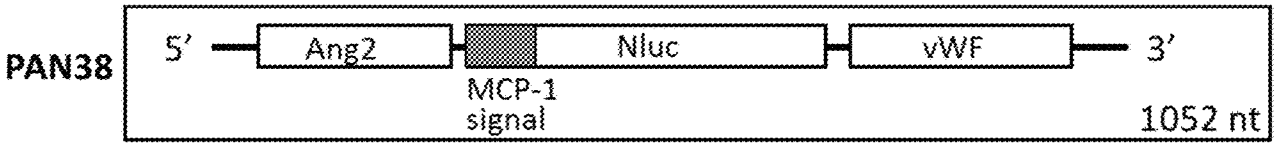

Fig. 47A

PAN38 aaagtgattgattcggatactgacactgtaggatctggggagagaggaacaaaggaccgtgaaagctgctctgtaaaagctgacacagccctcccaagtgagcaggactgttcttcc
cactgcaatctgacagtttactgcatgcctggagagaacacagcagtaaaaaccaggtttgctactggaaaaagaggaaagagaagactttcattgacggacccagccatggcagc
gtagcagccctgcgttttagacggcagcagctcgggactctggacgtgtgtttgccctcaagtttgctaagctgctggtttattactgaagaaagaatgaaagtctctgccgcccttctgt
gcctgctgctcatagcagccaccttcattccccaagggctcgctgtcttcacactcgaagatttcgttggggactggcgacagacagccggctacaacctggaccaagtccttgaacag
ggaggtgtgtccagtttgtttcagaatctcggggtgtccgtaactccgatccaaaggattgtcctgagcggtgaaaatgggctgaagatcgacatccatgtcatcatcccgtatgaagg
tctgagcggcgaccaaatgggccagatcgaaaaaatttttaaggtggtgtaccctgtggatgatcatcactttaaggtgatcctgcactatggcacactggtaatcgacggggttacgc
cgaacatgatcgactatttcggacggccgtatgaaggcatcgccgtgttcgacggcaaaaagatcactgtaacagggaccctgtggaacggcaacaaaattatcgacgagcgcctg
atcaaccccgacggctccctgctgttccgagtaaccatcaacggagtgaccggctggcggctgtgcgaacgcattctggcgtaaggctgctgcagctgcatgggtgcctgctgctgcct
gccttggcctgatggccaggccagagtgctgccagtcctctgcatgttctgctcttgtgcccttctgagcccacaataaaggctgagctcttatcttgcaaaaggc

Fig. 47B

PAN39

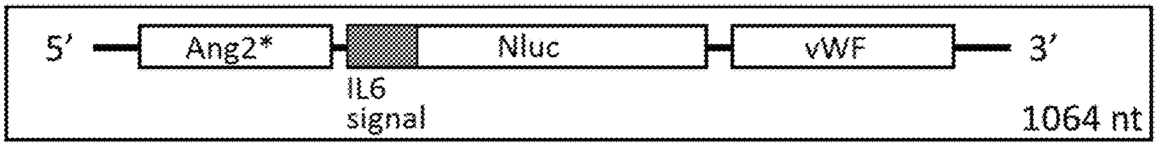

Fig. 48A

PAN39 aaagtgattgattcggatactgacactgtaggatctggggagagaggaacaaaggaccgtgaaagctgctctgtaaaagctgacacagccctcccaagtgagcaggactgttcttcc
cactgcaatctgacagtttactgccctggagagaacacagcagtaaaaaccaggtttgctactggaaaaagaggaaagagaagactttcattgacggacccagccgcagcgtagca
gccctgcgttttagacggcagcagctcgggactctggacgtgtgtttgccctcaagtttgctaagctgctggtttattactgaagaaagaatgaactccttctccacaagcgccttcggtc
cagttgccttctccctgggcctgctcctggtgttgcctgctgccttccctgccccagtcttcacactcgaagatttcgttggggactggcgacagacagccggctacaacctggaccaagt
ccttgaacagggaggtgtgtccagtttgtttcagaatctcggggtgtccgtaactccgatccaaaggattgtcctgagcggtgaaaatgggctgaagatcgacatccatgtcatcatcc
cgtatgaaggtctgagcggcgaccaaatgggccagatcgaaaaaatttttaaggtggtgtaccctgtggatgatcatcactttaaggtgatcctgcactatggcacactggtaatcga
cggggttacgccgaacatgatcgactatttcggacggccgtatgaaggcatcgccgtgttcgacggcaaaaagatcactgtaacagggaccctgtggaacggcaacaaaattatcg
acgagcgcctgatcaaccccgacggctccctgctgttccgagtaaccatcaacggagtgaccggctggcggctgtgcgaacgcattctggcgtaaggctgctgcagctgcatgggtgc
ctgctgctgcctgccttggcctgatggccaggccagagtgctgccagtcctctgcatgttctgctcttgtgcccttctgagcccacaataaaggctgagctcttatcttgcaaaaggc

Fig. 48B

PAN40

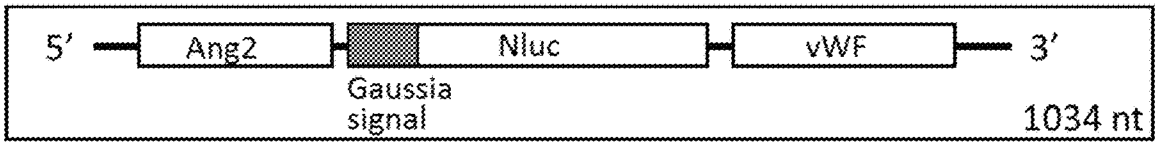

Fig. 49A

PAN40 aaagtgattgattcggatactgacactgtaggatctggggagagaggaacaaaggaccgtgaaagctgctctgtaaaagctgacacagccctcccaagtgagcaggactgttcttcc
cactgcaatctgacagtttactgcatgcctggagagaacacagcagtaaaaaccaggtttgctactggaaaaagaggaaagagaagactttcattgacggacccagccatggcagc
gtagcagccctgcgttttagacggcagcagctcgggactctggacgtgtgtttgccctcaagtttgctaagctgctggtttattactgaagaaagaatgggagtgaaagttctttttgcc
cttatttgtattgctgtggccgaggccgtcttcacactcgaagatttcgttggggactggcgacagacagccggctacaacctggaccaagtccttgaacagggaggtgtgtccagttt
gtttcagaatctcggggtgtccgtaactccgatccaaaggattgtcctgagcggtgaaaatgggctgaagatcgacatccatgtcatcatcccgtatgaaggtctgagcggcgaccaa
atgggccagatcgaaaaaatttttaaggtggtgtaccctgtggatgatcatcactttaaggtgatcctgcactatggcacactggtaatcgacggggttacgccgaacatgatcgacta
tttcggacggccgtatgaaggcatcgccgtgttcgacggcaaaaagatcactgtaacagggaccctgtggaacggcaacaaaattatcgacgagcgcctgatcaaccccgacggct
ccctgctgttccgagtaaccatcaacggagtgaccggctggcggctgtgcgaacgcattctggcgtaaggctgctgcagctgcatgggtgcctgctgctgcctgccttggcctgatggc
caggccagagtgctgccagtcctctgcatgttctgctcttgtgcccttctgagcccacaataaaggctgagctcttatcttgcaaaaggc

Fig. 49B

PAN41

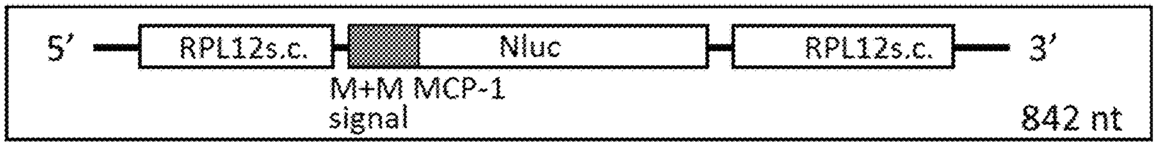

Fig. 50A

PAN41 catatcttcattcttcactctttcccccccccccccttatcctcctatctaatcctctcatctctctcctcctcttcctccaacaacaactaacaatggcagcaactacaacaatgaaagtctct
gccgcccttctgtgcctgctgctcatagcagccaccttcattccccaagggctcgctgtcttcacactcgaagatttcgttggggactggcgacagacagccggctacaacctggacca
agtccttgaacagggaggtgtgtccagtttgtttcagaatctcggggtgtccgtaactccgatccaaaggattgtcctgagcggtgaaaatgggctgaagatcgacatccatgtcatca
tcccgtatgaaggtctgagcggcgaccaaatgggccagatcgaaaaaatttttaaggtggtgtaccctgtggatgatcatcactttaaggtgatcctgcactatggcacactggtaatc
gacggggttacgccgaacatgatcgactatttcggacggccgtatgaaggcatcgccgtgttcgacggcaaaaagatcactgtaacagggaccctgtggaacggcaacaaaattat
cgacgagcgcctgatcaaccccgacggctccctgctgttccgagtaaccatcaacggagtgaccggctggcggctgtgcgaacgcattctggcgtaattttgagtaattttcaattttgt
ttttgtttttgtttttgttgttgggagttgttgtaatttggtaaatgttggggtcactaaaatcttttgttgcaattttagcaccttttttattagatatataaaattgggtttagatgtagttaa

Fig. 50B

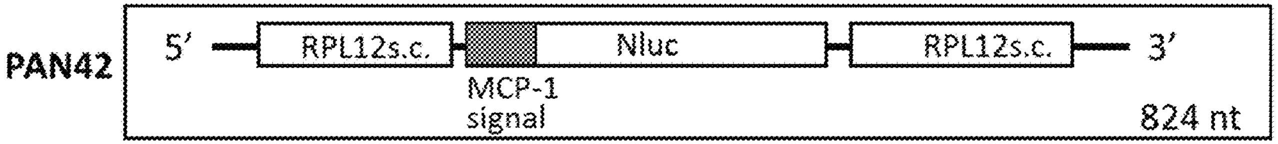

Fig. 51A

PAN42 catatcttcattcttcactctttccccccccccccttatcctcctatctaatcctctcatctctctcctcctcttcctccaacaacaactaacaatgaaagtctctgccgcccttctgtgcctgc
tgctcatagcagccaccttcattccccaagggctcgctgtcttcacactcgaagatttcgttggggactggcgacagacagccggctacaacctggaccaagtccttgaacagggagg
tgtgtccagtttgtttcagaatctcggggtgtccgtaactccgatccaaaggattgtcctgagcggtgaaaatgggctgaagatcgacatccatgtcatcatcccgtatgaaggtctgag
cggcgaccaaatgggccagatcgaaaaaatttttaaggtggtgtaccctgtggatgatcatcactttaaggtgatcctgcactatggcacactggtaatcgacggggttacgccgaac
atgatcgactatttcggacggccgtatgaaggcatcgccgtgttcgacggcaaaaagatcactgtaacagggaccctgtggaacggcaacaaaattatcgacgagcgcctgatcaac
cccgacggctccctgctgttccgagtaaccatcaacggagtgaccggctggcggctgtgcgaacgcattctggcgtaattttgagtaattttcaattttgtttttgtttttgtttttgttgttg
ggagttgttgtaatttggtaaatgttggggtcactaaaatcttttgttgcaattttagcaccttttttattagatatataaaattgggtttagatgtagttaa

Fig. 51B

PAN43

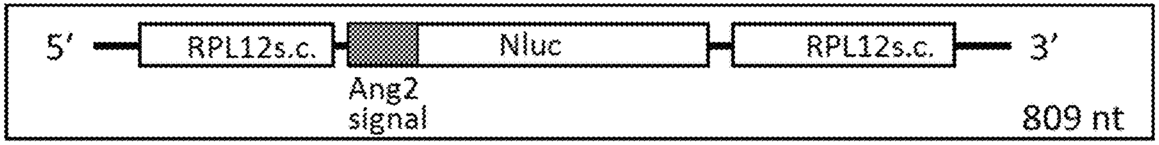

Fig. 52A

PAN43 catatcttcattcttcactctttccccccccccccttatcctcctatctaatcctctcatctctctcctcctcttcctccaacaacaactaacaatgtggcagattgttttctttactctgagctg
tgatcttgtcttggccgcagccgtcttcacactcgaagatttcgttggggactggcgacagacagccggctacaacctggaccaagtccttgaacagggaggtgtgtccagtttgtttca
gaatctcggggtgtccgtaactccgatccaaaggattgtcctgagcggtgaaaatgggctgaagatcgacatccatgtcatcatcccgtatgaaggtctgagcggcgaccaaatggg
ccagatcgaaaaaatttttaaggtggtgtaccctgtggatgatcatcactttaaggtgatcctgcactatggcacactggtaatcgacggggttacgccgaacatgatcgactatttcg
gacggccgtatgaaggcatcgccgtgttcgacggcaaaaagatcactgtaacagggaccctgtggaacggcaacaaaattatcgacgagcgcctgatcaaccccgacggctccctg
ctgttccgagtaaccatcaacggagtgaccggctggcggctgtgcgaacgcattctggcgtaattttgagtaattttcaattttgtttttgtttttgtttttgttgttgggagttgttgtaattt
ggtaaatgttggggtcactaaaatcttttgttgcaattttagcaccttttttattagatatataaaattgggtttagatgtagttaa

Fig. 52B

PAN44

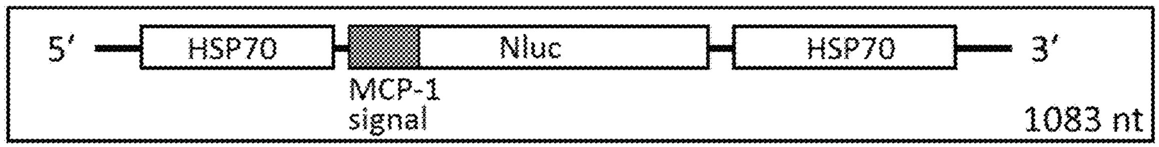

Fig. 53A

PAN44 ataaaagcccaggggcaagcggtccggataacggctagcctgaggagctgctgcgacagtccactaccttttcgagagtgactcccgttgtcccaaggcttcccagagcgaacctgt
gcggctgcaggcaccggcgcgtcgagtttccggcgtccggaaggaccgagctcttctcgcgaatccagtgttccgtttccagcccccaatctcagagcggagccgacagagagcagg
gaaccggcatgaaagtctctgccgcccttctgtgcctgctgctcatagcagccaccttcattccccaagggctcgctgtcttcacactcgaagatttcgttggggactggcgacagacag
ccggctacaacctggaccaagtccttgaacagggaggtgtgtccagtttgtttcagaatctcggggtgtccgtaactccgatccaaaggattgtcctgagcggtgaaaatgggctgaa
gatcgacatccatgtcatcatcccgtatgaaggtctgagcggcgaccaaatgggccagatcgaaaaaatttttaaggtggtgtaccctgtggatgatcatcactttaaggtgatcctgc
actatggcacactggtaatcgacggggttacgccgaacatgatcgactatttcggacggccgtatgaaggcatcgccgtgttcgacggcaaaaagatcactgtaacagggaccctgt
ggaacggcaacaaaattatcgacgagcgcctgatcaaccccgacggctccctgctgttccgagtaaccatcaacggagtgaccggctggcggctgtgcgaacgcattctggcgtaag
ggcctttccaagattgctgtttttgttttggagcttcaagactttgcatttcctagtatttctgtttgtcagttctcaatttcctgtgtttgcaatgttgaaatttttggtgaagtactgaactt
gcttttttccggtttctacatgcagagatgaatttatactgccatcttacgactatttcttctttttaatacacttaactcaggccatttttaagttggttacttcaaagtaaataaacttta
aaattc

Fig. 53B

PAN45

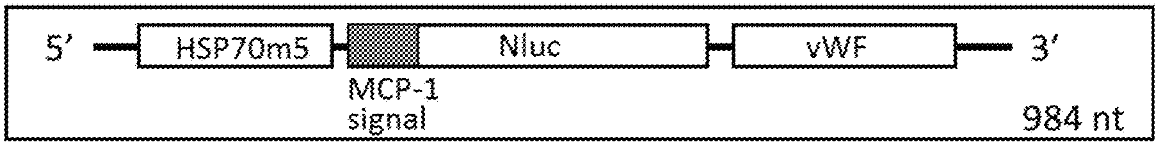

Fig. 54A

PAN45 gggctgggggagggtatataagccgagtaggcgacggtgaggtcgacgccggccaagacagcacagacagattgacctattggggtgtttcgcgagtgtgagagggaagcgccgc
ggcctgtatttctagacctgcccttcgcctggttcgtggcgccttgtgaccccgggcccctgccgcctgcaagtcggaaattgcgctgtgctcctgtgctacggcctgtggctggactgcc
tgctgctgcccaactggctggcaagatgaaagtctctgccgcccttctgtgcctgctgctcatagcagccaccttcattccccaagggctcgctgtcttcacactcgaagatttcgttggg
gactggcgacagacagccggctacaacctggaccaagtccttgaacagggaggtgtgtccagtttgtttcagaatctcggggtgtccgtaactccgatccaaaggattgtcctgagcg
gtgaaaatgggctgaagatcgacatccatgtcatcatcccgtatgaaggtctgagcggcgaccaaatgggccagatcgaaaaaatttttaaggtggtgtaccctgtggatgatcatca
ctttaaggtgatcctgcactatggcacactggtaatcgacggggttacgccgaacatgatcgactatttcggacggccgtatgaaggcatcgccgtgttcgacggcaaaaagatcact
gtaacagggaccctgtggaacggcaacaaaattatcgacgagcgcctgatcaaccccgacggctccctgctgttccgagtaaccatcaacggagtgaccggctggcggctgtgcga
acgcattctggcgtaaggctgctgcagctgcatgggtgcctgctgctgcctgccttggcctgatggccaggccagagtgctgccagtcctctgcatgttctgctcttgtgcccttctgagc
ccacaataaaggctgagctcttatcttgcaaaaggc

Fig. 54B

PAN46

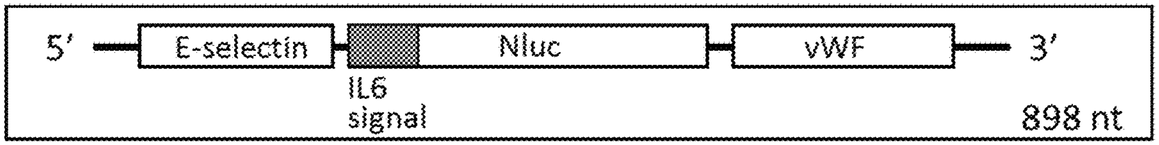

Fig. 55A

PAN46

Agctgttcttggctgacttcacatcaaaactcctatactgacctgagacagaggcagcagtgatacccacctgagagatcctgtgtttgaacaactgcttcccaaaacggaaagtattt
caagcctaaacctttgggtgaaaagaactcttgaagtcatgaactccttctccacaagcgccttcggtccagttgccttctccctgggcctgctcctggtgttgcctgctgccttccctgcc
ccagtcttcacactcgaagatttcgttggggactggcgacagacagccggctacaacctggaccaagtccttgaacagggaggtgtgtccagtttgtttcagaatctcggggtgtccgt
aactccgatccaaaggattgtcctgagcggtgaaaatgggctgaagatcgacatccatgtcatcatcccgtatgaaggtctgagcggcgaccaaatgggccagatcgaaaaaatttt
taaggtggtgtaccctgtggatgatcatcactttaaggtgatcctgcactatggcacactggtaatcgacggggttacgccgaacatgatcgactatttcggacggccgtatgaaggca
tcgccgtgttcgacggcaaaaagatcactgtaacagggaccctgtggaacggcaacaaaattatcgacgagcgcctgatcaaccccgacggctccctgctgttccgagtaaccatca
acggagtgaccggctggcggctgtgcgaacgcattctggcgtaaggctgctgcagctgcatgggtgcctgctgctgcctgccttggcctgatggccaggccagagtgctgccagtcctc
tgcatgttctgctcttgtgcccttctgagcccacaataaaggctgagctcttatcttgcaaaaggc

Fig. 55B

PAN47

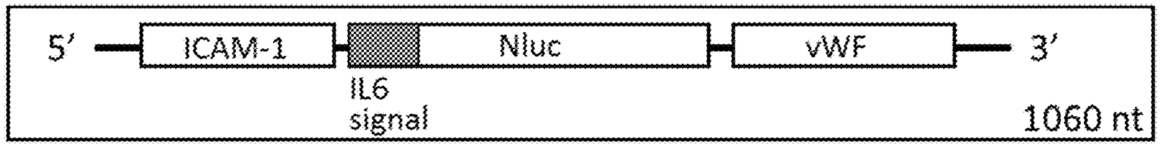

Fig. 56A

PAN47 caagcttagcctggccgggaaacgggaggcgtggaggccgggagcagcccccggggtcatcgccctgccaccgccgcccgattgctttagcttggaaattccggagctgaagcggc
cagcgagggaggatgaccctctcggcccgggcaccctgtcagtccggaaataactgcagcatttgttccggaggggaaggcgcgaggtttccgggaaagcagcaccgccccttggc
ccccaggtggctagcgctataaaggatcacgcgccccagtcgacgctgagctcctctgctactcagagttgcaacctcagcctcgctatgaactccttctccacaagcgccttcggtcc
agttgccttctccctgggcctgctcctggtgttgcctgctgccttccctgccccagtcttcacactcgaagatttcgttggggactggcgacagacagccggctacaacctggaccaagtc
cttgaacagggaggtgtgtccagtttgtttcagaatctcggggtgtccgtaactccgatccaaaggattgtcctgagcggtgaaaatgggctgaagatcgacatccatgtcatcatccc
gtatgaaggtctgagcggcgaccaaatgggccagatcgaaaaaatttttaaggtggtgtaccctgtggatgatcatcactttaaggtgatcctgcactatggcacactggtaatcgac
ggggttacgccgaacatgatcgactatttcggacggccgtatgaaggcatcgccgtgttcgacggcaaaaagatcactgtaacagggaccctgtggaacggcaacaaaattatcga
cgagcgcctgatcaaccccgacggctccctgctgttccgagtaaccatcaacggagtgaccggctggcggctgtgcgaacgcattctggcgtaaggctgctgcagctgcatgggtgcc
tgctgctgcctgccttggcctgatggccaggccagagtgctgccagtcctctgcatgttctgctcttgtgcccttctgagcccacaataaaggctgagctcttatcttgcaaaaggc

Fig. 56B

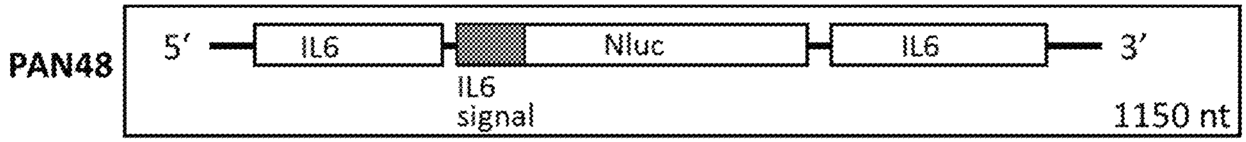

Fig. 57A

PAN48

Gtctcaatattagagtctcaacccccaataaatataggactggagatgtctgaggctcattctgccctggagcccaccgggaacgaaagagaagctctatctcccctccaggagccc
agctatgaactccttctccacaagcgccttcggtccagttgccttctccctggggctgctcctggtgttgcctgctgccttccctgccccagtcttcacactcgaagatttcgttggggact
ggcgacagacagccggctacaacctggaccaagtccttgaacagggaggtgtgtccagtttgtttcagaatctcggggtgtccgtaactccgatccaaaggattgtcctgagcggtga
aaatgggctgaagatcgacatccatgtcatcatcccgtatgaaggtctgagcggcgaccaaatgggccagatcgaaaaaatttttaaggtggtgtaccctgtggatgatcatcacttt
aaggtgatcctgcactatggcacactggtaatcgacggggttacgccgaacatgatcgactatttcggacggccgtatgaaggcatcgccgtgttcgacggcaaaaagatcactgta
acagggaccctgtggaacggcaacaaaattatcgacgagcgcctgatcaaccccgacggctccctgctgttccgagtaaccatcaacggagtgaccggctggcggctgtgcgaacg
cattctggcgtaacatgggcacctcagattgttgttgttaatgggcattccttcttctggtcagaaacctgtccactgggcacagaacttatgttgttctctatggagaactaaaagtatg
agcgttaggacactattttaattatttttaatttattaatatttaaatatgtgaagctgagttaatttatgtaagtcatatttatatttttaagaagtaccacttgaaacattttatgtattag
ttttgaaataataatggaaagtggctatgcagtttgaatatcctttgtttcagagccagatcatttcttggaaagtgtaggcttacctcaaataaatggctaacttatacatatttttaaag
aaatatttatattgtatttatataatgtataaatggtttttataccaataaatggcattttaaaaaattcagcaa

Fig. 57B

PAN49

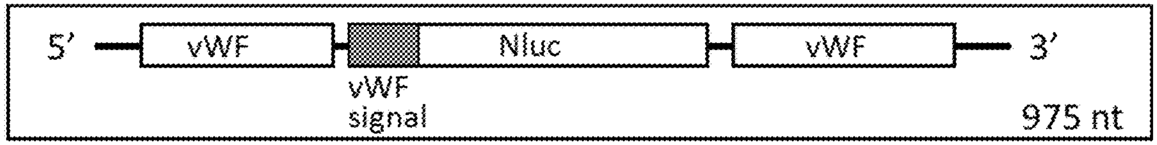

Fig. 58A

PAN49 gtggcagctcacagctattgtggtgggaaagggagggtggttggtggatgtcacagcttgggctttatctcccccagcagtggggactccacagcccctgggctacataacagcaaga
cagtccggagctgtagcagacctgattgagcctttgcagcagctgagagcatggcctagggtgggcggcaccattgtccagcagctgagtttcccagggaccttggagatagccgca
gccctcatttgcaggggaagatgattcctgccagatttgccggggtgctgcttgctctggccctcattttgccagggaccctttgtgtcttcacactcgaagatttcgttggggactggcg
acagacagccggctacaacctggaccaagtccttgaacagggaggtgtgtccagtttgtttcagaatctcggggtgtccgtaactccgatccaaaggattgtcctgagcggtgaaaat
gggctgaagatcgacatccatgtcatcatcccgtatgaaggtctgagcggcgaccaaatgggccagatcgaaaaaatttttaaggtggtgtaccctgtggatgatcatcactttaagg
tgatcctgcactatggcacactggtaatcgacggggttacgccgaacatgatcgactatttcggacggccgtatgaaggcatcgccgtgttcgacggcaaaaagatcactgtaacagg
gaccctgtggaacggcaacaaaattatcgacgagcgcctgatcaaccccgacggctccctgctgttccgagtaaccatcaacggagtgaccggctggcggctgtgcgaacgcattct
ggcgtaaggctgctgcagctgcatgggtgcctgctgctgcctgccttggcctgatggccaggccagagtgctgccagtcctctgcatgttctgctcttgtgcccttctgagcccacaata
aaggctgagctcttatcttgcaaaaggc

Fig. 58B

Homo sapiens angiopoietin 1 (ANGPT1; Ang-1), transcript variant 1, mRNA <NM_001146.4>

5′-UTR:

gccctaagccatcagcaatccttagtataggggcacactcatgcattcctgtcaagtcatcttgtgaaaggctgcctgcttccagcttggcttggatgtgcaaccttaataaaactcact
gaggtctgggagaaaatagcagatctgcagcagatagggtagaggaaagggtctagaatatgtacacgcagctgactcaggcaggctccatgctgaacggtcacacagagaggaa
acaataaatctcagctactatgcaataaatatctcaagttttaacgaagaaaaacatcattgcagtgaaataaaaaattttaaattttagaacaaagctaacaaatggctagttttct
atgattcttcttcaaacgctttctttgagggggaaagagtcaaacaaacaagcagttttacctgaaataaagaactagttttagaggtcagaagaaaggagcaagttttgcgagaggc
acggaaggagtgtgctggcagtaca

Fig. 59A sig_peptide:

nt:

atgacagttttcctttcctttgctttcctcgctgccattctgact aa:

MTVFLSFAFLAAILT

Fig. 59B

CDS (mat_peptide):

cacatagggtgcagcaatcagcgccgaagtccagaaaacagtgggagaagatataaccggattcaacatgggcaatgtgcctacactttcattcttccagaacacgatggcaactgt
cgtgagagtacgacagaccagtacaacacaaacgctctgcagagagatgctccacacgtggaaccggatttctcttcccagaaacttcaacatctggaacatgtgatggaaaattat
actcagtggctgcaaaaacttgagaattacattgtggaaaacatgaagtcggagatggcccagatacagcagaatgcagttcagaaccacacggctaccatgctggagataggaac
cagcctcctctctcagactgcagagcagaccagaaagctgacagatgttgagacccaggtactaaatcaaacttctcgacttgagatacagctgctggagaattcattatccacctac
aagctagagaagcaacttcttcaacagacaaatgaaatcttgaagatccatgaaaaaaacagtttattagaacataaaatcttagaaatggaaggaaaacacaaggaagagttgg
acaccttaaaggaagagaaagagaaccttcaaggcttggttactcgtcaaacatatataatccaggagctggaaaagcaattaaacagagctaccaccaacaacagtgtccttcag
aagcagcaactggagctgatggacacagtccacaaccttgtcaatctttgcactaaagaaggtgttttactaaagggaggaaaaagagaggaagagaaaccatttagagactgtgc
agatgtatatcaagctggttttaataaaagtggaatctacactatttatattaataatatgccagaacccaaaaaggtgttttgcaatatggatgtcaatgggggaggttggactgtaa
tacaacatcgtgaagatggaagtctagatttccaaagaggctggaaggaatataaaatgggttttggaaatccctccggtgaatattggctggggaatgagtttatttttgccattacc
agtcagaggcagtacatgctaagaattgagttaatggactgggaagggaaccgagcctattcacagtatgacagattccacataggaaatgaaaagcaaaactataggttgtattta
aaaggtcacactgggacagcaggaaaacagagcagcctgatcttacacggtgctgatttcagcactaaagatgctgataatgacaactgtatgtgcaaatgtgccctcatgttaaca
ggaggatggtggtttgatgcttgtggcccctccaatctaaatggaatgttctatactgcgggacaaaaccatggaaaactgaatgggataaagtggcactacttcaaagggcccagtt
actccttacgttccacaactatgatgattcgacctttagatttttga

Fig. 59C

3'-UTR:

aagcgcaatgtcagaagcgattatgaaagcaacaaagaaatccggagaagctgccaggtgagaaactgtttgaaaacttcagaagcaaacaatattgtctcccttccagcaataag
tggtagttatgtgaagtcaccaaggttcttgaccgtgaatctggagccgtttgagttcacaagagtctctacttggggtgacagtgctcacgtggctcgactatagaaaactccactgac
tgtcgggctttaaaaagggaagaaactgctgagcttgctgtgcttcaaactactactggaccttattttggaactatggtagccagatgataaatatggttaatttcatgtaaaacaga
aaaaaagagtgaaaaagagaatatacatgaagaatagaaacaagcctgccataatcctttggaaaagatgtattataccagtgaaaaggtgttatatctatgcaaacctactaaca
aattatactgttgcacaattttgataaaaatttagaacagcattgtcctctgagttggttaaatgttaatggatttcagaagcctaattccagtatcatacttactagttgatttctgcttac
ccatcttcaaatgaaaattccatttttgtaagccataatgaactgtagtacatggacaataagtgtgtggtagaaacaaactccattactctgatttttgatacagttttcagaaaaaga
aatgaacataatcaagtaaggatgtatgtggtgaaaacttaccacccccatactatggttttcatttactctaaaaactgattgaatgatatataaatatatttatagcctgagtaaagt
taaaagaatgtaaaatatatcatcaagttcttaaaataatatacatgcatttaatatttcctttgatattatacaggaaagcaatattttggagtatgttaagttgaagtaaaagcaagt
actctggagcagttcattttacagtatctacttgcatgtgtatacatacatgtaacttcattattttaaaaatatttttagaactccaatactcaccctgttatgtcttgctaatttaaatttt
gctaattaactgaaacatgcttaccagattcacactgttccagtgtctataaaagaaacactttgaagtctataaaaaataaaataattataaatatcattgtacatagcatgtttatat
ctgcaaaaaacctaatagctaattaatctggaatatgcaacattgtccttaattgatgcaaataacacaaatgctcaaagaaatctactatatcccttaatgaaatacatcattcttcat
atatttctccttcagtccattcccttaggcaatttttaatttttaaaaattattatcaggggagaaaaattggcaaaactattatatgtaagggaaatatatacaaaaagaaaattaatc
atagtcacctgactaagaaattctgactgctagttgccataaataactcaatggaaatattcctatgggataatgtattttaagtgaatttttggggtgcttgaagttactgcattatttta
tcaagaagtcttctctgcctgtaagtgtccaaggttatgacagtaaacagtttttattaaaacatgagtcactatgggatgagaaaattgaaataaagctactgggcctcctctcataa
aagagacagttgttggcaaggtagcaataccagtttcaaacttggtgacttgatccactatgccttaatggtttcctccatttgagaaaataaagctattcacattgttaagaaaaatac
tttttaaagtttaccatcaagtctttttatatttatgtgtctgtattctacccctttttgccttacaagtgatatttgcaggtattataccatttttctattcttggtggcttcttcatagcaggt
aagcctctccttctaaaaacttctcaactgttttcatttaagggaaagaaaatgagtattttgtcctttttgtgttcctacagacactttcttaaaccagtttttggataaagaatactatttc
caaactcatattacaaaaacaaaataaaataataaaaaaagaaagcatgatatttactgttttgttgtctgggtttgagaaatgaaatattgtttccaattatttataataaatcagtat
aaaatgttttatgattgttatgtgtattatgtaatacgtacatgtttatggcaatttaacatgtgtattcttttaattgtttcagaataggataattaggtattcgaattttgtctttaaaattc
atgtggtttctatgcaaagttcttcatatcatcacaacattatttgatttaaataaaattgaaagtaatatttgtgcaa

Fig. 59D

Homo sapiens angiopoietin 4 (ANGPT4; Ang-4), transcript variant 1, mRNA <NM_015985.3>

5'-UTR:

agacagaggtttgtagctgcagctgcaggcaagcctggccactgttggctgcagcaggacatcccaggcacagcccctagggctctgagcagacatccctcgccattgacacatcttc
ag

Fig. 60A sig_peptide:

nt:

atgctctcccagctagccatgctgcagggcagcctcctccttgtggttgccaccatgtctgtggct aa:

MLSQLAMLQGSLLLVVATMSVA

Fig. 60B

CDS (mat_peptide):

caacagacaaggcaggaggcggataggggctgcgagacacttgtagtccagcacggccactgtagctacaccttcttgctgcccaagtctgagccctgccctccggggcctgaggtc
tccagggactccaacaccctccagagagaatcactggccaacccactgcacctggggaagttgcccacccagcaggtgaaacagctggagcaggcactgcagaacaacacgcagt
ggctgaagaagctagagagggccatcaagacgatcttgaggtcgaagctggagcaggtccagcagcaaatggcccagaatcagacggcccccatgctagagctgggcaccagcct
cctgaaccagaccactgcccagatccgcaagctgaccgacatggaggctcagctcctgaaccagacatcaagaatggatgcccagatgccagagacctttctgtccaccaacaagct
ggagaaccagctgctgctacagaggcagaagctccagcagcttcagggccaaaacagcgcgctcgagaagcggttgcaggccctggagaccaagcagcaggaggagctggccag
catcctcagcaagaaggcgaagctgctgaacacgctgagccgccagagcgccgccctcaccaacatcgagcgcggcctgcgcggtgtcaggcacaactccagcctcctgcaggacc
agcagcacagcctgcgccagctgctggtgttgttgcggcacctggtgcaagaaagggctaacgcctcggccccggccttcataatggcaggtgagcaggtgttccaggactgtgcag
agatccagcgctctggggccagtgccagtggtgtctacaccatccaggtgtccaatgcaacgaagcccaggaaggtgttctgtgacctgcagagcagtggaggcaggtggaccctca
tccagcgccgtgagaatggcaccgtgaattttcagcggaactggaaggattacaaacagggcttcggagacccagctggggagcactggctgggcaatgaagtggtgcaccagctc
accagaagggcagcctactctctgcgtgtggagctgcaagactgggaaggccacgaggcctatgcccagtacgaacatttccacctgggcagtgagaaccagctatacaggctttct
gtggtcgggtacagcggctcagcagggcgccagagcagcctggtcctgcagaacaccagctttagcacccttgactcagacaacgaccactgtctctgcaagtgtgcccaagtgatg
tctggagggtggtggtttgacgcctgtggcctgtcaaacctcaacggcgtctactaccacgctcccgacaacaagtacaagatggacggcatccgctggcactacttcaagggcccca
gctactcactgcgtgcctctcgcatgatgatacggcctttggacatctaa

Fig. 60C

3'-UTR:

cgagcagctgtgccagaggctggaccacacaggagaagctcggacttggcactcctggacaacctggacccagatgcaagacactgtgccaccgccttccctgacaccctgggcttc
ctgagccagccctccttgacccagaagtccagaagggtcatctgcccccaactcccctccgtctgtgacatggagggtgttcggggcccatccctctgatgtagtcctcgcccctcttc
tctccctccccccttcaggggctccctgcctgagggtcacagtaccttgaatgggctgagaacagaccaaacttgattcccatgaccaatggtggggttgcaggcaggtgggaatgtatt
tgcacatcggaagctgcccagatggcccaggttctctcccttggattggcaagaaggccatctcccattctaagctcctgttccaagattttctagtcttgagatgtccttgaactttcttt
tcaagtctgaaggggctgcatccaccccttagtgggtgggttaatcattatttccccttcacacttcaccacttctaggttctaatgaccctagatctcagggtctttagacttcaccactt
ctaggctttaccacttcaccacttctaggctccaatgtttggagctcagggtctttaggagacccaaaaggacatgctccttcacctccagcatgtcctagaggatgtgtcacagggaat
aactatggcttgtctctaaaagtacctatgagcaatgagaaaaggaaacagcaggttaagtcaaagtgaacaggcactcttcactgcaggactgatcagagcctttaatatggccaa
gtgccttgtgactacccatgaaggggctagagtgggcagctttctccaaatttacttatttgaaaatgggctcggtttgtcccagagcatctcacaggactgtagatgctcttggacaaa
gctagtgctcccctggcataaggaggagccctacgaccccatccccaccccagctatactcaccctttttggctacaagggccacagtgacagcctcaaacaacctctaaaaacaact
ggaaataacctttcagttaaaacagataccatccctgaagaagggtctagaactaggtccctgtctgtgttataggctcatgtcctccaaggctccttcaagtcccaggaagctgatct
ctacctgggtggcttcccttaggactccctgtaacctcaactcccccaggctcaattacagggactgttaggcaggacatctgtctccaagtccagatcctctctgcctccaagccctaa
cccctagcctccctcccttccccatccagcagtgatgctgcctctgtggtggtaggtggggagctgcaggggaggagataaggcctctgcctgagtttgggagaccagggccctcata
gcttctttcagaggatggagtcagaaaggatccacagctactctgtcacctgcccccatcactgtgtcatgctgtctgccctgttgtcatcagccaacacccaggcatagccaggagcc
cacctgccctaccgccaggatacacctctgtcctcagaaggttttctcctggatgagactgagccaatgggaatggaccccttcatcccccctggctcgccccagccctgagtcccactc
tcagccgatccctgagtaaacccagcacagactgactttgatctcattcctgggaattagcactcttccccttcaagactcaaaggacatggttgctaatggtggcatttcaggcatgat
gggaaatctttaggggcagattgctgcccagagagctcaaatcgccttaagcagcatttgcccagcagacctttatttagcctctactgtgtgcagtgtggtgtggtgggcagggctttg
gagtcggacaaacctgctccagctctgacactttggtccagtggctcagcctctcaaggcaccagttatcttcacatcatcaaagcctcagttttcccatctgtaaaatggagatgataa
tattccttcctggctgggctatggcaaggaggaaatgagaccatgtatgtcatcttcttaatagagcctggcatgaagcaggtgcctaataaatgtttgtcctcaaagaggagaatggg

Fig. 60D (cont.)

gtgaggaaggcattccccagcacatgccgccccttctcctgcactcaggtgaggaaaaggcattttatttttgtatccacatcatttatttttctattgtagtttctaggctgactgcaagc
tagagaggagacagggcaaagctgtgaggcccagggacagaactcctctgggtgggttgaaggcccaagtccctctctactcccattttataagggggcaggaagctgatttgagtt
atcctcagacacctgttctttatgtaattttattttatttttttgagacagagtctcactctgtcacccaggctggagtgcagtggcatgatctcagatcactgcaatctctgcctcctggttc
aagtgattctcctacctcagcctcctgagtaatgggattacagacgcctaccaccacgcccggaaaacttttgtatttttagtagaaacgggttttcaccatgttggccaggctggtctc
aaactcctggcctcatgtgatccacctgcctcagcctcccaaagtgctgggattacaggcatgagccaccatacccagcctcagacacctgttcttaaatattcatccttctttcttacct
tccttcctcttccatgccaggactcaggtataagggatagaaattctagccctaaggaataaattgactcacataactggaaagtctaagggtaaaggcaagtgaggttagatccaga
ggctcaaatgatgtcagctccacctctcagcccctccatctgccccgttgacttcattctcagccaggatctttcctcacaagaaggctctggcagccccaggctcatgtcctcccagctc
agcatccctgacccggggagctccctcgtctccatgattccagtaaaggaatgattttctgcagccag

Fig. 60D

COMP-Ang1 <synthetic construct>

CDS (mat_peptide):

gggatcttagacctagccccacagatgcttcgagaactccaggagactaatgcggcgctgcaagacgtgagagagctcttgcgacagcaggtcaaggagatcaccttcctgaagaa
tacggtgatggaatgtgacgcttgcggaggctcccttgtcaatctttgcactaaagaaggtgttttactaaagggaggaaaaagagaggaagagaaaccatttagagactgtgcaga
tgtatatcaagctggttttaataaaagtggaatctacactatttatattaataatatgccagaacccaaaaaggtgttttgcaatatggatgtcaatgggggaggttggactgtaataca
acatcgtgaagatggaagtctagatttccaaagaggctggaaggaatataaaatgggttttggaaatccctccggtgaatattggctggggaatgagtttatttttgccattaccagtc
agaggcagtacatgctaagaattgagttaatggactgggaagggaaccgagcctattcacagtatgacagattccacataggaaatgaaaagcaaaactataggttgtatttaaaa
ggtcacactgggacagcaggaaaacagagcagcctgatcttacacggtgctgatttcagcactaaagatgctgataatgacaactgtatgtgcaaatgtgccctcatgttaacagga
ggatggtggtttgatgcttgtggcccctccaatctaaatggaatgttctatactgcgggacaaaaccatggaaaactgaatgggataaagtggcactacttcaaagggcccagttact
ccttacgttccacaactatgatgattcgacctttagatttttga

Fig. 61 hCOMP-Ang1 <synthetic construct>

CDS (mat_peptide):

gggatcttagacttgggcccgcagatgcttcgggaactgcaggaaaccaacgcggcgctgcaggacgtgcgggagctgctgcggcagcaggtcagggagatcacgttcctgaaaaa
cacggtgatggagtgtgacgcgtgcggaggctcccttgtcaatctttgcactaaagaaggtgttttactaaagggaggaaaaagagaggaagagaaaccatttagagactgtgcag
atgtatatcaagctggttttaataaaagtggaatctacactatttatattaataatatgccagaacccaaaaaggtgttttgcaatatggatgtcaatgggggaggttggactgtaatac
aacatcgtgaagatggaagtctagatttccaaagaggctggaaggaatataaaatgggttttggaaatccctccggtgaatattggctggggaatgagtttatttttgccattaccagt
cagaggcagtacatgctaagaattgagttaatggactgggaagggaaccgagcctattcacagtatgacagattccacataggaaatgaaaagcaaaactataggttgtatttaaa
aggtcacactgggacagcaggaaaacagagcagcctgatcttacacggtgctgatttcagcactaaagatgctgataatgacaactgtatgtgcaaatgtgccctcatgttaacagg
aggatggtggtttgatgcttgtggcccctccaatctaaatggaatgttctatactgcgggacaaaaccatggaaaactgaatgggataaagtggcactacttcaaagggcccagttac
tccttacgttccacaactatgatgattcgacctttagatttttga

Fig. 62

CMP-Ang1 <synthetic construct>

CDS (mat_peptide):

gggatcttagaggaagacccggccgcctgcgagtccctggtgaaattccaagccaaagtggaggggctgctgcaggccctgaccaggaaactggaagctgtgagtaagcggctggc
catcctggagaacacagttgtcggatcccttgtcaatcttgccactaaagaaggtgttttactaaagggaggaaaaagagaggaagagaaaccatttagagactgtgcagatgtata
tcaagctggttttaataaaagtggaatctacactatttatattaataatatgccagaacccaaaaaggtgttttgcaatatggatgtcaatggggggaggttggactgtaatacaacatc
gtgaagatggaagtctagatttccaaagaggctggaaggaatataaaatgggttttggaaatccctccggtgaatattggctggggaatgagtttatttttgccattaccagtcagagg
cagtacatgctaagaattgagttaatggactgggaagggaaccgagcctattcacagtatgacagattccacataggaaatgaaaagcaaaactataggttgtatttaaaaggtcac
actgggacagcaggaaaacagagcagcctgatcttacacggtgctgatttcagcactaaagatgctgataatgacaactgtatgtgcaaatgtgccctcatgttaacaggaggatgg
tggtttgatgcttgtggcccctccaatctaaatggaatgttctatactgcgggacaaaaccatggaaaactgaatgggataaagtggcactacttcaaagggcccagttactccttacg
ttccacaactatgatgattcgacctttagatttttga

Fig. 63

COMP-Ang2 <synthetic construct>

CDS (mat_peptide):

gggatcttagacctagccccacagatgcttcgagaactccaggagactaatgcggcgctgcaagacgtgagagagctcttgcgacagcaggtcaaggagatcaccttcctgaagaa
tacggtgatggaatgtgacgcttgcggaggctccttactgactatgatgtccacatcaaactcagctaaggaccccactgttgctaaagaagaacaaatcagcttcagagactgtgct
gaagtattcaaatcaggacacaccacgaatggcatctacacgttaacattccctaattctacagaagagatcaaggcctactgtgacatggaagctggaggaggcgggtggacaatt
attcagcgacgtgaggatggcagcgttgattttcagaggacttggaaagaatataaagtgggatttggtaacccttcaggagaatattggctgggaaatgagtttgtttcgcaactga
ctaatcagcaacgctatgtgcttaaaatacaccttaaagactgggaagggaatgaggcttactcattgtatgaacatttctatctctcaagtgaagaactcaattataggattcacctta
aaggacttacagggacagccggcaaaataagcagcatcagccaaccaggaaatgattttagcacaaaggatggagacaacgacaaatgtatttgcaaatgttcacaaatgctaac
aggaggctggtggtttgatgcatgtggtccttccaacttgaacggaatgtactatccacagaggcagaacacaaataagttcaacggcattaaatggtactactggaaaggctcagg
ctattcgctcaaggccacaaccatgatgatccgaccagcagatttctaa

Fig. 64

Homo sapiens TEK receptor tyrosine kinase (TEK), transcript variant 1, mRNA (TIE-2) <NM_000459.4>

CDS:

atggactctttagccagcttagttctctgtggagtcagcttgctcctttctggaactgtggaaggtgccatggacttgatcttgatcaattccctacctcttgtatctgatgctgaaacatct
ctcacctgcattgcctctgggtggcgcccccatgagcccatcaccataggaagggactttgaagccttaatgaaccagcaccaggatccgctggaagttactcaagatgtgaccagag
aatgggctaaaaaagttgtttggaagagagaaaaggctagtaagatcaatggtgcttatttctgtgaagggcgagttcgaggagaggcaatcaggatacgaaccatgaagatgcgt
caacaagcttccttcctaccagctactttaactatgactgtggacaagggagataacgtgaacatatctttcaaaaaggtattgattaaagaagaagatgcagtgatttacaaaaatg
gttccttcatccattcagtgccccggcatgaagtacctgatattctagaagtacacctgcctcatgctcagccccaggatgctggagtgtactcggccaggtatataggaggaaacctct
tcacctcggccttcaccaggctgatagtccggagatgtgaagcccagaagtggggacctgaatgcaaccatctctgtactgcttgtatgaacaatggtgtctgccatgaagatactgg
agaatgcatttgccctcctgggtttatgggaaggacgtgtgagaaggcttgtgaactgcacacgtttggcagaacttgtaaagaaaggtgcagtggacaagagggatgcaagtcttat
gtgttctgtctccctgacccctatgggtgttcctgtgccacaggctggaagggtctgcagtgcaatgaagcatgccaccctggtttttacgggccagattgtaagcttaggtgcagctgc
aacaatggggagatgtgtgatcgcttccaaggatgtctctgctctccaggatggcaggggctccagtgtgagagagaaggcataccgaggatgaccccaaagatagtggatttgcca
gatcatatagaagtaaacagtggtaaatttaatcccatttgcaaagcttctggctggccgctacctactaatgaagaaatgaccctggtgaagccggatgggacagtgctccatccaa
aagactttaaccatacggatcatttctcagtagccatattcaccatccaccggatcctcccccctgactcaggagtttgggtctgcagtgtgaacacagtggctgggatggtggaaaag
cccttcaacatttctgttaaagttcttccaaagcccctgaatgccccaaacgtgattgacactggacataactttgctgtcatcaacatcagctctgagccttactttggggatggaccaa
tcaaatccaagaagcttctatacaaacccgttaatcactatgaggcttggcaacatattcaagtgacaaatgagattgttacactcaactatttggaacctcggacagaatatgaactc
tgtgtgcaactggtccgtcgtggagagggtggggaagggcatcctggacctgtgagacgcttcacaacagcttctatcggactccctcctccaagaggtctaaatctcctgcctaaaa
gtcagaccactctaaatttgacctggcaaccaatatttccaagctcggaagatgacttttatgttgaagtggagagaaggtctgtgcaaaaaagtgatcagcagaatattaaagttcc

Fig. 65 (cont.)

aggcaacttgacttcggtgctacttaacaacttacatcccagggagcagtacgtggtccgagctagagtcaacaccaaggcccaggggaatggagtgaagatctcactgcttggac
ccttagtgacattcttcctcctcaaccagaaaacatcaagatttccaacattacacactcctcagctgtgatttcttggacaatattggatggctattctatttcttctattactatccgtta
caaggttcaaggcaagaatgaagaccagcacgttgatgtgaagataaagaatgccaccatcactcagtatcagctcaagggcctagagcctgaaacagcataccaggtggacattt
ttgcagagaacaacatagggtcaagcaacccagccttttctcatgaactggtgaccctcccagaatctcaagcaccagcggacctcggagggggaagatgctgcttatagccatcc
ttggctctgctggaatgacctgcctgactgtgctgttggcctttctgatcatattgcaattgaagagggcaaatgtgcaaaggagaatggcccaagccttccaaaacgtgagggaaga
accagctgtgcagttcaactcagggactctggccctaaacaggaaggtcaaaaacaacccagatcctacaatttatccagtgcttgactggaatgacatcaaatttcaagatgtgatt
ggggagggcaattttggccaagttcttaaggcgcgcatcaagaaggatgggttacggatggatgctgccatcaaaagaatgaaagaatatgcctccaaagatgatcacagggactt
tgcaggagaactggaagttctttgtaaacttggacaccatccaaacatcatcaatctcttaggagcatgtgaacatcgaggctacttgtacctggccattgagtacgcgccccatggaa
accttctggacttccttcgcaagagccgtgtgctggagacggacccagcatttgccattgccaatagcaccgcgtccacactgtcctcccagcagctccttcacttcgctgccgacgtgg
cccggggcatggactacttgagccaaaaacagtttatccacagggatctggctgccagaaacattttagttggtgaaaactatgtggcaaaaatagcagattttggattgtcccgagg
tcaagaggtgtatgtgaaaaagacaatgggaaggctcccagtgcgctggatggccatcgagtcactgaattacagtgtgtacacaaccaacagtgatgtatggtcctatggtgtgtta
ctatgggagattgttagcttaggaggcacaccctactgcgggatgacttgtgcagaactctacgagaagctgccccagggctacagactggagaagcccctgaactgtgatgatgag
gtgtatgatctaatgagacaatgctggcgggagaagccttatgagaggccatcatttgcccagatattggtgtccttaaacagaatgttagaggagcgaaagacctacgtgaatacc
acgctttatgagaagtttacttatgcaggaattgactgttctgctgaagaagcggcctag

Fig. 65

**Mutant Homo sapiens TEK receptor tyrosine kinase (TEK) (TIE2*; R849W)**

CDS:

atggactctttagccagcttagttctctgtggagtcagcttgctcctttctggaactgtggaaggtgccatggacttgatcttgatcaattccctacctcttgtatctgatgctgaaacatct
ctcacctgcattgcctctgggtggcgcccccatgagcccatcaccataggaagggactttgaagccttaatgaaccagcaccaggatccgctggaagttactcaagatgtgaccagag
aatgggctaaaaaagttgtttggaagagagaaaaggctagtaagatcaatggtgcttatttctgtgaagggcgagttcgaggagaggcaatcaggatacgaaccatgaagatgcgt
caacaagcttccttcctaccagctactttaactatgactgtggacaagggagataacgtgaacatatctttcaaaaaggtattgattaaagaagaagatgcagtgatttacaaaaatg
gttccttcatccattcagtgccccggcatgaagtacctgatattctagaagtacacctgcctcatgctcagccccaggatgctggagtgtactcggccaggtatataggaggaaacctct
tcacctcggccttcaccaggctgatagtccggagatgtgaagcccagaagtggggacctgaatgcaaccatctctgtactgcttgtatgaacaatggtgtctgccatgaagatactgg
agaatgcatttgccctcctgggtttatgggaaggacgtgtgagaaggcttgtgaactgcacacgtttggcagaacttgtaaagaaaggtgcagtggacaagagggatgcaagtcttat
gtgttctgtctccctgacccctatgggtgttcctgtgccacaggctggaagggtctgcagtgcaatgaagcatgccaccctggtttttacgggccagattgtaagcttaggtgcagctgc
aacaatggggagatgtgtgatcgcttccaaggatgtctctgctctccaggatggcaggggctccagtgtgagagagaaggcataccgaggatgaccccaaagatagtggatttgcca
gatcatatagaagtaaacagtggtaaatttaatcccatttgcaaagcttctggctggccgctacctactaatgaagaaatgaccctggtgaagccggatgggacagtgctccatccaa
aagactttaaccatacggatcatttctcagtagccatattcaccatccaccggatcctcccccctgactcaggagtttgggtctgcagtgtgaacacagtggctgggatggtggaaaag
cccttcaacatttctgttaaagttcttccaaagcccctgaatgccccaaacgtgattgacactggacataactttgctgtcatcaacatcagctctgagccttactttggggatggaccaa
tcaaatccaagaagcttctatacaaacccgttaatcactatgaggcttggcaacatattcaagtgacaaatgagattgttacactcaactatttggaacctcggacagaatatgaactc
tgtgtgcaactggtccgtcgtggagagggtggggaagggcatcctggacctgtgagacgcttcacaacagcttctatcggactccctcctccaagaggtctaaatctcctgcctaaaa
gtcagaccactctaaatttgacctggcaaccaatatttccaagctcggaagatgacttttatgttgaagtggagagaaggtctgtgcaaaaaagtgatcagcagaatattaaagttcc

Fig. 66 (cont.)

aggcaacttgacttcggtgctacttaacaacttacatcccagggagcagtacgtggtccgagctagagtcaacaccaaggcccagggggaatggagtgaagatctcactgcttggac
ccttagtgacattcttcctcctcaaccagaaaacatcaagatttccaacattacacactcctcagctgtgatttcttggacaatattggatggctattctatttcttctattactatccgtta
caaggttcaaggcaagaatgaagaccagcacgttgatgtgaagataaagaatgccaccatcactcagtatcagctcaagggcctagagcctgaaacagcataccaggtggacattt
ttgcagagaacaacatagggtcaagcaacccagccttttctcatgaactggtgaccctcccagaatctcaagcaccagcggacctcggagggggaagatgctgcttatagccatcc
ttggctctgctggaatgacctgcctgactgtgctgttggcctttctgatcatattgcaattgaagagggcaaatgtgcaaaggagaatggcccaagccttccaaaacgtgagggaaga
accagctgtgcagttcaactcagggactctggccctaaacaggaaggtcaaaaacaacccagatcctacaatttatccagtgcttgactggaatgacatcaaatttcaagatgtgatt
ggggagggcaattttggccaagttcttaaggcgcgcatcaagaaggatgggttatggatggatgctgccatcaaaagaatgaaagaatatgcctccaaagatgatcacagggacttt
gcaggagaactggaagttctttgtaaacttggacaccatccaaacatcatcaatctcttaggagcatgtgaacatcgaggctacttgtacctggccattgagtacgcgccccatggaa
accttctggacttccttcgcaagagccgtgtgctggagacggacccagcatttgccattgccaatagcaccgcgtccacactgtcctcccagcagctccttcacttcgctgccgacgtgg
cccggggcatggactacttgagccaaaaacagtttatccacagggatctggctgccagaaacattttagttggtgaaaactatgtggcaaaaatagcagattttggattgtcccgagg
tcaagaggtgtatgtgaaaaagacaatgggaaggctcccagtgcgctggatggccatcgagtcactgaattacagtgtgtacacaaccaacagtgatgtatggtcctatggtgtgtta
ctatgggagattgttagcttaggaggcacaccctactgcgggatgacttgtgcagaactctacgagaagctgccccagggctacagactggagaagcccctgaactgtgatgatgag
gtgtatgatctaatgagacaatgctggcgggagaagccttatgagaggccatcatttgcccagatattggtgtccttaaacagaatgttagaggagcgaaagacctacgtgaatacc
acgctttatgagaagtttacttatgcaggaattgactgttctgctgaagaagcggcctag

Fig. 66

PAN50

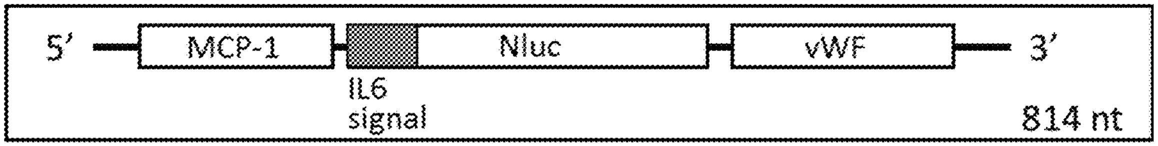

Fig. 67A

PAN50 gaggaaccgagaggctgagactaacccagaaacatccaattctcaaactgaagctcgcactctcgcctccagcatgaactccttctccacaagcgccttcggtccagttgccttctccc
tgggcctgctcctggtgttgcctgctgccttccctgccccagtcttcacactcgaagatttcgttggggactggcgacagacagccggctacaacctggaccaagtccttgaacaggga
ggtgtgtccagtttgtttcagaatctcggggtgtccgtaactccgatccaaaggattgtcctgagcggtgaaaatgggctgaagatcgacatccatgtcatcatcccgtatgaaggtctg
agcggcgaccaaatgggccagatcgaaaaaatttttaaggtggtgtaccctgtggatgatcatcactttaaggtgatcctgcactatggcacactggtaatcgacggggttacgccga
acatgatcgactatttcggacggccgtatgaaggcatcgccgtgttcgacggcaaaaagatcactgtaacagggaccctgtggaacggcaacaaaattatcgacgagcgcctgatca
accccgacggctccctgctgttccgagtaaccatcaacggagtgaccggctggcggctgtgcgaacgcattctggcgtaaggctgctgcagctgcatgggtgcctgctgctgcctgcct
tggcctgatggccaggccagagtgctgccagtcctctgcatgttctgctcttgtgcccttctgagcccacaataaaggctgagctcttatcttgcaaaaggc

Fig. 67B

PAN51

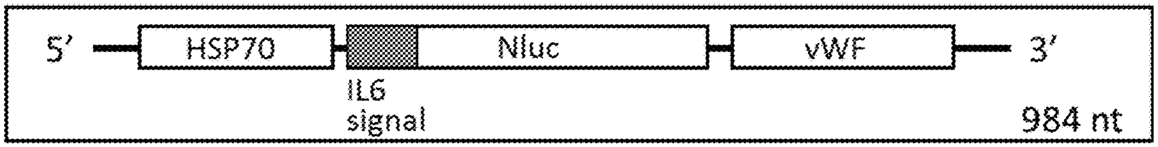

Fig. 68A

PAN51 ataaaagcccaggggcaagcggtccggataacggctagcctgaggagctgctgcgacagtccactaccttttttcgagagtgactcccgttgtcccaaggcttcccagagcgaacctgt
gcggctgcaggcaccggcgcgtcgagtttccggcgtccggaaggaccgagctcttctcgcgaatccagtgttccgtttccagcccccaatctcagagcggagccgacagagagcagg
gaaccggcatgaactccttctccacaagcgccttcggtccagttgccttctccctgggcctgctcctggtgttgcctgctgccttccctgccccagtcttcacactcgaagatttcgttggg
gactggcgacagacagccggctacaacctggaccaagtccttgaacagggaggtgtgtccagtttgtttcagaatctcggggtgtccgtaactccgatccaaaggattgtcctgagcg
gtgaaaatgggctgaagatcgacatccatgtcatcatcccgtatgaaggtctgagcggcgaccaaatgggccagatcgaaaaaatttttaaggtggtgtaccctgtggatgatcatca
ctttaaggtgatcctgcactatggcacactggtaatcgacggggttacgccgaacatgatcgactatttcggacggccgtatgaaggcatcgccgtgttcgacggcaaaaagatcact
gtaacagggaccctgtggaacggcaacaaaattatcgacgagcgcctgatcaaccccgacggctccctgctgttccgagtaaccatcaacggagtgaccggctggcggctgtgcga
acgcattctggcgtaaggctgctgcagctgcatgggtgcctgctgctgcctgccttggcctgatggccaggccagagtgctgccagtcctctgcatgttctgctcttgtgcccttctgagc
ccacaataaaggctgagctcttatcttgcaaaaggc

Fig. 68B

PAN52

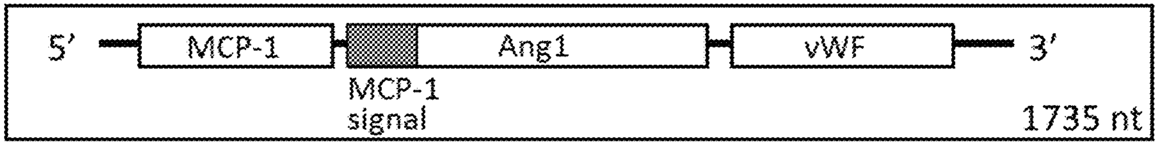

Fig.69A

PAN52 gaggaaccgagaggctgagactaacccagaaacatccaattctcaaactgaagctcgcactctcgcctccagcatgaaagtctctgccgcccttctgtgcctgctgctcatagcagcc
accttcattccccaagggctcgctcacatagggtgcagcaatcagcgccgaagtccagaaaacagtgggagaagatataaccggattcaacatgggcaatgtgcctacactttcatt
cttccagaacacgatggcaactgtcgtgagagtacgacagaccagtacaacacaaacgctctgcagagagatgctccacacgtggaaccggatttctcttcccagaaacttcaacat
ctggaacatgtgatggaaaattatactcagtggctgcaaaaacttgagaattacattgtggaaaacatgaagtcggagatggcccagatacagcagaatgcagttcagaaccacac
ggctaccatgctggagataggaaccagcctcctctctcagactgcagagcagaccagaaagctgacagatgttgagacccaggtactaaatcaaacttctcgacttgagatacagct
gctggagaattcattatccacctacaagctagagaagcaacttcttcaacagacaaatgaaatcttgaagatccatgaaaaaaacagtttattagaacataaaatcttagaaatgga
aggaaaacacaaggaagagttggacaccttaaaggaagagaaagagaaccttcaaggcttggttactcgtcaaacatatataatccaggagctggaaaagcaattaaacagagct
accaccaacaacagtgtccttcagaagcagcaactggagctgatggacacagtccacaaccttgtcaatctttgcactaaagaaggtgttttactaaagggaggaaaaagagagga
agagaaaccatttagagactgtgcagatgtatatcaagctggttttaataaaagtggaatctacactatttatattaataatatgccagaacccaaaaaggtgttttgcaatatggatg
tcaatgggggaggttggactgtaatacaacatcgtgaagatggaagtctagatttccaaagaggctggaaggaatataaaatgggttttggaaatccctccggtgaatattggctgg
ggaatgagtttatttttgccattaccagtcagaggcagtacatgctaagaattgagttaatggactgggaagggaaccgagcctattcacagtatgacagattccacataggaaatga
aaagcaaaactataggttgtatttaaaaggtcacactgggacagcaggaaaacagagcagcctgatcttacacggtgctgatttcagcactaaagatgctgataatgacaactgtat
gtgcaaatgtgccctcatgttaacaggaggatggtggtttgatgcttgtggcccctccaatctaaatggaatgttctatactgcgggacaaaaccatggaaaactgaatgggataaag
tggcactacttcaaagggcccagttactccttacgttccacaactatgatgattcgacctttagatttttgaggctgctgcagctgcatgggtgcctgctgctgcctgccttggcctgatgg
ccaggccagagtgctgccagtcctctgcatgttctgctcttgtgcccttctgagcccacaataaaggctgagctcttatcttgcaaaaggc

Fig. 69B

PAN53

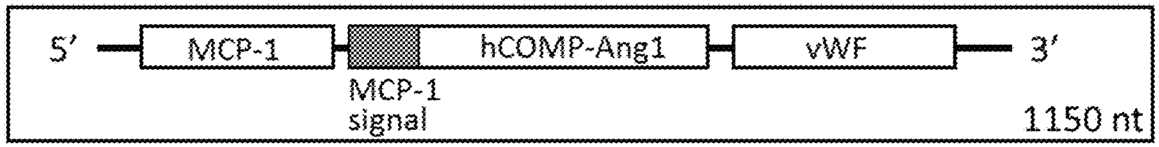

Fig. 70A

PAN53 gaggaaccgagaggctgagactaacccagaaacatccaattctcaaactgaagctcgcactctcgcctccagcatgaaagtctctgccgcccttctgtgcctgctgctcatagcagcc
accttcattccccaagggctcgctgggatcttagacttgggcccgcagatgcttcgggaactgcaggaaaccaacgcggcgctgcaggacgtgcgggagctgctgcggcagcaggtc
agggagatcacgttcctgaaaaacacggtgatggagtgtgacgcgtgcggaggctcccttgtcaatctttgcactaaagaaggtgttttactaaagggaggaaaaagagaggaaga
gaaaccatttagagactgtgcagatgtatatcaagctggttttaataaaagtggaatctacactatttatattaataatatgccagaacccaaaaaggtgttttgcaatatggatgtca
atggggaggttggactgtaatacaacatcgtgaagatggaagtctagatttccaaagaggctggaaggaatataaaatgggttttggaaatccctccggtgaatattggctgggga
atgagtttatttttgccattaccagtcagaggcagtacatgctaagaattgagttaatggactgggaagggaaccgagcctattcacagtatgacagattccacataggaaatgaaaa
gcaaaactataggttgtatttaaaaggtcacactgggacagcaggaaaacagagcagcctgatcttacacggtgctgatttcagcactaaagatgctgataatgacaactgtatgtgc
aaatgtgccctcatgttaacaggaggatggtggtttgatgcttgtggcccctccaatctaaatggaatgttctatactgcgggacaaaaccatggaaaactgaatgggataaagtggc
actacttcaaagggcccagttactccttacgttccacaactatgatgattcgacctttagatttttgaggctgctgcagctgcatgggtgcctgctgctgcctgccttggcctgatggcca
ggccagagtgctgccagtcctctgcatgttctgctcttgtgcccttctgagcccacaataaaggctgagctcttatcttgcaaaaggc

Fig. 70B

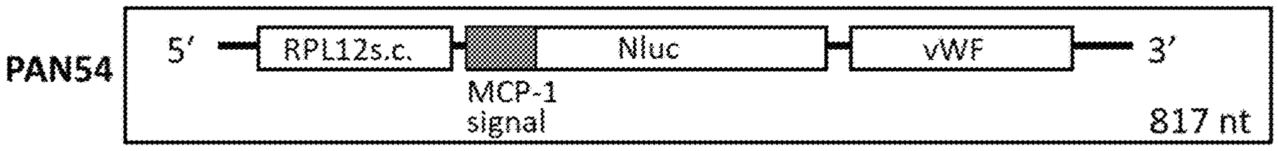

Fig. 86A

PAN54 catatcttcattcttcactctttcccccccccccccttatcctcctatctaatcctctcatctctctcctcctcttcctccaacaacaactaacaatgaaagtctctgccgcccttctgtgcctgc
tgctcatagcagccaccttcattccccaagggctcgctgtcttcacactcgaagatttcgttggggactggcgacagacagccggctacaacctggaccaagtccttgaacagggagg
tgtgtccagtttgtttcagaatctcggggtgtccgtaactccgatccaaaggattgtcctgagcggtgaaaatgggctgaagatcgacatccatgtcatcatcccgtatgaaggtctgag
cggcgaccaaatgggccagatcgaaaaaatttttaaggtggtgtaccctgtggatgatcatcactttaaggtgatcctgcactatggcacactggtaatcgacggggttacgccgaac
atgatcgactatttcggacggccgtatgaaggcatcgccgtgttcgacggcaaaaagatcactgtaacagggaccctgtggaacggcaacaaaattatcgacgagcgcctgatcaac
cccgacggctccctgctgttccgagtaaccatcaacggagtgaccggctggcggctgtgcgaacgcattctggcgtaaggctgctgcagctgcatgggtgcctgctgctgcctgccttg
gcctgatggccaggccagagtgctgccagtcctctgcatgttctgctcttgtgcccttctgagcccacaataaaggctgagctcttatcttgcaaaaggc

Fig. 86B

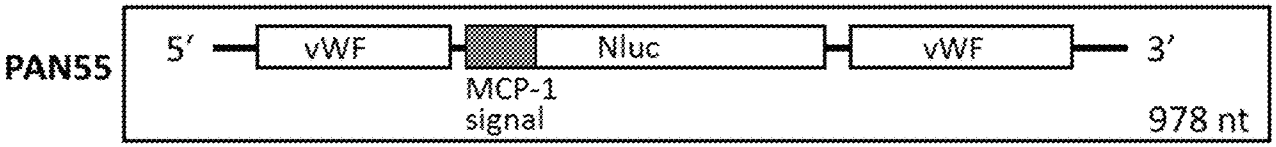

Fig. 87A

PAN55 gtggcagctcacagctattgtggtgggaaagggagggtggttggtggatgtcacagcttgggctttatctcccccagcagtggggactccacagcccctgggctacataacagcaaga
cagtccggagctgtagcagacctgattgagcctttgcagcagctgagagcatggcctagggtgggcggcaccattgtccagcagctgagtttcccagggaccttggagatagccgca
gccctcatttgcaggggaagatgaaagtctctgccgcccttctgtgcctgctgctcatagcagccaccttcattccccaagggctcgctgtcttcacactcgaagatttcgttggggactg
gcgacagacagccggctacaacctggaccaagtccttgaacagggaggtgtgtccagtttgtttcagaatctcggggtgtccgtaactccgatccaaaggattgtcctgagcggtgaa
aatgggctgaagatcgacatccatgtcatcatcccgtatgaaggtctgagcggcgaccaaatgggccagatcgaaaaaatttttaaggtggtgtaccctgtggatgatcatcacttta
aggtgatcctgcactatggcacactggtaatcgacggggttacgccgaacatgatcgactatttcggacggccgtatgaaggcatcgccgtgttcgacggcaaaaagatcactgtaac
agggaccctgtggaacggcaacaaaattatcgacgagcgcctgatcaaccccgacggctccctgctgttccgagtaaccatcaacggagtgaccggctggcggctgtgcgaacgcat
tctggcgtaaggctgctgcagctgcatgggtgcctgctgctgcctgccttggcctgatggccaggccagagtgctgccagtcctctgcatgttctgctcttgtgcccttctgagcccacaa
taaaggctgagctcttatcttgcaaaaggc

Fig. 87B

PAN56

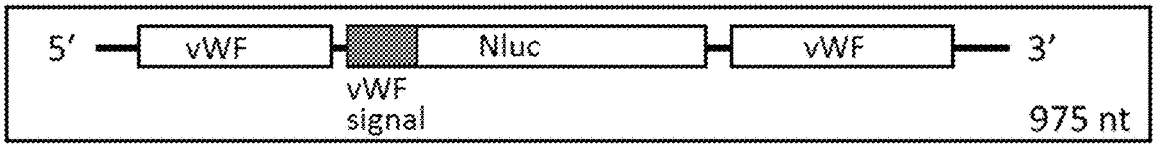

Fig. 88A

PAN56 gtggcagctcacagctattgtggtgggaaagggagggtggttggtggatgtcacagcttgggctttatctcccccagcagtggggactccacagcccctgggctacataacagcaaga
cagtccggagctgtagcagacctgattgagcctttgcagcagctgagagcatggcctagggtgggcggcaccattgtccagcagctgagtttcccagggaccttggagatagccgca
gccctcatttgcaggggaagatgattcctgccagatttgccggggtgctgcttgctctggccctcattttgccagggaccctttgtgtcttcacactcgaagatttcgttggggactggcg
acagacagccggctacaacctggaccaagtccttgaacagggaggtgtgtccagtttgtttcagaatctcggggtgtccgtaactccgatccaaaggattgtcctgagcggtgaaaat
gggctgaagatcgacatccatgtcatcatcccgtatgaaggtctgagcggcgaccaaatgggccagatcgaaaaaatttttaaggtggtgtaccctgtggatgatcatcactttaagg
tgatcctgcactatggcacactggtaatcgacggggttacgccgaacatgatcgactatttcggacggccgtatgaaggcatcgccgtgttcgacggcaaaaagatcactgtaacagg
gaccctgtggaacggcaacaaaattatcgacgagcgcctgatcaaccccgacggctccctgctgttccgagtaaccatcaacggagtgaccggctggcggctgtgcgaacgcattct
ggcgtaaggctgctgcagctgcatgggtgcctgctgctgcctgccttggcctgatggccaggccagagtgctgccagtcctctgcatgttctgctcttgtgcccttctgagcccacaata
aaggctgagctcttatcttgcaaaaggc

Fig. 88B

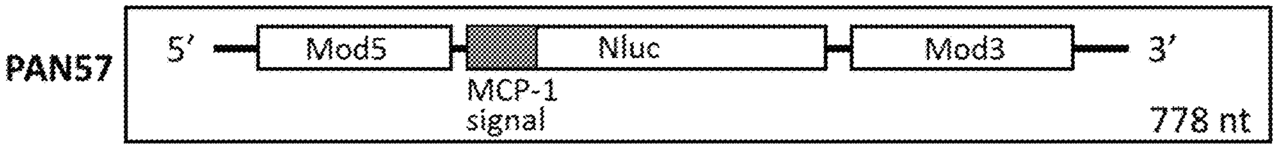

Fig. 89A

PAN57 gggaaataagagagaaaagaagagtaagaagaaatataagaccccggcgccgccaccatgaaagtctctgccgcccttctgtgcctgctgctcatagcagccaccttcattcccca
agggctcgctgtcttcacactcgaagatttcgttggggactggcgacagacagccggctacaacctggaccaagtccttgaacagggaggtgtgtccagtttgtttcagaatctcggg
gtgtccgtaactccgatccaaaggattgtcctgagcggtgaaaatgggctgaagatcgacatccatgtcatcatcccgtatgaaggtctgagcggcgaccaaatgggccagatcgaa
aaaatttttaaggtggtgtaccctgtggatgatcatcactttaaggtgatcctgcactatggcacactggtaatcgacggggttacgccgaacatgatcgactatttcggacggccgtat
gaaggcatcgccgtgttcgacggcaaaaagatcactgtaacagggaccctgtggaacggcaacaaaattatcgacgagcgcctgatcaaccccgacggctccctgctgttccgagta
accatcaacggagtgaccggctggcggctgtgcgaacgcattctggcgtaataataggctggagcctcggtggcctagcttcttgccccttgggcctccccccagcccctcctcccctt
cctgcacccgtacccccctccataaagtaggaaacactacagtggtctttgaataaagtctgagtgggcggc

Fig. 89B

PAN58

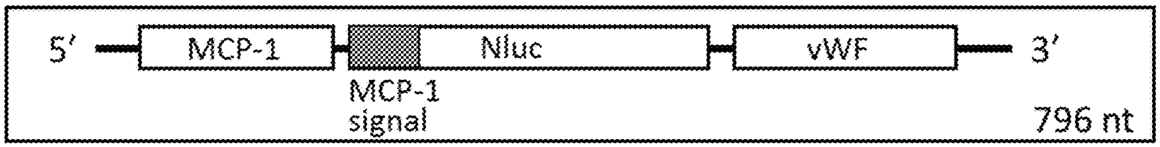

Fig. 90A

PAN58 gaggaaccgagaggctgagactaacccagaaacatccaattctcaaactgaagctcgcactctcgccgccaccatgaaagtctctgccgcccttctgtgcctgctgctcatagcagcc
accttcattccccaagggctcgctgtcttcacactcgaagatttcgttggggactggcgacagacagccggctacaacctggaccaagtccttgaacagggaggtgtgtccagtttgtt
tcagaatctcggggtgtccgtaactccgatccaaaggattgtcctgagcggtgaaaatgggctgaagatcgacatccatgtcatcatcccgtatgaaggtctgagcggcgaccaaatg
ggccagatcgaaaaaatttttaaggtggtgtaccctgtggatgatcatcactttaaggtgatcctgcactatggcacactggtaatcgacggggttacgccgaacatgatcgactattt
cggacggccgtatgaaggcatcgccgtgttcgacggcaaaaagatcactgtaacagggaccctgtggaacggcaacaaaattatcgacgagcgcctgatcaaccccgacggctccc
tgctgttccgagtaaccatcaacggagtgaccggctggcggctgtgcgaacgcattctggcgtaaggctgctgcagctgcatgggtgcctgctgctgcctgccttggcctgatggccag
gccagagtgctgccagtcctctgcatgttctgctcttgtgcccttctgagcccacaataaaggctgagctcttatcttgcaaaaggc

Fig. 90B

PAN59

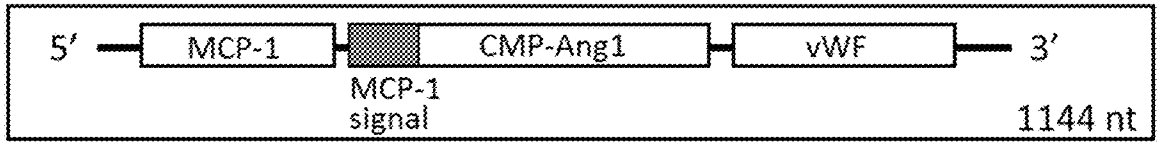

Fig. 91A

PAN59 gaggaaccgagaggctgagactaacccagaaacatccaattctcaaactgaagctcgcactctcgcctccagcatgaaagtctctgccgcccttctgtgcctgctgctcatagcagcc
accttcattccccaagggctcgctgggatcttagaggaagacccggccgcctgcgagtccctggtgaaattccaagccaaagtggaggggctgctgcaggccctgaccaggaaactg
gaagctgtgagtaagcggctggccatcctggagaacacagttgtcggctcccttgtcaatcttgccactaaagaaggtgttttactaaagggaggaaaaagagaggaagagaaacc
atttagagactgtgcagatgtatatcaagctggttttaataaaagtggaatctacactatttatattaataatatgccagaacccaaaaaggtgttttgcaatatggatgtcaatggggg
aggttggactgtaatacaacatcgtgaagatggaagtctagatttccaaagaggctggaaggaatataaaatgggttttggaaatccctccggtgaatattggctggggaatgagttt
atttttgccattaccagtcagaggcagtacatgctaagaattgagttaatggactgggaagggaaccgagcctattcacagtatgacagattccacataggaaatgaaaagcaaaac
tataggttgtatttaaaaggtcacactgggacagcaggaaaacagagcagcctgatcttacacggtgctgatttcagcactaaagatgctgataatgacaactgtatgtgcaaatgtg
ccctcatgttaacaggaggatggtggtttgatgcttgtggcccctccaatctaaatggaatgttctatactgcgggacaaaaccatggaaaactgaatgggataaagtggcactacttc
aaagggcccagttactccttacgttccacaactatgatgattcgacctttagatttttgaggctgctgcagctgcatgggtgcctgctgctgcctgccttggcctgatggccaggccaga
gtgctgccagtcctctgcatgttctgctcttgtgcccttctgagcccacaataaaggctgagctcttatcttgcaaaaggc

Fig. 91B

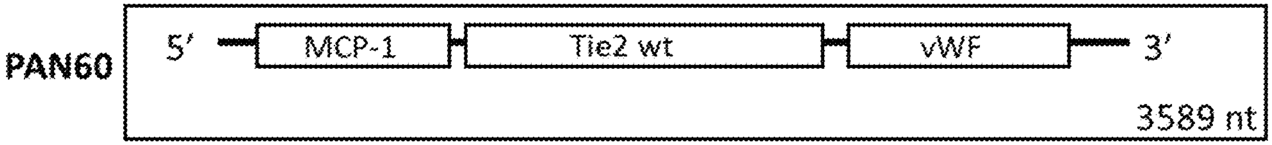

Fig. 95A

PAN60 gaggaaccgagaggctgagactaacccagaaacatccaattctcaaactgaagctcgcactctcgcctccagcatggactctttagccagcttagttctctgtggagtcagcttgctcc
tttctggaactgtggaaggtgccatggacttgatcttgatcaattccctacctcttgtatctgatgctgaaacatctctcacctgcattgcctctgggtggcgcccccatgagcccatcacc
ataggaagggactttgaagccttaatgaaccagcaccaggacccgctggaagttactcaagatgtgaccagagaatgggctaaaaaagttgtttggaagagagaaaaggctagta
agatcaatggtgcttatttctgtgaagggcgagttcgaggagaggcaatcaggatacgaaccatgaagatgcgtcaacaagcttccttcctaccagctactttaactatgactgtgga
caagggagataacgtgaacatatctttcaaaaaggtattgattaaagaagaagatgcagtgatttacaaaaatggttccttcatccattcagtgccccggcatgaagtacctgatattc
tagaagtacacctgcctcatgctcagccccaggatgctggagtgtactcggccaggtatataggaggaaacctcttcacctcggccttcaccaggctgatagtccggagatgtgaagc
ccagaagtggggacctgaatgcaaccatctctgtactgcttgtatgaacaatggtgtctgccatgaagatactggagaatgcatttgccctcctgggtttatgggaaggacgtgtgaga
aggcttgtgaactgcacacgtttggcagaacttgtaaagaaaggtgcagtggacaagagggatgcaagtcttatgtgttctgtctccctgacccctatgggtgttcctgtgccacaggc
tggaagggtctgcagtgcaatgaagcatgccaccctggtttttacgggccagattgtaagcttaggtgcagctgcaacaatggggagatgtgtgatcgcttccaaggatgtctctgctc
tccaggatggcaggggctccagtgtgagagagaaggcataccgaggatgaccccaaagatagtggatttgccagatcatatagaagtaaacagtggtaaatttaatcccatttgcaa
agcttctggctggccgctacctactaatgaagaaatgaccctggtgaagccggatgggacagtgctccatccaaaagactttaaccatacggatcatttctcagtagccatattcacca
tccacagaatcctccccctgactcaggagtttgggtctgcagtgtgaacacagtggctgggatggtggaaaagcccttcaacatttctgttaaagttcttccaaagcccctgaatgccc
caaacgtgattgacactggacataactttgctgtcatcaacatcagctctgagccttactttggggatggaccaatcaaatccaagaagcttctatacaaacccgttaatcactatgag
gcttggcaacatattcaagtgacaaatgagattgttacactcaactatttggaacctcggacagaatatgaactctgtgtgcaactggtccgtcgtggagagggtggggaagggcatc
ctggacctgtgagacgcttcacaacagcttctatcggactccctcctccaagaggtctaaatctcctgcctaaaagtcagaccactctaaatttgacctggcaaccaatatttccaagct
cggaagatgacttttatgttgaagtggagagaaggtctgtgcaaaaaagtgatcagcagaatattaaagttccaggcaacttgacttcggtgctacttaacaacttacatcccaggga
gcagtacgtggtccgagctagagtcaacaccaaggcccaggggaatggagtgaagatctcactgcttggacccttagtgacattcttcctcctcaaccagaaaacatcaagatttcc

Fig. 95B aacattacacactcctcagctgtgatttcttggacaatattggatggctattctatttcttctattactatccgttacaaggttcaaggcaagaatgaagaccagcacgttgatgtgaaga
taaagaatgccaccatcactcagtatcagctcaagggcctagagcctgaaacagcataccaggtggacatttttgcagagaacaacatagggtcaagcaacccagccttttctcatg
aactggtgaccctcccagaatctcaagcaccagcggacctcggagggggaagatgctgcttatagccatccttggctctgctggaatgacctgcctgactgtgctgttggcctttctg
atcatattgcaattgaagagggcaaatgtgcaaaggagaatggcccaagccttccaaaacgtgagggaagaaccagctgtgcagttcaactcagggactctggccctaaacaggaa
ggtcaaaaacaacccagatcctacaatttatccagtgcttgactggaatgacatcaaatttcaagatgtgattggggagggcaattttggccaagttcttaaggcgcgcatcaagaag
gatgggttacggatggatgctgccatcaaaagaatgaaagaatatgcctccaaagatgatcacagggactttgcaggagaactggaagttctttgtaaacttggacaccatccaaac
atcatcaatctcttaggagcatgtgaacatcgaggctacttgtacctggccattgagtacgcgccccatggaaaccttctggacttccttcgcaagagccgtgtgctggagacggaccc
agcatttgccattgccaatagcaccgcgtccacactgtcctcccagcagctccttcacttcgctgccgacgtggcccggggcatggactacttgagccaaaaacagtttatccacaggg
atctggctgccagaaacattttagttggtgaaaactatgtggcaaaaatagcagattttggattgtcccgaggtcaagaggtgtatgtgaaaaagacaatgggaaggctcccagtgc
gctggatggccatcgagtcactgaattacagtgtgtacacaaccaacagtgatgtatggtcctatggtgtgttactatgggagattgttagcttaggaggcacaccctactgcgggatg
acttgtgcagaactctacgagaagctgccccagggctacagactggagaagcccctgaactgtgatgatgaggtgtatgatctaatgagacaatgctggcgggagaagccttatgag
aggccatcatttgcccagatattggtgtccttaaacagaatgttagaggagcgaaagacctacgtgaataccacgctttatgagaagtttacttatgcaggaattgactgttctgctga
agaagcggcctagggctgctgcagctgcatgggtgcctgctgctgcctgccttggcctgatggccaggccagagtgctgccagtcctctgcatgttctgctcttgtgcccttctgagccc
acaataaaggctgagctcttatcttgcaaaaggc

Fig. 95B continued

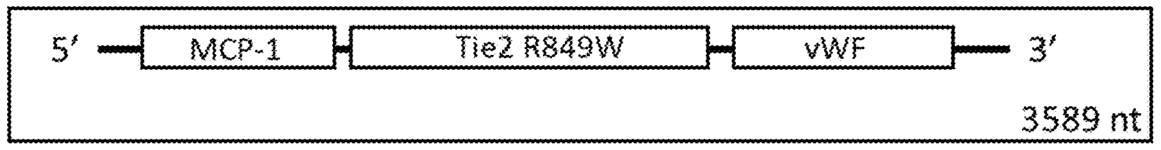

Fig. 96A

PAN61 gaggaaccgagaggctgagactaacccagaaacatccaattctcaaactgaagctcgcactctcgcctccagcatggactctttagccagcttagttctctgtggagtcagcttgctcc
tttctggaactgtggaaggtgccatggacttgatcttgatcaattccctacctcttgtatctgatgctgaaacatctctcacctgcattgcctctgggtggcgcccccatgagcccatcacc
ataggaagggactttgaagccttaatgaaccagcaccaggacccgctggaagttactcaagatgtgaccagagaatgggctaaaaagttgtttggaagagagaaaaggctagta
agatcaatggtgcttatttctgtgaagggcgagttcgaggagaggcaatcaggatacgaaccatgaagatgcgtcaacaagcttccttcctaccagctactttaactatgactgtgga
caagggagataacgtgaacatatctttcaaaaaggtattgattaaagaagaagatgcagtgatttacaaaaatggttccttcatccattcagtgccccggcatgaagtacctgatattc
tagaagtacacctgcctcatgctcagccccaggatgctggagtgtactcggccaggtatataggaggaaacctcttcacctcggccttcaccaggctgatagtccggagatgtgaagc
ccagaagtggggacctgaatgcaaccatctctgtactgcttgtatgaacaatggtgtctgccatgaagatactggagaatgcatttgccctcctgggtttatgggaaggacgtgtgaga
aggcttgtgaactgcacacgtttggcagaacttgtaaagaaaggtgcagtggacaagagggatgcaagtcttatgtgttctgtctccctgacccctatgggtgttcctgtgccacaggc
tggaagggtctgcagtgcaatgaagcatgccaccctggtttttacgggccagattgtaagcttaggtgcagctgcaacaatggggagatgtgtgatcgcttccaaggatgtctctgctc
tccaggatggcaggggctccagtgtgagagagaaggcataccgaggatgaccccaaagatagtggatttgccagatcatatagaagtaaacagtggtaaatttaatcccatttgcaa
agcttctggctggccgctacctactaatgaagaaatgaccctggtgaagccggatgggacagtgctccatccaaaagactttaaccatacggatcatttctcagtagccatattcacca
tccacagaatcctccccctgactcaggagtttgggtctgcagtgtgaacacagtggctgggatggtggaaaagcccttcaacatttctgttaaagttcttccaaagcccctgaatgccc
caaacgtgattgacactggacataactttgctgtcatcaacatcagctctgagccttactttggggatggaccaatcaaatccaagaagcttctatacaaacccgttaatcactatgag
gcttggcaacatattcaagtgacaaatgagattgttacactcaactatttggaacctcggacagaatatgaactctgtgtgcaactggtccgtcgtggagagggtggggaagggcatc
ctggacctgtgagacgcttcacaacagcttctatcggactccctcctccaagaggtctaaatctcctgcctaaaagtcagaccactctaaatttgacctggcaaccaatatttccaagct
cggaagatgacttttatgttgaagtggagagaaggtctgtgcaaaaaagtgatcagcagaatattaaagttccaggcaacttgacttcggtgctacttaacaacttacatcccaggga
gcagtacgtggtccgagctagagtcaacaccaaggcccaggggaatggagtgaagatctcactgcttggacccttagtgacattcttcctcctcaaccagaaaacatcaagatttcc

Fig. 96B aacattacacactcctcagctgtgatttcttggacaatattggatggctattctatttcttctattactatccgttacaaggttcaaggcaagaatgaagaccagcacgttgatgtgaaga
taaagaatgccaccatcactcagtatcagctcaagggcctagagcctgaaacagcataccaggtggacatttttgcagagaacaacatagggtcaagcaacccagccttttctcatg
aactggtgaccctcccagaatctcaagcaccagcggacctcggagggggaagatgctgcttatagccatccttggctctgctggaatgacctgcctgactgtgctgttggcctttctg
atcatattgcaattgaagagggcaaatgtgcaaaggagaatggcccaagccttccaaaacgtgagggaagaaccagctgtgcagttcaactcagggactctggccctaaacaggaa
ggtcaaaaacaacccagatcctacaatttatccagtgcttgactggaatgacatcaaatttcaagatgtgattggggagggcaattttggccaagttcttaaggcgcgcatcaagaag
gatgggttatggatggatgctgccatcaaaagaatgaaagaatatgcctccaaagatgatcacagggactttgcaggagaactggaagttctttgtaaacttggacaccatccaaac
atcatcaatctcttaggagcatgtgaacatcgaggctacttgtacctggccattgagtacgcgccccatggaaaccttctggacttccttcgcaagagccgtgtgctggagacggaccc
agcatttgccattgccaatagcaccgcgtccacactgtcctcccagcagctccttcacttcgctgccgacgtggcccggggcatggactacttgagccaaaaacagtttatccacaggg
atctggctgccagaaacattttagttggtgaaaactatgtggcaaaaatagcagattttggattgtcccgaggtcaagaggtgtatgtgaaaaagacaatgggaaggctcccagtgc
gctggatggccatcgagtcactgaattacagtgtgtacacaaccaacagtgatgtatggtcctatggtgtgttactatgggagattgttagcttaggaggcacaccctactgcgggatg
acttgtgcagaactctacgagaagctgccccagggctacagactggagaagcccctgaactgtgatgatgaggtgtatgatctaatgagacaatgctggcgggagaagccttatgag
aggccatcatttgcccagatattggtgtccttaaacagaatgttagaggagcgaaagacctacgtgaataccacgctttatgagaagtttacttatgcaggaattgactgttctgctga
agaagcggcctagggctgctgcagctgcatgggtgcctgctgctgcctgccttggcctgatggccaggccagagtgctgccagtcctctgcatgttctgctcttgtgcccttctgagccc
acaataaaggctgagctcttatcttgcaaaaggc

Fig. 96B continued

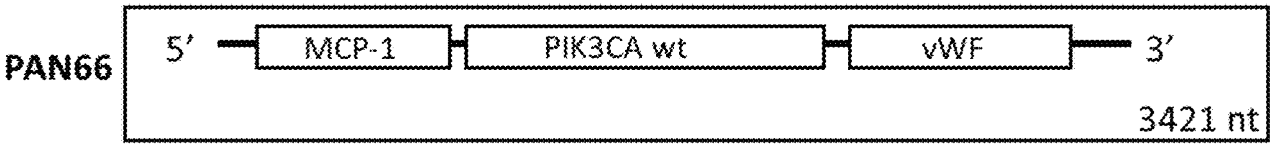

Fig. 97A

PAN66 gaggaaccgagaggctgagactaacccagaaacatccaattctcaaactgaagctcgcactctcgcctccagcatgcctccacgaccatcatcaggtgaactgtggggcatccactt
gatgcccccaagaatcctagtagaatgtttactaccaaatggaatgatagtgactttagaatgcctccgtgaggctacattaataaccataaagcatgaactatttaaagaagcaaga
aaatacccccctccatcaacttcttcaagatgaatcttcttacattttcgtaagtgttactcaagaagcagaaagggaagaatttttttgatgaaacaagacgactttgtgaccttcggcttt
ttcaaccctttttaaaagtaattgaaccagtaggcaaccgtgaagaaaagatcctcaatcgagaaattggttttgctatcggcatgccagtgtgtgaatttgatatggttaaagatcca
gaagtacaggacttccgaagaaatattctgaacgtttgtaaagaagctgtggatcttagggacctcaattcacctcatagtagagcaatgtatgtctatcctccaaatgtagaatcttc
accagaattgccaaagcacatatataataaattagataaagggcaaataatagtggtgatctgggtaatagtttctccaaataatgacaagcagaagtatactctgaaaatcaacca
tgactgtgtaccagaacaagtaattgctgaagcaatcaggaaaaaaactcgaagtatgttgctatcctctgaacaactaaaactctgtgttttagaatatcagggcaagtatattttaa
aagtgtgtggatgtgatgaatacttcctagaaaaatatcctctgagtcagtataagtatataagaagctgtataatgcttgggaggatgcccaatttgatgttgatggctaaagaaagc
ctttattctcaactgccaatggactgttttacaatgccatcttattccagacgcatttccacagctacaccatatatgaatggagaaacatctacaaaatccctttgggttataaatagtg
cactcagaataaaaattctttgtgcaacctacgtgaatgtaaatattcgagacattgataagatctatgttcgaacaggtatctaccatggaggagaacccttatgtgacaatgtgaac
actcaaagagtaccttgttccaatcccaggtggaatgaatggctgaattatgatatatacattcctgatcttcctcgtgctgctcgactttgcctttccatttgctctgttaaaggccgaaa
gggtgctaaagaggaacactgtccattggcatggggaaatataaacttgtttgattacacagacactctagtatctggaaaaatggctttgaatctttggccagtacctcatggattag
aagatttgctgaaccctattggtgttactggatcaaatccaaataaagaaactccatgcttagagttggagtttgactggttcagcagtgtggtaaagttcccagatatgtcagtgattg
aagagcatgccaattggtctgtatcccgagaagcaggatttagctattcccacgcaggactgagtaacagactagctagagacaatgaattaagggaaaatgacaaagaacagctc
aaagcaatttctacacgagatcctctctctgaaatcactgagcaggagaaagattttctatggagtcacagacactattgtgtaactatccccgaaattctacccaaattgcttctgtct
gttaaatggaattctagagatgaagtagcccagatgtattgcttggtaaaagattggcctccaatcaaacctgaacaggctatggaacttctggactgtaattacccagatcctatggt

Fig. 97B tcgaggttttgctgttcggtgcttggaaaaatatttaacagatgacaaactttctcagtatttaattcagctagtacaggtcctaaaatatgaacaatatttggataacttgcttgtgaga
tttttactgaagaaagcattgactaatcaaaggattgggcactttttcttttggcatttaaaatctgagatgcacaataaaacagttagccagaggtttggcctgcttttggagtcctatt
gtcgtgcatgtgggatgtatttgaagcacctgaataggcaagtcgaggcaatggaaaagctcattaacttaactgacattctcaaacaggagaagaaggatgaaacacaaaaggta
cagatgaagtttttagttgagcaaatgaggcgaccagatttcatggatgctctacagggctttctgtctcctctaaaccctgctcatcaactaggaaacctcaggcttgaagagtgtcga
attatgtcctctgcaaaaaggccactgtggttgaattgggagaacccagacatcatgtcagagttactgtttcagaacaatgagatcatctttaaaaatggggatgatttacggcaag
atatgctaacacttcaaattattcgtattatggaaaatatctggcaaaatcaaggtcttgatcttcgaatgttaccttatggttgtctgtcaatcggtgactgtgtgggacttattgaggtg
gtgcgaaattctcacactattatgcaaattcagtgcaaaggcggcttgaaaggtgcactgcagttcaacagccacacactacatcagtggctcaaagacaagaacaaaggagaaat
atatgatgcagccattgacctgtttacacgttcatgtgctggatactgtgtagctaccttcattttgggaattggagatcgtcacaatagtaacatcatggtgaaagacgatggacaact
gtttcatatagattttggacactttttggatcacaagaagaaaaaatttggttataaacgagaacgtgtgccatttgttttgacacaggatttcttaatagtgattagtaaaggagccca
agaatgcacaaagacaagagaatttgagaggtttcaggagatgtgttacaaggcttatctagctattcgacagcatgccaatctcttcataaatcttttctcaatgatgcttggctctgg
aatgccagaactacaatcttttgatgacattgcatacattcgaaagaccctagccttagataaaactgagcaagaggctttggagtatttcatgaaacaaatgaatgatgcacatcat
ggtggctggacaacaaaaatggattggatcttccacacaattaaacagcatgcattgaactgaggctgctgcagctgcatgggtgcctgctgctgcctgccttggcctgatggccagg
ccagagtgctgccagtcctctgcatgttctgctcttgtgcccttctgagcccacaataaaggctgagctcttatcttgcaaaaggc

Fig. 97B continued a)

Mod5 sequence (5'-UTR): (underlined in Fig 89; PAN57)

gggaaataagagagaaaagaagagtaagaagaaatataagaccccggcgccgccacc b)

Mod3 sequence (3'-UTR): (underlined in Fig 89; PAN57)

taataggctggagcctcggtggcctagcttcttgccccttgggcctccccccagcccctcctccccttcctgcacccgtacccccctccataaagtaggaaacactacagtggtctttgaat
aaagtctgagtgggcggc c)

5'-Primer for PAN57:

taatacgact cactatagggaaataagagagaaaagaa d)

3'-Primer for PAN57:

tttttttttt tttttttttt tttttttttt tttttttttt tttttttttt tttttttttt tttttttttt tttttttttt tttttttttt tttttttttt tttttttttt tttttttttt gccgcccactcagacttta e)

5'-Primer for constructs PAN55, PAN56 (Figures 87 und 88).

taatacgact cactatagggtggcagctcacagctatt

Fig. 100

RECOMBINANT NUCLEIC ACID CONSTRUCT

CROSS REFERENCE TO RELATED APPLICATIONS

This application is a continuation of International Application No. PCT/EP2019/071173, filed on Aug. 7, 2019, which claims priority to Application No. EP 18188489.1 filed on Aug. 10, 2018, Application No. EP 18194023.0 filed on Sep. 12, 2018, and Application No. EP 18248243.0 filed on Dec. 28, 2018, the entire contents of which are hereby incorporated by reference.

SEQUENCE LISTING

The instant application contains a Sequence Listing which has been submitted electronically in computer readable form (CRF) and is hereby incorporated by reference in its entirety. Said Sequence Listing, created on Oct. 21, 2024, is named P 10045 PCT_Sequence listing_21102024_ST25 and is 225 bytes in size.

The present invention is related to a recombinant nucleic acid construct, a vector, preferably an expression vector, comprising a recombinant nucleic acid construct, a cell comprising the recombinant nucleic acid construct and/or the vector, a delivery vehicle comprising the recombinant nucleic acid construct, a pharmaceutical composition comprising the recombinant nucleic acid construct, the recombinant nucleic acid construct for use in a method for the treatment and/or prevention of a disease, the recombinant nucleic acid construct for use in a method for restoring a cellular function of a cell, a method for the treatment and/or prevention of a disease and a method for restoring a cellular function of a cell.

Nucleic acid molecules serve various purposes in biological systems. One out of several purposes is to store genetic information, another one is to convey genetic information from deoxyribonucleic acid to the ribosome where such genetic information is translated into an amino acid sequence. The latter step involves the use of messenger ribonucleic acid (mRNA).

mRNA shows a very basic design in eukaryotic cells and typically comprises, in 5'→3' direction, a Cap structure, a 5' untranslated region (5' UTR), a coding sequence typically starting with a AUG codon attached to a coding sequence (CDS) terminating with a stop codon, a 3' untranslated region (3' UTR) and a poly-A-tail.

mRNA based therapy have been proposed as therapeutics since the beginning of the biotech. In principle, the administered mRNA sequence can cause a cell to make a protein, which in turn could directly treat a disease or could function as a vaccine; more indirectly the protein could interfere with an element of a pathway in such way that the pathway is either inhibited or stimulated, thereby treating or ameliorating a disease.

The problem underlying the present invention is the provision of a recombinant nucleic acid construct, preferably of an mRNA, whereby such recombinant nucleic acid construct allows for high expression of the coding sequence of the recombinant nucleic acid construct.

Another problem underlying the present invention is the provision of a recombinant nucleic acid construct, preferably of an mRNA, whereby such recombinant nucleic acid construct allows for the expression of the coding sequence of the recombinant nucleic acid construct in an endothelial cell.

These and other problems underlying the present invention are solved by the subject matter of the attached independent claims; preferred embodiments may be taken from the attached dependent claims.

Additionally, and more specifically, the problem underlying the present invention is solved in a first aspect, which is also the first embodiment of the first aspect, by a recombinant nucleic acid construct comprising in 5'→3' direction a 5' UTR, a coding region coding for an effector molecule, and a 3' UTR, wherein the 5' UTR is selected from the group comprising a 5' UTR of a gene coding for MCP-1 or a derivative thereof having a nucleotide identity of at least 85%, a 5' UTR of a gene coding for RPL12s.c. or a derivative thereof having a nucleotide identity of at least 85%, a 5' UTR of a gene coding for Ang-2 or a derivative thereof having a nucleotide identity of at least 85%, a 5' UTR of a gene coding for HSP70 or a derivative thereof having a nucleotide identity of at least 85%, a 5' UTR of a gene coding for H3.3. or a derivative thereof having a nucleotide identity of at least 85%, a 5' UTR of a gene coding for Galectin-9 or a derivative thereof having a nucleotide identity of at least 85%, a 5' UTR of a gene coding for GADD34 or a derivative thereof having a nucleotide identity of at least 85%, a 5' UTR of a gene coding for EDN1 or a derivative thereof having a nucleotide identity of at least 85%, a 5' UTR of a gene coding for HSP70m5 or a derivative thereof having a nucleotide identity of at least 85%, a 5' UTR of a gene coding for E-selectin or a derivative thereof having a nucleotide identity of at least 85% a 5' UTR of a gene coding for ICAM-1 or a derivative thereof having a nucleotide identity of at least 85%, a 5' UTR of a gene coding for IL-6 or a derivative thereof having a nucleotide identity of at least 85% and a 5' UTR of a gene coding for vWF or a derivative thereof having a nucleotide identity of at least 85%;

wherein 3' UTR is selected from the group comprising a 3' UTR of a gene coding for vWF or a derivative thereof having a nucleotide identity of at least 85%, a 3' UTR of a gene coding for MCP-1 or a derivative thereof having a nucleotide identity of at least 85%, a 3' UTR of a gene coding for RPL12s.c. or a derivative thereof having a nucleotide identity of at least 85%, a 3' UTR of a gene coding for HSP70 or a derivative thereof having a nucleotide identity of at least 85%, a 3' UTR of a gene coding for H3.3. or a derivative thereof having a nucleotide identity of at least 85%, a 3' UTR of a gene coding for GADD34 or a derivative thereof having a nucleotide identity of at least 85%, a 3' UTR of a gene coding for EDN1 or a derivative thereof having a nucleotide identity of at least 85%, and a 3' UTR of a gene coding for IL-6 or a derivative thereof having a nucleotide identity of at least 85%, wherein the effector molecule is effective in restoring a cellular function of a cell or is effective in exercising a therapeutic effect in or on a cell, and wherein the recombinant nucleic acid construct is different from a wild type mRNA coding for the effector molecule.

In a second embodiment of the first aspect, which is also an embodiment of the first embodiment of the first aspect, the 5' UTR and the 3' UTR of the recombinant construct are of different origin, preferably are from different endogenous species.

In a third embodiment of the first aspect, which is also an embodiment of the first and second embodiment of the first aspect, the 5' UTR and the 3' UTR of the recombinant construct are of the same origin, preferably are from the same endogenous genes species.

In a fourth embodiment of the first aspect, which is also an embodiment of the first, second and third embodiment of the first aspect, a) the 5' UTR is a 5' UTR of a gene coding for MCP-1 or a derivative thereof having a nucleotide identity of at least 85%, and wherein the 3' UTR is selected from the group comprising a 3' UTR of a gene coding for vWF or a derivative thereof having a nucleotide identity of at least 85%, a 3' UTR of a gene coding for HSP70 or a derivative thereof having a nucleotide identity of at least 85%, a 3' UTR of a gene coding for RPL12s.c. or a derivative thereof having a nucleotide identity of at least 85%, and a 3' UTR of a gene coding for MCP-1 or a derivative thereof having a nucleotide identity of at least 85%.

b) the 5' UTR is a 5' UTR of a gene coding for RPL12s.c. or a derivative thereof having a nucleotide identity of at least 85%, and wherein the 3' UTR is selected from the group comprising a 3' UTR of a gene coding for vWF or a derivative thereof having a nucleotide identity of at least 85%, a 3' UTR of a gene coding for HSP70 or a derivative thereof having a nucleotide identity of at least 85%, a 3' UTR of a gene coding for RPL12s.c. or a derivative thereof having a nucleotide identity of at least 85% and a 3' UTR of a gene coding for MCP-1 or a derivative thereof having a nucleotide identity of at least 85%, c) the 5' UTR is a 5' UTR of a gene coding for ANG-2 or a derivative thereof having a nucleotide identity of at least 85%, and wherein the 3' UTR is selected from the group comprising a 3' UTR of a gene coding for HSP70 or a derivative thereof having a nucleotide identity of at least 85%, a 3' UTR of a gene coding for RPL12s.c. or a derivative thereof having a nucleotide identity of at least 85%, a 3' UTR of a gene coding for vWF or a derivative thereof having a nucleotide identity of at least 85% and a 3' UTR of a gene coding for MCP-1 or a derivative thereof having a nucleotide identity of at least 85%, or d) the 5' UTR is a 5' UTR of a gene coding for HSP70 or a derivative thereof having a nucleotide identity of at least 85%, and wherein the 3' UTR is selected from the group comprising a 3' UTR of a gene coding for HSP70 or a derivative thereof having a nucleotide identity of at least 85%, a 3' UTR of a gene coding for RPL12s.c. or a derivative thereof having a nucleotide identity of at least 85%, a 3' UTR of a gene coding for vWF or a derivative thereof having a nucleotide identity of at least 85% and a 3' UTR of a gene coding for MCP-1 or a derivative thereof having a nucleotide identity of at least 85%.

In a fifth embodiment of the first aspect, which is also an embodiment of the first, second and third embodiment of the first aspect, a) the 3'UTR is a 3' UTR of a gene coding for vWF or a derivative thereof having a nucleotide identity of at least 85% and the 5' UTR is selected from the group comprising a 5' UTR of a gene coding for MCP-1 or a derivative thereof having a nucleotide identity of at least 85%, a 5' UTR of a gene coding for RPL12s.c. or a derivative thereof having a nucleotide identity of at least 85%, a 5' UTR of a gene coding for HSP70 or a derivative thereof having a nucleotide identity of at least 85%, a 5' UTR of a gene coding for ANG-2 of a derivative thereof having a nucleotide identity of at least 85%, b) the 3'UTR is a 3' UTR of a gene coding for HSP70 or a derivative thereof having a nucleotide identity of at least 85% and the 5' UTR is selected from the group comprising a 5' UTR of a gene coding for HSP70 or a derivative thereof having a nucleotide identity of at least 85% a 5' UTR of a gene coding for RPL12s.c. or a derivative thereof having a nucleotide identity of at least 85%, a 5' UTR of a gene coding for ANG-2 of a derivative thereof having a nucleotide identity of at least 85%, and a 5' UTR of a gene coding for MCP-1 or a derivative thereof having a nucleotide identity of at least 85%, c) the 3'UTR is a 3' UTR of a gene coding for RPL12s.c. or a derivative thereof having a nucleotide identity of at least 85% and the 5' UTR is selected from the group comprising a 5' UTR of a gene coding for HSP70 or a derivative thereof having a nucleotide identity of at least 85% a 5' UTR of a gene coding for RPL12s.c. or a derivative thereof having a nucleotide identity of at least 85%, a 5' UTR of a gene coding for ANG-2 of a derivative thereof having a nucleotide identity of at least 85%, and a 5' UTR of a gene coding for MCP-1 or a derivative thereof having a nucleotide identity of at least 85%, or d) the 3'UTR is a 3' UTR of a gene coding for MCP-1 or a derivative thereof having a nucleotide identity of at least 85% and the 5' UTR is selected from the group comprising a 5' UTR of a gene coding for HSP70 or a derivative thereof having a nucleotide identity of at least 85%, a 5' UTR of a gene coding for RPL12s.c. or a derivative thereof having a nucleotide identity of at least 85%, a 5' UTR of a gene coding for ANG-2 of a derivative thereof having a nucleotide identity of at least 85%, and a 5' UTR of a gene coding for MCP-1 or a derivative thereof having a nucleotide identity of at least 85%.

In a sixth embodiment of the first aspect, which is also an embodiment of the first, second, third, fourth and fifth embodiment of the first aspect, the construct is one selected from the group comprising a construct, wherein the 5' UTR is a 5' UTR of a gene coding for MCP-1 or a derivative thereof having a nucleotide identity of at least 85%, and the 3' UTR is a 3' UTR of a gene coding for vWF or a derivative thereof having a nucleotide identity of at least 85%, a construct, wherein the 5' UTR is a 5' UTR of a gene coding for RPL12s.c. or a derivative thereof having a nucleotide identity of at least 85%, and the 3' UTR is a 3' UTR of a gene coding for vWF or a derivative thereof having a nucleotide identity of at least 85%, a construct, wherein the 5' UTR is a 5' UTR of a gene coding for MCP-1 or a derivative thereof having a nucleotide identity of at least 85%, and the 3' UTR is a 3' UTR of a gene coding for MCP-1 or a derivative thereof having a nucleotide identity of at least 85%, a construct, wherein the 5' UTR is a 5' UTR of a gene coding for ANG-2 or a derivative thereof having a nucleotide identity of at least 85%, and the 3' UTR is a 3' UTR of a gene coding for vWF or a derivative thereof having a nucleotide identity of at least 85%, a construct, wherein the 5' UTR is a 5' UTR of a gene coding for RPL12s.c. or a derivative thereof having a nucleotide identity of at least 85%, and the 3' UTR is a 3' UTR of a gene coding for RPL12s.c. or a derivative thereof having a nucleotide identity of at least 85%, a construct, wherein the 5' UTR is a 5' UTR of a gene coding for HSP70 or a derivative thereof having a nucleotide identity of at least 85%, and the 3' UTR is a 3' UTR of a gene coding for HSP70 or a derivative thereof having a nucleotide identity of at least 85%, a construct, wherein the 5' UTR is a 5' UTR of a gene coding for H3.3. or a derivative thereof having a nucleotide identity of at least 85%, and the 3' UTR is a 3' UTR of a gene coding for H3.3. or a derivative thereof having a nucleotide identity of at least 85%, and a construct, wherein the 5' UTR is a 5' UTR of a gene coding for Galectin 9 or a derivative thereof having a nucleotide identity of at least 85%, and the 3' UTR is a 3' UTR of a gene coding for Galectin 9 or a derivative thereof having a nucleotide identity of at least 85%.

In a seventh embodiment of the first aspect, which is also an embodiment of the first, second, third, fourth, fifth and sixth embodiment of the first aspect, the construct comprises a poly-A tail, preferably at the 3' terminal end of the recombinant nucleic acid construct.

In an eighth embodiment of the first aspect, which is also an embodiment of the first, second, third, fourth, fifth, sixth and seventh embodiment of the first aspect, the construct comprises a CAP structure, preferably at the 5' terminal end of the recombinant nucleic acid construct.

In a ninth embodiment of the first aspect, which is also an embodiment of the first, second, third, fourth, fifth, sixth, seventh and eighth embodiment of the first aspect, the construct comprises a IRES (internal ribosomal entry site) sequence, preferably at the 5' terminal end of the recombinant nucleic acid construct.

In a tenth embodiment of the first aspect, which is also an embodiment of the first, second, third, fourth, fifth, sixth, seventh, eighth and ninth embodiment of the first aspect, the construct comprises nucleic acid sequence coding for a signal peptide, preferably the signal peptide is in-frame with nucleic acid sequence coding for a signal peptide and is arranged between the 5' UTR and the coding region coding for an effector molecule.

In an eleventh embodiment of the first aspect, which is also an embodiment of the tenth embodiment of the first aspect, the signal peptide allows secretion of the effector molecule.

In a $12^{th}$ embodiment of the first aspect, which is also an embodiment of the tenth and the eleventh embodiment of the first aspect, the nucleotide sequence coding for a signal peptide is selected from the group comprising a nucleotide sequence coding for a signal peptide of MCP-1 or a derivative thereof having a nucleotide identity of at least 85%, nucleotide sequence coding for a signal peptide of IL-6 or a derivative thereof having a nucleotide identity of at least 85%, a nucleotide sequence coding for a signal peptide of Ang-2 or a derivative thereof having a nucleotide identity of at least 85%, and a nucleotide sequence coding for a signal peptide of Ang-1 or a derivative thereof having a nucleotide identity of at least 85%.

In a$13^{th}$ embodiment of the first aspect, which is also an embodiment of the first, second, third, fourth, fifth, sixth, seventh, eighth, ninth, tenth, eleventh and $12^{th}$ embodiment of the first aspect, the cell a cellular function of which is restored and/or the cell in or on which a therapeutic effect is exercised is an endothelial cell, preferably a vascular endothelial cell, more preferably the vascular endothelial cell is a microvascular endothelial cell.

In $14^{th}$ embodiment of the first aspect, which is also an embodiment of the first, second, third, fourth, fifth, sixth, seventh, eighth, ninth, tenth, eleventh, $12^{th}$ and $13^{th}$ embodiment of the first aspect, the cellular function is one which can be restored by an effector molecule having anti-permeability effect of endothelial cells, an anti-vascular leakage effect, an anti-apoptotic effect of endothelial cells or an anti-inflammatory effect of endothelial cells or an anti-stress response effect, preferably the effect is linked to or associated with the Tie-2 signalling pathway, VEGF-receptor pathway, NOTCH signalling pathway, PI3-kinase pathway, eNOS signalling pathway, sirtuin-dependent metabolic and energy homeostasis pathway, oxidative stress pathway, shear stress response pathway, ET-1 signal transduction pathway, NO-mediated signal transduction pathway, and mechanochemical transduction pathway.

More specifically, the problem underlying the present invention is solved in a second aspect, which is also a first embodiment of the second aspect, by a recombinant nucleic acid construct comprising in 5'→3' direction a 5' non-translated region, a coding region coding for an effector molecule, and a 3' non-translated region, wherein the effector molecule is effective in restoring a cellular function of a cell, for use in a method for the treatment and/or prevention of a disease, wherein the effector molecule is expressed by an endothelial cell. In an embodiment and as preferably used herein restoring a cellular function comprises and, respectively, encompasses killing of a cell, more preferably killing of tumor endothelial cells and/or tumor cells; in another embodiment and as preferably used herein, restoring cellular function comprises and, respectively, encompasses neoangiogenesis, more preferably neoangiogenesis in case of vascular diseases.

In a second embodiment of the second aspect which is also an embodiment of the first embodiment of the second aspect, the treatment and/or prevention of a disease involves restoration of the cellular function of a cell.

More specifically, the problem underlying the present invention is solved in a third aspect, which is also a first embodiment of the third aspect, by a recombinant nucleic acid construct comprising in 5'→3' direction a 5' non-translated region, a coding region coding for an effector molecule, and a 3' non-translated region, wherein the effector molecule is effective in restoring a cellular function of a cell, for use in a method for restoring the cellular function of a cell, wherein the effector molecule is expressed by an endothelial cell.

More specifically, the problem underlying the present invention is solved in a fourth aspect, which is also a first embodiment of the fourth aspect, by a recombinant nucleic acid construct comprising in 5'→3' direction a 5' non-translated region, a coding region coding for an effector molecule, and a 3' non-translated region, wherein the effector molecule is effective in exercising a therapeutic effect in or on a cell, for use in a method for the treatment and/or prevention of a disease, wherein the effector molecule is expressed by an endothelial cell.

In a second embodiment of the fourth aspect which is also an embodiment of the first embodiment of the fourth aspect, the treatment and/or prevention of a disease involves restoration of a cellular function of a cell.

More specifically, the problem underlying the present invention is solved in a fifth aspect, which is also a first embodiment of the fifth aspect, by a recombinant nucleic acid construct comprising in 5'→3' direction a 5' non-translated region, a coding region coding for an effector molecule, and a 3' non-translated region, wherein the effector molecule is effective in exercising a therapeutic effect in or on a cell, for use of in a method for restoring a cellular function of a cell, wherein the effector molecule is expressed by an endothelial cell.

In a third embodiment of the second aspect which is also an embodiment of the first and second embodiment of the second aspect, in a second embodiment of the third aspect which is also an embodiment of the first embodiment of the third aspect, in a third embodiment of the fourth aspect which is also an embodiment of the first and second embodiment of the fourth aspect, and in a second embodiment of the fifth aspect which is also an embodiment of the first embodiment of the fifth aspect, the effector molecule is expressed in the method by an endothelial cell.

In a fourth embodiment of the second aspect which is also an embodiment of the first, second and third embodiment of the second aspect, in a third embodiment of the third aspect which is also an embodiment of the first and the second embodiment of the third aspect, in a fourth embodiment of the fourth aspect which is also an embodiment of the first, second and third embodiment of the fourth aspect, and in a third embodiment of the fifth aspect which is also an embodiment of the first and second embodiment of the fifth aspect, the endothelial cell is a vascular endothelial cell, preferably the vascular endothelial cell is a microvascular endothelial cell.

In a fifth embodiment of the second aspect which is also an embodiment of the first, second, third and fourth embodiment of the second aspect, in a fourth embodiment of the third aspect which is also an embodiment of the first, second and third embodiment of the third aspect, in a fifth embodiment of the fourth aspect which is also an embodiment of the first, second, third and fourth embodiment of the fourth aspect, and in a fourth embodiment of the fifth aspect which is also an embodiment of the first, second and third embodiment of the fifth aspect, the endothelial cell is a non-dividing endothelial cell, a non-proliferating endothelial cell or a resting endothelial cell. In an embodiment thereof and as preferably used herein the endothelial is a vascular endothelial cell, a lymphatic endothelial cells, an endothelial stem cell (ESC) or an endothelial progenitor cells (EPC).

In a sixth embodiment of the second aspect which is also an embodiment of the first, second, third, fourth and fifth embodiment of the second aspect, in a fifth embodiment of the third aspect which is also an embodiment of the first, second, third and fourth embodiment of the third aspect, in a sixth embodiment of the fourth aspect which is also an embodiment of the first, second, third, fourth and fifth embodiment of the fourth aspect, and in a fifth embodiment of the fifth aspect which is also an embodiment of the first, second, third and fourth embodiment of the fifth aspect, the endothelial cell is a senescent endothelial cell.

In a seventh embodiment of the second aspect which is also an embodiment of the first, second, third, fourth, fifth and sixth embodiment of the second aspect, in a sixth embodiment of the third aspect which is also an embodiment of the first, second, third, fourth and fifth embodiment of the third aspect, in a seventh embodiment of the fourth aspect which is also an embodiment of the first, second, third, fourth, fifth and sixth embodiment of the fourth aspect, and in a sixth embodiment of the fifth aspect which is also an embodiment of the first, second, third, fourth and fifth embodiment of the fifth aspect, the endothelial cell is impaired by age and/or showing stress-related defects.

In an eighth embodiment of the second aspect which is also an embodiment of the first, second, third, fourth, fifth, sixth and seventh embodiment of the second aspect, in a seventh embodiment of the third aspect which is also an embodiment of the first, second, third, fourth, fifth and sixth embodiment of the third aspect, in an eighth embodiment of the fourth aspect which is also an embodiment of the first, second, third, fourth, fifth, sixth and seventh embodiment of the fourth aspect, and in a seventh embodiment of the fifth aspect which is also an embodiment of the first, second, third, fourth, fifth and sixth embodiment of the fifth aspect, the recombinant nucleic acid construct additionally comprises one element selected from the group comprising a cap structure, an IRES sequence, a further start codon providing sequence, a nucleic acid sequence coding for a signal peptide and a poly-A tail.

In a ninth embodiment of the second aspect which is also an embodiment of the first, second, third, fourth, fifth, sixth, seventh and eighth embodiment of the second aspect, in an eighth embodiment of the third aspect which is also an embodiment of the first, second, third, fourth, fifth, sixth and seventh embodiment of the third aspect, in a ninth embodiment of the fourth aspect which is also an embodiment of the first, second, third, fourth, fifth, sixth, seventh and eighth embodiment of the fourth aspect, and in an eighth embodiment of the fifth aspect which is also an embodiment of the first, second, third, fourth, fifth, sixth and seventh embodiment of the fifth aspect, wherein the recombinant nucleic acid construct is one selected from the group comprising in 5'→3' direction a)—a 5' non-translated region,
a coding region coding for an effector molecule,
a 3' non-translated region, and
a poly-A tail;

b)—a 5' non-translated region,
a further start codon providing sequence,
a coding region coding for an effector molecule,
a 3' non-translated region, and
a poly-A tail;

c)—a cap structure,
a 5' non-translated region,
a coding region coding for an effector molecule, and
a 3' non-translated region;

d)—a cap structure,
a 5' non-translated region,
a further start codon providing sequence,
a coding region coding for an effector molecule, and
a 3' non-translated region;

e)—an IRES sequence,
a 5' non-translated region,
a coding region coding for an effector molecule, and
a 3' non-translated region;

f)—an IRES sequence,
a 5' non-translated region,
a further start codon providing sequence,
a coding region coding for an effector molecule, and
a 3' non-translated region;

g)—a cap structure,
a 5' non-translated region,
a coding region coding for an effector molecule,
a 3' non-translated region, and
a poly-A tail;

h)—a cap structure,
a 5' non-translated region,
a further start codon providing sequence,
a coding region coding for an effector molecule,
a 3' non-translated region, and
a poly-A tail;

i)—an IRES sequence,
a 5' non-translated region,
a coding region coding for an effector molecule,
a 3' non-translated region, and
a poly-A tail;

j)—an IRES sequence,
a 5' non-translated region,
a further start codon providing sequence,
a coding region coding for an effector molecule,
a 3' non-translated region, and
a poly-A tail;

k)—a 5' non-translated region,
a nucleic acid sequence coding for a signal peptide,
a coding region coding for an effector molecule,
a 3' non-translated region, and
a poly-A tail;

l)—a 5' non-translated region,
a further start codon providing sequence,
a nucleic acid sequence coding for a signal peptide,
a coding region coding for an effector molecule,
a 3' non-translated region, and
a poly-A tail;

m)—a cap structure,
a 5' non-translated region,
a nucleic acid sequence coding for a signal peptide,
a coding region coding for an effector molecule, and
a 3' non-translated region;
a cap structure
a 5' non-translated region,
a further start codon providing sequence,
a nucleic acid sequence coding for a signal peptide,
a coding region coding for an effector molecule, and
a 3' non-translated region;

o)—an IRES sequence,
a 5' non-translated region,
a nucleic acid sequence coding for a signal peptide,
a coding region coding for an effector molecule, and
a 3' non-translated region;

p)—an IRES sequence,
a 5' non-translated region,
a further start codon providing sequence,
a nucleic acid sequence coding for a signal peptide,
a coding region coding for an effector molecule, and
a 3' non-translated region;

q)—a cap structure,
a 5' non-translated region,
a nucleic acid sequence coding for a signal peptide,
a coding region coding for an effector molecule,
a 3' non-translated region, and
a poly-A tail;

r)—a cap structure,
a 5' non-translated region,
a further start codon providing sequence,
a nucleic acid sequence coding for a signal peptide,
a coding region coding for an effector molecule,
a 3' non-translated region, and
a poly-A tail;

s)—an IRES sequence,
a 5' non-translated region,
a nucleic acid sequence coding for a signal peptide,
a coding region coding for an effector molecule,
a 3' non-translated region, and
a poly-A tail; and t)—an IRES sequence,
a 5' non-translated region,
a further start codon providing sequence,
a nucleic acid sequence coding for a signal peptide,
a coding region coding for an effector molecule,
a 3' non-translated region, and
a poly-A tail.

In a tenth embodiment of the second aspect which is also an embodiment of the first, second, third, fourth, fifth, sixth, seventh, eighth and ninth embodiment of the second aspect, in an ninth embodiment of the third aspect which is also an embodiment of the first, second, third, fourth, fifth, sixth, seventh and eighth embodiment of the third aspect, in a tenth embodiment of the fourth aspect which is also an embodiment of the first, second, third, fourth, fifth, sixth, seventh, eighth and ninth embodiment of the fourth aspect, and in an ninth embodiment of the fifth aspect which is also an embodiment of the first, second, third, fourth, fifth, sixth, seventh and eighth embodiment of the fifth aspect, the recombinant nucleic acid comprises in 5'→3' direction a cap structure,
a 5' non-translated region,
a nucleic acid sequence coding for a signal peptide,
a coding region coding for an effector molecule,
a 3' non-translated region, and
a poly-A tail.

In an eleventh embodiment of the second aspect which is also an embodiment of the first, second, third, fourth, fifth, sixth, seventh, eighth, ninth and tenth embodiment of the second aspect, in a tenth embodiment of the third aspect which is also an embodiment of the first, second, third, fourth, fifth, sixth, seventh, eighth and ninth embodiment of the third aspect, in an eleventh embodiment of the fourth aspect which is also an embodiment of the first, second, third, fourth, fifth, sixth, seventh, eighth, ninth and tenth embodiment of the fourth aspect, and in a tenth embodiment of the fifth aspect which is also an embodiment of the first, second, third, fourth, fifth, sixth, seventh, eighth and ninth embodiment of the fifth aspect, the recombinant nucleic acid comprises in 5'→3' direction an IRES sequence,
a 5' non-translated region,
a nucleic acid sequence coding for a signal peptide,
a coding region coding for an effector molecule,
a 3' non-translated region, and
a poly-A tail.

In a 12th embodiment of the second aspect which is also an embodiment of the first, second, third, fourth, fifth, sixth, seventh, eighth, ninth, tenth and eleventh embodiment of the second aspect, in an eleventh embodiment of the third aspect which is also an embodiment of the first, second, third, fourth, fifth, sixth, seventh, eighth, ninth and tenth embodiment of the third aspect, in a 12th embodiment of the fourth aspect which is also an embodiment of the first, second, third, fourth, fifth, sixth, seventh, eighth, ninth, tenth and eleventh embodiment of the fourth aspect, and in an eleventh embodiment of the fifth aspect which is also an embodiment of the first, second, third, fourth, fifth, sixth, seventh, eighth, ninth and tenth embodiment of the fifth aspect, recombinant nucleic acid comprises in 5'→3' direction a cap structure,
a 5' non-translated region,
a further start codon providing sequence,
a nucleic acid sequence coding for a signal peptide,
a coding region coding for an effector molecule, a 3' non-translated region, and a poly-A tail.

In a $13^{th}$ embodiment of the second aspect which is also an embodiment of the first, second, third, fourth, fifth, sixth, seventh, eighth, ninth, tenth, eleventh and $12^{th}$ embodiment of the second aspect, in a $12^{th}$ embodiment of the third aspect which is also an embodiment of the first, second, third, fourth, fifth, sixth, seventh, eighth, ninth, tenth and eleventh embodiment of the third aspect, in a $13^{th}$ embodiment of the fourth aspect which is also an embodiment of the first, second, third, fourth, fifth, sixth, seventh, eighth, ninth, tenth, eleventh and $12^{th}$ embodiment of the fourth aspect, and in an $12^{th}$ embodiment of the fifth aspect which is also an embodiment of the first, second, third, fourth, fifth, sixth, seventh, eighth, ninth, tenth and eleventh embodiment of the fifth aspect, the recombinant nucleic acid comprises in 5'→3' direction an IRES sequence, a 5' non-translated region, a further start codon providing sequence, a nucleic acid sequence coding for a signal peptide, a coding region coding for an effector molecule, a 3' non-translated region, and a poly-A tail.

In a $14^{th}$ embodiment of the second aspect which is also an embodiment of the first, second, third, fourth, fifth, sixth, seventh, eighth, ninth, tenth, eleventh, $12^{th}$ and $13^{th}$ embodiment of the second aspect, in a $13^{th}$ embodiment of the third aspect which is also an embodiment of the first, second, third, fourth, fifth, sixth, seventh, eighth, ninth, tenth, eleventh and $12^{th}$ embodiment of the third aspect, in a $14^{th}$ embodiment of the fourth aspect which is also an embodiment of the first, second, third, fourth, fifth, sixth, seventh, eighth, ninth, tenth, eleventh, $12^{th}$ and $13^{th}$ embodiment of the fourth aspect, and in an $13^{th}$ embodiment of the fifth aspect which is also an embodiment of the first, second, third, fourth, fifth, sixth, seventh, eighth, ninth, tenth, eleventh and $12^{th}$ embodiment of the fifth aspect, the further start codon providing sequence is in-frame with the coding region coding for an effector molecule.

In a $15^{th}$ embodiment of the second aspect which is also an embodiment of the first, second, third, fourth, fifth, sixth, seventh, eighth, ninth, tenth, eleventh, $12^{th}$, $13^{th}$ and $14^{th}$ embodiment of the second aspect, in a $14^{th}$ embodiment of the third aspect which is also an embodiment of the first, second, third, fourth, fifth, sixth, seventh, eighth, ninth, tenth, eleventh, $12^{th}$ and $13^{th}$ embodiment of the third aspect, in a $15^{th}$ embodiment of the fourth aspect which is also an embodiment of the first, second, third, fourth, fifth, sixth, seventh, eighth, ninth, tenth, eleventh, $12^{th}$, $13^{th}$ and $14^{th}$ embodiment of the fourth aspect, and in an $14^{th}$ embodiment of the fifth aspect which is also an embodiment of the first, second, third, fourth, fifth, sixth, seventh, eighth, ninth, tenth, eleventh $12^{th}$ and $13^{th}$ embodiment of the fifth aspect, the 5' non-translated region is a 5' UTR.

In a $16^{th}$ embodiment of the second aspect which is also an embodiment of the first, second, third, fourth, fifth, sixth, seventh, eighth, ninth, tenth, eleventh, $12^{th}$, $13^{th}$, $14^{th}$ and $15^{th}$ embodiment of the second aspect, in a $15^{th}$ embodiment of the third aspect which is also an embodiment of the first, second, third, fourth, fifth, sixth, seventh, eighth, ninth, tenth, eleventh, $12^{th}$, $13^{th}$ and $14^{th}$ embodiment of the third aspect, in a $16^{th}$ embodiment of the fourth aspect which is also an embodiment of the first, second, third, fourth, fifth, sixth, seventh, eighth, ninth, tenth, eleventh, $12^{th}$, $13^{th}$, $14^{th}$ and $15^{th}$ embodiment of the fourth aspect, and in an $15^{th}$ embodiment of the fifth aspect which is also an embodiment of the first, second, third, fourth, fifth, sixth, seventh, eighth, ninth, tenth, eleventh $12^{th}$, $13^{th}$ and $14^{th}$ embodiment of the fifth aspect, the 5' non-translated region is from a eukaryotic organism, preferably a mammalian organism, more preferably a mammalian organism selected from the group comprising human, non-human primate such as cynomolgus, chimpanzee rhesus monkey, rat and mouse. In an alternative embodiment the 5' non-translated region is from a viral gene, preferably the virus is a virus capable of infecting a eukaryotic organism.

In a $17^{th}$ embodiment of the second aspect which is also an embodiment of the first, second, third, fourth, fifth, sixth, seventh, eighth, ninth, tenth, eleventh, $12^{th}$, $13^{th}$, $14^{th}$, $15^{th}$ and $16^{th}$ embodiment of the second aspect, in a $16^{th}$ embodiment of the third aspect which is also an embodiment of the first, second, third, fourth, fifth, sixth, seventh, eighth, ninth, tenth, eleventh, $12^{th}$, $13^{th}$, $14^{th}$ and $15^{th}$ embodiment of the third aspect, in a $17^{th}$ embodiment of the fourth aspect which is also an embodiment of the first, second, third, fourth, fifth, sixth, seventh, eighth, ninth, tenth, eleventh, $12^{th}$, $13^{th}$, $14^{th}$, $15^{th}$ and $16^{th}$ embodiment of the fourth aspect, and in an $16^{th}$ embodiment of the fifth aspect which is also an embodiment of the first, second, third, fourth, fifth, sixth, seventh, eighth, ninth, tenth, eleventh $12^{th}$, $13^{th}$, $14^{th}$ and $15^{th}$ embodiment of the fifth aspect, the 5' UTR is selected from the group comprising a 5' UTR of a gene coding for MCP-1 or a derivative thereof having a nucleotide identity of at least 85%, a 5' UTR of a gene coding for RPL12s.c. or a derivative thereof having a nucleotide identity of at least 85%, a 5' UTR of a gene coding for Ang-2 or a derivative thereof having a nucleotide identity of at least 85%, a 5' UTR of a gene coding for HSP70 or a derivative thereof having a nucleotide identity of at least 85%, a 5' UTR of a gene coding for H3.3. or a derivative thereof having a nucleotide identity of at least 85%, and a 5' UTR of a gene coding for Galectin-9 or a derivative thereof having a nucleotide identity of at least 85%.

In an $18^{th}$ embodiment of the second aspect which is also an embodiment of the first, second, third, fourth, fifth, sixth, seventh, eighth, ninth, tenth, eleventh, $12^{th}$, $13^{th}$, $14^{th}$, $15^{th}$, $16^{th}$ and $17^{th}$ embodiment of the second aspect, in a $17^{th}$ embodiment of the third aspect which is also an embodiment of the first, second, third, fourth, fifth, sixth, seventh, eighth, ninth, tenth, eleventh, $12^{th}$, $13^{th}$, $14^{th}$, $15^{th}$ and $16^{th}$ embodiment of the third aspect, in an $18^{th}$ embodiment of the fourth aspect which is also an embodiment of the first, second, third, fourth, fifth, sixth, seventh, eighth, ninth, tenth, eleventh, $12^{th}$, $13^{th}$, $14^{th}$, $15^{th}$, $16^{th}$ and $17^{th}$ embodiment of the fourth aspect, and in an $17^{th}$ embodiment of the fifth aspect which is also an embodiment of the first, second, third, fourth, fifth, sixth, seventh, eighth, ninth, tenth, eleventh $12^{th}$, $13^{th}$, $14^{th}$ and $15^{th}$, $16^{th}$ embodiment of the fifth aspect, the 3' non-translated region is a 3'-UTR.

In a $19^{th}$ embodiment of the second aspect which is also an embodiment of the first, second, third, fourth, fifth, sixth, seventh, eighth, ninth, tenth, eleventh, $12^{th}$, $13^{th}$, $14^{th}$, $15^{th}$ $16^{th}$, $17^{th}$ and $18^{th}$ embodiment of the second aspect, in an $18^{th}$ embodiment of the third aspect which is also an embodiment of the first, second, third, fourth, fifth, sixth, seventh, eighth, ninth, tenth, eleventh, $12^{th}$, $13^{th}$, $14^{th}$, $15^{th}$, $16^{th}$ and $17^{th}$ embodiment of the third aspect, in a $19^{th}$ embodiment of the fourth aspect which is also an embodiment of the first, second, third, fourth, fifth, sixth, seventh, eighth, ninth, tenth, eleventh, $12^{th}$, $13^{th}$, $14^{th}$, $15^{th}$, $16^{th}$, $17^{th}$ and $18^{th}$ embodiment of the fourth aspect, and in an $18^{th}$ embodiment of the fifth aspect which is also an embodiment of the first, second, third, fourth, fifth, sixth, seventh, eighth, ninth, tenth, eleventh $12^{th}$, $13^{th}$, $14^{th}$ and $15^{th}$, $16^{th}$, $17^{th}$ embodiment of the fifth aspect, the 3' non-translated region is from a eukaryotic organism, preferably a mammalian organism, more preferably a mammalian organism selected from the group comprising human, non-human primate such as cynomolgus, chimpanzee rhesus monkey, rat and mouse. In an alternative embodiment the 5' non-translated region is from a viral gene, preferably the virus is a virus capable of infecting a eukaryotic organism.

In a $20^{th}$ embodiment of the second aspect which is also an embodiment of the first, second, third, fourth, fifth, sixth, seventh, eighth, ninth, tenth, eleventh, $12^{th}$, $13^{th}$, $14^{th}$, $15^{th}$, $16^{th}$, $17^{th}$, $18^{th}$ and $19^{th}$ embodiment of the second aspect, in a $19^{th}$ embodiment of the third aspect which is also an embodiment of the first, second, third, fourth, fifth, sixth, seventh, eighth, ninth, tenth, eleventh, $12^{th}$, $13^{th}$, $14^{th}$, $15^{th}$, $16^{th}$, $17^{th}$ and $18^{th}$ embodiment of the third aspect, in a $20^{th}$ embodiment of the fourth aspect which is also an embodiment of the first, second, third, fourth, fifth, sixth, seventh, eighth, ninth, tenth, eleventh, $12^{th}$, $13^{th}$, $14^{th}$, $15^{th}$, $16^{th}$, $17^{th}$, $18^{th}$ and $19^{th}$ embodiment of the fourth aspect, and in a $19^{th}$ embodiment of the fifth aspect which is also an embodiment of the first, second, third, fourth, fifth, sixth, seventh, eighth, ninth, tenth, eleventh $12^{th}$, $13^{th}$, $14^{th}$, $15^{th}$, $16^{th}$, $17^{th}$ and $18^{th}$ embodiment of the fifth aspect, the 3' UTR is selected from the group comprising a 3' UTR of a gene coding for vWF or a derivative thereof having a nucleotide identity of at least 85%, a 3' UTR of a gene coding for MCP-1 or a derivative thereof having a nucleotide identity of at least 85%, a 3' UTR of a gene coding for RPL12s.c. or a derivative thereof having a nucleotide identity of at least 85%, a 3' UTR of a gene coding for HSP70 or a derivative thereof having a nucleotide identity of at least 85%, and a 3' UTR of a gene coding for H3.3. or a derivative thereof having a nucleotide identity of at least 85%.

In a $21^{st}$ embodiment of the second aspect which is also an embodiment of the first, second, third, fourth, fifth, sixth, seventh, eighth, ninth, tenth, eleventh, $12^{th}$, $13^{th}$, $14^{th}$, $15^{th}$, $16^{th}$, $17^{th}$, $18^{th}$, $19^{th}$ and $20^{th}$ embodiment of the second aspect, in a $20^{th}$ embodiment of the third aspect which is also an embodiment of the first, second, third, fourth, fifth, sixth, seventh, eighth, ninth, tenth, eleventh, $12^{th}$, $13^{th}$, $14^{th}$, $15^{th}$, $16^{th}$, $17^{th}$, $18^{th}$ and $19^{th}$ embodiment of the third aspect, in a $21^{st}$ embodiment of the fourth aspect which is also an embodiment of the first, second, third, fourth, fifth, sixth, seventh, eighth, ninth, tenth, eleventh, $12^{th}$, $13^{th}$, $14^{th}$, $15^{th}$, $16^{th}$, $17^{th}$, $18^{th}$ $19^{th}$ and $20^{th}$ embodiment of the fourth aspect, and in a $20^{th}$ embodiment of the fifth aspect which is also an embodiment of the first, second, third, fourth, fifth, sixth, seventh, eighth, ninth, tenth, eleventh $12^{th}$, $13^{th}$, $14^{th}$ $15^{th}$, $16^{th}$, $17^{th}$, $18^{th}$ and $19^{th}$ embodiment of the fifth aspect, the 5' UTR and 3' UTR of the recombinant nucleic acid construct are of different origin, preferably are from different species.

In a $22^{nd}$ embodiment of the second aspect which is also an embodiment of the first, second, third, fourth, fifth, sixth, seventh, eighth, ninth, tenth, eleventh, $12^{th}$, $13^{th}$, $14^{th}$, $15^{th}$ $16^{th}$, $17^{th}$, $18^{th}$, $19^{th}$, $20^{th}$ and $21^{st}$ embodiment of the second aspect, in a $21^{st}$ embodiment of the third aspect which is also an embodiment of the first, second, third, fourth, fifth, sixth, seventh, eighth, ninth, tenth, eleventh, $12^{th}$, $13^{th}$, $14^{th}$, $15^{th}$, $16^{th}$, $17^{th}$, $18^{th}$, $19^{th}$ and $20^{th}$ embodiment of the third aspect, in a $22^{nd}$ embodiment of the fourth aspect which is also an embodiment of the first, second, third, fourth, fifth, sixth, seventh, eighth, ninth, tenth, eleventh, $12^{th}$, $13^{th}$, $14^{th}$, $15^{th}$, $16^{th}$, $17^{th}$, $18^{th}$ $19^{th}$, $20^{th}$ and $21^{st}$ embodiment of the fourth aspect, and in a $21^{st}$ embodiment of the fifth aspect which is also an embodiment of the first, second, third, fourth, fifth, sixth, seventh, eighth, ninth, tenth, eleventh $12^{th}$, $13^{th}$, $14^{th}$ $15^{th}$, $16^{th}$, $17^{th}$, $18^{th}$, $19^{th}$ and $20^{th}$ embodiment of the fifth aspect, the 5' UTR and 3' UTR of the recombinant nucleic acid construct are of the same origin, preferably are from the same species.

In a $23^{rd}$ embodiment of the second aspect which is also an embodiment of the first, second, third, fourth, fifth, sixth, seventh, eighth, ninth, tenth, eleventh, $12^{th}$, $13^{th}$, $14^{th}$, $15^{th}$ $16^{th}$, $17^{th}$, $18^{th}$, $19^{th}$, $20^{th}$, $21^{st}$ and $22^{nd}$ embodiment of the second aspect, in a $22^{nd}$ embodiment of the third aspect which is also an embodiment of the first, second, third, fourth, fifth, sixth, seventh, eighth, ninth, tenth, eleventh, $12^{th}$, $13^{th}$, $14^{th}$, $15^{th}$, $16^{th}$, $17^{th}$, $18^{th}$, $19^{th}$ $20^{th}$ and $21^{st}$ embodiment of the third aspect, in a $23^{rd}$ embodiment of the fourth aspect which is also an embodiment of the first, second, third, fourth, fifth, sixth, seventh, eighth, ninth, tenth, eleventh, $12^{th}$, $13^{th}$, $14^{th}$, $15^{th}$, $16^{th}$, $17^{th}$, $18^{th}$ $19^{th}$ and $20^{th}$, $21^{st}$ and $22^{nd}$ embodiment of the fourth aspect, and in a $22^{nd}$ embodiment of the fifth aspect which is also an embodiment of the first, second, third, fourth, fifth, sixth, seventh, eighth, ninth, tenth, eleventh $12^{th}$, $13^{th}$, $14^{th}$ $15^{th}$, $16^{th}$, $17^{th}$ $18^{th}$, $19^{th}$, $20^{th}$ and $21^{st}$ embodiment of the fifth aspect, a) the 5' UTR is a 5' UTR of a gene coding for MCP-1 or a derivative thereof having a nucleotide identity of at least 85%, and wherein the 3' UTR is selected from the group comprising a 3' UTR of a gene coding for vWF or a derivative thereof having a nucleotide identity of at least 85%, a 3' UTR of a gene coding for HSP70 or a derivative thereof having a nucleotide identity of at least 85%, a 3' UTR of a gene coding for RPL12s.c. or a derivative thereof having a nucleotide identity of at least 85%, and a 3' UTR of a gene coding for MCP-1 or a derivative thereof having a nucleotide identity of at least 85%.

b) the 5' UTR is a 5' UTR of a gene coding for RPL12s.c. or a derivative thereof having a nucleotide identity of at least 85%, and wherein the 3' UTR is selected from the group comprising a 3' UTR of a gene coding for vWF or a derivative thereof having a nucleotide identity of at least 85%, a 3' UTR of a gene coding for HSP70 or a derivative thereof having a nucleotide identity of at least 85%, a 3' UTR of a gene coding for RPL12s.c. or a derivative thereof having a nucleotide identity of at least 85%, and a 3' UTR of a gene coding for MCP-1 or a derivative thereof having a nucleotide identity of at least 85%, c) the 5' UTR is a 5' UTR of a gene coding for HSP70 or a derivative thereof having a nucleotide identity of at least 85%, and wherein the 3' UTR is selected from the group comprising a 3' UTR of a gene coding for HSP70 or a derivative thereof having a nucleotide identity of at least 85%, a 3' UTR of a gene coding for RPL12s.c. or a derivative thereof having a nucleotide identity of at least 85%, a 3' UTR of a gene coding for vWF or a derivative thereof having a nucleotide identity of at least 85% and a 3' UTR of a gene coding for MCP-1 or a derivative thereof having a nucleotide identity of at least 85%, or d) the 5' UTR is a 5' UTR of a gene coding for ANG-2 or a derivative thereof having a nucleotide identity of at least 85%, and wherein the 3' UTR is selected from the group comprising a 3' UTR of a gene coding for HSP70 or a derivative thereof having a nucleotide identity of at least 85%, a 3' UTR of a gene coding for RPL12s.c. or a derivative thereof having a nucleotide identity of at least 85%, a 3' UTR of a gene coding for vWF or a derivative thereof having a nucleotide identity of at least 85% and a 3' UTR of a gene coding for MCP-1 or a derivative thereof having a nucleotide identity of at least 85%.

In a 24$^{th}$ embodiment of the second aspect which is also an embodiment of the first, second, third, fourth, fifth, sixth, seventh, eighth, ninth, tenth, eleventh, 12$^{th}$, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$ and 23$^{rd}$ embodiment of the second aspect, in a 23$^{rd}$ embodiment of the third aspect which is also an embodiment of the first, second, third, fourth, fifth, sixth, seventh, eighth, ninth, tenth, eleventh, 12$^{th}$, 13$^{th}$, 14$^{th}$, 15$^{th}$, 16$^{th}$, 17$^{th}$, 18$^{th}$, 19$^{th}$, 20$^{th}$, 21$^{st}$ and 22$^{nd}$ embodiment of the third aspect, in a 24$^{th}$ embodiment of the fourth aspect which is also an embodiment of the first, second, third, fourth, fifth, sixth, seventh, eighth, ninth, tenth, eleventh, 12$^{th}$, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$ and 23$^{rd}$ embodiment of the fourth aspect, and in a 23$^{rd}$ embodiment of the fifth aspect which is also an embodiment of the first, second, third, fourth, fifth, sixth, seventh, eighth, ninth, tenth, eleventh 12$^{th}$, 13$^{th}$, 14$^{th}$ 15$^{th}$, 16$^{th}$, 17$^{th}$, 18$^{th}$, 19$^{th}$, 20$^{th}$, 21$^{st}$ and 22$^{nd}$ embodiment of the fifth aspect, a) 3'UTR is a 3' UTR of a gene coding for vWF or a derivative thereof having a nucleotide identity of at least 85% and the 5' UTR is selected from the group comprising a 5' UTR of a gene coding for MCP-1 or a derivative thereof having a nucleotide identity of at least 85%, a 5' UTR of a gene coding for RPL12s.c. or a derivative thereof having a nucleotide identity of at least 85%, a 5' UTR of a gene coding for HSP70 or a derivative thereof having a nucleotide identity of at least 85%, and a 5' UTR of a gene coding for ANG-2 of a derivative thereof having a nucleotide identity of at least 85%, and, b) 3'UTR is a 3' UTR of a gene coding for HSP70 or a derivative thereof having a nucleotide identity of at least 85% and the 5' UTR is selected from the group comprising a 5' UTR of a gene coding for HSP70 or a derivative thereof having a nucleotide identity of at least 85% a 5' UTR of a gene coding for RPL12s.c. or a derivative thereof having a nucleotide identity of at least 85%, a 5' UTR of a gene coding for ANG-2 of a derivative thereof having a nucleotide identity of at least 85%, and a 5' UTR of a gene coding for MCP-1 or a derivative thereof having a nucleotide identity of at least 85%, c) 3'UTR is a 3' UTR of a gene coding for RPL12s.c. or a derivative thereof having a nucleotide identity of at least 85% and the 5' UTR is selected from the group comprising a 5' UTR of a gene coding for HSP70 or a derivative thereof having a nucleotide identity of at least 85% a 5' UTR of a gene coding for RPL12s.c. or a derivative thereof having a nucleotide identity of at least 85%, a 5' UTR of a gene coding for ANG-2 of a derivative thereof having a nucleotide identity of at least 85%, and a 5' UTR of a gene coding for MCP-1 or a derivative thereof having a nucleotide identity of at least 85%, or d) 3'UTR is a 3' UTR of a gene coding for MCP-1 or a derivative thereof having a nucleotide identity of at least 85% and the 5' UTR is selected from the group comprising a 5' UTR of a gene coding for HSP70 or a derivative thereof having a nucleotide identity of at least 85%, a 5' UTR of a gene coding for RPL12s.c. or a derivative thereof having a nucleotide identity of at least 85%, a 5' UTR of a gene coding for ANG-2 of a derivative thereof having a nucleotide identity of at least 85%, and a 5' UTR of a gene coding for MCP-1 or a derivative thereof having a nucleotide identity of at least 85%.

In a 25$^{th}$ embodiment of the second aspect which is also an embodiment of the first, second, third, fourth, fifth, sixth, seventh, eighth, ninth, tenth, eleventh, 12$^{th}$, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$ and 24$^{th}$ embodiment of the second aspect, in a 24$^{th}$ embodiment of the third aspect which is also an embodiment of the first, second, third, fourth, fifth, sixth, seventh, eighth, ninth, tenth, eleventh, 12$^{th}$, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$ and 23$^{rd}$ embodiment of the third aspect, in a 25$^{th}$ embodiment of the fourth aspect which is also an embodiment of the first, second, third, fourth, fifth, sixth, seventh, eighth, ninth, tenth, eleventh, 12$^{th}$, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$ and 24$^{th}$ embodiment of the fourth aspect, and in a 24$^{th}$ embodiment of the fifth aspect which is also an embodiment of the first, second, third, fourth, fifth, sixth, seventh, eighth, ninth, tenth, eleventh 12$^{th}$, 13$^{th}$, 14$^{th}$ 15$^{th}$, 16$^{th}$, 17$^{th}$, 18$^{th}$, 19$^{th}$, 20$^{th}$, 21$^{st}$, 22$^{nd}$ and 23$^{rd}$ embodiment of the fifth aspect, the construct is one selected from the group comprising a construct, wherein the 5' UTR is a 5' UTR of a gene coding for MCP-1 or a derivative thereof having a nucleotide identity of at least 85%, and the 3' UTR is a 3' UTR of a gene coding for vWF or a derivative thereof having a nucleotide identity of at least 85%, a construct, wherein the 5' UTR is a 5' UTR of a gene coding for RPL12s.c. or a derivative thereof having a nucleotide identity of at least 85%, and the 3' UTR is a 3' UTR of a gene coding for vWF or a derivative thereof having a nucleotide identity of at least 85%, a construct, wherein the 5' UTR is a 5' UTR of a gene coding for MCP-1 or a derivative thereof having a nucleotide identity of at least 85%, and the 3' UTR is a 3' UTR of a gene coding for MCP-1 or a derivative thereof having a nucleotide identity of at least 85%, a construct, wherein the 5' UTR is a 5' UTR of a gene coding for ANG-2 or a derivative thereof having a nucleotide identity of at least 85%, and the 3' UTR is a 3' UTR of a gene coding for vWF or a derivative thereof having a nucleotide identity of at least 85%, a construct, wherein the 5' UTR is a 5' UTR of a gene coding for RPL12s.c. or a derivative thereof having a nucleotide identity of at least 85%, and the 3' UTR is a 3' UTR of a gene coding for RPL12s.c. or a derivative thereof having a nucleotide identity of at least 85%, a construct, wherein the 5' UTR is a 5' UTR of a gene coding for HSP70 or a derivative thereof having a nucleotide identity of at least 85%, and the 3' UTR is a 3' UTR of a gene coding for HSP70 or a derivative thereof having a nucleotide identity of at least 85%, a construct, wherein the 5' UTR is a 5' UTR of a gene coding for H3.3. or a derivative thereof having a nucleotide identity of at least 85%, and the 3' UTR is a 3' UTR of a gene coding for H3.3. or a derivative thereof having a nucleotide identity of at least 85%, or a construct, wherein the 5' UTR is a 5' UTR of a gene coding for Galectin 9 or a derivative thereof having a nucleotide identity of at least 85%, and the 3' UTR is a 3' UTR of a gene coding for Galectin 9 or a derivative thereof having a nucleotide identity of at least 85%.

In a 26$^{th}$ embodiment of the second aspect which is also an embodiment of the first, second, third, fourth, fifth, sixth, seventh, eighth, ninth, tenth, eleventh, 12$^{th}$, 13$^{th}$, 14$^{th}$, 15$^{th}$, 16th, 17th, 18th, 19th, 20th, 21st, 22nd, 23rd, 24th and 25th embodiment of the second aspect, in a 25th embodiment of the third aspect which is also an embodiment of the first, second, third, fourth, fifth, sixth, seventh, eighth, ninth, tenth, eleventh, 12th, 13th, 14th, 15th, 16th, 17th, 18th 19th, 20th, 21st, 22nd, 23rd and 24th embodiment of the third aspect, in a 26th embodiment of the fourth aspect which is also an embodiment of the first, second, third, fourth, fifth, sixth, seventh, eighth, ninth, tenth, eleventh, 12th, 13th, 14th, 15th, 16th, 17th, 18th, 19th, 20th, 21st, 22nd, and 23rd, 24th and 25th embodiment of the fourth aspect, and in a 25th embodiment of the fifth aspect which is also an embodiment of the first, second, third, fourth, fifth, sixth, seventh, eighth, ninth, tenth, eleventh 12th, 13th, 14th 15th, 16th, 17th, 18th, 19th, 20th, 21st, 22nd, 23rd and 24th embodiment of the fifth aspect, the construct comprises a poly-A tail.

In a 27th embodiment of the second aspect which is also an embodiment of the first, second, third, fourth, fifth, sixth, seventh, eighth, ninth, tenth, eleventh, 12th, 13th, 14th, 15th, 16th, 17th, 18th, 19th, 20th, 21st, 22nd, 23rd, 24th, 25th and 26th embodiment of the second aspect, in a 26th embodiment of the third aspect which is also an embodiment of the first, second, third, fourth, fifth, sixth, seventh, eighth, ninth, tenth, eleventh, 12th, 13th, 14th, 15th, 16th, 17th, 18th, 19th, 20th, 21st, 22nd, 23rd, 24th and 25th embodiment of the third aspect, in a 27th embodiment of the fourth aspect which is also an embodiment of the first, second, third, fourth, fifth, sixth, seventh, eighth, ninth, tenth, eleventh, 12th, 13th, 14th, 15th, 16th, 17th, 18th, 19th, 20th, 21st, 22nd, 23rd, 24th, 25th and 26th embodiment of the fourth aspect, and in a 26th embodiment of the fifth aspect which is also an embodiment of the first, second, third, fourth, fifth, sixth, seventh, eighth, ninth, tenth, eleventh 12th, 13th, 14th 15th, 16th, 17th, 18th, 19th, 20th, 21st, 22nd, 23rd, 24th and 25th embodiment of the fifth aspect, the construct comprises CAP structure.

In a 28th embodiment of the second aspect which is also an embodiment of the first, second, third, fourth, fifth, sixth, seventh, eighth, ninth, tenth, eleventh, 12th, 13th, 14th, 15th, 16th, 17th, 18th, 19th, 20th, 21st, 22nd and 23rd, 24th, 25th, 26th and 27th embodiment of the second aspect, in a 27th embodiment of the third aspect which is also an embodiment of the first, second, third, fourth, fifth, sixth, seventh, eighth, ninth, tenth, eleventh, 12th, 13th, 14th, 15th, 16th, 17th, 18th, 19th, 20th, 21st, 22nd, 23rd, 24th, 25th and 26th embodiment of the third aspect, in a 28th embodiment of the fourth aspect which is also an embodiment of the first, second, third, fourth, fifth, sixth, seventh, eighth, ninth, tenth, eleventh, 12th, 13th, 14th, 15th, 16th, 17th, 18th, 19th, 20th, 21st, 22nd, 23rd, 24th, 25th, 26th and 27th embodiment of the fourth aspect, and in a 27th embodiment of the fifth aspect which is also an embodiment of the first, second, third, fourth, fifth, sixth, seventh, eighth, ninth, tenth, eleventh 12th, 13th, 14th 15th, 16th, 17th, 18th, 19th, 20th, 21st, 22nd, 23rd, 24th, 25th and 26th embodiment of the fifth aspect, the construct comprises one or more IRESs (internal ribosomal entry sites) sequences. In a preferred embodiment, the IRES sequences replaced the Cap structure.

In a 29th embodiment of the second aspect which is also an embodiment of the first, second, third, fourth, fifth, sixth, seventh, eighth, ninth, tenth, eleventh, 12th, 13th, 14th, 15th, 16th, 17th, 18th, 19th, 20th, 21st, 22nd and 23rd, 24th, 25th, 26th, 27th and 28th embodiment of the second aspect, in a 28th embodiment of the third aspect which is also an embodiment of the first, second, third, fourth, fifth, sixth, seventh, eighth, ninth, tenth, eleventh, 12th, 13th, 14th, 15th, 16th, 17th, 18th, 19th, 20th, 21st, 22nd, 23rd, 24th, 25th, 26th and 27th embodiment of the third aspect, in a 29th embodiment of the fourth aspect which is also an embodiment of the first, second, third, fourth, fifth, sixth, seventh, eighth, ninth, tenth, eleventh, 12th, 13th, 14th, 15th, 16th, 17th, 18th, 19th, 20th, 21st, 22nd, 23rd, 24th, 25th, 26th, 27th and 28th embodiment of the fourth aspect, and in a 28th embodiment of the fifth aspect which is also an embodiment of the first, second, third, fourth, fifth, sixth, seventh, eighth, ninth, tenth, eleventh 12th, 13th, 14th 15th, 16th, 17th, 18th, 19th, 20th, 21st, 22nd, 23rd, 24th, 25th, 26th and 27th embodiment of the fifth aspect, the construct comprises nucleic acid sequence coding for a signal peptide.

In a 30th embodiment of the second aspect which is also an embodiment of the first, second, third, fourth, fifth, sixth, seventh, eighth, ninth, tenth, eleventh, 12th, 13th, 14th, 15th, 16th, 17th, 18th, 19th, 20th, 21st, 22nd and 23rd, 24th, 25th, 26th, 27th, 28th and 29th embodiment of the second aspect, in a 29th embodiment of the third aspect which is also an embodiment of the first, second, third, fourth, fifth, sixth, seventh, eighth, ninth, tenth, eleventh, 12th, 13th, 14th, 15th, 16th, 17th, 18th, 19th, 20th, 21st, 22nd, 23rd, 24th, 25th, 26th, 27th and 28th embodiment of the third aspect, in a 30th embodiment of the fourth aspect which is also an embodiment of the first, second, third, fourth, fifth, sixth, seventh, eighth, ninth, tenth, eleventh, 12th, 13th, 14th, 15th, 16th, 17th, 18th, 19th, 20th, 21st, 22nd, 23rd, 24th, 25th, 26th, 27th 28th and 29th embodiment of the fourth aspect, and in a 29th embodiment of the fifth aspect which is also an embodiment of the first, second, third, fourth, fifth, sixth, seventh, eighth, ninth, tenth, eleventh 12th, 13th, 14th 15th, 16th, 17th, 18th, 19th, 20th, 21st, 22nd, 23rd, 24th, 25th 26th, 27th and 28th embodiment of the fifth aspect, the signal peptide allows secretion of the effector molecule.

In a 31st embodiment of the second aspect which is also an embodiment of the first, second, third, fourth, fifth, sixth, seventh, eighth, ninth, tenth, eleventh, 12th, 13th, 14th, 15th 16th, 17th, 18th, 19th, 20th, 21st, 22nd and 23rd, 24th, 25th, 26th, 27th, 28th, 29th and 30th embodiment of the second aspect, in a 30th embodiment of the third aspect which is also an embodiment of the first, second, third, fourth, fifth, sixth, seventh, eighth, ninth, tenth, eleventh, 12th, 13th, 14th, 15th, 16th, 17th, 18th, 19th, 20th, 21st, 22nd, 23rd, 24th, 25th, 26th, 27th, 28th and 29th embodiment of the third aspect, in a 31st embodiment of the fourth aspect which is also an embodiment of the first, second, third, fourth, fifth, sixth, seventh, eighth, ninth, tenth, eleventh, 12th, 13th, 14th, 15th, 16th, 17th, 18th, 19th, 20th, 21st, 22nd, 23rd, 24th, 25th, 26th, 27th, 28th, 29th and 30th embodiment of the fourth aspect, and in a 30th embodiment of the fifth aspect which is also an embodiment of the first, second, third, fourth, fifth, sixth, seventh, eighth, ninth, tenth, eleventh 12th, 13th, 14th 15th, 16th, 17th, 18th, 19th, 20th, 21st, 22nd, 23rd, 24th, 25th, 26th, 27th, 28th and 29th embodiment of the fifth aspect, the nucleotide sequence coding for a signal peptide is selected from the group comprising a nucleotide sequence coding for a signal peptide of MCP-1 or a derivative thereof having a nucleotide identity of at least 85%, nucleotide sequence coding for a signal peptide of IL-6 or a derivative thereof having a nucleotide identity of at least 85%, a nucleotide sequence coding for a signal peptide of Ang-2 or a derivative thereof having a nucleotide identity of at least 85%, and a nucleotide sequence coding for a signal peptide of Ang-1 or a derivative thereof having a nucleotide identity of at least 85%.

In an embodiment of the first, second, third, fourth and fifth aspect, including any embodiment thereof, the cell a cellular function of which is restored and/or the cell in or on which a therapeutic effect is exercised is an endothelial cell, preferably a vascular endothelial cell, more preferably the vascular endothelial cell is a microvascular endothelial cell.

In an embodiment of the first, second, third, fourth and fifth aspect, including any embodiment thereof, the endothelial cell is a non-dividing endothelial cell, a non-proliferating endothelial cell or a resting endothelial cell.

In an embodiment of the first, second, third, fourth and fifth aspect, including any embodiment thereof, the endothelial cell is an endothelial cell stimulated by an inflammatory stimulus.

In an embodiment of the first, second, third, fourth and fifth aspect, including any embodiment thereof, the endothelial cell is a senescent endothelial cell.

In an embodiment of the first, second, third, fourth and fifth aspect, including any embodiment thereof, the endothelial cell is impaired by age and/or showing stress-related defects.

In an embodiment of the first, second, third, fourth and fifth aspect, including any embodiment thereof, the cellular function is one which can be restored by an effector molecule having anti-permeability effect of endothelial cells, an anti-vascular leakage effect, an anti-apoptotic effect of endothelial cells or an anti-inflammatory effect of endothelial cells or an anti-stress response effect. In an embodiment thereof, the effector molecule stimulates vessel survival, inhibits regression, inhibits apoptosis, stimulates migration, stimulates remodelling, stimulates angiogenesis, stimulates tube-formation/invasion, stimulates proliferation, inhibits leucocyte adhesion, inhibits adhesion molecule expression, inhibits tissue factor expression, inhibits NFKappaB activity or promotes monolayer integrity.

In an embodiment of the first, second, third, fourth and fifth aspect, including any embodiment thereof, the effect is linked to or associated with the Tie-2 signalling pathway, VEGF-receptor pathway, NOTCH signalling pathway, PI3-kinase pathway, eNOS signalling pathway, sirtuin-dependent metabolic and energy homeostasis pathway, oxidative stress pathway, shear stress response pathway, ET-1 signal transduction pathway, NO-mediated signal transduction pathway, and mechanochemical transduction pathway, preferably the pathway is selected from the group comprising Ang/Tie-2 signalling pathway, VEGF/VEGF receptor pathway and Notch/Notch ligand pathway.

In an embodiment of the first, second, third, fourth and fifth aspect, including any embodiment thereof, the effector molecule is an element of a pathway, wherein the pathway is selected from the group comprising the Tie-2 signalling pathway, VEGF-Receptor pathway, NOTCH signalling pathway, PI3-kinase pathway, eNOS signalling pathway, sirtuin-dependent metabolic and energy homeostasis pathway, oxidative stress pathway, shear stress response pathway ET-1 signal transduction pathway, NO-mediated signal transduction pathway, and mechanochemical transduction pathway.

In an embodiment of the first, second, third, fourth and fifth aspect, including any embodiment thereof, the effector molecule is selected from the group comprising Ang-1, Ang-4, COMP-Ang-1, hCOMP-Ang-1, COMP-Ang-1, COMP-ANG-2, Tie-2 receptor, Tie-1 receptor, PI3-kinase, preferably constitutive active PI3-kinase, hyperactive Tie-2 receptor (e.g. R849W), VE-cadherin, GRB2, GRB7, GRB14, GRB7, IQGAP1, RAC1, RAP1, DOK2, ABIN1 and ABIN2, KLF2 (Krueppel-like factor 2), alpha5 beta1 integrin, CD73, Akt 1, Akt 2 and Akt 3.

In an embodiment of the first, second, third, fourth and fifth aspect, including any embodiment thereof, the cellular function is vascular leakage and, preferably, the pathway is the Tie-2 pathway.

In an embodiment of the first, second, third, fourth and fifth aspect, including any embodiment thereof, the effector molecule is selected from the group comprising VEGF, VEGF-A, VEGF-B, PDGF, bFGF, Sirtuin, eNOS, RAS and c-MYC.

In an embodiment of the first, second, third, fourth and fifth aspect, including any embodiment thereof, wherein the effector molecule restores vascular regeneration or provides for vascular regeneration, preferably vascular endothelial vascular regeneration In an embodiment of the first, second, third, fourth and fifth aspect, including any embodiment thereof, the cell a cellular function of which is restored and/or the cell in or on which a therapeutic effect is exercised is a non-endothelial cell.

In an embodiment of the first, second, third, fourth and fifth aspect, including any embodiment thereof, the non-endothelial cell is selected from the group comprising epithelial cells, alveolar macrophages, Alveolar type I cells, alveolar type II cells, alveolar macrophages, Pneumocytes, lung epithelial cells, hematopoietic cells, bone marrow cells, bone cells, stem cells, mesenchymal cells, neural cells, glia cells, neuron cells, Astrocytes, cells of the peripheral nervous system, cardiac cells, adipocytes, vascular smooth muscle cells, cardiomyocytes, skeletal muscle cells, beta cells, pituitary cells, synovial lining cells, ovarian cells, testicular cells, B cells, T cells, reticulocytes, leukocytes, granulocytes, macrophages, neutrophils, antigen presenting cells (dendritic cells), fibroblasts, hepatocytes, tumor cells and combination thereof.

In an embodiment of the first, second, third, fourth and fifth aspect, including any embodiment thereof, the effector molecule is selected from the group comprising a tumor death ligand, a factor involved in hematopoiesis and blood clotting, a stem cell factor, a growth factors and a cytokine.

In an embodiment of the first, second, third, fourth and fifth aspect, including any embodiment thereof, the tumor death ligand is selected from the group comprising IL-12, members of the TNF gene superfamily of death ligand proteins such as Apo2L/TRAIL, IL-13, IL-10, IL-8, IL-2, interferon beta, secreted frizzled-related protein (SFRP) 1, SFRP 2, SFRP 3, SFRP 4 and SFRP5.

In an embodiment of the first, second, third, fourth and fifth aspect, including any embodiment thereof, wherein the factor involved in hematopoiesis and blood clotting is selected from the group comprising erythropoietin, Factor VII, Factor VIII, Factor IX and heparan-N-sulfatase.

In an embodiment of the first, second, third, fourth and fifth aspect, including any embodiment thereof, the stem cell factor is selected from the group comprising Oct4, Sox2, Klf4 and c-Myc.

In an embodiment of the first, second, third, fourth and fifth aspect, including any embodiment thereof, the growth factor and cytokine is selected from the group comprising adrenomedullin, angiopoietin family, autocrine motility factor, bone morphogenetic proteins, ciliary neurotrophic factor (CNTF), leukemia inhibitory factor (LIF), interleukin-6 (IL-6), macrophage colony-stimulating factor (m-CSF), granulocyte colony-stimulating factor (G-CSF), granulocyte macrophage colony-stimulating factor (GM-CSF), epidermal growth factor (EGF), ephrins, erythropoietin (EPO), fibroblast growth factor family (FGF1-23), somatotropin, GDNF family of ligands (such as glial cell line-derived neurotrophic factor (GDNF), neurturin, persephin, and artemin), growth differentiation factor-9 (GDF9), hepatocyte growth factor (HGF), hepatoma-derived growth factor (HDGF), insulin, insulin-like growth factors-1 and-2 (IGF-1; IGF-2), keratinocyte growth factor (KGF), migration-stimulating factor (MSF), macrophage-stimulating protein (MSP), also known as hepatocyte growth factor-like protein (HGFLP), myostatin (GDF-8), neuregulins 1-4 (NRG1-4), neurotrophins (brain-derived neurotrophic factor (BDNF), nerve growth factor (NGF), neurotrophin-3 (NT-3), neurotrophin-4 (NT-4)), placental growth factor (PGF), platelet-derived growth factor (PDGF), renalase (RNLS)-anti-apoptotic survival factor, T-cell growth factor (TCGF), thrombopoietin (TPO), transforming growth factor alpha (TGF-α), transforming growth factor beta (TGF-β), tumor necrosis factor-alpha (TNF-α), vascular endothelial growth factor family (VEGF), Wnt Signaling Pathway signaling glycoproteins (WNT1, WNT2, WNT2B, WNT3, WNT3A, WNT4, WNT5A, WNT5B, WNT6, WNT7A, WNT7B, WNT8A, WNT8B, WNT9A, WNT9B, WNT10A, WNT10B, WNT11, WNT16), granulocyte colony-stimulating factor (G-CSF), granulocyte macrophage colony-stimulating factor (GM-CSF), interferon-alfa, interferon-beta, interleukin 2 (IL-2), Interleukin 11 (IL-11), Interferon-gamma, IL-1, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-35 and IL-36.

In an embodiment of the first, second, third, fourth and fifth aspect, including any embodiment thereof, the disease is characterized by or caused by vascular leakage, preferably leakage of vascular endothelial cells, more preferably leakage of micro vascular endothelial cells.

In an embodiment of the first, second, third, fourth and fifth aspect, including any embodiment thereof, a subject suffering from the disease shows inflammation in the lung.

In an embodiment of the first, second, third, fourth and fifth aspect, including any embodiment thereof, the disease wherein the disease is selected from the group comprising pneumonia, sepsis and trauma.

In an embodiment of the first, second, third, fourth and fifth aspect, including any embodiment thereof, a subject suffering from the disease shows acute respiratory distress syndrome (ARDS).

In an embodiment of the first, second, third, fourth and fifth aspect, including any embodiment thereof, disease is pneumonia, preferably pneumonia selected from the group comprising severe community-acquired pneumonia (sCAP), community acquired pneumonia (CAP), hospital-acquired pneumonia (HAP).

In an embodiment of the first, second, third, fourth and fifth aspect, including any embodiment thereof, the disease is characterized by or shows lung damage.

In an embodiment of the first, second, third, fourth and fifth aspect, including any embodiment thereof, lung damage is immediate lung damage.

In an embodiment of the first, second, third, fourth and fifth aspect, including any embodiment thereof, immediate lung damage results from inhalation of toxic gases, toxic lung edema, lung infection of a virus or bacterium, aspiration of stomach contents, aspiration of fresh water, aspiration of salt water, pulmonary contusion, fat embolism, amniotic fluid embolism and inhalation of hyperbaric oxygen.

In an embodiment of the first, second, third, fourth and fifth aspect, including any embodiment thereof, lung damage is indirect lung damage.

In an embodiment of the first, second, third, fourth and fifth aspect, including any embodiment thereof, indirect lung damage results from sepsis, bacteremia, endotoxinemia, severe trauma, polytrauma including shock, burns, pancreatitis, malaria tropica, drugs and immunosuppression, chronic alcohol abuse, chronic pulmonary diseases, low pH of serum.

In an embodiment of the first, second, third, fourth and fifth aspect, including any embodiment thereof, the disease or effect is vascular regeneration or longevity, wherein preferably the effector molecule is selected from the group comprising VEGF, VEGF-A, VEGF-B, PDGF, bFGF, Sirtuin (Sirt 1), PPAR-gamma, AMPK, eNOS, RAS, c-MYC, FOXO3, PI3 kinase*, Akt, Akt* (* indicates fusion or truncated versions of the proteins to generate hyperactive and constitutively active derivatives of the kinases), adenosine A1 receptor, adenosine A2A receptor, adenosine A2B receptor, telomerase, Yamanaka factors (namely Oct4, sox2, klf4, c-My).

In an embodiment of the first, second, third, fourth and fifth aspect, including any embodiment thereof, the effector molecule is an antiapoptotic factor, preferably protecting normal, i.e. non-diseased endothelium, wherein the antiapoptotic factor is preferably selected from the group comprising PTEN, survivin, IAP, cIAP2 and XIAP, neuroglobin (binds cytochrome c), prosurvival pro-teins Bcl-2, Bcl-x1, Bcl-w, mcl-1 A1, NR-13, BHRF1, LMW5-HL, ORF16, KS-Bcl-2, Elb-19K and P53.

In an embodiment of the first, second, third, fourth and fifth aspect, including any embodiment thereof, the effector molecule is an apoptotic factor, preferably targeting tumor endothelium, wherein the apoptotic factor is preferably selected from the group comprising PTEN, survivin, IAP, cIAP2 and XIAP, neuroglobin (binds cytochrome c), pro-survival proteins Bcl-2, Bcl-x1, Bcl-w, mcl-1 A1, NR-13, BHRF1, LMW5-HL, ORF16, KS-BC1-2, E1b-19K, P53.

In an embodiment of the first, second, third, fourth and fifth aspect, including any embodiment thereof, the effector molecule is a tumor death ligand, preferably the tumor death ligand is proapoptotic or anti-angiogenic, more preferably the tumor death ligand is selected from the group comprising Members of the TNF gene superfamily of death ligand proteins such as TNF-alpha, Fas-L, Apo2L/TRAIL, IL-12, IL-13, IL-10, IL-8, IL-2, secreted frizzled-related protein (SFRP) family (SFRP1, 2, 3, 4, 5), ELTD1, TGF-β, TNF-a, IL-6, PTEN, p53 and other tumor suppressor genes with proapoptotic function, thrombospondin C, TIMP-1, TIMP-2, interferon-alpha, interferon-beta, interferon-gamma, Ang-1 and derivatives with Tie-2 agonistic function, cytochrome c, BH3-only proteins, pro-apoptotic Bcl-2 proteins Bad, Bid, Bax, Bak and Bim, Apaf1, procaspase-8, -9 -10, caspases 2, 3, 6, 7, 8, 9 and 10.

In an embodiment of the first, second, third, fourth and fifth aspect, including any embodiment thereof, the effector molecule is anti-inflammatory, preferably the effector molecule is selected from the group comprising IkappaB and derivative with mutated phosphorylation sites, PI3 kinase and Akt kinases and hyperactive forms.

In an embodiment of the first, second, third, fourth and fifth aspect, including any embodiment thereof, the effector molecule is active in blood coagulation and/or hematopoiesis, preferably the effector molecule is selected from the group comprising erythropoietin, factor VII, factor VIII, factor IX and heparan-N-sulfatase.

In an embodiment of the first, second, third, fourth and fifth aspect, including any embodiment thereof, the effector molecule is a gene editing nuclease such as Cas9.

In an embodiment of the first, second, third, fourth and fifth aspect, including any embodiment thereof, the effector molecule is coding for a therapeutic antibody or a decoy.

In an embodiment of the first, second, third, fourth and fifth aspect, including any embodiment thereof, the effector molecule is effective as a tumor vaccine, preferably the effector molecule is an antigen eliciting an immune response against a tumor cell.

In an embodiment of the first, second, third, fourth and fifth aspect, including any embodiment thereof, the effector molecule is a secreted protein In an embodiment of the first, second, third, fourth and fifth aspect, including any embodiment thereof, the effector molecule is effective as an autocrine factor.

In an embodiment of the first, second, third, fourth and fifth aspect, including any embodiment thereof, the effector molecule is effective as a paracrine factor.

In an embodiment of the first, second, third, fourth and fifth aspect, including any embodiment thereof, the recombinant nucleic acid construct consists of ribonucleotides.

In an embodiment of the first, second, third, fourth and fifth aspect, including any embodiment thereof, the recombinant nucleic acid construct consists of deoxyribonucleotides.

In an embodiment of the first, second, third, fourth and fifth aspect, including any embodiment thereof, the recombinant nucleic acid construct consists of ribonucleotides and deoxyribonucleotides.

More specifically, the problem underlying the present invention is solved in a sixth aspect which is also a first embodiment of the sixth aspect, by a vector comprising a recombinant nucleic acid construct of the first aspect, including any embodiment thereof, and/or a recombinant nucleic acid construct as described in connection with each and any aspect, including any embodiment thereof, preferably of the second, third, fourth and fifth aspect.

In a second embodiment of the sixth aspect which is also an embodiment of the first embodiment of the sixth aspect, the vector is an expression vector.

In a third embodiment of the sixth aspect which is also an embodiment of the second embodiment of the sixth aspect, the vector allows expression of the recombinant nucleic acid construct in a cell, preferably an endothelial cell, more preferably the vector is a plasmid or a virus.

More specifically, the problem underlying the present invention is solved in a seventh aspect which is also a first embodiment of the seventh aspect, by a cell comprising a recombinant nucleic acid construct according to the first, second, third, fourth and fifth aspect, including any embodiment thereof, and/or a vector according to the seventh aspect, including any embodiment thereof.

In a second embodiment of the seventh aspect which is also an embodiment of the first embodiment of the seventh aspect, the cell is an endothelial cell or a mesenchymal stem cell.

In a third embodiment of the seventh aspect which is also an embodiment of the first and second embodiment of the seventh aspect, the cell is a recombinant cell.

In a fourth embodiment of the seventh aspect which is also an embodiment of the first, second and third embodiment of the seventh aspect, the cell is an isolated cell.

More specifically, the problem underlying the present invention is solved in an eighth aspect which is also a first embodiment of the eighth aspect, by a delivery vehicle comprising a recombinant nucleic acid construct according to the first, second, third, fourth and fifth aspect, including any embodiment thereof, wherein the delivery vehicle is a cationic lipid delivery particle.

In a second embodiment of the eighth aspect which is also an embodiment of the first embodiment of the eighth aspect, the particle is a nanoparticle.

In a third embodiment of the eighth aspect which is also an embodiment of the first and second embodiment of the eighth aspect, the average size of the nanoparticle is from about 30 nm to about 200 nm, preferably from about 30 nm to about 140 nm and more preferably from about 30 nm to about 60 nm.

More specifically, the problem underlying the present invention is solved in a ninth aspect which is also a first embodiment of the ninth aspect, by a composition comprising a recombinant nucleic acid construct according to the first, second, third, fourth and fifth aspect, including any embodiment thereof, a vector according to the sixth aspect, including any embodiment thereof, a cell according to the seventh aspect, including any embodiment thereof, and/or a delivery vehicle according to the eight aspect, including any embodiment thereof. In a preferred embodiment, the composition is a pharmaceutical composition comprising a pharmaceutically acceptable excipient.

More specifically, the problem underlying the present invention is also solved in a tenth aspect by the use in the manufacture of a medicament of a recombinant nucleic acid construct according to the first, second, third, fourth and fifth aspect, including any embodiment thereof, a vector according to the sixth aspect, including any embodiment thereof, a cell according to the seventh aspect, including any embodiment thereof, a cell according to the seventh aspect, including any embodiment thereof, and/or a delivery vehicle according to the eight aspect, including any embodiment thereof. In an embodiment thereof, the medicament is for the treatment of a disease, preferably a disease described herein in connection with the second, third, fourth and fifth aspect, including any embodiment thereof.

More specifically, the problem underlying the present invention is also solved in an eleventh aspect by a method for treating a subject, preferably a human subject, wherein the method comprises administering to the subject a therapeutically effective amount of a recombinant nucleic acid construct according to the first, second, third, fourth and fifth aspect, including any embodiment thereof, a vector according to the sixth aspect, including any embodiment thereof, a cell according to the seventh aspect, including any embodiment thereof, a delivery vehicle according to the eight aspect, including any embodiment thereof and/or a composition according to the ninth aspect, including any embodiment thereof. In an embodiment thereof, the method is for the treatment of a disease, preferably a disease described herein in connection with the second, third, fourth and fifth aspect, including any embodiment thereof.

More specifically, the problem underlying the present invention is also solved in an twelfth aspect by a method for vaccinating a subject, preferably a human subject, wherein the method comprises administering to the subject an amount effective to elicit in a or the subject an immune response, preferably a desired immune response, of a recombinant nucleic acid construct according to the first, second, third, fourth and fifth aspect, including any embodiment thereof, a vector according to the sixth aspect, including any embodiment thereof, a cell according to the seventh aspect, including any embodiment thereof, a delivery vehicle according to the eight aspect, including any embodiment thereof and/or a composition according to the ninth aspect, including any embodiment thereof. In an embodiment thereof, the method is for the treatment of a disease, preferably a disease described herein in connection with the second, third, fourth and fifth aspect, including any embodiment thereof. In a preferred embodiment, the effector molecule is one which is capable of or suitable for eliciting such immune response.

In an embodiment and as preferably used herein, a heterologous construct or recombinant construct is a construct which as such is not existing in a wild type biological system such as a virus, a cell, a tissue, an organ or an organism. More preferably, a heterologous construct or a recombinant construct is one, where at least one element contained in the construct is not combined with a coding region for the effector, wherein said element is selected from the group consisting of a 5' non-translated region, a 3' non-translated region, a cap structure, a signal sequence and a poly-A tail. Preferably, the 5' non-translated region is a 5' UTR and the 3' non-translated region is a 3' UTR.

In an embodiment and as preferably used herein, a therapeutic method or a method for the treatment and/or prevention of a disease is a therapy.

In an embodiment of each and any aspect of the present invention, the coding region coding for an effector molecule is expressed by an endothelial cell. In preferred embodiment thereof, the endothelial cell expressing the effector molecule is an endothelial cell the function of which is impaired. In an alternative preferred embodiment, the endothelial cell expressing the effector molecule is an endothelial cell the function of which is not impaired; in such case, the effector molecule is exported or secreted by the effector molecule producing endothelial cell and exerts its effect on any other cell, typically any other endothelial cell, whereby such other cell is one the function of which is impaired. In a preferred embodiment, an impaired function of a cell is function of such cell which is to be restored in according with the present invention in its various aspect.

As preferably used herein, a derivative of a sequence which displays the same function as the parent sequence; preferably the parent sequence is a or the wild type sequence. In a preferred embodiment, the sequence of the derivative and of the parent case have an identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. It is within the present invention that the derivative is a truncated version of the parent sequence. Such truncation may exist at the 5' end, the 3' end or both the 5' end and the 3' end. If reference is made to a parent sequence in terms of identity, such identity preferable refers to a stretch of subsequent nucleotides shared by both the derivative and the parent sequence with the sequence of the parent sequence serving as the reference sequence.

In an embodiment and as preferably used herein, a coding region coding for an effector molecule comprises or consists of a nucleic acid sequence coding to said effector molecule.

In an embodiment and as preferably used herein, a 5' non-translated region is a 5' non-translated sequence.

In an embodiment and as preferably used herein, a 3' non-translated region is a 5' non-translated sequence.

In an embodiment and as preferably used herein, the indication of any source of any one of the elements contained in the recombinant nucleic acid construct of the invention is to be understood as a substitute of or an alternative description of a nucleotide sequence. Such nucleotide sequence is preferably the one of the respective wild type sequence, more preferably the one of the respective human wild type sequence. It will be appreciated by a person skilled in the art that other species than man may provide such wild type sequence; in an embodiment of the present invention such wild type sequence for such other species than man may be used in the practicing of the present invention. It will also be appreciated by a person skilled in the art that such wild type sequence may be taken from publicly available data bases such as GenBank. The wild type sequence may be subject to changes over time, typically to correct sequencing errors. In an embodiment of the invention, the sequence is the one described in said publicly available data bases such as GenBank at the date of filing of the instant application. To the extent various respective wild type sequences exist, each and any such wild type sequence shall be encompassed by the present invention. In another embodiment, where there is more than one wild type sequences and the more than one wild type sequence is provided by different groups of people such as different geographically defined groups of people and/or different genetically defined groups of people, the wild type sequence prevailing in the most comprehensive group of said different groups of people may be regarded as the wild type sequence.

In an embodiment of the present invention and as preferably used herein, if reference is made to a derivative of a 5' UTR of a gene indicating that the derivative has a nucleotide identity of at least 85%, identity is identity referring or relative to the 5' UTR of the gene.

In an embodiment of the present invention and as preferably used herein, if reference is made to a derivative of a 3' UTR of a gene indicating that the derivative has a nucleotide identity of at least 85%, identity is identity referring or relative to the 3' UTR of the gene.

In an embodiment and as preferably used herein, a signal peptide is a peptide which mediates directly or indirectly the transfer or secretion of a polypeptide or a protein fused or attached to the signal peptide into the extracellular space, whereupon, preferably, the signal sequence is removed from the polypeptide and protein, respectively.

In an embodiment of the present invention, the recombinant nucleic acid construct is a recombinant nucleic acid construct disclosed in the Figs, more specifically a recombinant nucleic acid construct disclosed in FIG. 40 (PAN29), FIG. 90 (PAN58), FIG. 86 (PAN54), FIG. 67 (PAN50), FIG. 45 (PAN34), FIG. 44 (PAN33), FIG. 39 (PAN28), FIG. 37 (PAN12), FIG. 88 (PAN56).

In an embodiment of the present invention and as preferably used herein, a decoy is a mRNA encoded protein which binds a ligand and neutralizes the signaling activity.

In an embodiment and as preferably used herein, a poly-A tail is a nucleotide sequence comprising or consisting of a plurality of A's covalently attached to each other, whereby such covalent linkage is preferably a phosphodiester linkage. In an embodiment thereof, the poly-A tail comprises about 20 to about 240 As (i.e. adenosinphosphates) nucleotides, preferably about 60 to 120 As, more preferable about 100 to 140 As and most preferably about 120 As.

The poly A tail is thought to stabilize natural messengers and synthetic sense RNA. Therefore, in one embodiment a long poly A tail can be added to an mRNA molecule thus rendering the RNA more stable. Poly A tails can be added using a variety of art-recognized techniques. For example, long poly A tails can be added to synthetic or in vitro transcribed RNA using poly A polymerase (Yokoe, et al. Nature Biotechnology. 1996; 14:1252-1256). A transcription vector can also encode long poly A tails. In addition, poly A tails can be added by transcription directly from PCR products. Poly A may also be ligated to the 3' end of a sense RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)). In one embodiment, the length of the poly A tail is at least about 90, 200, 300, 400 at least 500 nucleotides. In one embodiment, the length of the poly A tail is adjusted to control the stability of a modified sense mRNA molecule of the invention and, thus, the transcription of protein. For example, since the length of the poly A tail can influence the half-life of a sense mRNA molecule, the length of the poly A tail can be adjusted to modify the level of resistance of the mRNA to nucleases and thereby control the time course of protein expression in a cell. In one embodiment, the stabilized nucleic acid molecules are sufficiently resistant to in vivo degradation (e.g., by nucleases), such that they may be delivered to the target cell without a transfer vehicle. In yet another embodiment the nucleic acid molecule can be purified by means of HPLC in order to remove double-stranded RNA contaminants and thus to reduce innate immune system activation (see e.g. Kariko et al., Nucleic Acids Res. 2011 November; 39(21):e142).

In an embodiment and as preferably used herein, the CAP structure is a nucleotide sequence forming a CAP structure which is known to a person skilled in the art. In eukaryotic cells the CAP-structure consists of a m7G(5')ppp(5')G 5'-5'-triphosphate linkage structure. The first two ribose sugars at the 5'-end of the mRNA can be methylated in the 2'-position which is known as CAP-1 (in case the first of the two ribose sugars is methylated) and CAP-2 structure (in case the second of the two ribose sugars is methylated). The CAP-structure can be incorporated during the mRNA transcription or post-transcriptionally by using capping and 2'-O-Methyltransferase enzymes and S-adenosylmethionine (SAM) as a methyl donor. In addition, a phosphatase treatment can be used in order to remove immune stimulatory 5'-phosphates.

In a preferred embodiment of the recombinant nucleic acid construct according to each and any aspect, including any embodiment thereof, the recombinant nucleic acid construct is an mRNA.

In an embodiment of each and any aspect of the present invention, including any embodiment thereof, a 5' UTR of a gene coding for MCP-1 comprises a nucleotide sequence of SEQ ID NO: 20.

In an embodiment of each and any aspect of the present invention, including any embodiment thereof, a 3' UTR of a gene coding for MCP-1 comprises a nucleotide sequence of SEQ ID NO: 23.

In an embodiment of each and any aspect of the present invention, including any embodiment thereof, a 5' UTR of a gene coding for RPL12s.c. comprises a nucleotide sequence of SEQ ID NO: 24.

In an embodiment of each and any aspect of the present invention, including any embodiment thereof, a 3' UTR of a gene coding for RPL12s.c. comprises a nucleotide sequence of SEQ ID NO: 25.

In an embodiment of each and any aspect of the present invention, including any embodiment thereof, a 5' UTR of a gene coding for Ang-2 comprises a nucleotide sequence of SEQ ID NO: 26.

In an embodiment of each and any aspect of the present invention, including any embodiment thereof, a 3' UTR of a gene coding for Ang-2 comprises a nucleotide sequence of SEQ ID NO: 29.

In an embodiment of each and any aspect of the present invention, including any embodiment thereof, a 5' UTR of a gene coding for HSP70 comprises a nucleotide sequence of SEQ ID NO: 38 or 40.

In an embodiment of each and any aspect of the present invention, including any embodiment thereof, a 3' UTR of a gene coding for HSP70 comprises a nucleotide sequence of SEQ ID NO: 39 or 43.

In an embodiment of each and any aspect of the present invention, including any embodiment thereof, a 5' UTR of a gene coding for H3.3. comprises a nucleotide sequence of SEQ ID NO: 44.

In an embodiment of each and any aspect of the present invention, including any embodiment thereof, a 3' UTR of a gene coding for H3.3. comprises a nucleotide sequence of SEQ ID NO: 45.

In an embodiment of each and any aspect of the present invention, including any embodiment thereof, a 5' UTR of a gene coding for Galectin-9 (LHALS9) comprises a nucleotide sequence of SEQ ID NO: 46.

In an embodiment of each and any aspect of the present invention, including any embodiment thereof, a 3' UTR of a gene coding for Galectin-9 (LHALS9) comprises a nucleotide sequence of SEQ ID NO: 47.

In an embodiment of each and any aspect of the present invention, including any embodiment thereof, a 5' UTR of a gene coding for IL-6 comprises a nucleotide sequence of SEQ ID NO: 30.

In an embodiment of each and any aspect of the present invention, including any embodiment thereof, a 3' UTR of a gene coding for IL-6 comprises a nucleotide sequence of SEQ ID NO: 33.

In an embodiment of each and any aspect of the present invention, including any embodiment thereof, a 5' UTR of a gene coding for vWF comprises a nucleotide sequence of SEQ ID NO: 34.

In an embodiment of each and any aspect of the present invention, including any embodiment thereof, a 3' UTR of a gene coding for vWF comprises a nucleotide sequence of SEQ ID NO: 37.

In an embodiment of each and any aspect of the present invention, including any embodiment thereof, a 5' UTR of a gene coding for Ang-1 comprises a nucleotide sequence of SEQ ID NO: 83.

In an embodiment of each and any aspect of the present invention, including any embodiment thereof, a 3' UTR of a gene coding for Ang-1 comprises a nucleotide sequence of SEQ ID NO: 88.

In an embodiment of each and any aspect of the present invention, including any embodiment thereof, a 5' UTR of a gene coding for Ang-4 comprises a nucleotide sequence of SEQ ID NO: 89.

In an embodiment of each and any aspect of the present invention, including any embodiment thereof, a 3' UTR of a gene coding for Ang-4 comprises a nucleotide sequence of SEQ ID NO: 94.

In an embodiment of each and any aspect of the present invention, including any embodiment thereof, a 5' UTR of construct PAN57 comprises a nucleotide sequence of SEQ ID NO: 120.

In an embodiment of each and any aspect of the present invention, including any embodiment thereof, a 3' UTR of construct PAN57 comprises a nucleotide sequence of SEQ ID NO: 121.

In an embodiment of each and any aspect of the present invention, including any embodiment thereof, the various combinations of a 5' UTR and a 3' UTR as realized in each and any of the specific constructs disclosed herein is a combination of 5' UTR and a 3' UTR which may be realized in recombinant nucleic acid construct irrespective of any other constituent and in particular irrespective of any coding region coding for an effector molecule contained in a recombinant nucleic acid construct of the invention.

In an embodiment of each and any aspect of the present in invention, including any embodiment thereof, and as preferably used herein, an endogenous gene is a gene contained in any cell described herein. In accordance therewith, a recombinant nucleic acid construct where the 5' UTR and the 3' UTR are from different endogenous genes, comprises a 5' UTR from a first gene of a cell and a 3' UTR from a second gene of a cell, for example the 5' UTR is from a gene encoding MCP-1 or Ang-2, and the 3' UTR is from a gene coding for vWF. Said cell may be the same cell or a different cell and/or said cell may be the same kind of cell or a different kind of cell. Preferably, the cell is of human origin.

In a preferred embodiment of the recombinant nucleic acid construct according to each and any aspect, including any embodiment thereof, the recombinant nucleic acid construct is a recombinant nucleic acid molecule.

It is within the present invention defined by each and any aspect, including any embodiment thereof, that the nucleotides forming the recombinant nucleic acid molecule may be modified. Suitable modifications include alterations in one or more nucleotides of a codon such that the codon encodes the same amino acid but is more stable than the codon found in the wild-type version of the nucleic acid. For example, an inverse relationship between the stability of RNA and a higher number cytidines (C's) and/or uridines (U's) residues has been demonstrated, and RNA devoid of C and U residues have been found to be stable to most RNases (Heidenreich, et al. J Biol Chem 269, 2131-8 (1994)). In some embodiments, the number of C and/or U residues in an mRNA sequence is reduced. In another embodiment, the number of C and/or U residues is reduced by substitution of one codon encoding a particular amino acid for another codon encoding the same or a related amino acid. Contemplated modifications to the mRNA nucleic acids of the present invention also include the incorporation of pseudouridine, N1-methyl-pseudouridine, 5-methoxyuridine and 5'-Methylcytidine. The incorporation of such modified nucleotides into the recombinant nucleic acid construct, preferably the mRNA of the present invention may enhance stability and translational capacity, as well as diminishing immunogenicity in vivo. (See, e.g., Kariko, K., et al., Molecular Therapy 16 (11): 1833-1840 (2008)). Substitutions and modifications to the recombinant nucleic acid construct of the present invention, particularly at the level of the individual nucleotide of the recombinant nucleic acid construct, may be performed by methods readily known to one of ordinary skill in the art.

The constraints on reducing the number of C and U residues in a sequence will likely be greater within the coding region of an mRNA, compared to an untranslated region, (i.e., it will likely not be possible to eliminate all of the C and U residues present in the message while still retaining the ability of the message to encode the desired amino acid sequence). The degeneracy of the genetic code, however presents an opportunity to allow the number of C and/or U residues that are present in the sequence to be reduced, while maintaining the same coding capacity (i.e., depending on which amino acid is encoded by a codon, several different possibilities for modification of RNA sequences may be possible). For example, the codons for Gly can be altered to GGA or GGG instead of GGU or GGC.

The term modification also includes, for example, the incorporation of non-nucleotide linkages or modified nucleotides into the nucleic acid sequences of the present invention (e.g., modifications to one or both the 3' and 5' ends of an mRNA molecule encoding a functional protein or enzyme). Such modifications include the addition of bases to a nucleic acid sequence (e.g., the inclusion of a poly A tail or a longer poly A tail), the alteration of the 3' UTR or the 5' UTR, complexing the nucleic acid with an agent (e.g., a protein or a complementary nucleic acid molecule), and inclusion of elements which change the structure of a nucleic acid molecule (e.g., which form secondary structures).

The delivery vehicle according to the eighth aspect is preferably based on a composition of one or more suitable lipids (e.g. liposomes) which in combination with the recombinant nucleic acid construct according to the present invention result in overall cationic-lipid-nucleic acid particles (cLNPs). Such cLNPs can be used for functionally transferring a nucleic acid, particularly an mRNA, into endothelial cells of the mammalian vasculature.

Lipid-nucleic acid nanoparticles (LNPs) formed by complexation of nucleic acids such as the recombinant nucleic acid construct of the present invention with cationic lipids in combination with other lipidic components, such as zwitterionic phospholipids, cholesterol and PEGylated lipids, have already been used to block degradation of RNAs in plasma and to facilitate the functional cellular uptake of the RNAs.

However, in a therapeutic context, particularly in view of parenteral therapeutic applications, the overall charge of the lipid-nucleic acid nanoparticles, characterized by the Zeta-potential, is essential in directing the organ distribution of the nanoparticles. Someone skilled in the art will appreciate that overall neutrally charged LNPs are almost exclusively taken up by organs of the reticuloendothelial system, particularly by the liver and spleen. On the other hand, it is also known to those skilled in the art, that overall positively charged lipid nanoparticles are particularly useful to functionally deliver a pharmaceutical payload into cells of the mammalian vasculature.

Those skilled in the art will also appreciate that free nucleic acids, particularly mRNAs, are immune stimulatory if applied intravenously.

Thus, in view of parenteral therapeutic applications a thorough and stable complexation of the nucleic acid inside the lipidic nanoparticle will be essential in order to prevent undesired immunogenic side reactions. Furthermore, it is also known to those skilled in the art that the size of the lipid-nucleic acid nanoparticle is crucial in suppressing the reticuloendothelial clearance of the particles.

It has recently been described that highly potent limit sized siRNA LNPs (~30 nm mean particle size) can be prepared using a microfluidic mixing process based on a staggered herringbone micromixer (SHM) device (Belliveau et al.; Molecular Therapy-Nucleic Acids (2012) 1(8)).

Due to the millisecond mixing of the lipids and the nucleic acid such as the recombinant nucleic acid construct of the invention on a nanoliter scale, the resulting particles are characterized by a very tight packaging of the nucleic acid inside a dense, solid particle core. On the contrary, those skilled in the art will appreciate that macrofluidic mixing processes using T-type connectors, generally result in larger nanoparticles with a more heterogeneous, multilamellar morphology.

In an embodiment, the present invention provides novel positively charged lipid-nucleic acid nanoparticles comprising a nucleic acid such as recombinant nucleic acid construct of the invention for the functional delivery of said recombinant nucleic acid construct of the invention, particularly mRNA, into cells of the mammalian vasculature, particularly into endothelial cells of the lung vasculature.

In an embodiment of the various aspects of the present invention, including any embodiment thereof, a cationic lipid selected from the group comprising β-(L-Arginyl)-L-2,3-diamino propionic acid-N-palmityl-N-oleyl-amide, L-Arginyl-β-alanine-N-palmityl-N-oleyl-amide, DOTAP (N-[1-(2,3-Dioleoyloxy) propyl]-N,N,N-trimethylammonium methyl-chloride), DOTMA (1,2-di-O-octadecenyl-3-trimethylammonium propane (chloride salt)) or DC-cholesterol is combined with neutral lipids and further shielding lipid components bearing a polyethylene glycol (PEG) modification. The neutral lipid can be either a zwitterionic phospholipid selected from a group comprising Diphytanoyl-PE (1,2-Diphytanoyl-sn-glycero-3-phosphoethanolamine), DOPE (1,2-Dioleoyl-sn-glycero-3-phosphoethanolamine), DLPE (1,2-Lauroyl-sn-glycero-3-phosphoethanolamine), DMPE, POPE, DSPE or an uncharged sterol lipid selected from a group comprising cholesterol and stigmasterol. The PEGylated lipid component is selected from a group comprising methoxyPEG-DSPE, methoxyPEG-DLG, methoxyPEG-DMG, methoxyPEG-DPG, methoxyPEG-DSG, methoxyPEG-c-DMA, methoxyPEG-C8-Ceramide, methoxyPEG-C16-Ceramide. In a particular embodiment the chain length of the PEG-chain corresponds to a molecular weight in the range of 750 Da to 5000 Da, preferably in a range of 1500 Da to 3000 Da.

In another embodiment of the present invention, the molar ratio of the lipids in the lipid mixture is in a range of 20-80 mol % cationic lipid, 10-70 mol % neutral lipid and 1-10 mol % PEGylated lipid, preferably in a range of 35-65 mol % cationic lipid, 35-65 mol % neutral lipid and 1-5 mol % PEGylated lipid (with the overall lipid content being set as 100%).

In a preferred embodiment, the cationic lipid is β-(L-Arginyl)-L-2,3-diamino propionic acid-N-palmityl-N-oleyl-amide or L-Arginyl-β-alanine-N-palmityl-N-oleyl-amide, the neutral lipid is the phospholipid Diphytanoyl-PE and the PEGylated lipid is methoxyPEG2000-DSPE. The molar ratio is 50 mol % cationic lipid, 49 mol % Diphytanoyl-PE and 1 mol % mPEG2000-DSPE (1,2-distearoyl-sn-glycero-3-phosphoethanolamine-N-[methoxy (polyethylene glycol)-2000] (sodium salt)).

In yet another embodiment, the mixture of above mentioned lipids is dissolved in a water miscible solvent selected from a group comprising ethanol, acetone, 1-butanol, 2-butanol, tert.-butanol, 3-methyl-1-butanol, 2-methyl-1-propanol, 1-propanol, 2-propanol, dimethylsulfoxide, preferably from a group comprising ethanol, tert.-butanol and 1-butanol.

The dissolved lipid mixture is subsequently rapidly mixed with a dissolution of a nucleic acid such as the recombinant nucleic acid construct of the invention in an aqueous solvent, resulting in the formation of lipid-nucleic acid nanoparticles (LNPs). In a preferred embodiment of the present invention, the mixing is performed using a microfluidic mixing device, particularly using a staggered herringbone-type mixing chamber, e.g. NanoAssemblr™ (Precision NanoSystems Inc.; Vancouver, Canada) device.

In yet another embodiment, the mass ratio of total lipids to nucleic acid nucleic acid such as the recombinant nucleic acid construct of the invention is in a range of 5 to 60, preferably in a range of 15 to 40 and the volumetric mixing ratio of aqueous nucleic acid solution to organic total lipid solution is in the range of 1:1 to 6:1, preferably in the range of 2:1 to 4:1. The mixing flow-rate of the solutions is in the range of 5 ml/min to 25 ml/min, preferably in a range of 10 ml/min to 20 ml/min.

In a certain embodiment of the invention the organic solvent of the resulting mixture is removed after the mixing step by dialysis or by tangential flow filtration using ultrafiltration membranes, whereby the ultrafiltration membranes can be either hollow fiber membranes or flat-screen membranes. The pore size of the ultrafiltration membrane corresponds to a molecular weight cutoff in the range of 1500 Da to 500.000 Da, preferably in a range of 1500 Da to 100.000 Da and even more preferably in a range of 1500 Da to 30.000 Da. Within the tangential flow filtration step it is also possible to concentrate the LNPs to a desired concentration.

The mean particle size of the resulting LNPs can be measured using dynamic light scattering (DLS) technologies and is preferably in the range of 15 nm to 400 nm, more preferably in a range of 25 nm to 200 nm and even more preferable the particles have a size in the range of 25 nm to 100 nm. The overall particle charge of the LNPs is positive and the Zeta-potential of the particles is preferably in a range between +5 mV to +60 mV, more preferably in a range of +25 mV to +60 mV.

In certain embodiments, the delivery vehicle of the invention is a liposomal transfer vehicle, e.g. a lipid nanoparticle or a lipidoid nanoparticle. In one embodiment, the transfer vehicle may be selected and/or prepared to optimize delivery of the recombinant nucleic acid construct of the invention to a target cell. For example, if the target cell is an endothelial cell, the properties of the transfer vehicle (e.g., size, charge and/or pH) may be optimized to effectively deliver such transfer vehicle to the target cell, reduce immune clearance and/or promote retention in that target cell. Alternatively, if the target cell is in the central nervous system (e.g., mRNA such as the recombinant nucleic acid construct of the invention administered for the treatment of neurodegenerative diseases may specifically target brain or spinal tissue), selection and preparation of the transfer vehicle must consider penetration of, and retention within, the blood brain barrier and/or the use of alternate means of directly delivering such transfer vehicle to such target cell. In one embodiment, the compositions of the present invention may be combined with agents that facilitate the transfer of exogenous mRNA (e.g., agents which disrupt or improve the permeability of the blood brain barrier and thereby enhance the transfer of exogenous mRNA to the target cells).

Liposomes (e.g., liposomal lipid nanoparticles) are known to be particularly suitable for their use as transfer vehicles of diagnostic or therapeutic compounds in vivo (Lasic, Trends Biotechnol, 16:307-321, 1998; Drummond et al, Pharmacol. Rev., 51:691-743, 1999) and are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol, 16:307-321, 1998). Bilayer membranes of the liposomes can also be formed by amphiphilic polymers and surfactants (e.g., polymerosomes, niosomes, etc.). Such liposomes may also be used as the lipid moiety in the delivery vehicle of the present invention comprising a recombinant nucleic acid construct of the present invention.

It is to be acknowledged that any feature related to the recombinant nucleic acid construct as disclosed in connection with a particular aspect of the present invention is equally an embodiment of the recombinant nucleic acid construct of each and any other aspect of the present invention, including any embodiment thereof. More specifically, any embodiment of the recombinant nucleic acid construct disclosed in connection with the first aspect is also an embodiment of the recombinant nucleic acid construct of the second, third and fourth aspect; similarly, any embodiment of the recombinant nucleic acid construct disclosed in connection with the second, third and fourth aspect is also an embodiment of the recombinant nucleic acid construct of the first aspect.

It is generally acknowledged in the art that the UTRs flanking a coding region do not interfere with the coding region and, more specifically, that the UTRs may, in principle, be exchanged without interfering with the expression of the coding region (see, e.g. WO 2017/100551 A1; Trepotec et al.; Tissue Engineering Part A, Vol 0 Nr ja (April 2018) (https://doi.org/10.1089/ten.TEA.2017.0485)

BRIEF DESCRIPTION OF THE DRAWINGS

The present invention is further illustrated by the following Figs. and Examples form which further features, embodiments and advantages of the present invention may be taken.

FIG. 7A shows the 5' primers (SEQ ID NOs 1-9, respectively) used for the 5' UTRs of the indicated gene; the first column indicates in connection with which construct such primer is to be used, the second column indicates the origin of the 5' UTR, and the third column indicates the position where the primer hybridizes to the nucleotide sequence.

FIG. 7B shows the 3' primers (SEQ ID NOs 10-19, respectively) used for the 3' UTRs of the indicated gene; the first column indicates in connection with which construct such primer is to be used, the second column indicates the origin of the 3' UTR, and the third column indicates the position where the primer hybridizes to the nucleotide sequence.

FIG. 15A shows the 5' UTR nucleotide sequence (SEQ ID NO:20) of the mRNA of human MCP-1 which is also referred to as *Homo sapiens* C—C motif chemokine ligand 2 (CCL2) (GenBank entry NM_002982.3).

FIG. 15B shows both the nucleotide sequence (SEQ ID NO:21) and the amino acid sequence of the signal peptide sequence of human MCP-1 (SEQ ID NO:22).

FIG. 15C shows the 3' UTR nucleotide sequence (SEQ ID NO:23) of the mRNA of human MCP-1.

FIG. 16A shows the 5' UTR nucleotide sequence (SEQ ID NO:24) of the mRNA of the 50S ribosomal protein L12, chloroplastic (LOC110782793), of *Spinacia oleracea* which is also referred to as RPL12s.c. (GenBank entry XM_021987044.1).

FIG. 16B shows the 3' UTR (SEQ ID NO:25) from the mRNA of the 50S ribosomal protein L12, chloroplastic (LOC110782793), of *Spinacia oleracea*.

FIG. 17A shows the 5' UTR nucleotide sequence (SEQ ID NO:26) of the mRNA of human angiopoietin 2 which is also referred to as ANGPT2 or Ang-2, transcript variant 1 (GenBank entry NM_001147.2).

FIG. 17B shows both the nucleotide sequence (SEQ ID NO:27) and the amino acid sequence (SEQ ID NO:28) of the signal sequence of the mRNA of human Ang-2.

FIG. 17C shows the 3' UTR nucleotide sequence (SEQ ID NO:29) of the mRNA of human Ang-2.

FIG. 18A shows the 5' UTR nucleotide sequence (SEQ ID NO:30) of the mRNA of human interleukin 6 (IL-6), transcript variant 1 (GenBank entry NM_000600.4).

FIG. 18B shows both the nucleotide sequence (SEQ ID NO:31) and the amino acid sequence (SEQ ID NO:32) of the signal sequence of the mRNA of human IL-6.

FIG. 18C shows the 3' UTR nucleotide sequence (SEQ ID NO:33) of the mRNA of human IL-6.

FIG. 19A shows the 5' UTR nucleotide sequence (SEQ ID NO:34) of the mRNA of human von Willebrand factor (vWF) (GenBank entry NM_000552.4).

FIG. 19B shows both the nucleotide sequence (SEQ ID NO:35) and the amino acid sequence (SEQ ID NO:36) of the signal sequence of the mRNA of von Willebrand factor (vWF).

FIG. 19C shows the 3' UTR nucleotide sequence (SEQ ID NO:37) of the mRNA of von Willebrand factor (vWF).

FIG. 20A shows the 5' UTR nucleotide sequence (SEQ ID NO:38) of the mRNA of human heat shock protein family A (Hsp70) member 1A, also referred to as HSPA1A (GenBank entry NM_005345.5).

FIG. 20B shows the 3' UTR nucleotide sequence (SEQ ID NO:39) of the mRNA of human HSPA1A.

FIG. 21A shows the 5' UTR nucleotide sequence (SEQ ID NO:40) of the mRNA of human heat shock protein family A (Hsp70) member 5, also referred to as HSPA5, (GenBank entry NM_005347.4).

FIG. 21B shows both the nucleotide sequence (SEQ ID NO:41) and the amino acid sequence (SEQ ID NO:42) of the signal sequence of the mRNA of human HSPA5.

FIG. 21B shows both the nucleotide sequence (SEQ ID NO:41) and the amino acid sequence (SEQ ID NO:42) of the signal sequence of the mRNA of human HSPA5.

FIG. 21C shows the 3' UTR nucleotide sequence (SEQ ID NO:43) of the mRNA of human HSPA1A.

FIG. 22A shows the 5' UTR nucleotide sequence (SEQ ID NO:44) of the mRNA of human H3 histone family member 3A (H3F3A), also referred to as H3.3, (GenBank entry NM_002107.4).

FIG. 22B shows the 3' UTR nucleotide sequence (SEQ ID NO:45) of the mRNA of human H3.3.

FIG. 23A shows the 5' UTR nucleotide sequence (SEQ ID NO:46) of the mRNA of human galectin-9 (LGALS9), transcript variant 1 (GenBank entry NM_009587.2).

FIG. 23B shows the 3' UTR nucleotide sequence (SEQ ID NO:47) of the mRNA of human galectin-9.

FIG. 24A shows the basic structure and FIG. 24B shows the nucleotide sequence (SEQ ID NO: 48) of recombinant nucleic acid construct PAN01.

FIG. 25A shows the basic structure and FIG. 25B shows the basic structure and nucleotide sequence (SEQ ID NO:49) of recombinant nucleic acid construct PAN03.

FIG. 26A shows the basic structure and FIG. 26B shows the basic structure and nucleotide sequence (SEQ ID NO:50) of recombinant nucleic acid construct PAN04.

FIG. 27A shows the basic structure and FIG. 27B shows the basic structure and nucleotide sequence (SEQ ID NO:51) of recombinant nucleic acid construct PAN06.

FIG. 28A shows the basic structure and FIG. 28B shows the basic structure and nucleotide sequence (SEQ ID NO:52) of recombinant nucleic acid construct PAN36.

FIG. 29A shows the basic structure and FIG. 29B shows the basic structure and nucleotide sequence (SEQ ID NO:53) of recombinant nucleic acid construct PAN37.

FIG. 30A shows the basic structure and FIG. 30B shows nucleotide sequence (SEQ ID NO: 54) of recombinant nucleic acid construct PAN02.

FIG. 31A shows the basic structure and FIG. 31B shows nucleotide sequence (SEQ ID NO: 55) of recombinant nucleic acid construct PAN05.

FIG. 32A shows the basic structure and FIG. 32B shows the basic structure and nucleotide sequence (SEQ ID NO:56) of recombinant nucleic acid construct PAN07.

FIG. 33A shows the basic structure and FIG. 33B shows the basic structure and nucleotide sequence (SEQ ID NO:57) of recombinant nucleic acid construct PAN08.

FIG. 34A shows the basic structure and FIG. 34B shows the basic structure and nucleotide sequence (SEQ ID NO:58) of recombinant nucleic acid construct PAN09.

FIG. 35A shows the basic structure and FIG. 35B shows the basic structure and nucleotide sequence (SEQ ID NO:59) of recombinant nucleic acid construct PAN10.

FIG. 36A shows the basic structure and FIG. 36B shows the basic structure and nucleotide sequence (SEQ ID NO:60) of recombinant nucleic acid construct PAN11.

FIG. 37A shows the basic structure and FIG. 37B shows the basic structure and nucleotide sequence (SEQ ID NO:61) of recombinant nucleic acid construct PAN12.

FIG. 38A shows the basic structure and FIG. 38B shows the basic structure and nucleotide sequence (SEQ ID NO:61) of recombinant nucleic acid construct PAN13.

FIG. 39A shows the basic structure and FIG. 39B shows the basic structure and nucleotide sequence (SEQ ID NO:63) of recombinant nucleic acid construct PAN28.

FIG. 40A shows the basic structure and FIG. 40B shows the basic structure and nucleotide sequence (SEQ ID NO:64) of recombinant nucleic acid construct PAN29.

FIG. 41A shows the basic structure and FIG. 41B shows the basic structure and nucleotide sequence (SEQ ID NO:65) of recombinant nucleic acid construct PAN30.

FIG. 42A shows the basic structure and FIG. 42B shows the basic structure and nucleotide sequence (SEQ ID NO:66) of recombinant nucleic acid construct PAN31.

FIG. 43A shows the basic structure and FIG. 43B shows the basic structure and nucleotide sequence (SEQ ID NO:67) of recombinant nucleic acid construct PAN32.

FIG. 44A shows the basic structure and FIG. 44B shows the basic structure and nucleotide sequence (SEQ ID NO:68) of recombinant nucleic acid construct PAN33.

FIG. 45A shows the basic structure and FIG. 45B shows the basic structure and nucleotide sequence (SEQ ID NO:69) of recombinant nucleic acid construct PAN34.

FIG. 46A shows the basic structure and FIG. 46B shows the basic structure and nucleotide sequence (SEQ ID NO:70) of recombinant nucleic acid construct PAN35.

FIG. 47A shows the basic structure and FIG. 47B shows the basic structure and nucleotide sequence (SEQ ID NO:71) of recombinant nucleic acid construct PAN38.

FIG. 48A shows the basic structure and FIG. 48B shows the basic structure and nucleotide sequence (SEQ ID NO:72) of recombinant nucleic acid construct PAN39.

FIG. 49A shows the basic structure and FIG. 49B shows the basic structure and nucleotide sequence (SEQ ID NO:73) of recombinant nucleic acid construct PAN40.

FIG. 50A shows the basic structure and FIG. 50B shows the basic structure and nucleotide sequence (SEQ ID NO:74) of recombinant nucleic acid construct PAN41.

FIG. 51A shows the basic structure and FIG. 51B shows the basic structure and nucleotide sequence (SEQ ID NO:75) of recombinant nucleic acid construct PAN42.

FIG. 52A shows the basic structure and FIG. 52B shows the basic structure and nucleotide sequence (SEQ ID NO:76) of recombinant nucleic acid construct PAN43.

FIG. 53A shows the basic structure and FIG. 53B shows the basic structure and nucleotide sequence (SEQ ID NO:77) of recombinant nucleic acid construct PAN44.

FIG. 54A shows the basic structure and FIG. 54B shows the basic structure and nucleotide sequence (SEQ ID NO:78) of recombinant nucleic acid construct PAN45.

FIG. 55A shows the basic structure and FIG. 55B shows the basic structure and nucleotide sequence (SEQ ID NO:79) of recombinant nucleic acid construct PAN46.

FIG. 56A shows the basic structure and FIG. 57B shows the basic structure and nucleotide sequence (SEQ ID NO:80) of recombinant nucleic acid construct PAN47.

FIG. 57A shows the basic structure and FIG. 58B shows the basic structure and nucleotide sequence (SEQ ID NO:81) of recombinant nucleic acid construct PAN48.

FIG. 58 shows the basic structure and nucleotide sequence (SEQ ID NO:82) of recombinant nucleic acid construct PAN49.

FIG. 59A shows the nucleotide sequence (SEQ ID NO:83) of mRNA of human angiopoietin 1, also referred to as ANGPT1 or Ang-1, transcript variant 1, GenBank entry NM_001146.4.

FIG. 59B shows both the nucleotide sequence (SEQ ID NO:84) and the amino acid sequence (SEQ ID NO:85) of the mRNA of human Ang-1.

FIG. 59C shows the coding sequence (CDS) (SEQ ID NO:86) of the mature peptide of mRNA of human Ang-1.

FIG. 59D shows the 3' UTR nucleotide sequence (SEQ ID NO:88) of the mRNA of human Ang-1.

FIG. 60A shows the nucleotide sequence (SEQ ID NO:89) of mRNA of human angiopoietin 4, also referred to as ANGPT4 or Ang-4, transcript variant 1, GenBank entry NM_015985.3.

FIG. 60B shows both the nucleotide sequence (SEQ ID NO:90) and the amino acid sequence (SEQ ID NO:91) of the mRNA of human Ang-4.

FIG. 60C shows the coding sequence (CDS) (SEQ ID NO:92) of the mature peptide of mRNA of human Ang-4.

FIG. 60D shows the 3' UTR nucleotide sequence (SEQ ID NO:94) of the mRNA of human Ang-4.

FIG. 61 shows the nucleotide sequence (SEQ ID NO:95) coding for COMP-Ang1 which is a synthetic construct.

FIG. 62 shows the nucleotide sequence (SEQ ID NO:97) coding for hCOMP-Ang1 which is a synthetic construct.

FIG. 63 shows the nucleotide sequence (SEQ ID NO:99) coding for CMP-Ang1 which is a synthetic construct.

FIG. 64 shows the nucleotide sequence (SEQ ID NO:100) coding for COMP-Ang2 which is a synthetic construct.

FIG. 65 shows the coding nucleotide sequence (SEQ ID NO:101) of mRNA of human TEK receptor tyrosine kinase (TEK), transcript variant 1, also referred to as Tie-2, GenBank entry.

FIG. 66 shows the coding nucleotide sequence (SEQ ID NO:103) of mRNA of human mutant TEK receptor tyrosine kinase (TEK), which is also referred to as TIE* having a R849W mutation.

FIG. 67A shows the basic structure and FIG. 67B shows the basic structure and nucleotide sequence (SEQ ID NO:105) of recombinant nucleic acid construct PAN50.

FIG. 68A shows the basic structure and FIG. 68B shows the basic structure and nucleotide sequence (SEQ ID NO:106) of recombinant nucleic acid construct PAN51.

FIG. 69A shows the basic structure and FIG. 69B shows the basic structure and nucleotide sequence (SEQ ID NO:107) of recombinant nucleic acid construct PAN52.

FIG. 70A shows the basic structure and FIG. 70B shows the basic structure and nucleotide sequence (SEQ ID NO:108) of recombinant nucleic acid construct PAN53.

FIG. 86A shows the basic structure and FIG. 86B shows the basic structure and nucleotide sequence (SEQ ID NO:109) of recombinant nucleic acid construct PAN54.

FIG. 87A shows the basic structure and FIG. 87B shows the basic structure and nucleotide sequence (SEQ ID NO:110) of recombinant nucleic acid construct PAN55.

FIG. 88A shows the basic structure and FIG. 88B shows the basic structure and nucleotide sequence (SEQ ID NO:111) of recombinant nucleic acid construct PAN56.

FIG. 89A shows the basic structure and FIG. 89B shows the basic structure and nucleotide sequence (SEQ ID NO:112) of recombinant nucleic acid construct PAN57.

FIG. 90A shows the basic structure and FIG. 90B shows the basic structure and nucleotide sequence (SEQ ID NO:113) of recombinant nucleic acid construct PAN58.

FIG. 91A shows the basic structure and FIG. 91B shows the basic structure and nucleotide sequence (SEQ ID NO:114) of recombinant nucleic acid construct PAN59.

The human embryonic kidney 293 cell line (HEK293) is grown in EMEM (EBSS)+2 mM Glutamine+1% Non Essential Amino Acids (NEAA)+10% FCS culture medium. Subculture Routine is to split sub-confluent cultures (70-80%) 1:2 to 1:6 i.e. seeding at 2-5×10,000 cells/cm$^2$ using 0.25% trypsin or trypsin/EDTA; 5% $CO_2$; 37° C. mRNA transfection are performed with the Lipofectamine™ MessengerMAX™ Transfection Reagent (Invitrogen™) according to the manufactures protocol.

Figure 94:
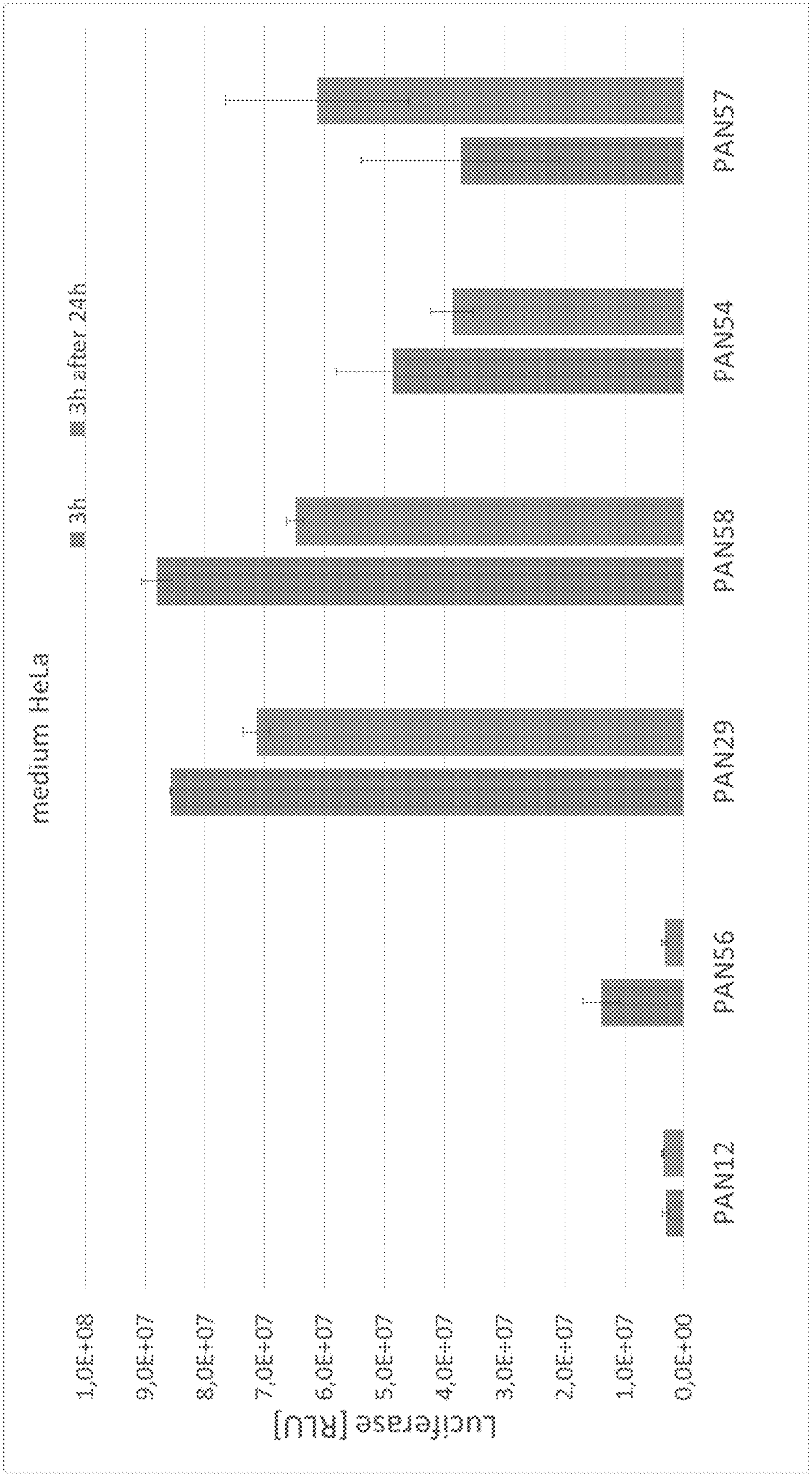

FIG. 94 is a bar diagram showing expression of luciferase, indicated as RLU (relative light units) of luciferase in medium, by the indicated recombinant nucleic acid constructs in HeLa cells, where luciferase is used as the effector molecule after 3 hours (left column). An additional 3-hours luciferase activity value is assessed 24 hours (right column) post transfection, after washing of the cells and supplementing the cells with fresh medium.

FIG. 95A shows the basic structure and FIG. 95B shows the basic structure and nucleotide sequence (SEQ ID NO:115) of recombinant nucleic acid construct PAN60.

FIG. 96A shows the basic structure and FIG. 96B shows the basic structure and nucleotide sequence (SEQ ID NO:116) of recombinant nucleic acid construct PAN61.

FIG. 97A shows the basic structure and FIG. 97B shows the basic structure and nucleotide sequence (SEQ ID NO:117) of recombinant nucleic acid construct PAN66.

Figure 98:
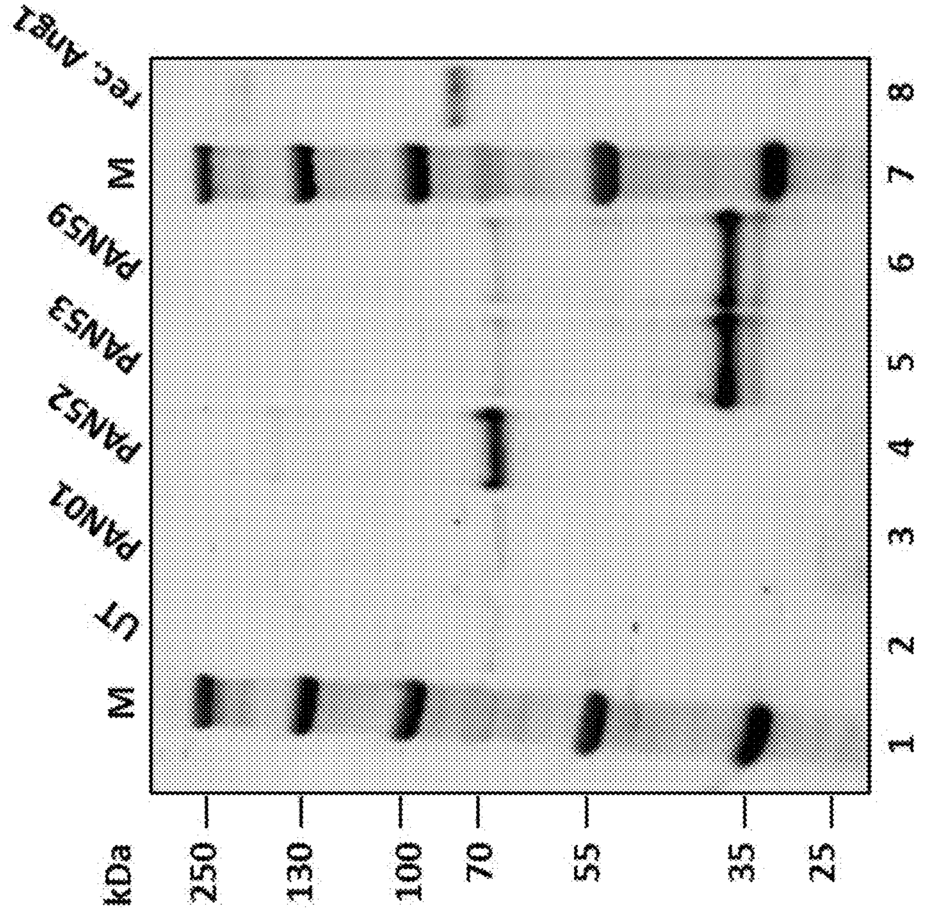

FIG. 98 shows Western Blot analysis of protein lysates from HPMEC cells transfected with indicated PAN mRNA constructs. Cells were transfected with 1 μg the mRNAs and harvested after 6 hours. Total cell lysates were separated by SDS-PAGE and analyzed by immunoblot using anti-Ang1 antibody. M, Marker; UT, untreated cells, rec. Ang1, recombinant hAng1.

Figure 99:
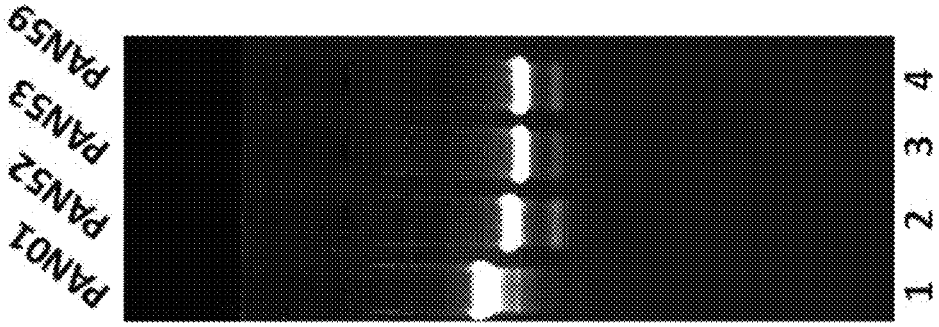

FIG. 99 shows Agarose gels of mRNAs after in vitro transcription. 2 μg of indicated mRNAs were separated by agarose gel electrophoresis and visualized by ethidium bromide staining and UV illumination.

FIG. 100 shows the sequences of: a) the 5'UTR of PAN57 (SEQ ID NO:120); b) the 3'UTR of PAN57 (SEQ ID NO:121); c) the 5'PCR-Primer for PAN57 (SEQ ID NO:122); d) the 3'PCR-Primer for PAN57 (SEQ ID NO: 123) and e) the 5'PCR-Primer for PAN55, PAN56 (SEQ ID NO:124).

DETAILED DESCRIPTION

Figure 1:
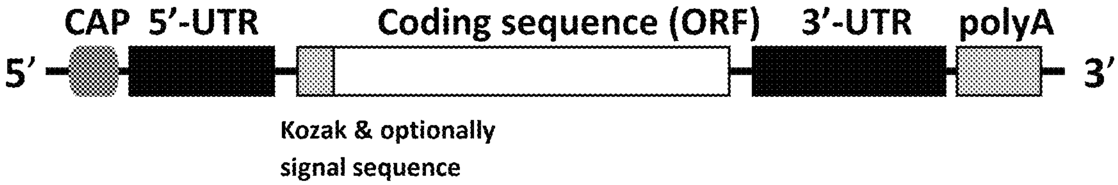
FIG. 1 is a schematic representation of conventional mRNA molecule structure.

FIG. 1 is a schematic representation of conventional mRNA molecule structure. Eukaryotic including mammalian mRNAs consist of a cap region, a 5' untranslated region (UTR), the coding sequence (CDS) with an open reading frame (ORF) starting with a consensus Kozak sequence for optimal translation initiation and in case of secreted proteins followed by an signal peptide leader sequences, a 3' UTR, and a poly A-tail (>120 nt) at the 3' end.

Figure 2:
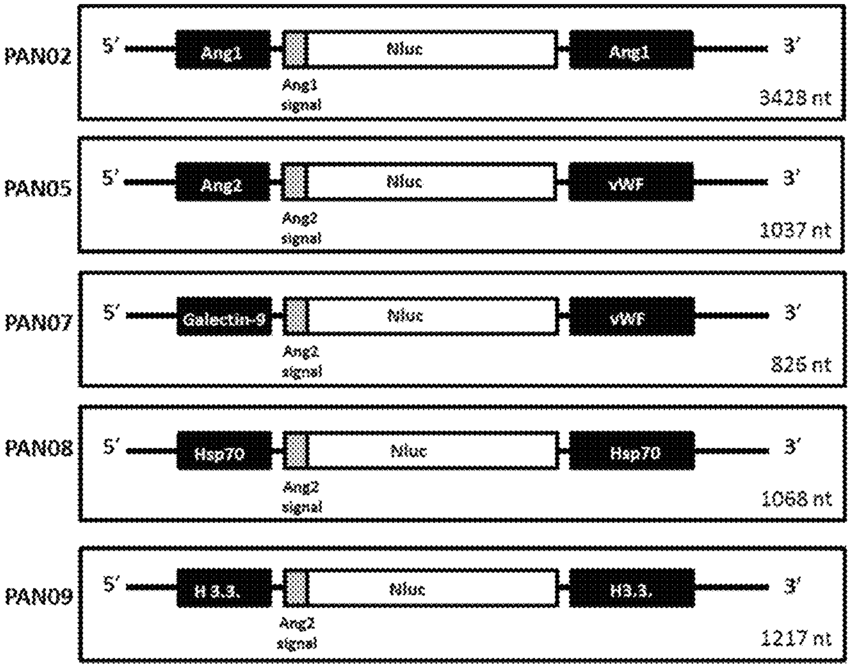
FIG. 2 is a schematic representation of selected examples for mRNA constructs with the coding sequence with an open reading frame being the one of Nano-luciferase, namely PAN02, PAN05, PAN07, PAN08, PAN09, PAN10, PAN11, PAN12, 13, PAN28, PAN29, PAN30, PAN31, PAN32, PAN33, PAN34, PAN35, PAN36, PAN37, PAN38, PAN39, PAN40, PAN41, PAN42, PAN43, PAN44, PAN45, PAN46, PAN47, PAN48 and PAN49.
Figure 2:
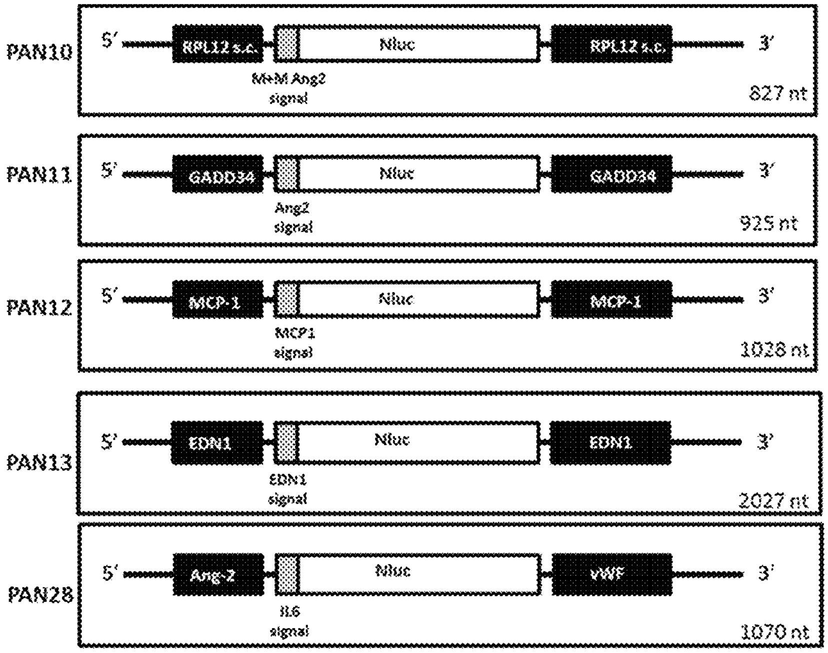
Figure 2:
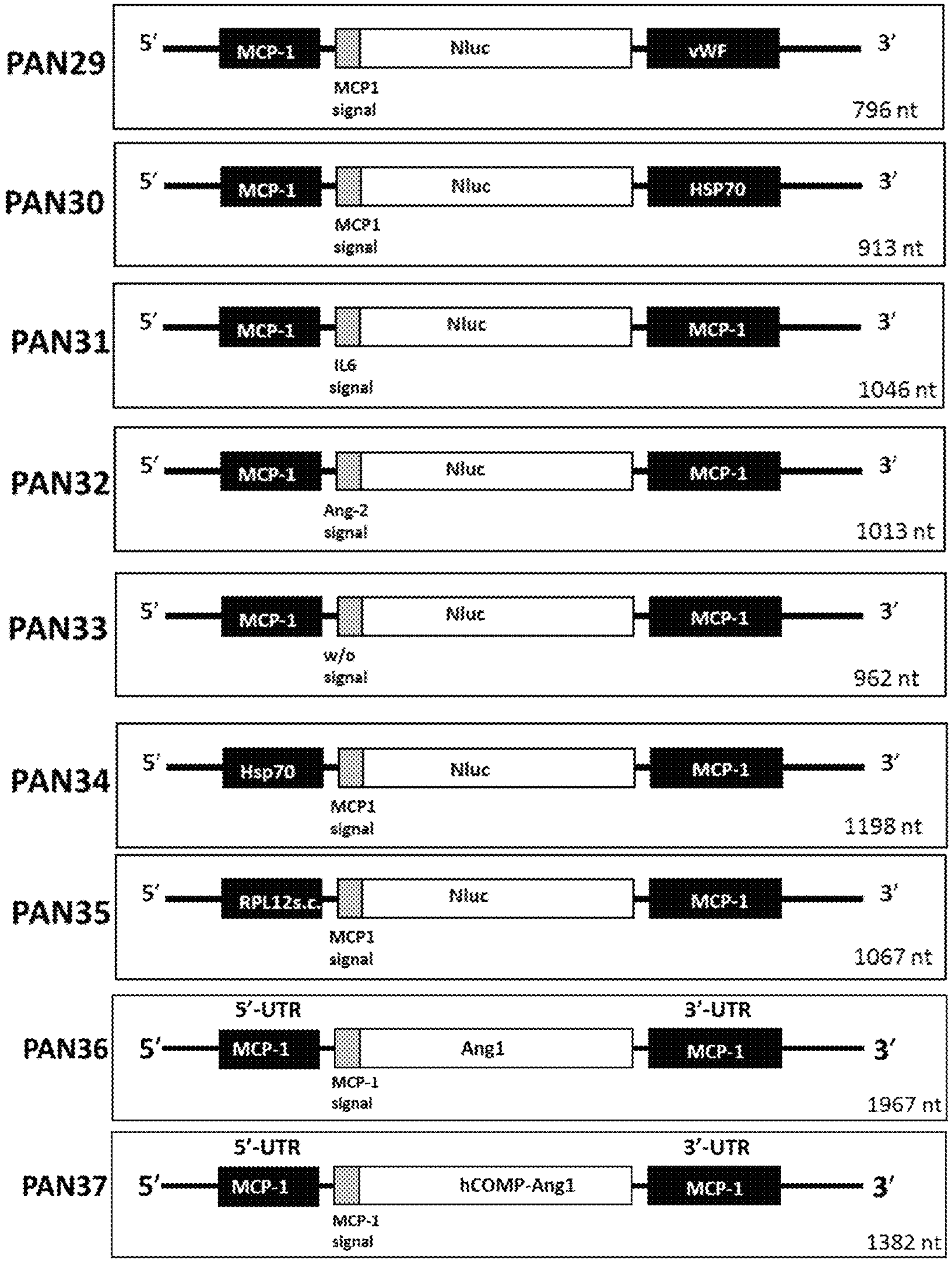
Figure 2:
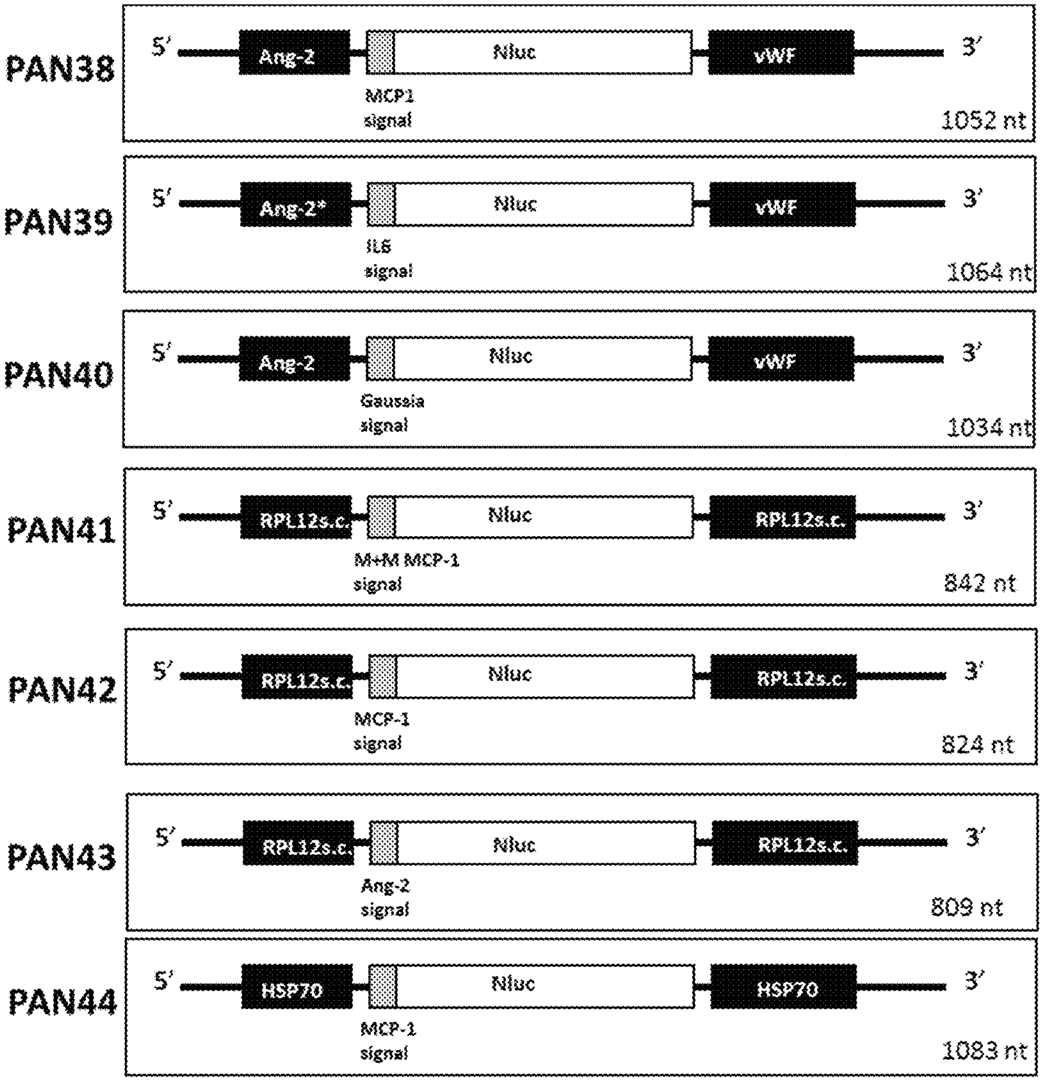
Figure 2:
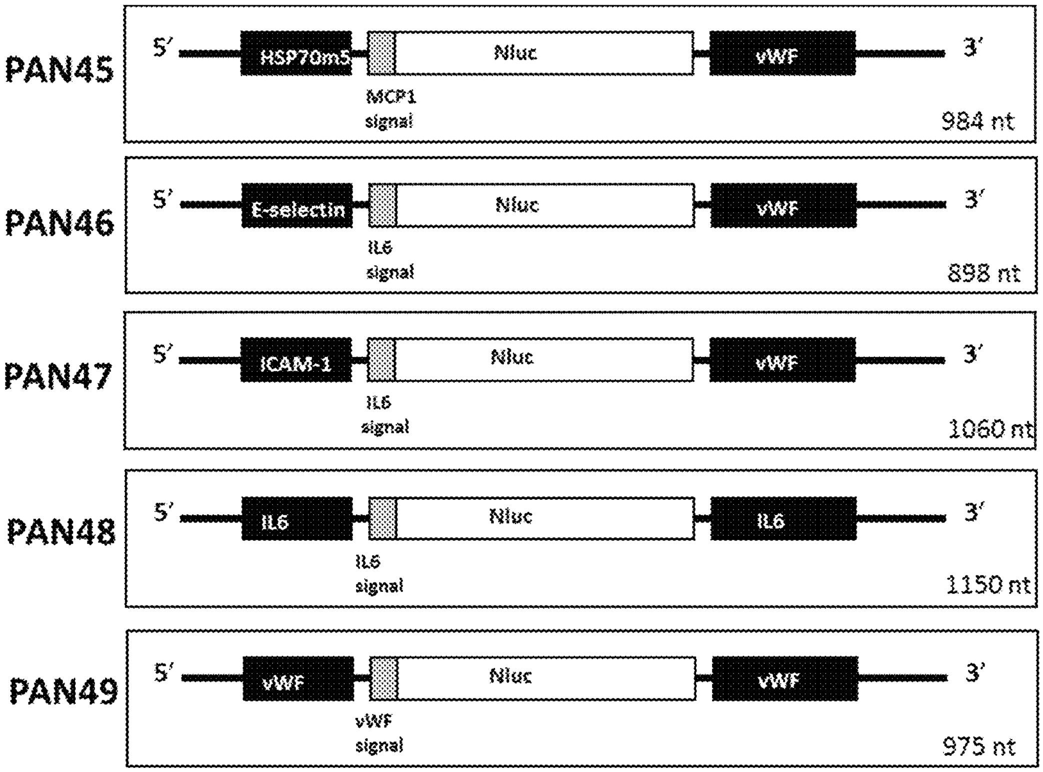

FIG. 2 is a schematic representation of selected examples for mRNA constructs with the coding sequence with an open reading frame being the one of Nano-luciferase. It is within the present invention that for each and any of the indicated mRNA constructs the coding region comprising a sequence with an open reading frame for Nano-luciferase may be replaced by a coding regions comprising a sequence coding for an effector molecule, particularly by a coding region comprising a sequence coding for an effector molecule disclosed herein; in a preferred embodiment thereof, the effector molecule is Ang1 or COMP-Ang1. In accordance with the present invention, the recombinant nucleic acid constructs are designed as follows:

Recombinant nucleic acid construct PAN02 comprises as the 5' non-translated region the 5' UTR of Ang1, as the nucleic acid sequence coding for a signal peptide the nucleic acid sequence coding for a signal peptide of Ang1, as the coding region coding for an effector molecule the coding region coding for Nano luciferase, and as the 3' non-translated region the 3' UTR of Ang1.

Recombinant nucleic acid construct PAN05 comprises as the 5' non-translated region the 5' UTR of Ang2, as the nucleic acid sequence coding for a signal peptide the nucleic acid sequence coding for a signal peptide of Ang2, as the coding region coding for an effector molecule the coding region coding for Nano luciferase, and as the 3' non-translated region the 3' UTR of von Willebrand Factor (vWF).

Recombinant nucleic acid construct PAN07 comprises as the 5' non-translated region the 5' UTR of Galectin-9, as the nucleic acid sequence coding for a signal peptide the nucleic acid sequence coding for a signal peptide of Ang2, as the coding region coding for an effector molecule the coding region coding for Nano luciferase, and as the 3' non-translated region the 3' UTR of von Willebrand Factor (vWF).

Recombinant nucleic acid construct PAN08 comprises as the 5' non-translated region the 5' UTR of Hsp70, as the nucleic acid sequence coding for a signal peptide the nucleic acid sequence coding for a signal peptide of Ang2, as the coding region coding for an effector molecule the coding region coding for Nano luciferase, and as the 3' non-translated region the 3' UTR of HSP70.

Recombinant nucleic acid construct PAN09 comprises as the 5' non-translated region the 5' UTR of H3.3, as the nucleic acid sequence coding for a signal peptide the nucleic acid sequence coding for a signal peptide of Ang2, as the coding region coding for an effector molecule the coding region coding for Nano luciferase, and as the 3' non-translated region the 3' UTR of H3.3.

Recombinant nucleic acid construct PAN10 comprises as the 5' non-translated region the 5' UTR of RPL12s.c., as the nucleic acid sequence coding for a signal peptide the nucleic acid sequence coding for a signal peptide of Ang2, as the coding region coding for an effector molecule the coding region coding for Nano luciferase, and as the 3' non-translated region the 3' UTR of RPL12s.c. This construct additionally comprises another start codon preceding the start codon of the coding region for Nano-luciferase in-frame.

Recombinant nucleic acid construct PAN11 comprises as the 5' non-translated region the 5' UTR of GADD34, as the nucleic acid sequence coding for a signal peptide the nucleic acid sequence coding for a signal peptide of Ang2, as the coding region coding for an effector molecule the coding region coding for Nano luciferase, and as the 3' non-translated region the 3' UTR of GADD34.

Recombinant nucleic acid construct PAN12 comprises as the 5' non-translated region the 5' UTR of MCP-1 as the nucleic acid sequence coding for a signal peptide the nucleic acid sequence coding for a signal peptide of MCP-1, as the coding region coding for an effector molecule the coding region coding for Nano luciferase, and as the 3' non-translated region the 3' UTR of MCP-1.

Recombinant nucleic acid construct PAN13 comprises as the 5' non-translated region the 5' UTR of EDN1, as the nucleic acid sequence coding for a signal peptide the nucleic acid sequence coding for a signal peptide of EDN1, as the coding region coding for an effector molecule the coding region coding for Nano luciferase, and as the 3' non-translated region the 3' UTR of EDN1.

Recombinant nucleic acid construct PAN28 comprises as the 5' non-translated region the 5' UTR of Ang2, as the nucleic acid sequence coding for a signal peptide the nucleic acid sequence coding for a signal peptide of IL-6, as the coding region coding for an effector molecule the coding region coding for Nano luciferase, and as the 3' non-translated region the 3' UTR of vWF.

Recombinant nucleic acid construct PAN29 comprises as the 5' non-translated region the 5' UTR of MCP-1, as the nucleic acid sequence coding for a signal peptide the nucleic acid sequence coding for a signal peptide of MCP-1, as the coding region coding for an effector molecule the coding region coding for Nano luciferase, and as the 3' non-translated region the 3' UTR of von Willebrand Factor (vWF).

Recombinant nucleic acid construct PAN30 comprises as the 5' non-translated region the 5' UTR of MCP-1, as the nucleic acid sequence coding for a signal peptide the nucleic acid sequence coding for a signal peptide of MCP-1, as the coding region coding for an effector molecule the coding region coding for Nano luciferase, and as the 3' non-translated region the 3' UTR of HSP70.

Recombinant nucleic acid construct PAN31 comprises as the 5' non-translated region the 5' UTR of MCP-1, as the nucleic acid sequence coding for a signal peptide the nucleic acid sequence coding for a signal peptide of IL-6, as the coding region coding for an effector molecule the coding region coding for Nano luciferase, and as the 3' non-translated region the 3' UTR of MCP-1.

Recombinant nucleic acid construct PAN32 comprises as the 5' non-translated region the 5' UTR of MCP-1, as the nucleic acid sequence coding for a signal peptide the nucleic acid sequence coding for a signal peptide of Ang2, as the coding region coding for an effector molecule the coding region coding for Nano luciferase, and as the 3' non-translated region the 3' UTR of MCP-1.

Recombinant nucleic acid construct PAN33 comprises as the 5' non-translated region the 5' UTR of MCP-1, no nucleic acid sequence coding for a signal peptide, as the coding region coding for an effector molecule the coding region coding for Nano luciferase, and as the 3' non-translated region the 3' UTR of MCP-1.

Recombinant nucleic acid construct PAN34 comprises as the 5' non-translated region the 5' UTR of Hsp70, as the nucleic acid sequence coding for a signal peptide the nucleic acid sequence coding for a signal peptide of MCP-1, as the coding region coding for an effector molecule the coding region coding for Nano luciferase, and as the 3' non-translated region the 3' UTR of MCP-1.

Recombinant nucleic acid construct PAN35 comprises as the 5' non-translated region the 5' UTR of RPL 12 s.c. (spinach chloroplast), as the nucleic acid sequence coding for a signal peptide the nucleic acid sequence coding for a signal peptide of MCP-1, as the coding region coding for an effector molecule the coding region coding for Nano luciferase, and as the 3' non-translated region the 3' UTR of MCP-1.

Recombinant nucleic acid construct PAN36 comprises as the 5' non-translated region the 5' UTR of MCP-1, as the nucleic acid sequence coding for a signal peptide the nucleic acid sequence coding for a signal peptide of MCP-1, as the coding region coding for an effector molecule the coding region coding for Ang1, and as the 3' non-translated region the 3' UTR of MCP-1.

Recombinant nucleic acid construct PAN37 comprises as the 5' non-translated region the 5' UTR of MCP-1, as the nucleic acid sequence coding for a signal peptide the nucleic acid sequence coding for a signal peptide of MCP-1, as the coding region coding for an effector molecule the coding region coding for hCOMP-Ang1, and as the 3' non-translated region the 3' UTR of MCP-1.

Recombinant nucleic acid construct PAN38 comprises as the 5' non-translated region the 5' UTR of Ang2, as the nucleic acid sequence coding for a signal peptide the nucleic acid sequence coding for a signal peptide of MCP-1, as the coding region coding for an effector molecule the coding region coding for Nano luciferase, and as the 3' non-translated region the 3' UTR of von Willebrand Factor (vWF).

Recombinant nucleic acid construct PAN39 comprises as the 5' non-translated region the 5' UTR of Ang2* (Ang2 5'-UTR with deleted upstream ATGs), as the nucleic acid sequence coding for a signal peptide the nucleic acid sequence coding for a signal peptide of IL-6, as the coding region coding for an effector molecule the coding region coding for Nano luciferase, and as the 3' non-translated region the 3' UTR of von Willebrand Factor (vWF).

Recombinant nucleic acid construct PAN40 comprises as the 5' non-translated region the 5' UTR of Ang2, as the nucleic acid sequence coding for a signal peptide the nucleic acid sequence coding for a signal peptide of *Gaussia* luciferase, as the coding region coding for an effector molecule the coding region coding for Nano luciferase, and as the 3' non-translated region the 3' UTR of von Willebrand Factor (vWF).

Recombinant nucleic acid construct PAN41 comprises as the 5' non-translated region the 5' UTR of RPL12 s.c., as the nucleic acid sequence coding for a signal peptide the nucleic acid sequence coding for a signal peptide of MCP-1 with an additional upstream ATG for translational start, as the coding region coding for an effector molecule the coding region coding for Nano luciferase, and as the 3' non-translated region the 3' UTR of RPL12 s.c. This construct additionally comprises another start codon preceding the start codon of the coding region for Nano-luciferase in-frame.

Recombinant nucleic acid construct PAN42 comprises as the 5' non-translated region the 5' UTR of RPL12 s.c., as the nucleic acid sequence coding for a signal peptide the nucleic acid sequence coding for a signal peptide of MCP-1, as the coding region coding for an effector molecule the coding region coding for Nano luciferase, and as the 3' non-translated region the 3' UTR of RPL12 s.c.

Recombinant nucleic acid construct PAN43 comprises as the 5' non-translated region the 5' UTR of RPL12 s.c., as the nucleic acid sequence coding for a signal peptide the nucleic acid sequence coding for a signal peptide of Ang2, as the coding region coding for an effector molecule the coding region coding for Nano luciferase, and as the 3' non-translated region the 3' UTR of RPL12 s.c.

Recombinant nucleic acid construct PAN44 comprises as the 5' non-translated region the 5' UTR of Hsp70, as the nucleic acid sequence coding for a signal peptide the nucleic acid sequence coding for a signal peptide of MCP-1, as the coding region coding for an effector molecule the coding region coding for Nano luciferase, and as the 3' non-translated region the 3' UTR of Hsp70.

Recombinant nucleic acid construct PAN45 comprises as the 5' non-translated region the 5' UTR of Hsp70m5, as the nucleic acid sequence coding for a signal peptide the nucleic acid sequence coding for a signal peptide of MCP-1, as the coding region coding for an effector molecule the coding region coding for Nano luciferase, and as the 3' non-translated region the 3' UTR of von Willebrand Factor (vWF).

Recombinant nucleic acid construct PAN46 comprises as the 5' non-translated region the 5' UTR of E-selectin, as the nucleic acid sequence coding for a signal peptide the nucleic acid sequence coding for a signal peptide of IL-6, as the coding region coding for an effector molecule the coding region coding for Nano luciferase, and as the 3' non-translated region the 3' UTR of von Willebrand Factor (vWF).

Recombinant nucleic acid construct PAN47 comprises as the 5' non-translated region the 5' UTR of ICAM1, as the nucleic acid sequence coding for a signal peptide the nucleic acid sequence coding for a signal peptide of IL-6, as the coding region coding for an effector molecule the coding region coding for Nano luciferase, and as the 3' non-translated region the 3' UTR of von Willebrand Factor (vWF).

Recombinant nucleic acid construct PAN48 comprises as the 5' non-translated region the 5' UTR of IL-6, as the nucleic acid sequence coding for a signal peptide the nucleic acid sequence coding for a signal peptide of IL-6, as the coding region coding for an effector molecule the coding region coding for Nano luciferase, and as the 3' non-translated region the 3' UTR of IL-6).

Recombinant nucleic acid construct PAN49 comprises as the 5' non-translated region the 5' UTR of von Willebrand Factor (vWF), as the nucleic acid sequence coding for a signal peptide the nucleic acid sequence coding for a signal peptide of von Willebrand Factor (vWF), as the coding region coding for an effector molecule the coding region coding for Nano luciferase, and as the 3' non-translated region the 3' UTR of von Willebrand Factor (vWF).

Figure 3:
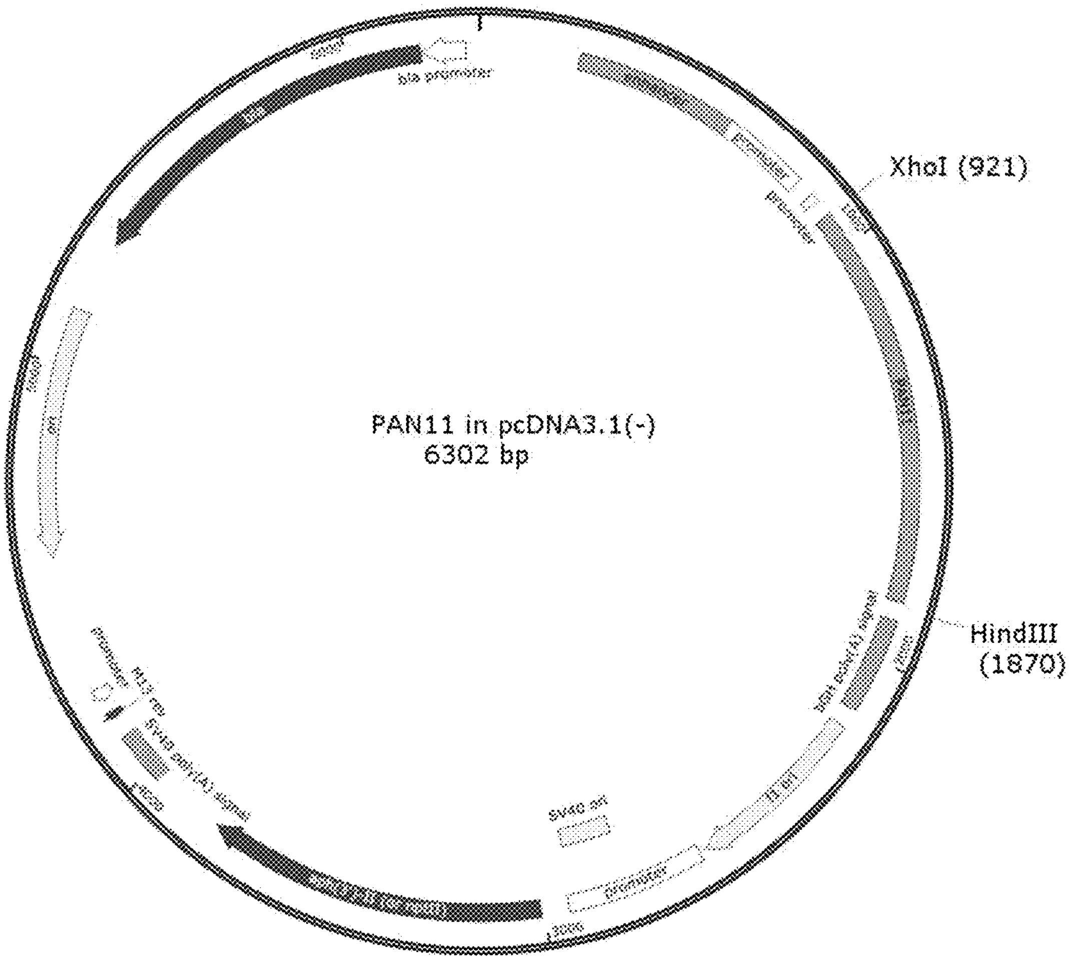
FIG. 3 is a restriction map of plasmid pcDNA3.1(-) containing construct PAN11.

FIG. 3 shows a restriction map of a plasmid pcDNA3.1(-) used as an illustrative example for a plasmid for the expression of an exemplary recombinant nucleic acid construct of the present invention, whereby such exemplary recombinant nucleic acid construct is construct PAN 11; restriction sites XhoI/HindIII are shown.

Figure 4:
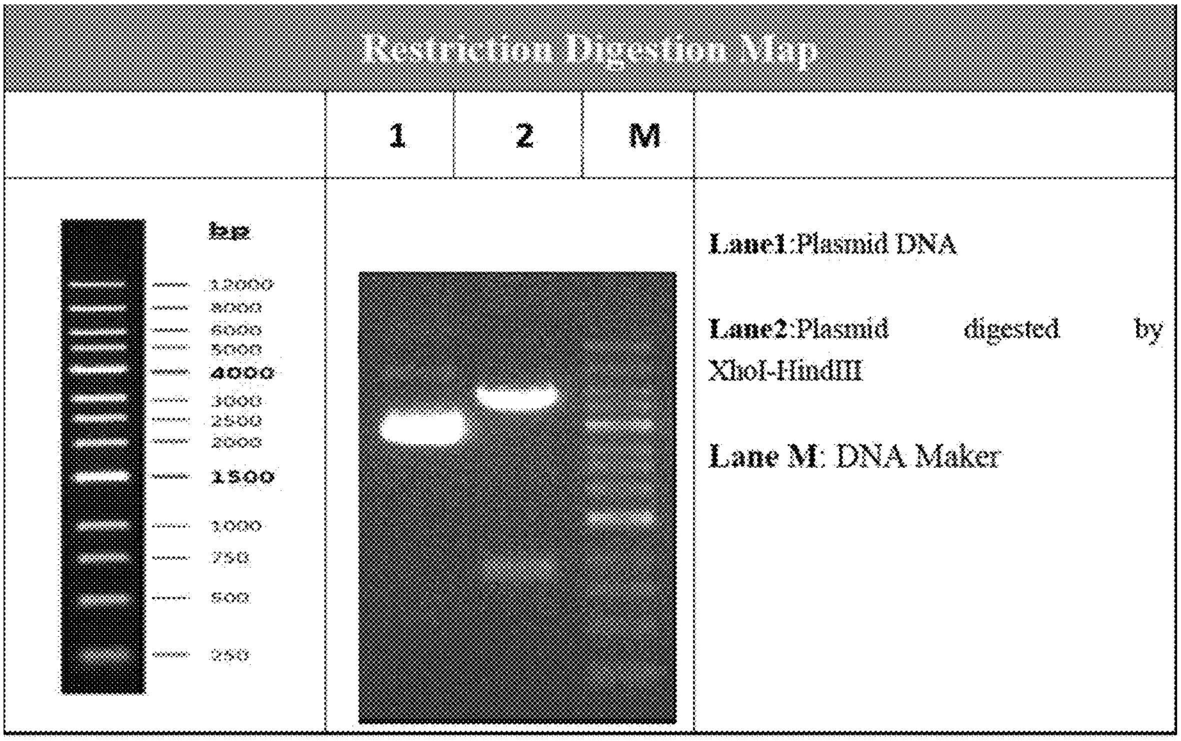
FIG. 4 is a restriction digest map of plasmid pdDNA3.1(-) of FIG. 3.

FIG. 4 shows a restriction digestion map of the PAN11 expressing pcDNA3.1-plasmid of FIG. 3; the insert represents PAN11 sequence with engineered 5' and 3' UTR, signal sequence and the coding region coding for Nano-Luciferase.

Figure 5:
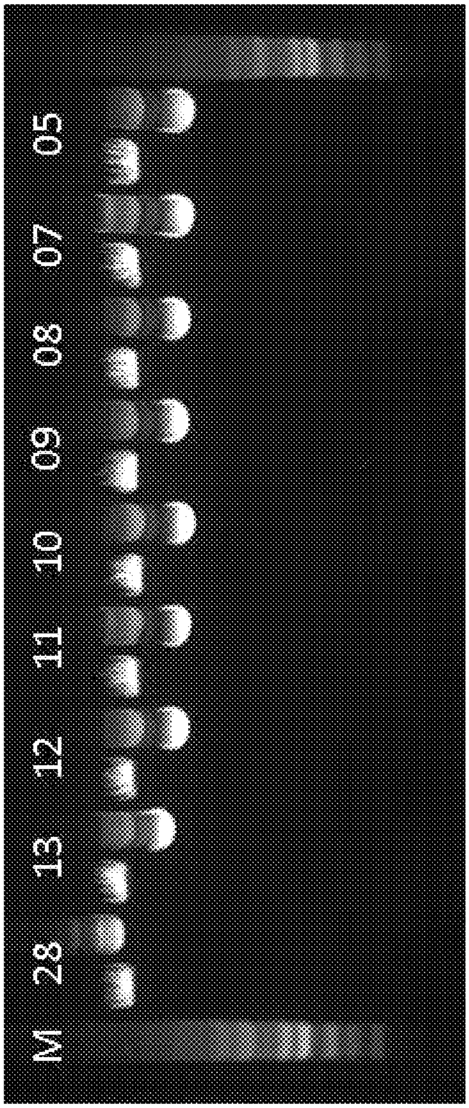
FIG. 5 is an 1% agarose gel stained with EtBr showing the non-linearized (uncut, supercoiled, right lanes) and linearization product (left lanes) of pcDNA3.1(-) plasmids containing constructs PAN28 ("28"), PAN13 ("13"), PAN12 ("12"), PAN11 ("11"), PAN10 ("10"), PAN09 ("09"), PAN08 ("08"), PAN07 ("07") and PAN05 ("05") upon BamHI restriction.

FIG. 5 is an 1% agarose gel stained with EtBr showing the non-linearized (uncut, supercoiled, right lanes) and linearization product (left lanes) of pcDNA3.1(-) plasmids upon BamHI restriction of the constructs PAN28 ("28"), PAN13 ("13"), PAN12 ("12"), PAN11 ("11"), PAN10 ("10"), PAN09 ("09"), PAN08 ("08"), PAN07 ("07") and PAN05 ("05").

Figure 6:
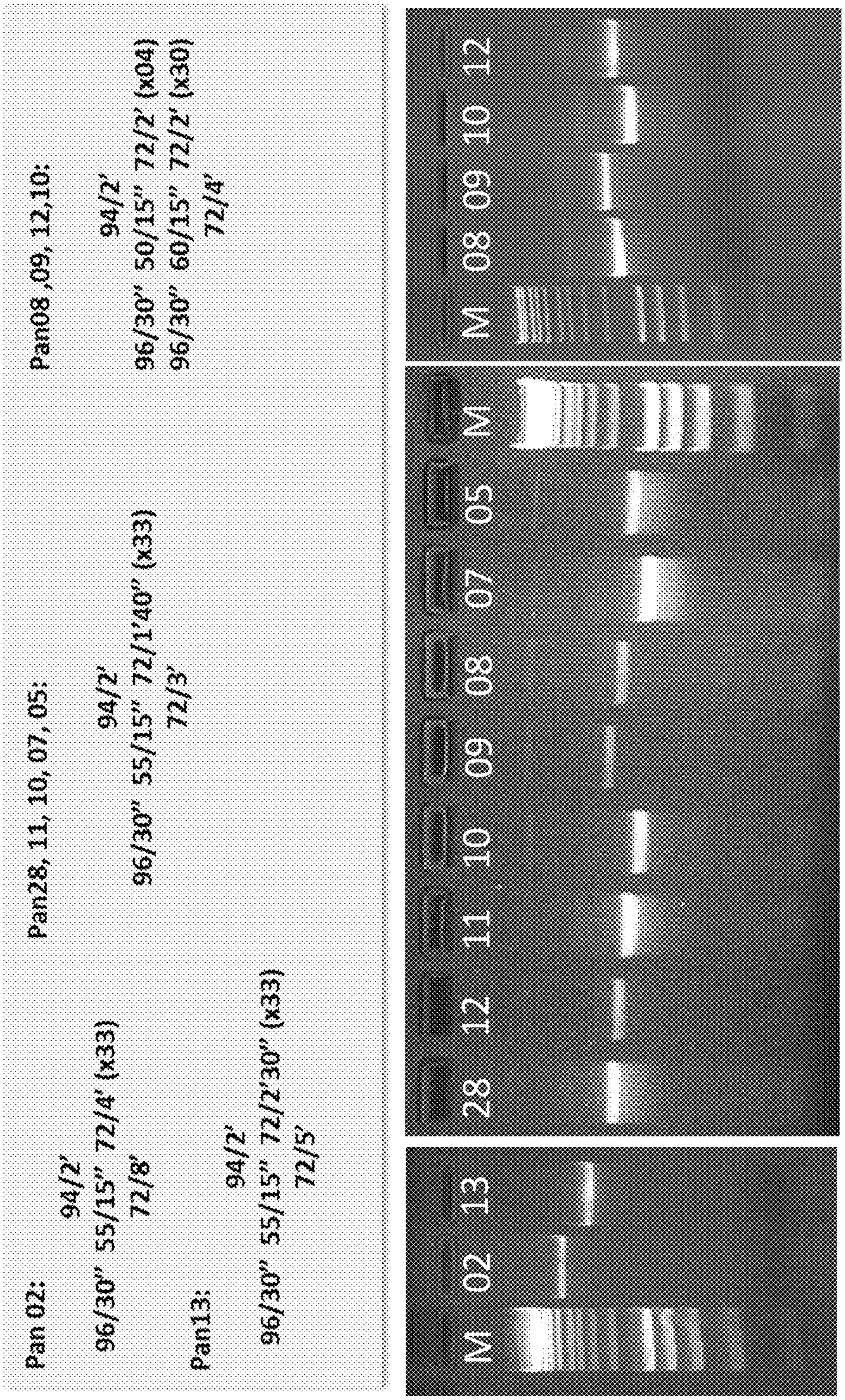
FIG. 6 shows 1% agarose gels stained with EtBr showing PCR products of Poly-A tailing PCRs for the addition of 120 nt of Poly-A tail.

FIG. 6 shows 1% agarose gels stained with EtBr showing PCR products of Poly-A tailing PCRs for the addition of 120 nt of Poly-A tail by 120 nt long poly-T 3' primer flanking the different recombinant nucleic acid constructs. On top are the optimized PCR conditions for the indicated recombinant nucleic acid constructs. For example, for Pan02 the conditions are as follows: denaturation for 2 minutes at 94° C. 33 cycles of 30 seconds at 96° C., 15 seconds at 55° C. and 4 minutes at 72° C. Final extension for 8 minutes at 72° C.

Figure 8:
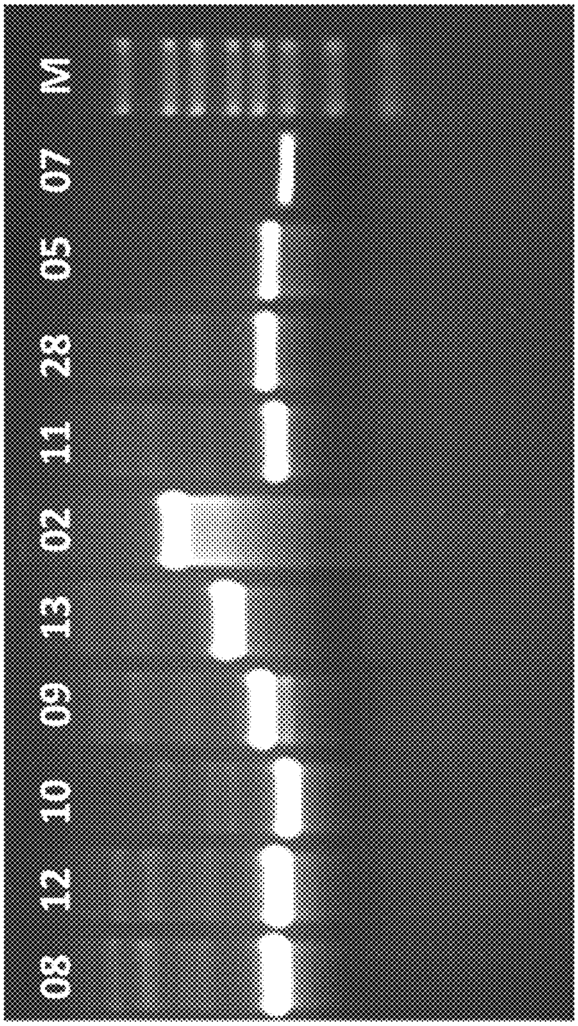
FIG. 8 is an image of a non-denaturing agarose gel after EtBr staining showing the in vitro mRNA transcripts of various construct.
Figure 9B:
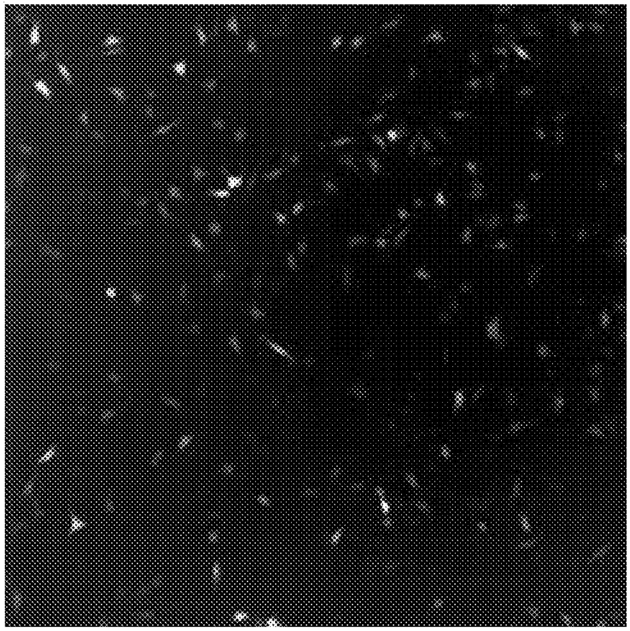
FIGS. 9A and 9B are photographs of fluorescence microscopy 24 h post transfection of HeLa cells transfected with 0.5 μg (FIG. 9A) and 0.1 μg (FIG. 9B) of a commercially, enhanced mRNA version of the producing green fluorescent protein (TriLINK Biotechnology).
Figure 9A:
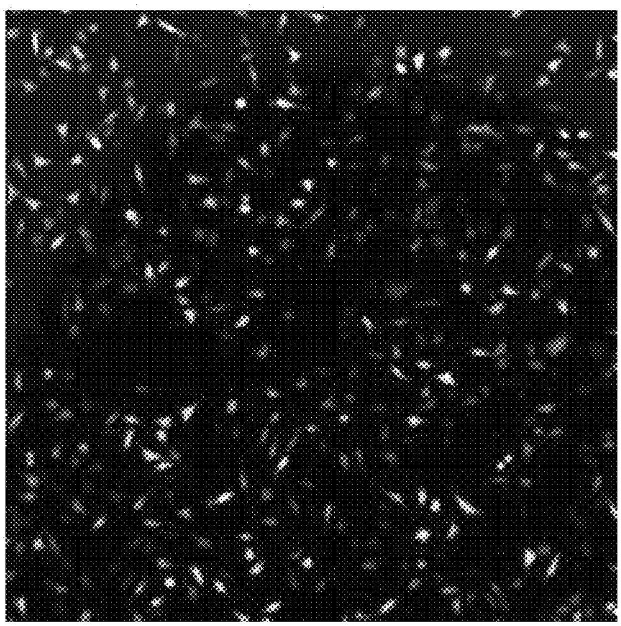
Figure 10:
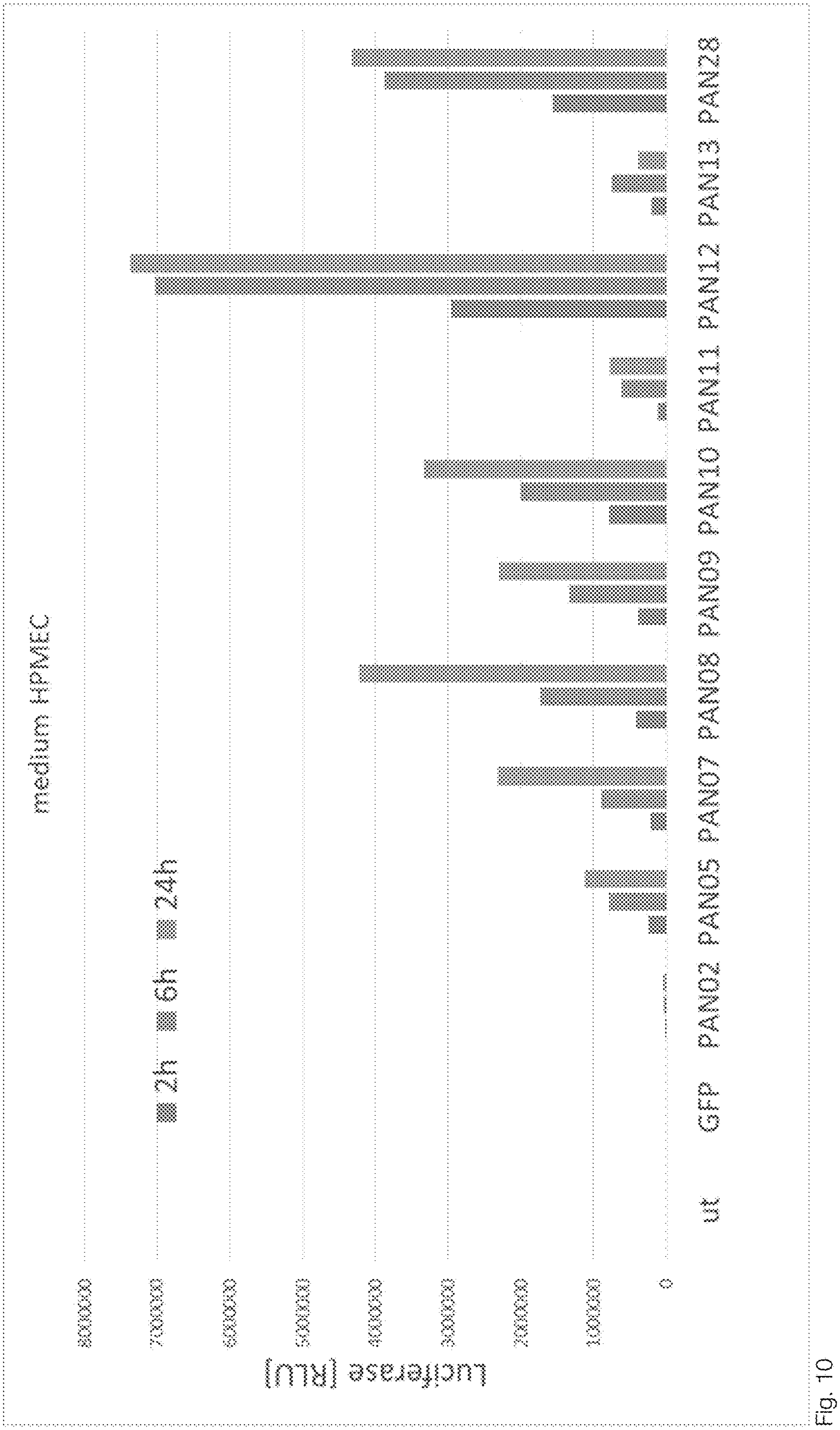
FIG. 10 is a bar diagram showing expression of luciferase, indicated as RLU (relative light units) of luciferase in medium, by the indicated recombinant nucleic acid constructs in HPMEC where luciferase is used as the effector molecule after 2 hours (left column), 6 hours (middle column) and 24 hours (right column) post transfection.
Figure 11:
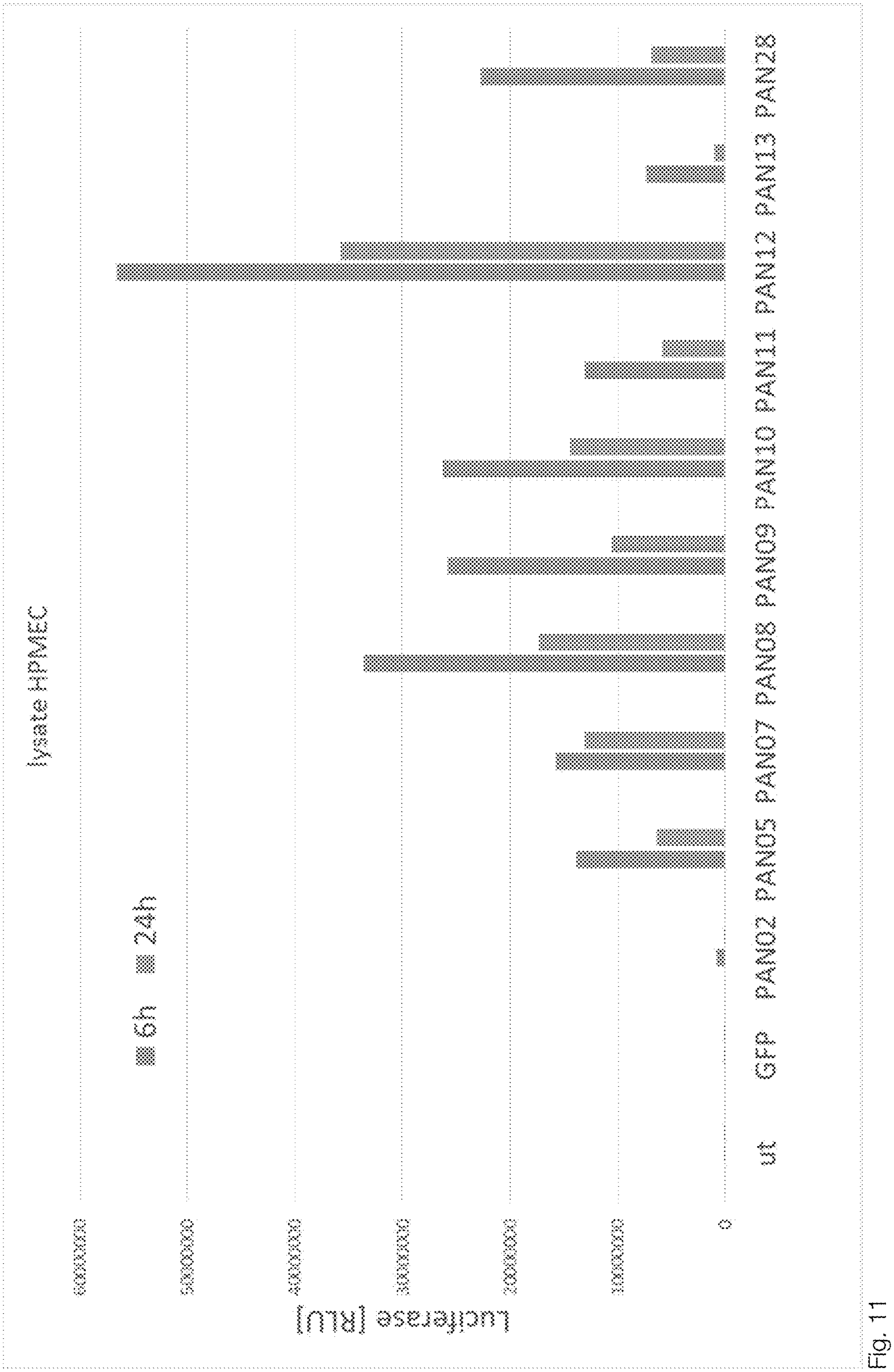
FIG. 11 is a bar diagram showing expression of luciferase, indicated as RLU (relative light units) of luciferase in whole cell lysates of HPMEC, by the indicated recombinant nucleic acid constructs in HPMEC, where luciferase is used as the effector molecule after, 6 hours (left column) and 24 hours (right column) post transfection.
Figure 12:
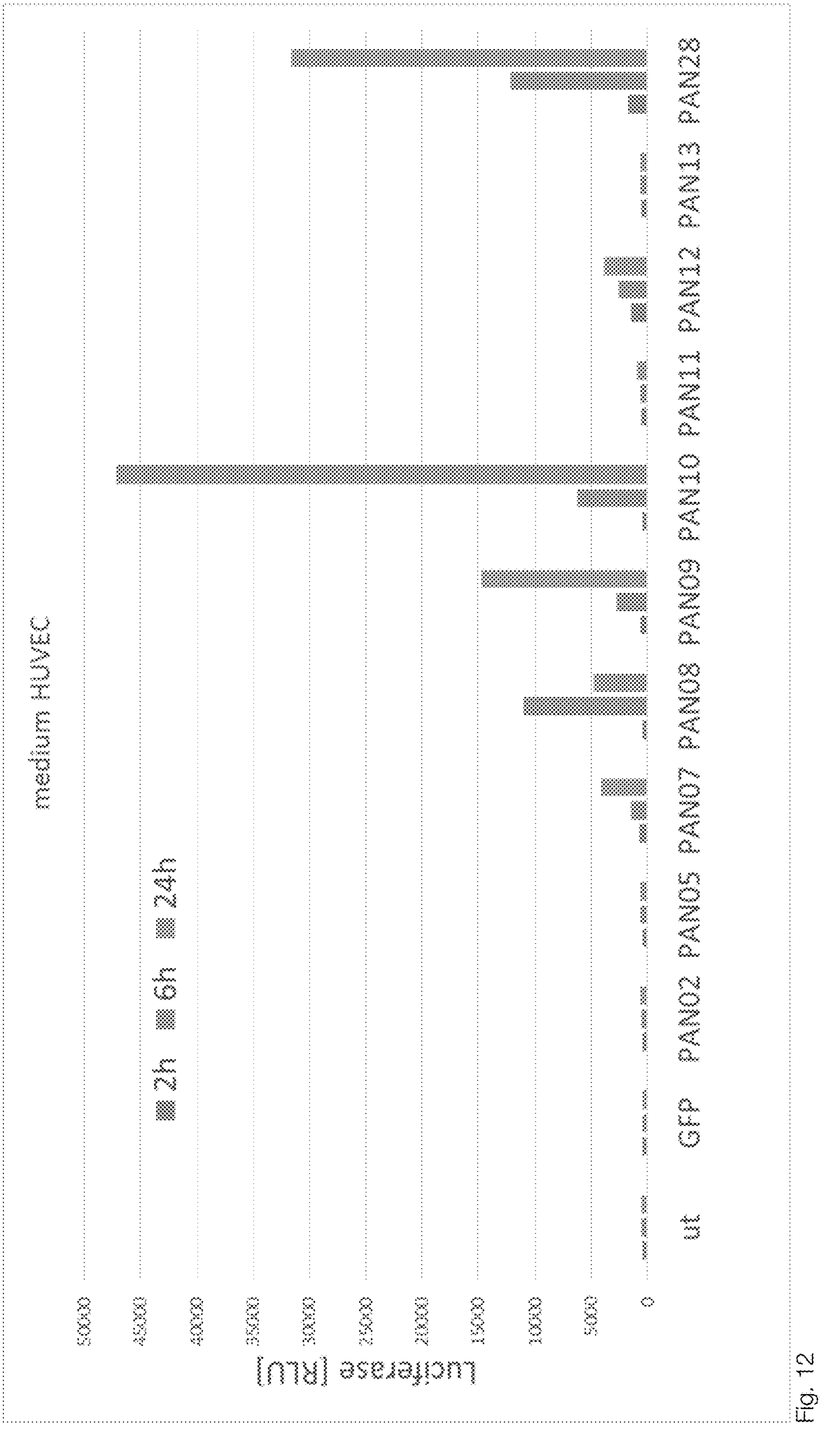
FIG. 12 is a bar diagram showing expression of luciferase, indicated as RLU (relative light units) of luciferase in medium, by the indicated recombinant nucleic acid constructs in HUVEC where luciferase is used as the effector molecule after 2 hours (left column), 6 hours (middle column) and 24 hours (right column) post transfection.
Figure 13:
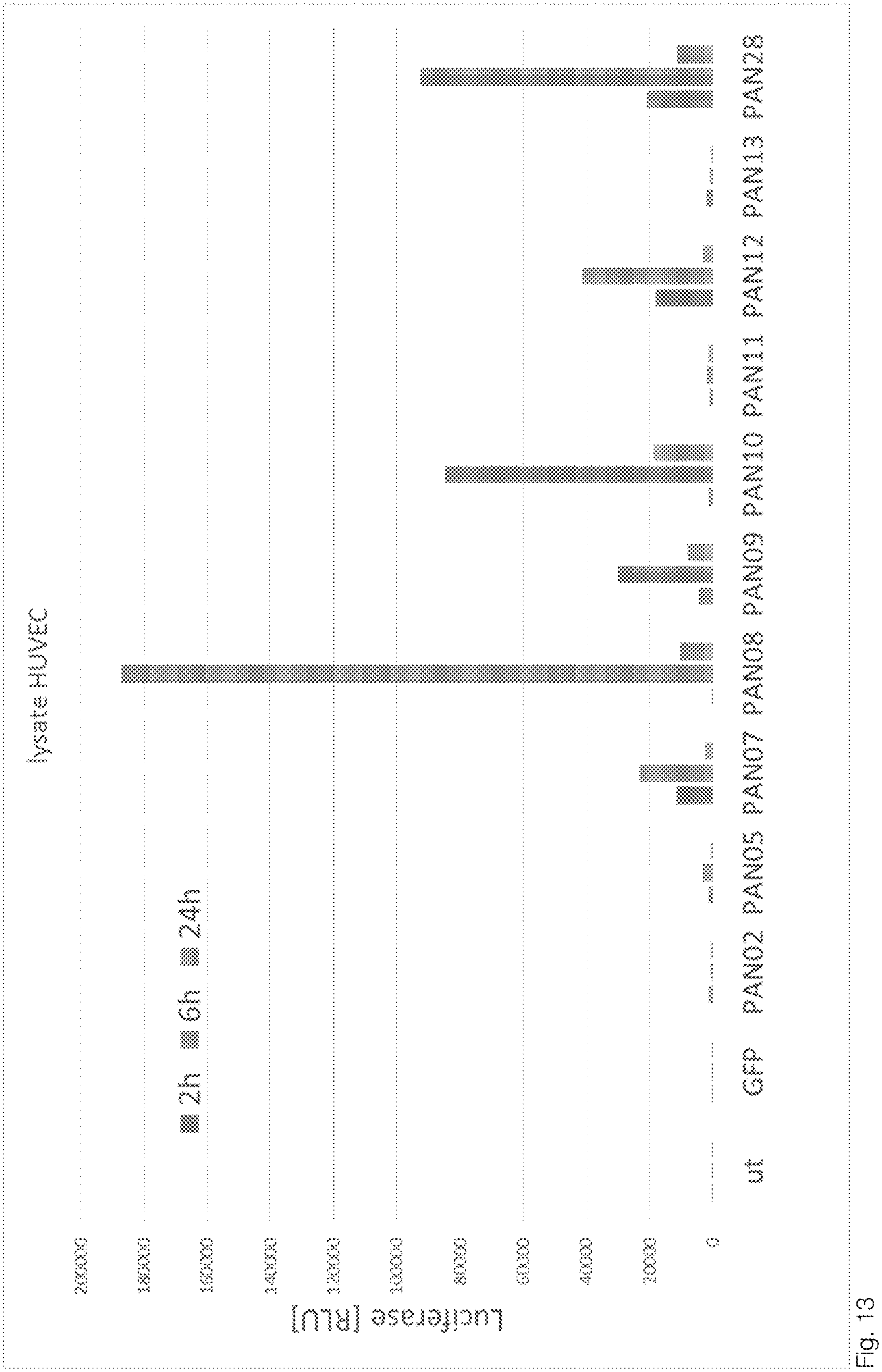
FIG. 13 is a bar diagram showing expression of luciferase, indicated as RLU (relative light units)] of luciferase in whole cell lysates of HUVEC, by the indicated recombinant nucleic acid constructs after lysis of HUVEC, where luciferase is used as the effector molecule after 2 hours (left column), 6 hours (middle column) and 24 hours (right column) post transfection.
Figure 14:
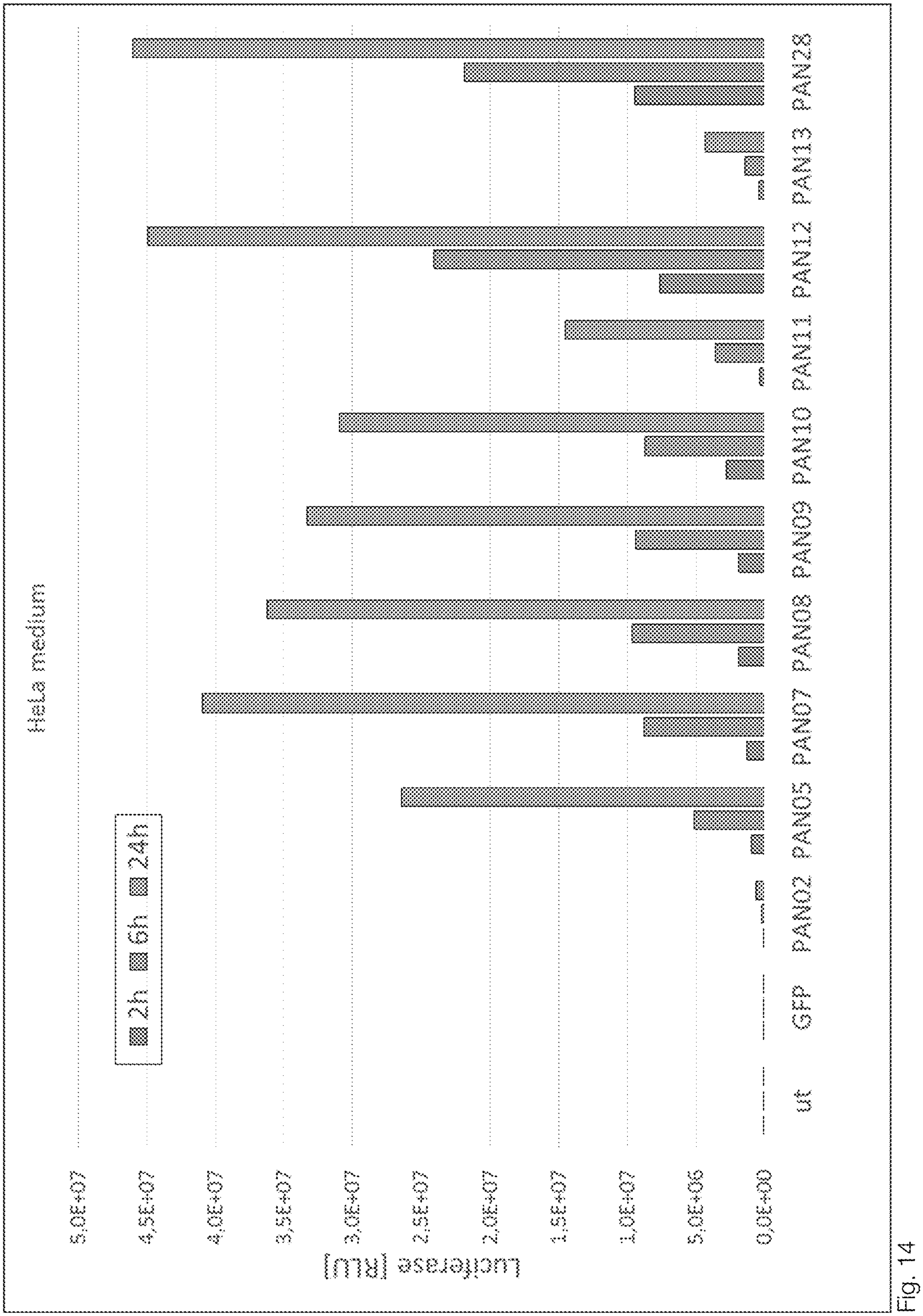
FIG. 14 is a bar diagram showing expression of luciferase, indicated as RLU [(relative light units) of luciferase in medium, by the indicated recombinant nucleic acid constructs in HeLa cells where luciferase is used as the effector molecule after 2 hours (left column), 6 hours (middle column) and 24 hours (right column) post transfection.

FIG. 8 is an image of a 1% non-denaturing agarose gel stained with EtBr showing the in vitro transcribed mRNAs of constructs PAN28 ("28"), PAN13 ("13"), PAN12 ("12"), PAN11 ("11"), PAN10 ("10"), PAN09 ("09"), PAN08 ("08"), PAN07 ("07") and PAN05 ("05"). M: is a lane with a high range RiboRuler RNA ladder. From this FIG. 8 may be taken that the transcribed mRNAs were intact and, more specifically, were not degraded.

FIG. 24 shows the basic structure and nucleotide sequence of recombinant nucleic acid construct PAN01. PANI is an embodiment of the present invention comprising as the 5' non-translated region the 5' UTR of Ang1, as the nucleic acid sequence coding for a signal peptide the nucleic acid sequence coding for a signal peptide of Ang1, as the coding region coding for an effector molecule the coding region coding for Ang1, and as the 3' non-translated region the 3' UTR of Ang1.

FIG. 25 shows the basic structure and nucleotide sequence of recombinant nucleic acid construct PAN03. PAN03 is an embodiment of the present invention comprising as the 5' non-translated region the 5' UTR of Ang1, as the nucleic acid sequence coding for a signal peptide the nucleic acid sequence coding for a signal peptide of Ang1, as the coding region coding for an effector molecule the coding region coding for COMP-Ang1, and as the 3' non-translated region the 3' UTR of Ang1.

FIG. 26 shows the basic structure and nucleotide sequence of recombinant nucleic acid construct PAN04. PAN04 is an embodiment of the present invention comprising as the 5' non-translated region the 5' UTR of Ang2, as the nucleic acid sequence coding for a signal peptide the nucleic acid sequence coding for a signal peptide of Ang2, as the coding region coding for an effector molecule the coding region coding for Ang1, and as the 3' non-translated region the 3' UTR of von Willebrand Factor (vWF).

FIG. 27 shows the basic structure and nucleotide sequence of recombinant nucleic acid construct PAN06. PAN06 is an embodiment of the present invention comprising as the 5' non-translated region the 5' UTR of Ang2, as the nucleic acid sequence coding for a signal peptide the nucleic acid sequence coding for a signal peptide of Ang2, as the coding region coding for an effector molecule the coding region coding for COMP-Ang1, and as the 3' non-translated region the 3' UTR of von Willebrand Factor (vWF).

FIG. 28 shows the basic structure and nucleotide sequence of recombinant nucleic acid construct PAN36. PAN36 is an embodiment of the present invention comprising as the 5' non-translated region the 5' UTR of MCP-1, as the nucleic acid sequence coding for a signal peptide the nucleic acid sequence coding for a signal peptide of MCP-1, as the coding region coding for an effector molecule the coding region coding for Ang1, and as the 3' non-translated region the 3' UTR of MCP-1.

FIG. 67 shows recombinant nucleic acid construct PAN50 which is another embodiment of an mRNA of the present invention comprising as the 5' non-translated region the 5' UTR of MCP-1, as the nucleic acid sequence coding for a signal peptide the nucleic acid sequence coding for a signal peptide of IL-6, as the coding region coding for an effector molecule the coding region coding for Nano luciferase, and as the 3' non-translated region the 3' UTR of von Willebrand Factor (vWF).

FIG. 68 shows recombinant nucleic acid construct PAN51 which is another embodiment of an mRNA of the present invention comprising as the 5' non-translated region the 5' UTR of HSP70, as the nucleic acid sequence coding for a signal peptide the nucleic acid sequence coding for a signal peptide of IL-6, as the coding region coding for an effector molecule the coding region coding for Nano luciferase (NLuc), and as the 3' non-translated region the 3' UTR of von Willebrand Factor (vWF).

FIG. 69 shows recombinant nucleic acid construct PAN52 which is another embodiment of an mRNA of the present invention comprising as the 5' non-translated region the 5' UTR of MCP-1, as the nucleic acid sequence coding for a signal peptide the nucleic acid sequence coding for a signal peptide of MCP-1, as the coding region coding for an effector molecule the coding region coding for Ang1, and as the 3' non-translated region the 3' UTR of von Willebrand Factor (vWF).

FIG. 70 shows recombinant nucleic acid construct PAN53 which is another embodiment of an mRNA of the present invention comprising as the 5' non-translated region the 5' UTR of MCP-1, as the nucleic acid sequence coding for a signal peptide the nucleic acid sequence coding for a signal peptide of MCP-1, as the coding region coding for an effector molecule the coding region coding for hCOMP-Ang1, and as the 3' non-translated region the 3' UTR of von Willebrand Factor (vWF).

Figure 71B:
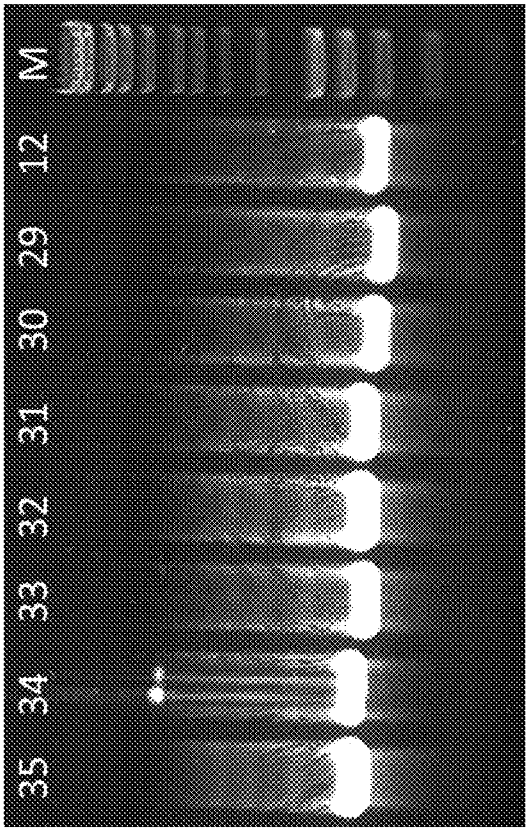
FIG. 71B is an image of a non-denaturing agarose gel after EtBr staining showing the in vitro mRNA transcripts of various construct.
Figure 71A:
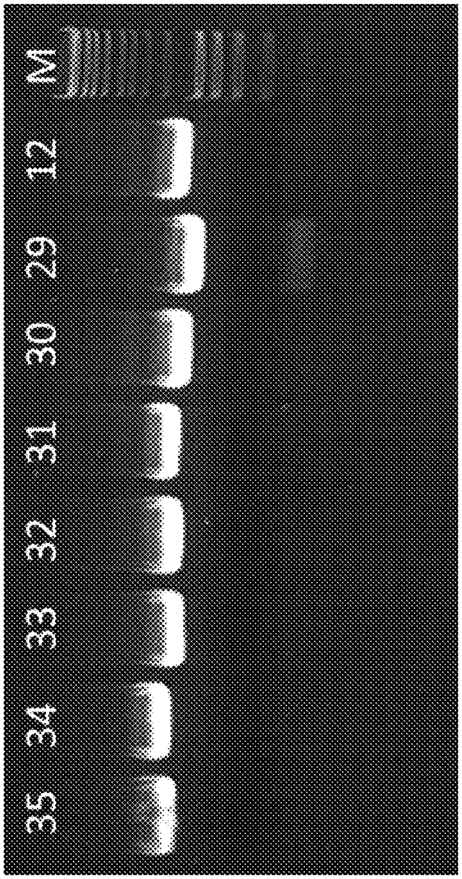
FIG. 71A is an image of a non-denaturing agarose gel after EtBr staining showing the tail-PCR products of various construct.
Figure 72:
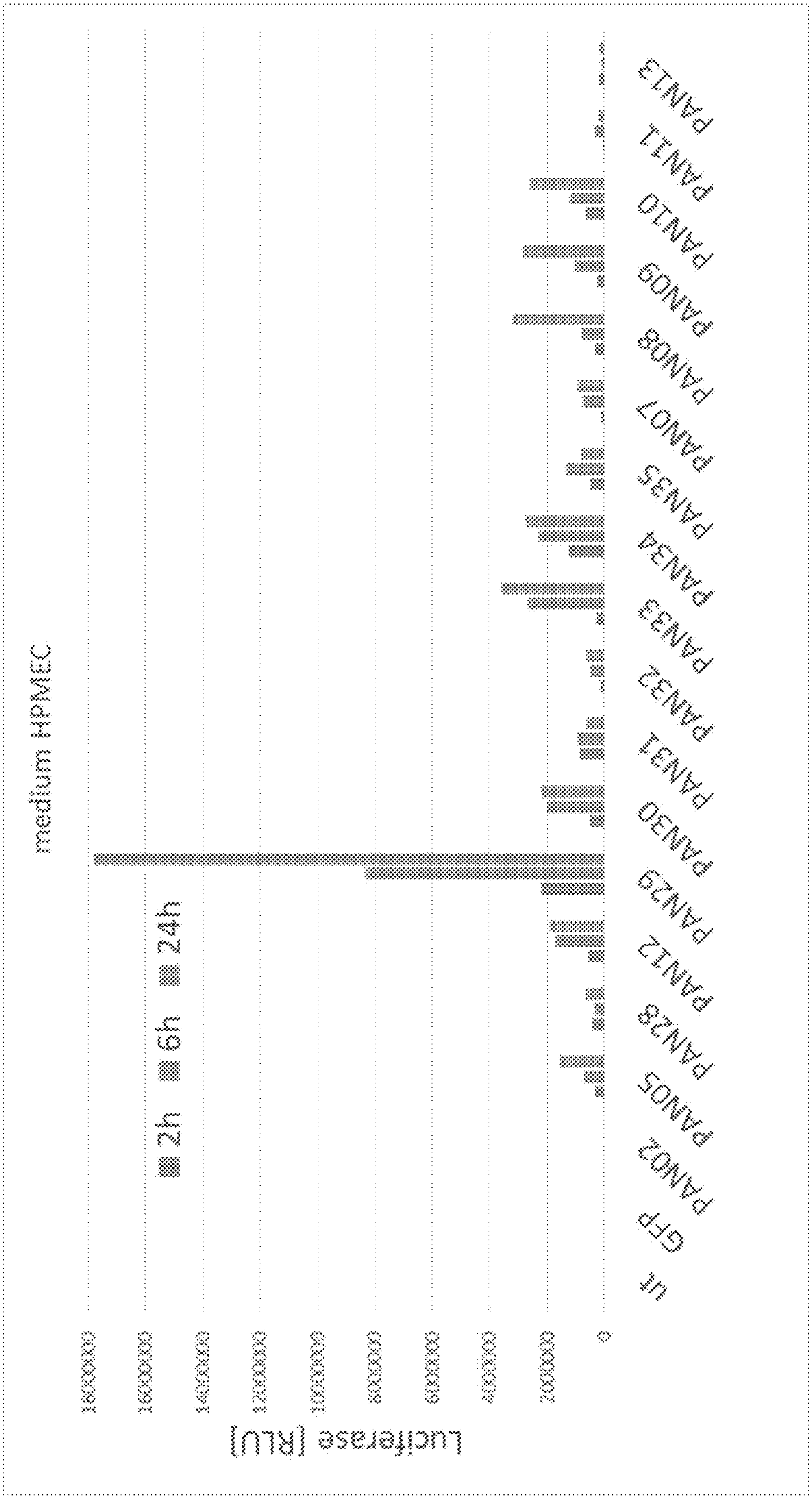
FIG. 72 is a bar diagram showing expression of luciferase, indicated as RLU (relative light units) of luciferase in medium, by the indicated recombinant nucleic acid constructs in HPMEC where luciferase is used as the effector molecule after 2 hours (left column), 6 hours (middle column) and 24 hours (right column) post transfection.
Figure 73:
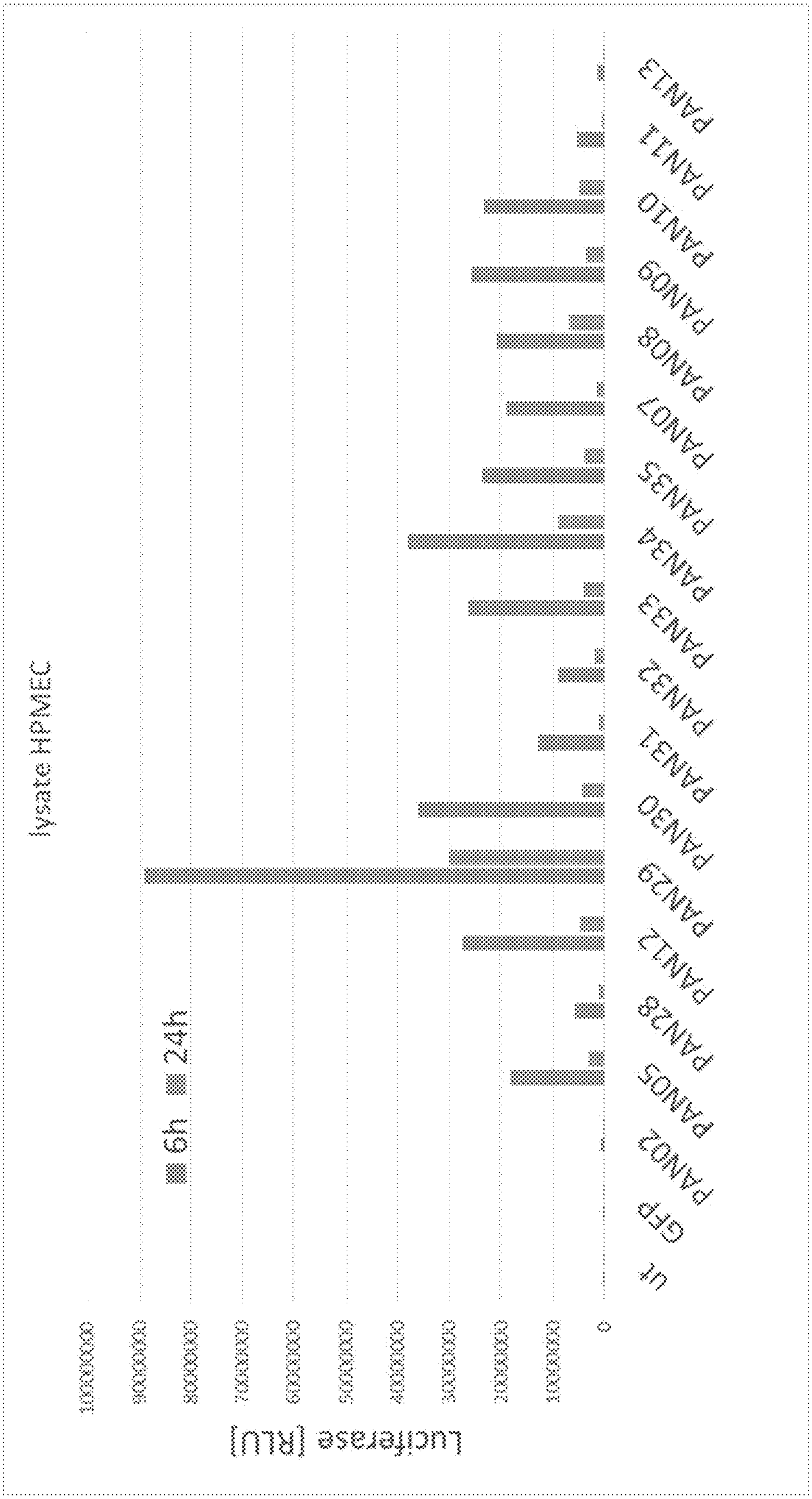
FIG. 73 is a bar diagram showing expression of luciferase, indicated as RLU (relative light units) of luciferase in whole cell lysates of HPMEC, by the indicated recombinant nucleic acid constructs in HPMEC, where luciferase is used as the effector molecule after 6 hours (left column) and 24 hours (right column) post transfection.
Figure 74A:
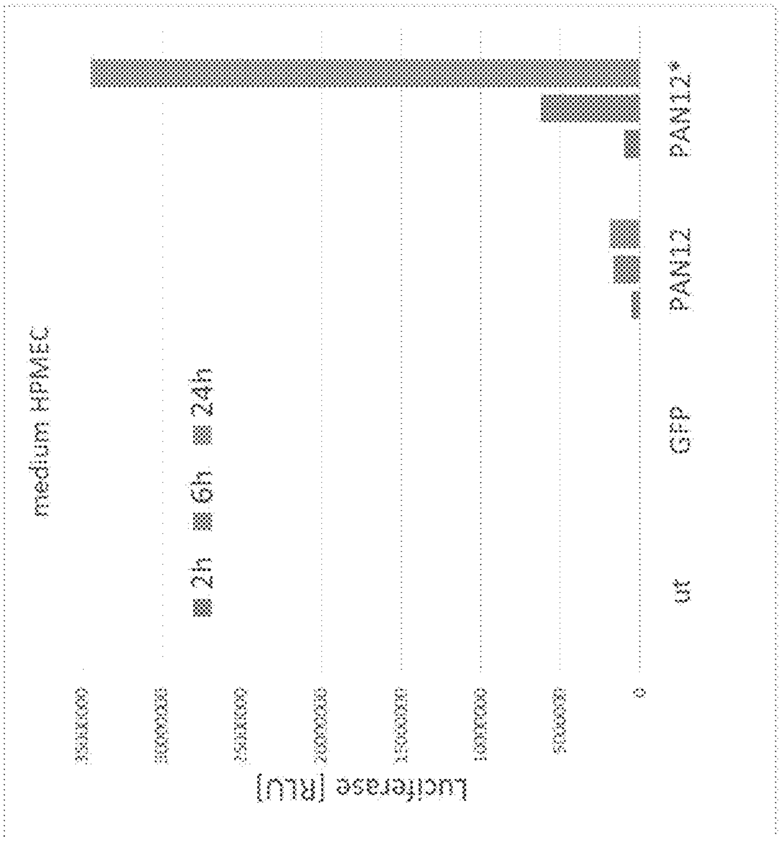
FIG. 74A (left) is a bar diagram showing expression of luciferase, indicated as RLU (relative light units) of luciferase in medium, by the indicated recombinant nucleic acid constructs in HPMEC (transfected with GFP mRNA, PAN12 mRNA and PAN12* mRNA) where luciferase is used as the effector molecule after 2 hours (left column), 6 hours (middle column) and 24 hours (right column) post transfection. In PAN12* 100% of uridine and 100% cytidine nucleotides are replaced by pseudo-uridine and 5-methyl-cytidine, respectively.
Figure 74B:
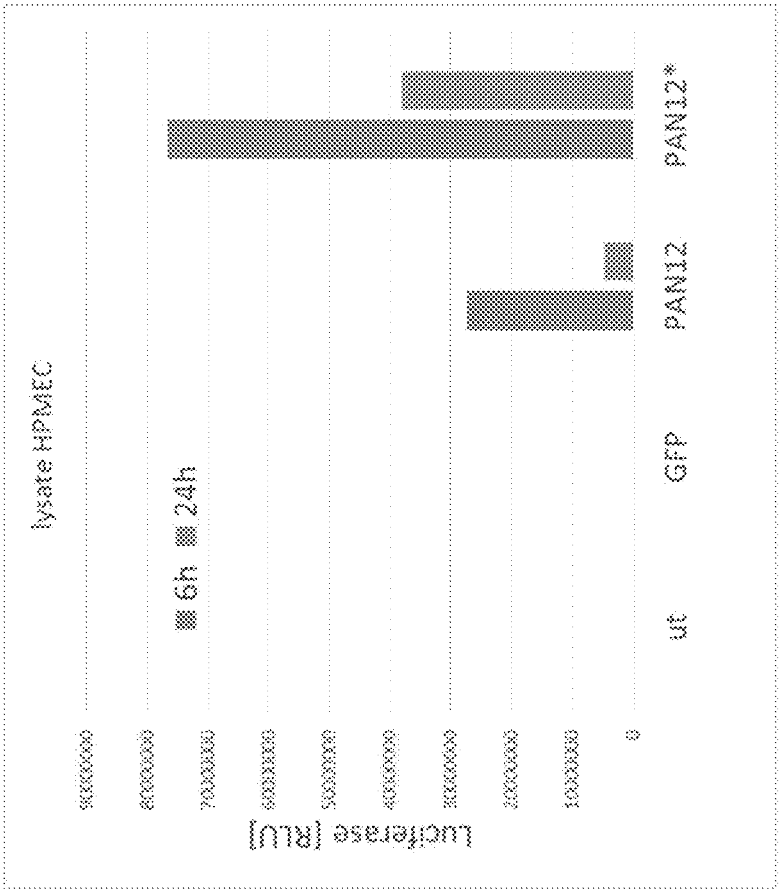
FIG. 74B (right) is a bar diagram showing expression of luciferase, indicated as RLU (relative light units) of luciferase in cell lysates, by the indicated recombinant nucleic acid constructs in HPMEC (transfected with GFP mRNA, PAN12 mRNA and PAN12* mRNA) where luciferase is used as the effector molecule after 6 hours (left column) and 24 hours (right column) post transfection. In PAN12* 100% of uridine and 100% cytidine nucleotides are replaced by pseudo-uridine and 5-methyl-cytidine, respectively.
Figure 75:
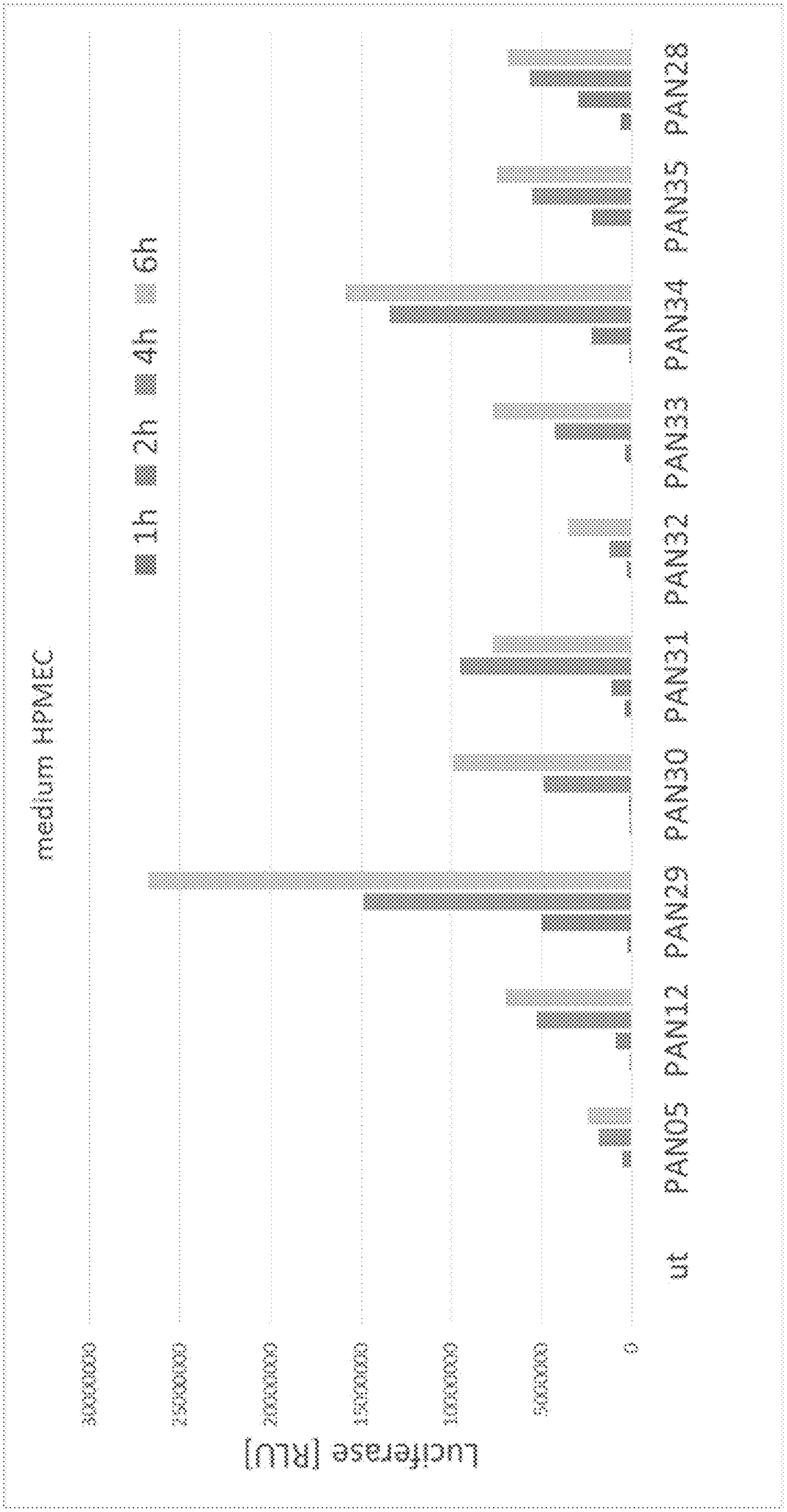
FIG. 75 is a bar diagram showing expression of luciferase, indicated as RLU (relative light units) of luciferase in medium, by the indicated recombinant nucleic acid constructs in HPMEC where luciferase is used as the effector molecule after 1 hour, 2 hours, 4 hours and 24 hours post transfection (from left to right, with 1 hour results being shown to the utmost left side and 24 hours result being shown to the utmost right side).
Figure 76:
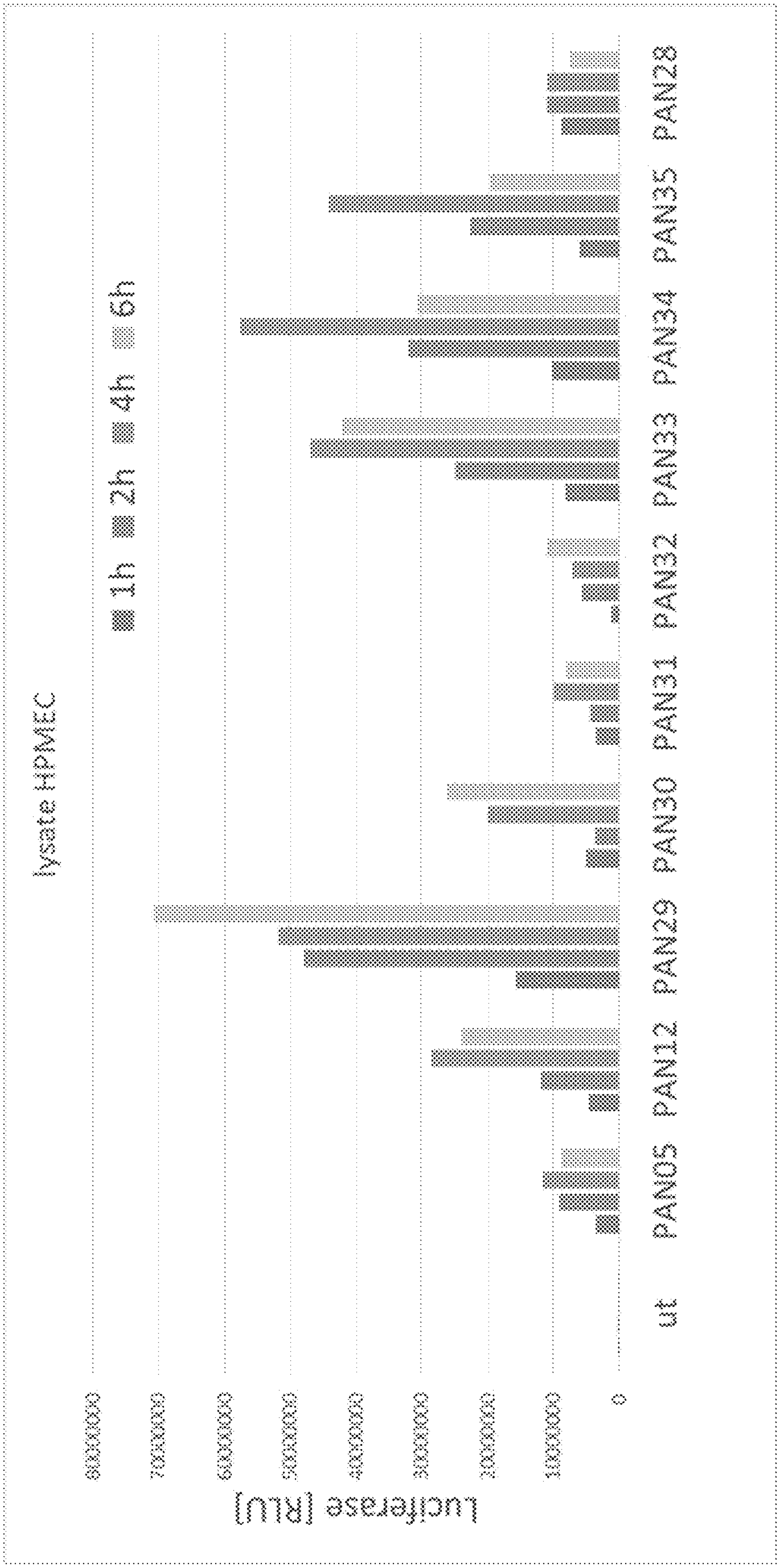
FIG. 76 is a bar diagram showing expression of luciferase, indicated as RLU (relative light units) of luciferase in whole cell lysates of HPMEC, by the indicated recombinant nucleic acid constructs in HPMEC, where luciferase is used as the effector molecule after 1 hour, 2 hours, 4 hours and 24 hours post transfection (from left to right, with 1 hour results being shown to the utmost left side and 24 hours result being shown to the utmost right side).
Figure 77B:
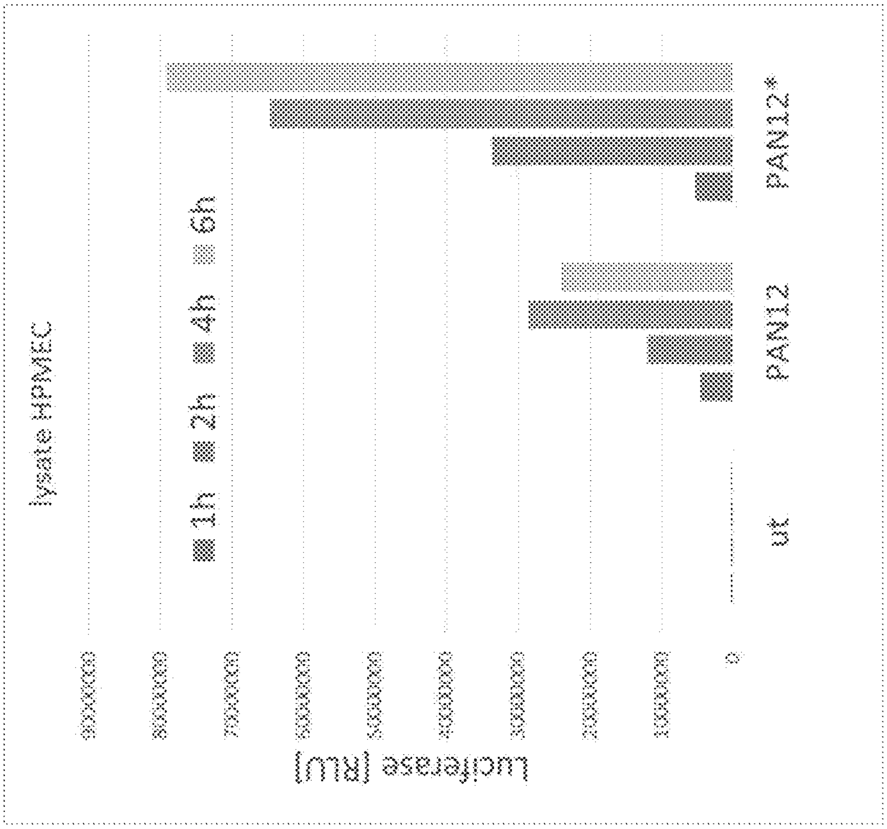
FIG. 77B (right) is a bar diagram showing expression of luciferase, indicated as RLU (relative light units) of luciferase in cell lysates, by the indicated recombinant nucleic acid constructs in HPMEC (transfected with GFP mRNA, PAN12 mRNA and PAN12* mRNA) where luciferase is used as the effector molecule after 1 hour, 2 hours, 4 hours and 24 hours post transfection (from left to right, with 1 hour results being shown to the utmost left side and 24 hours result being shown to the utmost right side). In PAN12* 100% of uridine and 100% cytidine nucleotides are replaced by pseudo-uridine and 5-methyl-cytidine, respectively.
Figure 77A:
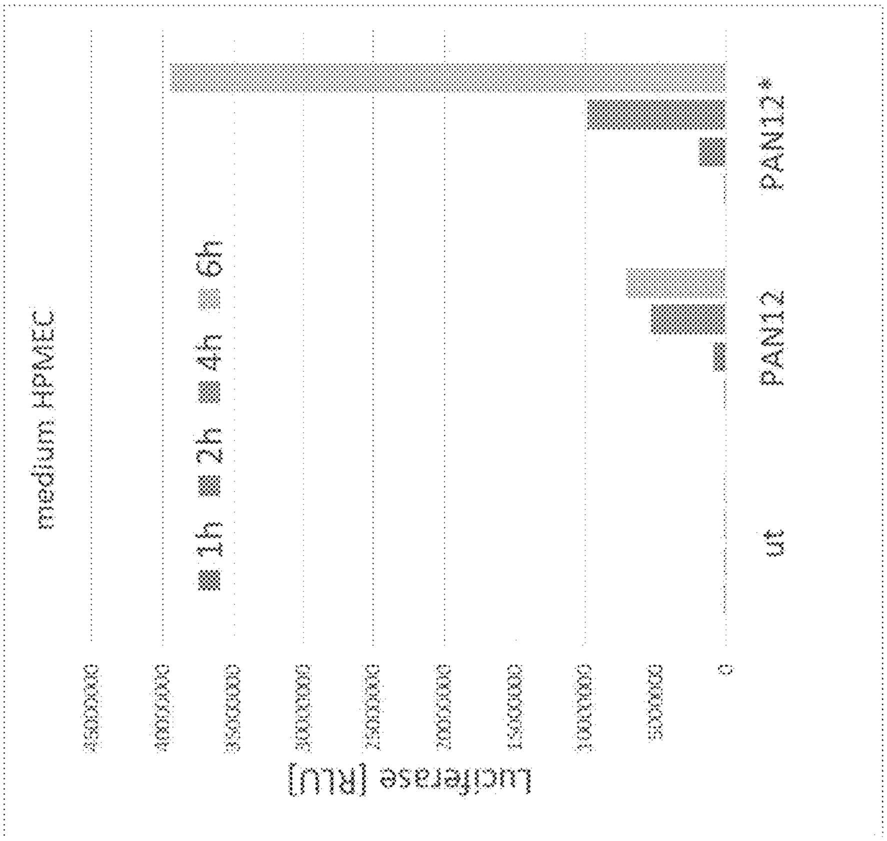
FIG. 77A (left) is a bar diagram showing expression of luciferase, indicated as RLU (relative light units) of luciferase in medium, by the indicated recombinant nucleic acid constructs in HPMEC (transfected with GFP mRNA, PAN12 mRNA and PAN12* mRNA) where luciferase is used as the effector molecule after 1 hour, 2 hours, 4 hours and 24 hours post transfection (from left to right, with 1 hour results being shown to the utmost left side and 24 hours result being shown to the utmost right side). In PAN12* 100% of uridine and 100% cytidine nucleotides are replaced by pseudo-uridine and 5-methyl-cytidine, respectively.
Figure 78:
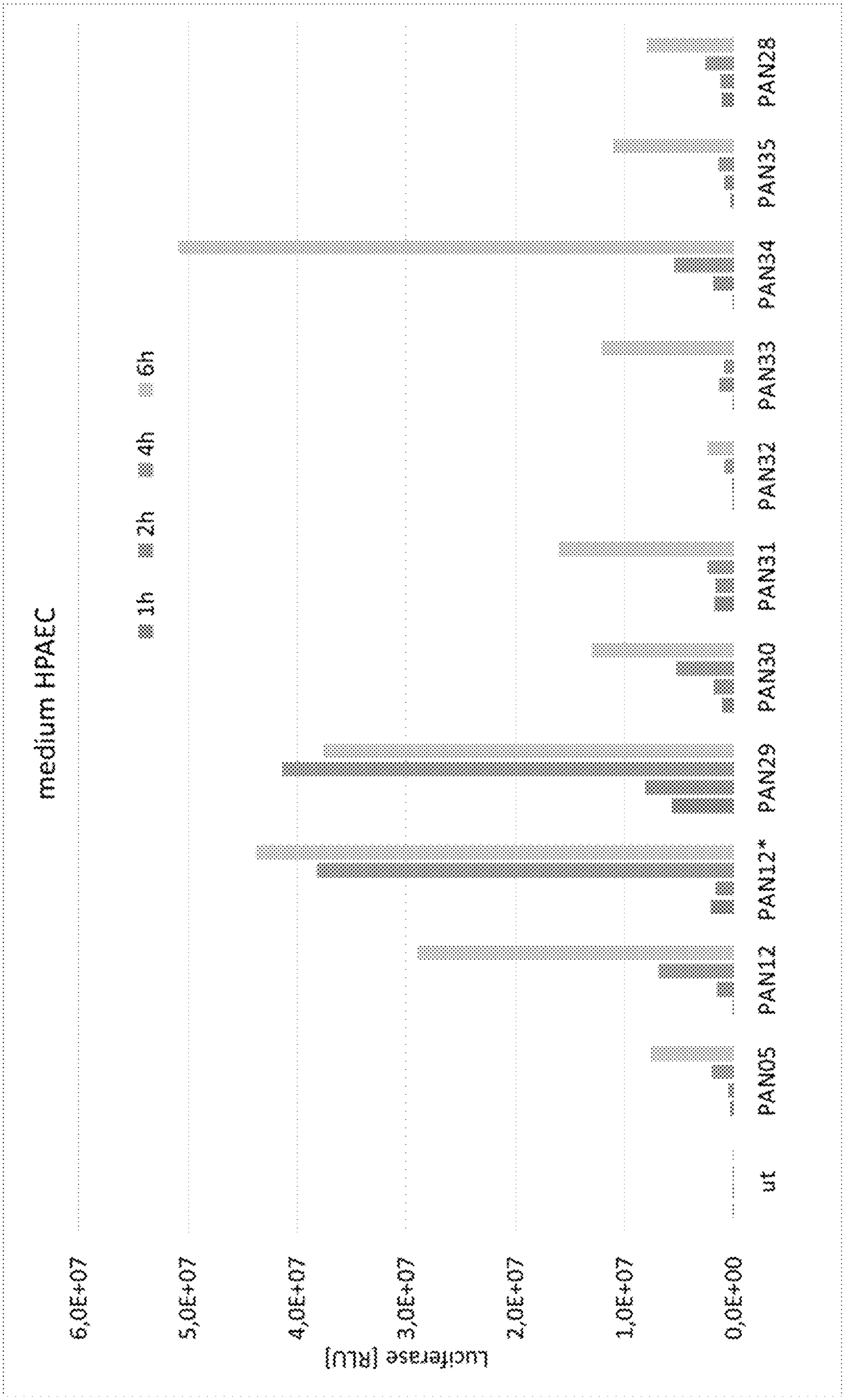
FIG. 78 is a bar diagram showing expression of luciferase, indicated as RLU (relative light units) of luciferase in medium, by the indicated recombinant nucleic acid constructs in HPAEC where luciferase is used as the effector molecule after 1 hour, 2 hours, 4 hours and 24 hours post transfection (from left to right, with 1 hour results being shown to the utmost left side and 24 hours result being shown to the utmost right side).
Figure 79:
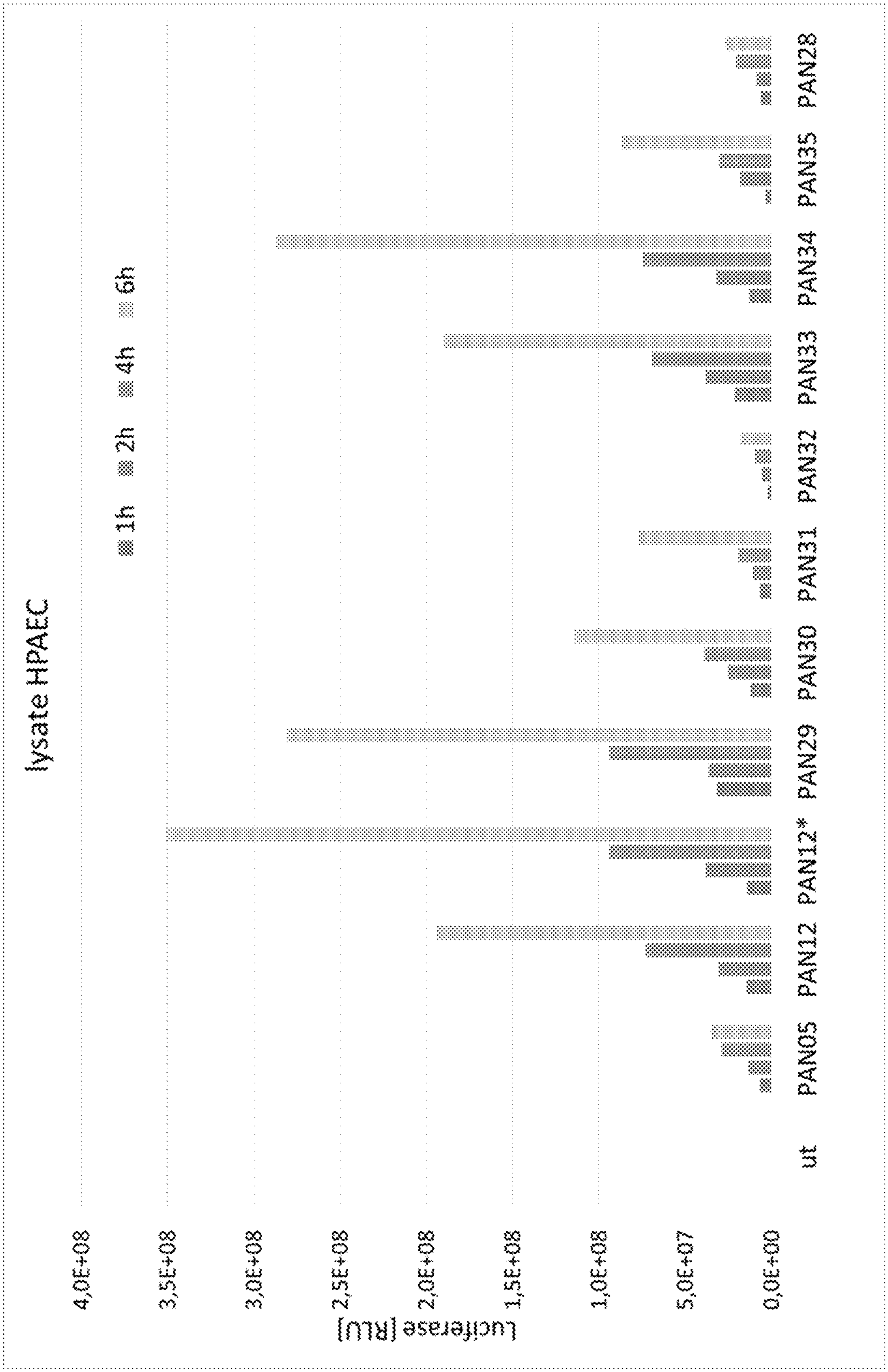
FIG. 79 is a bar diagram showing expression of luciferase, indicated as RLU (relative light units) of luciferase in whole cell lysates of HPAEC, by the indicated recombinant nucleic acid constructs in HPAEC, where luciferase is used as the effector molecule after 1 hour, 2 hours, 4 hours and 24 hours post transfection (from left to right, with 1 hour results being shown to the utmost left side and 24 hours result being shown to the utmost right side).
Figure 80:
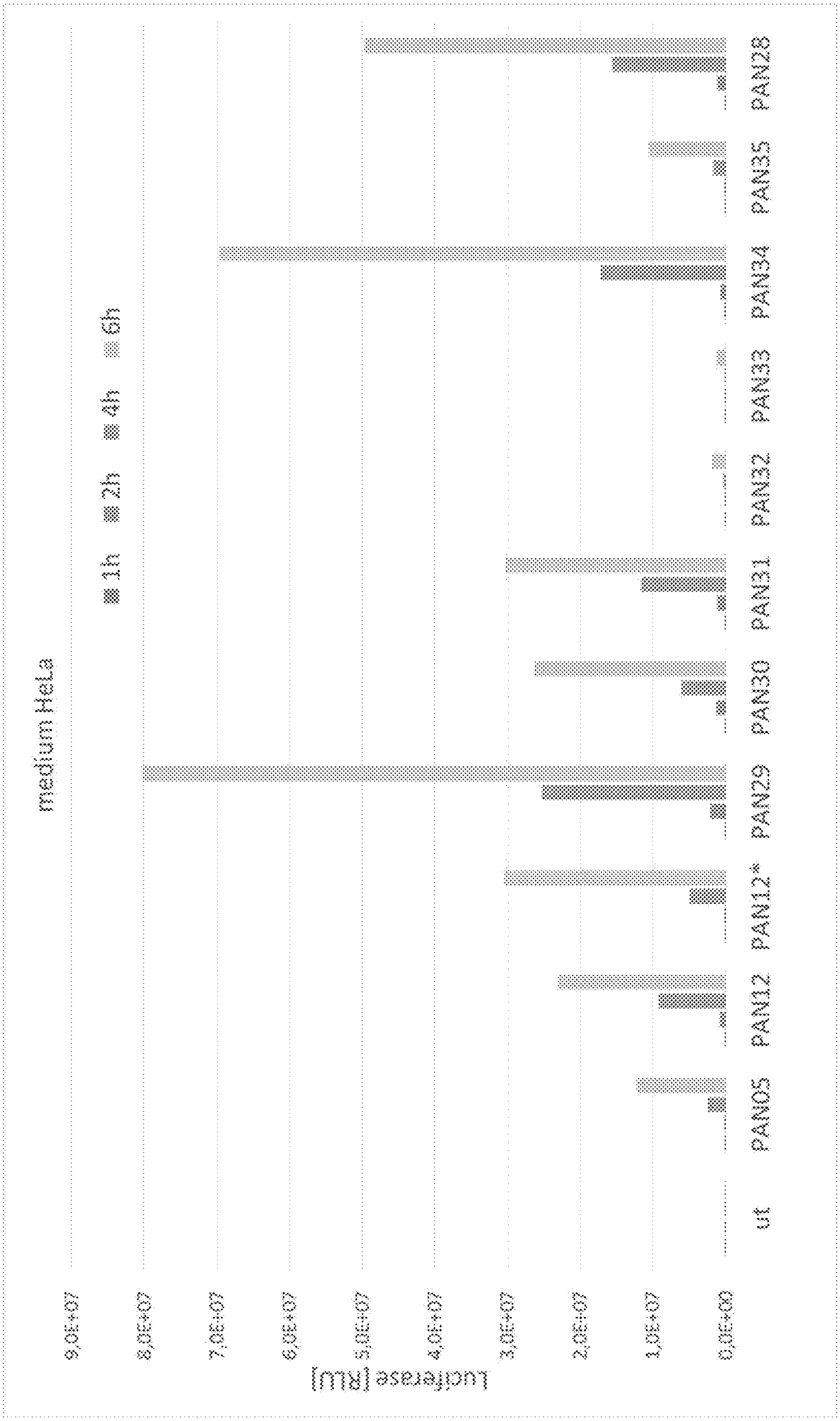
FIG. 80 is a bar diagram showing expression of luciferase, indicated as RLU (relative light units) of luciferase in medium, by the indicated recombinant nucleic acid constructs in HeLa cells where luciferase is used as the effector molecule after 1 hour, 2 hours, 4 hours and 24 hours post transfection (from left to right, with 1 hour results being shown to the utmost left side and 24 hours result being shown to the utmost right side).
Figure 81:
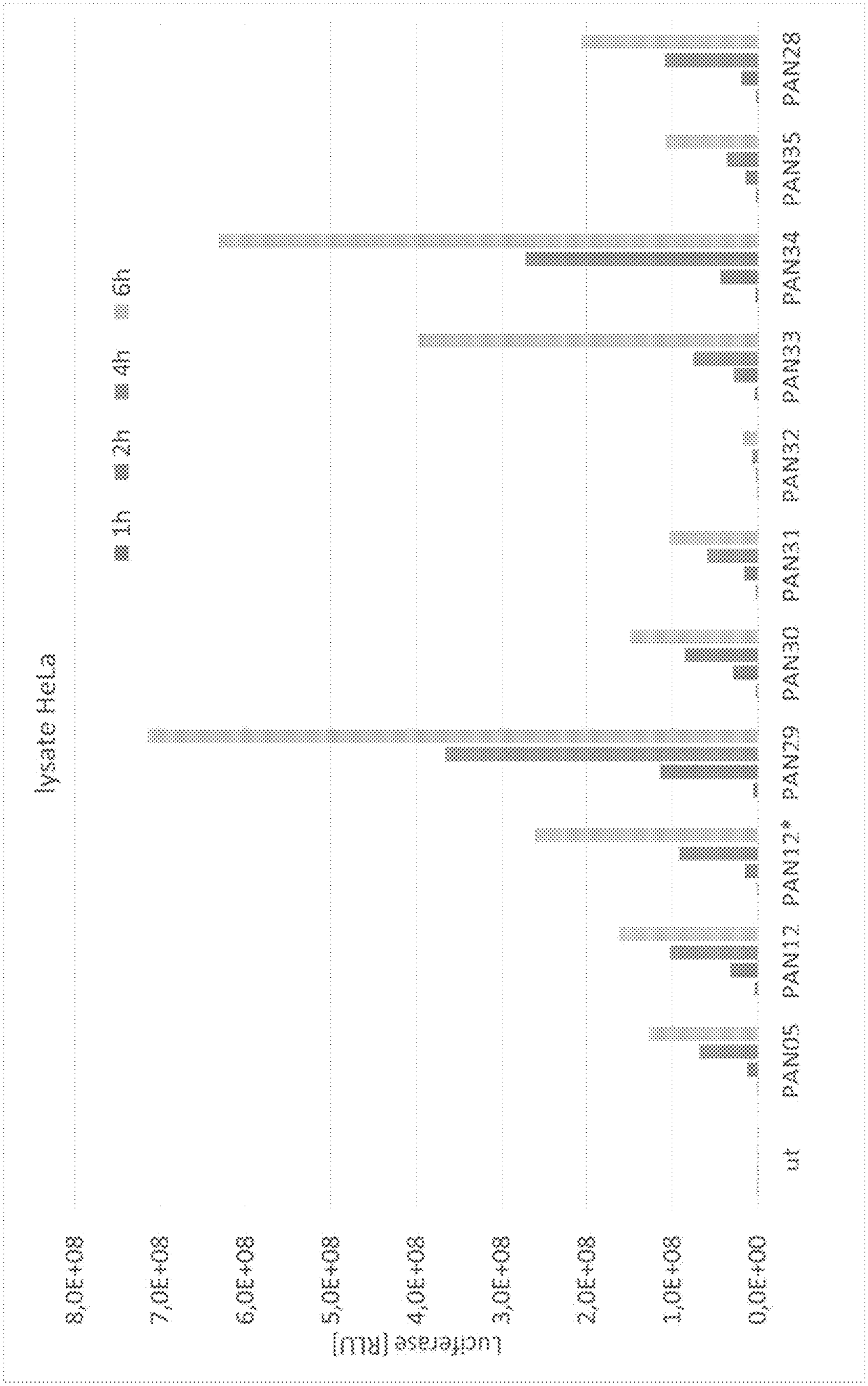
FIG. 81 is a bar diagram showing expression of luciferase, indicated as RLU (relative light units) of luciferase in whole cell lysates of Hela cells, by the indicated recombinant nucleic acid constructs in HeLA cells, where luciferase is used as the effector molecule after 1 hour, 2 hours, 4 hours and 24 hours post transfection (from left to right, with 1 hour results being shown to the utmost left side and 24 hours result being shown to the utmost right side).
Figure 82:
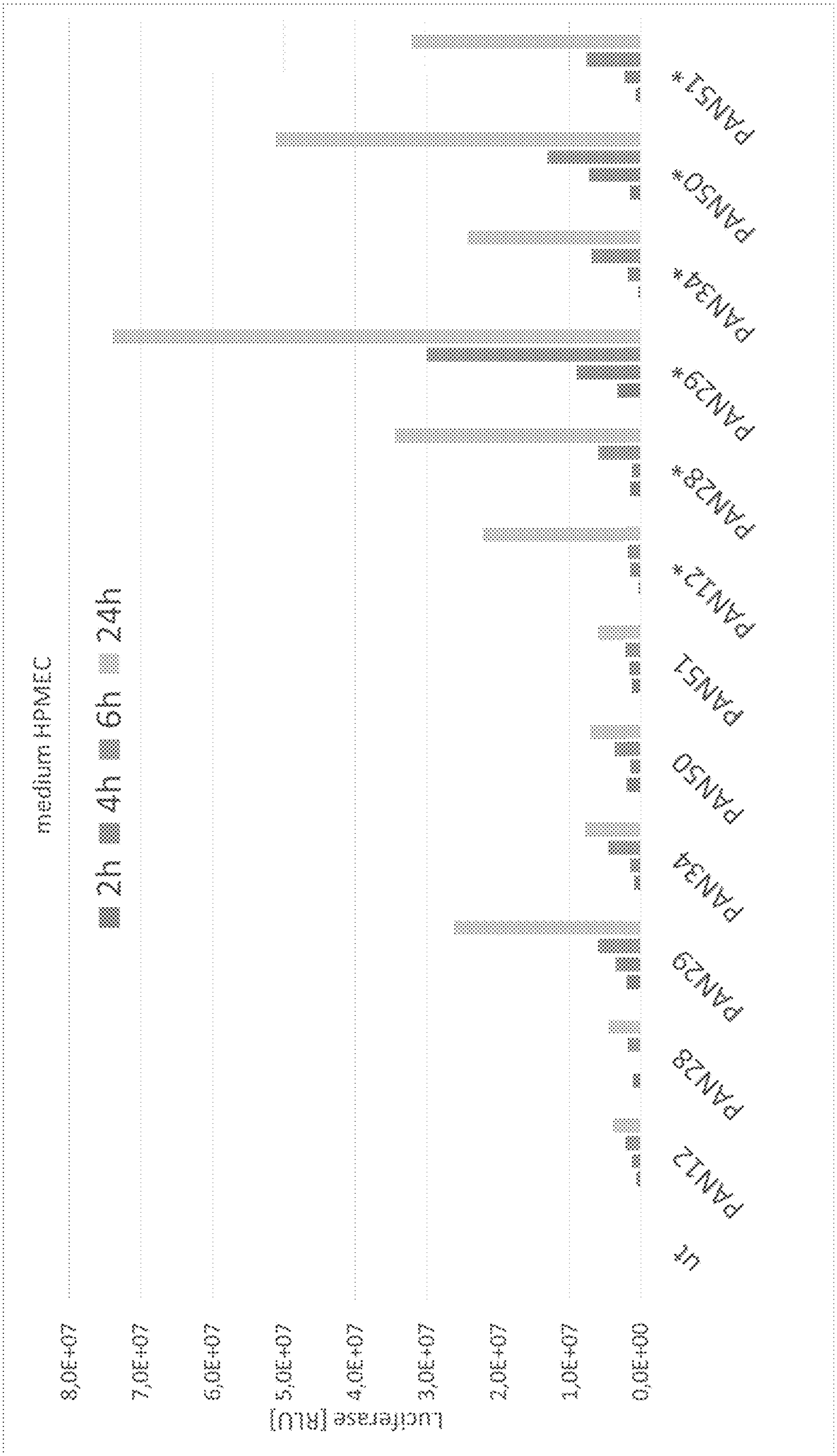
FIG. 82 is a bar diagram showing expression of luciferase, indicated as RLU (relative light units) of luciferase in medium, by the indicated recombinant nucleic acid constructs in HPMEC where luciferase is used as the effector molecule after 2 hours, 4 hours, 6 hours and 24 hours post transfection (from left to right, with 1 hour results being shown to the utmost left side and 24 hours result being shown to the utmost right side). In constructs PAN12*, PAN28*, PAN29*, PAN34*, PAN50* and PAN51*100% of uridine and 100% cytidine nucleotides are replaced by pseudo-uridine and 5-methyl-cytidine, respectively.
Figure 83:
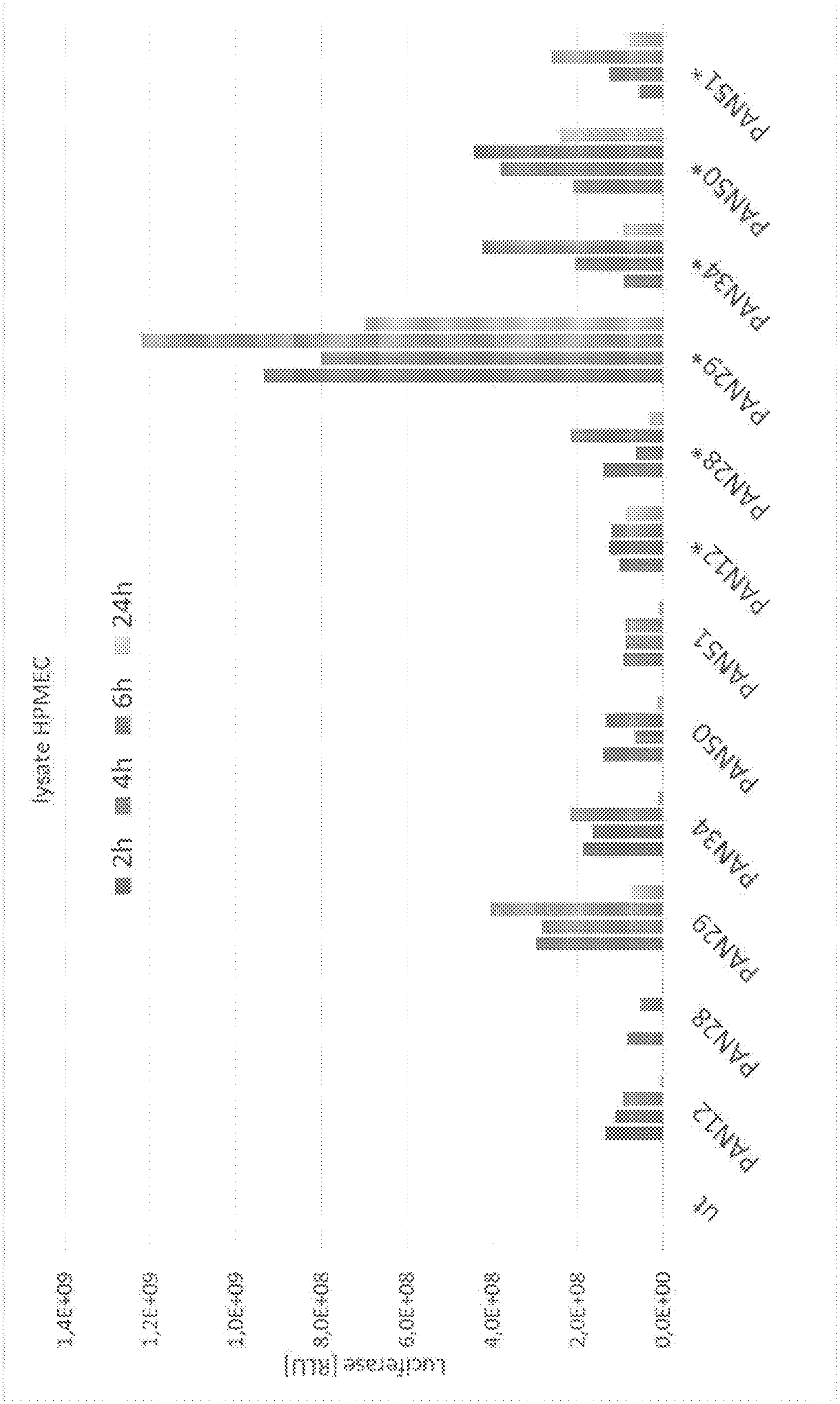
FIG. 83 is a bar diagram showing expression of luciferase, indicated as RLU (relative light units) of luciferase in whole cell lysates of HPMEC, by the indicated recombinant nucleic acid constructs in HPMEC, where luciferase is used as the effector molecule after 2 hours, 4 hours, 6 hours and 24 hours post transfection (from left to right, with 1 hour results being shown to the utmost left side and 24 hours result being shown to the utmost right side). In constructs PAN12*, PAN28*, PAN29*, PAN34*, PAN50* and PAN51*100% of uridine and 100% cytidine nucleotides are replaced by pseudo-uridine and 5-methyl-cytidine, respectively.
Figure 84:
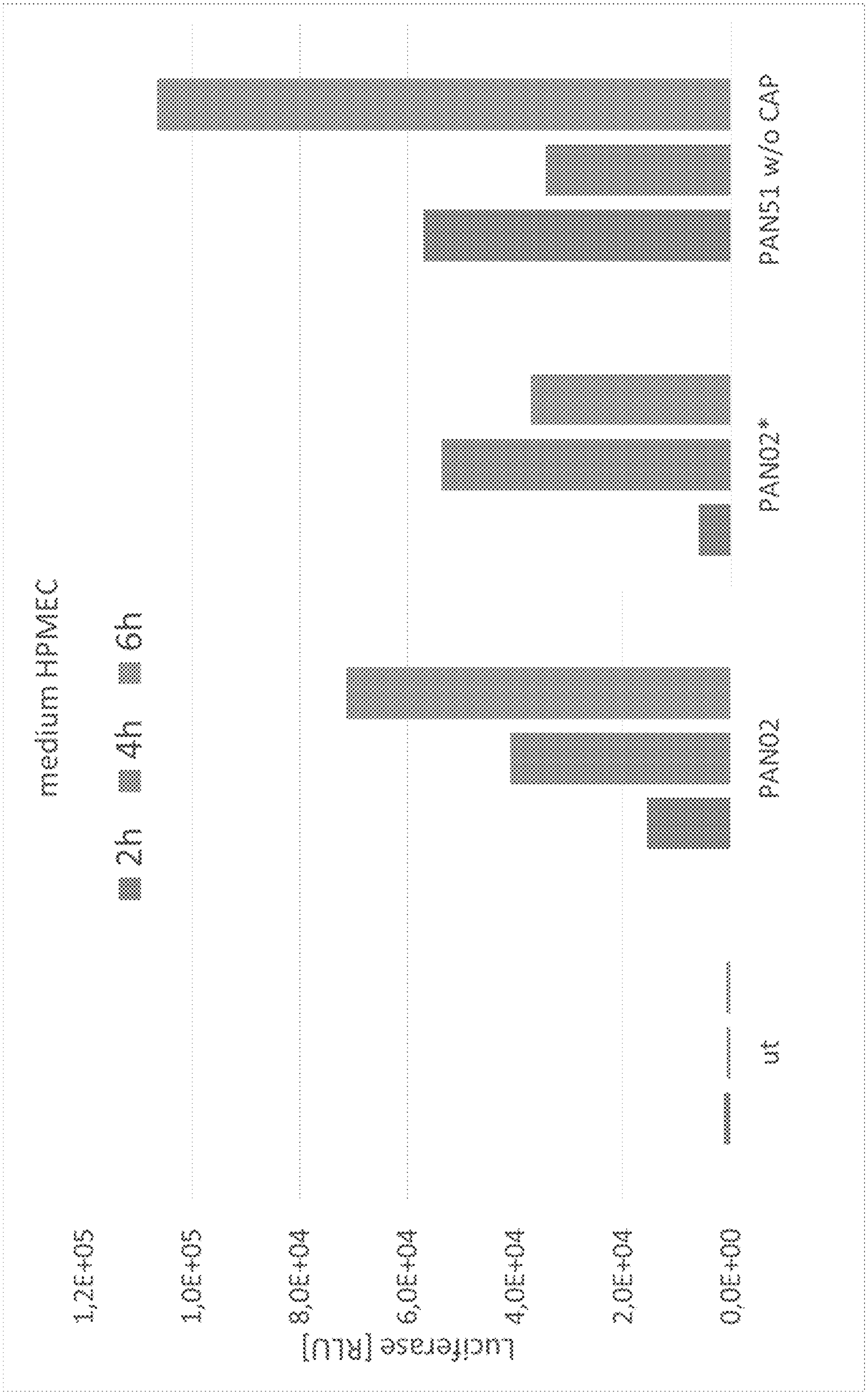
FIG. 84 is a bar diagram showing expression of luciferase, indicated as RLU (relative light units) of luciferase in medium, by the indicated recombinant nucleic acid constructs in HPMEC where luciferase is used as the effector molecule after 2 hours (left column), 4 hours (middle column) and 6 hours (right column) post transfection. In construct PAN02*, 100% of uridine and 100% cytidine nucleotides are replaced by pseudo-uridine and 5-methyl-cytidine, respectively; and in construct PAN51 w/o CAP the mRNA sequence is the one of construct PAN51, but without any 5'-capping structure.
Figure 85:
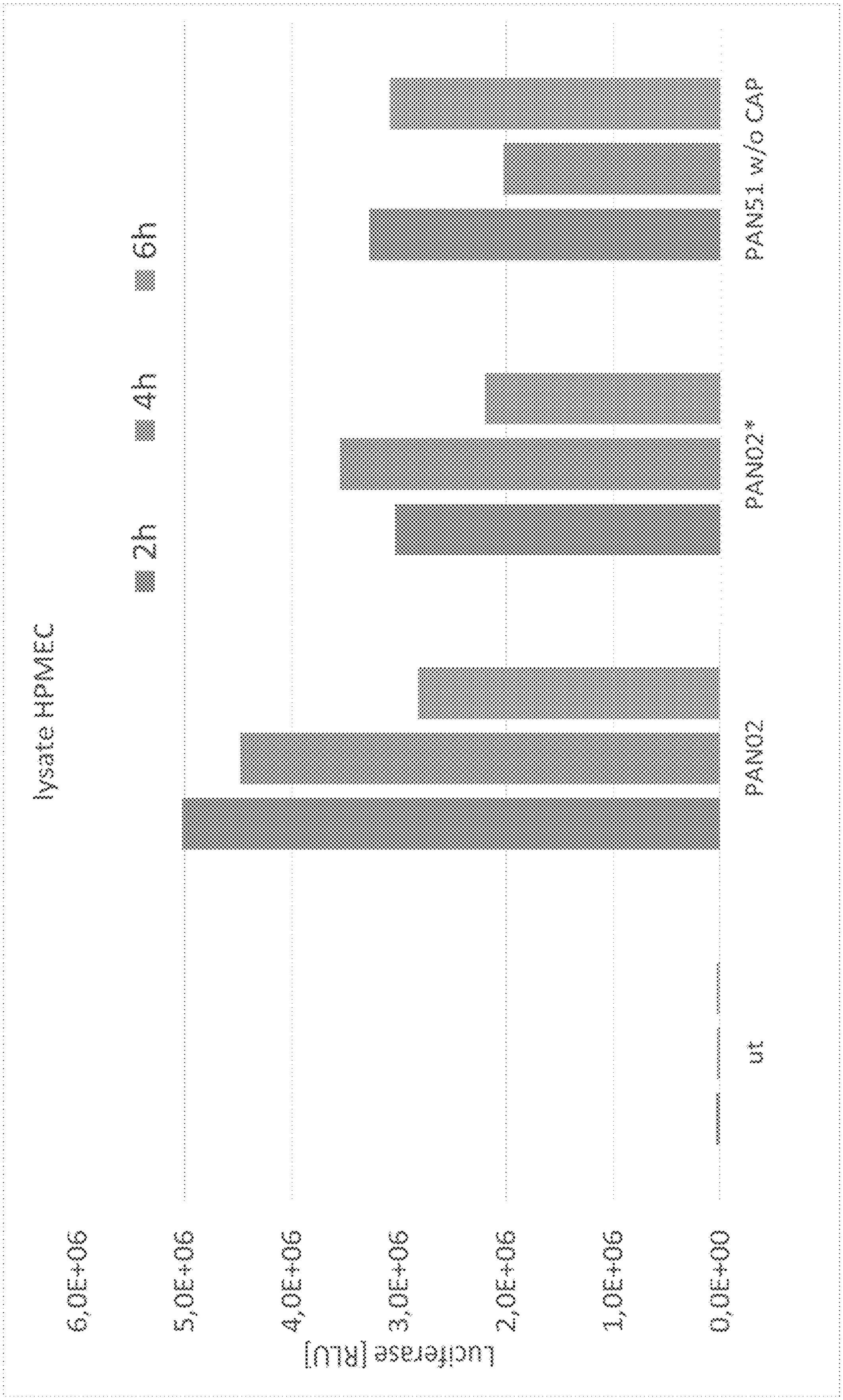
FIG. 85 is a bar diagram showing expression of luciferase, indicated as RLU (relative light units) of luciferase in whole cell lysates of HPMEC, by the indicated recombinant nucleic acid constructs in HPMEC, where luciferase is used as the effector molecule after 2 hours (left column) 4 hours (middle column) and 6 hours (right column) post transfection. In construct PAN02*, 100% of uridine and 100% cytidine nucleotides are replaced by pseudo-uridine and 5-methyl-cytidine, respectively; and in construct PAN51 w/o CAP the mRNA sequence is the one of construct PAN51, but without any 5'-capping structure.

FIG. 71A is an image of a 1% non-denaturing agarose gel stained with EtBr showing the tail-PCR products of constructs PAN35 ("35"), PA34 ("34"), PAN33 ("33"), PAN32 ("32"), PAN31 ("31"), PAN30 ("30"), PAN29 ("29") and PAN12 ("12"). M: is a lane with a high range RiboRuler RNA ladder. From this FIG. 71A may be taken that the transcribed mRNAs were intact and, more specifically, were not degraded.

FIG. 71B is an image of a 1% non-denaturing agarose gel stained with EtBr showing the in vitro mRNA transcripts of constructs PAN35 ("35"), PA34 ("34"), PAN33 ("33"), PAN32 ("32"), PAN31 ("31"), PAN30 ("30"), PAN29 ("29") and PAN12 ("12"). M: is a lane with a high range RiboRuler RNA ladder. From this FIG. 71B may be taken that the transcribed mRNAs were intact and, more specifically, were not degraded.

FIG. 86 shows recombinant nucleic acid construct PAN54 which is another embodiment of an mRNA of the present invention comprising as the 5' non-translated region the 5' UTR of RPL12s.c. as the nucleic acid sequence coding for a signal peptide the nucleic acid sequence coding for a signal peptide of MCP-1, as the coding region coding for an effector molecule the coding region coding for Nano-Luciferase (NLuc), and as the 3' non-translated region the 3' UTR of von Willebrand Factor (vWF).

FIG. 87 shows recombinant nucleic acid construct PAN55 which is another embodiment of an mRNA of the present invention comprising as the 5' non-translated region the 5' UTR of vWF, as the nucleic acid sequence coding for a signal peptide the nucleic acid sequence coding for a signal peptide of MCP-1, as the coding region coding for an effector molecule the coding region coding for Nano Luciferase (NLuc), and as the 3' non-translated region the 3' UTR of von Willebrand Factor (vWF).

FIG. 88 shows recombinant nucleic acid construct PAN56 which is another embodiment of an mRNA of the present invention comprising as the 5' non-translated region the 5' UTR of vWF, as the nucleic acid sequence coding for a signal peptide the nucleic acid sequence coding for a signal peptide of vWF, as the coding region coding for an effector molecule the coding region coding for Nano Luciferase (NLuc), and as the 3' non-translated region the 3' UTR of von Willebrand Factor (vWF).

FIG. 89 shows recombinant nucleic acid construct PAN57 which is another embodiment of an mRNA of the present invention comprising as the 5' non-translated region a synthetic nucleic acid sequence as described in Jiang, Lei et al. (2018). Systemic messenger RNA as an etiological treatment for acute intermittent *porphyria*. Nature Medicine. 24, 1899-2909 (2018), as the nucleic acid sequence coding for a signal peptide the nucleic acid sequence coding for a signal peptide of MCP-1, as the coding region coding for an effector molecule the coding region coding for Nano Luciferase (NLuc), and as the 3' non-translated region the 3' UTR a nucleic acid sequence as described in Jiang, Lei et al. (2018). Systemic messenger RNA as an etiological treatment for acute intermittent *porphyria*. Nature Medicine. 24; 1899-1909 (2018). The 5'- and 3' sequences are shown underlined and in bold.

FIG. 90 shows recombinant nucleic acid construct PAN58 which is another embodiment of an mRNA of the present invention comprising as the 5' non-translated region the 5' UTR of MCP-1, as the nucleic acid sequence coding for a signal peptide the nucleic acid sequence coding for a signal peptide of MCP-1, as the coding region coding for an effector molecule the coding region coding for Nano Luciferase (NLuc), and as the 3' non-translated region the 3' UTR of von Willebrand Factor (vWF). In addition, PAN58 comprises a consensus Kozak sequence (GCCACC) in the six bases upstream of the start AUG.

FIG. 91 shows recombinant nucleic acid construct PAN59 which is another embodiment of an mRNA of the present invention comprising as the 5' non-translated region the 5' UTR of MCP-1, as the nucleic acid sequence coding for a signal peptide the nucleic acid sequence coding for a signal peptide of MCP-1, as the coding region coding for an effector molecule the coding region coding for CMP-Ang1, and as the 3' non-translated region the 3' UTR of von Willebrand Factor (vWF).

FIG. 95 shows recombinant nucleic acid construct PAN60 which is another embodiment of an mRNA of the present invention comprising as the 5' non-translated region the 5' UTR of MCP-1, as the coding region coding for an effector molecule the coding region coding for wild type (wt) Tie2, and as the 3' non-translated region the 3' UTR of von Willebrand Factor (vWF).

FIG. 96 shows recombinant nucleic acid construct PAN61 which is another embodiment of an mRNA of the present invention comprising as the 5' non-translated region the 5' UTR of MCP-1, as the coding region coding for an effector molecule the coding region coding for Tie2 mutant R849W, and as the 3' non-translated region the 3' UTR of von Willebrand Factor (vWF).

FIG. 97 shows recombinant nucleic acid construct PAN66 which is another embodiment of an mRNA of the present invention comprising as the 5' non-translated region the 5' UTR of MCP-1, as the coding region coding for an effector molecule the coding region coding for wild type PIK3CA which is, according to GenBank *Homo sapiens* phosphatidylinositol-4,5-bisphosphate 3-kinase catalytic subunit alpha (PIK3CA) with the respective reference number being 006218.4, and as the 3' non-translated region the 3' UTR of von Willebrand Factor (vWF).

The SEQ ID NOs: of the sequence listing are related to the instant disclosure as summarized in Table 1.

TABLE 1

| Seq ID No: | Subject to FIG. | Further information |
|---|---|---|
| 1 | 7A | 5'Primer |
| 2 | 7A | 5'Primer |
| 3 | 7A | 5'Primer |
| 4 | 7A | 5'Primer |
| 5 | 7A | 5'Primer |
| 6 | 7A | 5'Primer |
| 7 | 7A | 5'Primer |
| 8 | 7A | 5'Primer |
| 9 | 7A | 5'Primer |
| 10 | 7A | 5'Primer |
| 11 | 7B | 3'Primer |
| 12 | 7B | 3'Primer |
| 13 | 7B | 3'Primer |
| 14 | 7B | 3'Primer |

TABLE 1-continued

| Seq ID No: | Subject to FIG. | Further information |
|---|---|---|
| 15 | 7B | 3'Primer |
| 16 | 7B | 3'Primer |
| 17 | 7B | 3'Primer |
| 18 | 7B | 3'Primer |
| 19 | 7B | 3'Primer |
| 20 | 15A | 5'UTR MCP1 |
| 21 | 15B | SP (signal peptide) nucleotide sequence of MCP1 |
| 22 | 15B | SP amino acid sequence of MCP1 |
| 23 | 15C | 3'UTR of MCP1 |
| 24 | 16A | 5'UTR of RPL12 |
| 25 | 16B | 3'UTR of RPL12 |
| 26 | 17A | 5'UTR of Ang2 |
| 27 | 17B | SP (signal peptide) nucleotide sequence of Ang2 |
| 28 | 17B | SP (signal peptide) amino acid sequence of Ang2 |
| 29 | 17C | 3'UTR of Ang2 |
| 30 | 18A | 5'UTR of IL6 |
| 31 | 18B | SP (signal peptide) nucleotide sequence of IL6 |
| 32 | 18B | SP (signal peptide) amino acid sequence of IL6 |
| 33 | 18C | 3'UTR of IL6 |
| 34 | 19A | 5'UTR of vWF |
| 35 | 19B | SP(signal peptide) nucleotide sequence of vWF |
| 36 | 19B | SP (signal peptide) amino aicd sequence of vWF |
| 37 | 19C | 3'UTR of vWF |
| 38 | 20A | 5'UTR of HSP70 A1 |
| 39 | 20B | 3'UTR of HSP70 A1 |
| 40 | 21A | 5'UTR of HSP70 A5 |
| 41 | 21B | SP (signal peptide) nucleotide sequence of HSP70 A5 |
| 42 | 21B | SP (signal peptide) amino acid sequence of HSP70 A5 |
| 43 | 21C | 3'UTR of HSP70 A5 |
| 44 | 22A | 5'UTR of H3.3 |
| 45 | 22B | 3'UTR of H3.3 |
| 46 | 23A | 5'UTR of LGALS9 |
| 47 | 23B | 3'UTR of LGALS9 |
| 48 | 24 | Construct PAN01 |
| 49 | 25 | Construct PAN03 |
| 50 | 26 | Construct PAN04 |
| 51 | 27 | Construct PAN06 |
| 52 | 28 | Construct PAN36 |
| 53 | 29 | Construct PAN37 |
| 54 | 30 | Construct PAN02 |
| 55 | 31 | Construct PAN05 |
| 56 | 32 | Construct PAN07 |
| 57 | 33 | Construct PAN08 |
| 58 | 34 | Construct PAN09 |
| 59 | 35 | Construct PAN10 |
| 60 | 36 | Construct PAN11 |
| 61 | 37 | Construct PAN12 |
| 62 | 38 | Construct PAN13 |
| 63 | 39 | Construct PAN28 |
| 64 | 40 | Construct PAN29 |
| 65 | 41 | Construct PAN30 |
| 66 | 42 | Construct PAN31 |
| 67 | 43 | Construct PAN32 |
| 68 | 44 | Construct PAN33 |
| 69 | 45 | Construct PAN34 |
| 70 | 46 | Construct PAN35 |
| 71 | 47 | Construct PAN38 |
| 72 | 48 | Construct PAN39 |
| 73 | 49 | Construct PAN40 |
| 74 | 50 | Construct PAN41 |
| 75 | 51 | Construct PAN42 |
| 76 | 52 | Construct PAN43 |
| 77 | 53 | Construct PAN44 |
| 78 | 54 | Construct PAN45 |
| 79 | 55 | Construct PAN46 |
| 80 | 56 | Construct |
| 81 | 57 | Construct PAN48 |
| 82 | 58 | Construct PAN49 |
| 83 | 59A | 5'UTR of Ang1 |
| 84 | 59B | SP (signal peptide) nucleotide sequence of Ang1 |
| 85 | 59B | SP (signal peptide) amino acid sequence of Ang1 |
| 86 | 59C | CDS of Ang1 (mature peptide + stop codon) |
| 87 | — | Amino acid sequence derived from SEQ ID No. 86 |
| 88 | 59D | 3'UTR of Ang1 |

TABLE 1-continued

| Seq ID No: | Subject to FIG. | Further information |
|---|---|---|
| 89 | 60A | 5'UTR of Ang4 |
| 90 | 60B | SP (signal peptide) nucleotide sequence of Ang4 |
| 91 | 60B | SP (signal peptide) amino acid sequecne of Ang4 |
| 92 | 60C | CDS of Ang4 (mature peptide + stop codon) |
| 93 | — | Amino acid sequence derived from SEQ ID No. 92 |
| 94 | 60D | 3'UTR of Ang4 |
| 95 | 61 | COMP-Ang1 CDS (mature pep + stop codon) (rat) |
| 96 | — | Amino acid sequence derived from SEQ ID No. 95 |
| 97 | 62 | hCOMP-Ang1 CDS (mature pep + stop codon) (human) |
| 98 | — | Amino acid sequence derived from SEQ ID No. 97 |
| 99 | 63 | CMP-Ang1 CDS (mat peptide + stop codon) |
| 100 | 64 | COMP-Ang2 CDS (mat peptide + stop codon) |
| 101 | 65 | Tie2 CDS (start + mat pep + stop codon) |
| 102 | — | Amino acid sequence derived from SEQ ID No. 101 |
| 103 | 66 | Tie2* CDS (R849W)(start + mat pep + stop codon) |
| 104 | — | Amino acid sequence derived from SEQ ID No. 103 |
| 105 | 67 | Construct PAN50 |
| 106 | 68 | Construct PAN51 |
| 107 | 69 | Construct PAN52 |
| 108 | 70 | Construct PAN53 |
| 109 | 86 | Construct PAN54 |
| 110 | 87 | Construct PAN55 |
| 111 | 88 | Construct PAN56 |
| 112 | 89 | Construct PAN57 (Mod) |
| 113 | 90 | Construct PAN58 |
| 114 | 91 | Construct PAN59 |
| 115 | 95 | Construct PAN60 (Tie2 wt) |
| 116 | 96 | Construct PAN61 (Tie2 R849W) |
| 117 | 97 | Construct PAN66 (PIK3CA wt) |
| 118 | | Construct CDS (start + mat pep+stop codon) PIK3CA |
| 119 | | CDS (mature peptide + stop cod) Nluc |
| 120 | 100a | 5'UTR of (PAN57) |
| 121 | 100b | 3'UTR of (PAN57) |
| 122 | 7B | 3'Primer for constructs PAN01-PAN03 |
| 123 | 100c | 5'Primer for construct PAN57 |
| 124 | 100d | 3'Primer for construct PAN57 |
| 125 | 100e | 5'Primer for construct PAN55 (FIG. 87) and PAN56 (FIG. 88) |

Example 1: Materials and Methods

Plasmid Template Generation by Gene Synthesis and Cloning

Sequences encoding Nluc reporter protein, Ang-1 protein and derivatives thereof (e.g. COMP-Ang-1, CMP-Ang-1) with different signal peptides were flanked by different heterologous 5' and 3' UTRs and were designed and produced by gene synthesis by BioCat (Heidelberg) and cloned (Xho1-BamHI) into pcDNA3.1-(Thermo Fisher).

Sequences encoding wt Tie-2 and sequences with the specified Tie-2 mutation in the coding region flanked by different heterologous 5' and 3' UTRs were designed (see FIGS. 95 and 96) and produced by gene synthesis by BioCat (Heidelberg) and cloned (Xho1-BamHI) into pcDNA3.1-(Thermo Fisher).

In Vitro Transcription from PCR Products to Generate Polyadenylated mRNAs

In vitro transcription is the synthesis of RNA transcripts by RNA polymerase from a linear DNA template containing the corresponding promoter sequence (T7, T3, SP6) and the gene to be transcribed. A typical transcription reaction consists of the template DNA, RNA polymerase, ribonucleotide triphosphates, RNase inhibitor and buffer containing Mg2+ ions. Linearized plasmid DNA, PCR products and synthetic DNA oligonucleotides can be used as templates for transcription as long as they have the T7 promoter sequence upstream of the gene to be transcribed. In order to generate DNA templates with a poly-(A) tail a tail-PCR using 5' primers containing T7 RNA polymerase sequences and 3' primers with a 120 nt Poly-T sequence were synthesized and purified (BioSpring, Frankfurt).

The Linear DNA templates for in vitro transcription were generated by PCR from linearized plasmid. Plasmids were digested with BamHI that cut once 3-terminal in the vector backbone to produce a linearized vector that can be used as the template for the poly-(A) tail PCR. 5 μg plasmid are digested for 2 h at 37° C. with 5 U BamHI restriction enzyme in 50 μl and 1× HF Buffer. Small Aliquots of digested mix were analyzed by gel electrophoresis to check for complete digestion of the plasmid (see, for example, FIG. 5 for constructs PAN28 (“28”), PAN13 (“13”), PAN12 (“12”), PAN11 (“11”), PAN10 (“10”), PAN09 (“09”), PAN08 (“08”), PAN07 (“07”) and PAN05 (“05”)). The restriction enzyme is heat-inactivated by incubating at 80° C. for 20 min and the digested plasmid is purified by a PCR purification column following the manufacturer’s protocol (NucleoSpin Gel and PCR clean-up, Macherey-Nagel). The linearized plasmid can be stored at −20° C. for several months and can be used for PCR template generation. The purpose of linearization was to eliminate circular templates that could potentially generate run-on transcripts during the IVT reaction.

Addition of poly-(A) tail by PCR was performed by using Hot StarHiFidelity polymerase (Qiagen) or Taq DNA Polymerase (Roche) following the manufacturer’s protocol. For this purpose, Adapter primers containing T7 promoter sequences and 3' Poly A tail sequences (120 nt) were used to amplify linear DNA-templates. Each of the adapter primers had overlap sequences which fused regulatory sequences necessary for translation and transcription to the gene of interest (see, for example, FIGS. 7*a* and 7*b*). A typical 50 μl PCR reaction contained final concentrations of 200 μM (of each) dNTP, 0.5 μM for each primer, 50 ng linearized plasmid DNA, 1×PCR reaction buffer (1.5 mM MgCl2) and 1.25 U Taq DNA Polymerase per reaction (0.25 μl of 5 U/μl). The specific PCR cycle programs or thermal profiles were adjusted according to the Tm of the primer pairs, according to the expected length of the PCR product and according to the used thermal cycler. The quality of the PCR products was checked by analyzing an aliquot by gel electrophoresis and the reactions are purified by commercial PCR purification kits ((NucleoSpin Gel and PCR clean-up, Macherey-Nagel).

In Vitro Transcription Reaction

Addition of a 5' end cap structure to the RNA is an important process in eukaryotes. It is essential for RNA stability, efficient translation, nuclear transport and splicing. The process involved addition of a 7-methylguanosine cap at the 5' triphosphate end of the RNA. RNA capping can be carried out post-transcriptionally using capping enzymes or co-transcriptionally using cap analogs such as ARCA (Jena Bioscience) or CleanCap (Trilink Biotechnologies) or EZ-Cap (ApexBio). In the enzymatic method, the mRNA may be capped using the vaccinia virus mRNA capping enzyme (NEB) as per manufacturer’s protocol. The enzyme adds on a 7-methylguanosine cap at the 5' end of the RNA using GTP and S-adenosyl methionine as donors (cap-0 structure). Both methods yield functionally active capped RNA suitable for transfection or other applications. In addition, a 2'-O-Methyltransferase can be used to introduce cap-1 and cap-2 structures.

In the example described below, the T7 High Yield Transcription Kit (Thermo Scientific) was used to synthesize capped RNA transcripts (PAN 01-XX) using cap analogs co-transriptionally.

The DNA template for the transcription reaction was a linearized plasmid or a PCR product. For the capped RNA the reaction at room temperature was set up in the following order:

| Component | Volume (μl) | Final |
|---|---|---|
| Nuclease free water* | To 20 | |
| 5X Reaction Buffer | 4 | 1X |
| ATP (100 mM) | 2 | 10 mM |
| CTP (100 mM) or 5'-Methylcytidine-5'-Triphophate (100 mM) | 2 | 10 mM |
| UTP (100 mM) or Pseudouridine-5'-Triphosphate (100 mM) or 5-Methoxyuridine-5'-Triphosphate (100 mM) N1-Methyl-pseudouridine (100 mM) | 2 | 10 mM |
| GTP (30 mM) | 2 | 3 mM |
| 3'-0-Me-m$^7$G(5')ppp(5')G cap analog (ARCA; Anti Reverse Cap Analog) (100 mM) | 2 | 10 mM |
| Template DNA* | X | 1 μg |
| T7 RNA Polymerase Mix | 2 | |
| Total | 20 | |

1 μg DNA was added and the total reaction volume to 20 μl was obtained by adding nuclease free water. The amount of water to be added varied based on the concentration of the template DNA. The reactions at were well mixed by vortexing and incubated at 37° C. for 2 hours in a dry air incubator. The transcription reactions were treated with DNase I to remove the DNA template before proceeding with purification as follows:

1. 70 μl nuclease free water was added to the transcription reactions followed by 10 μl of DNase I reaction buffer.
2. 2 μl DNase I were added to the reactions.
3. The reaction was incubated at 37° C. for 15 minutes.

Column Purification of Capped mRNA

1. The capped RNA was purified using the MEGAclearKit as per the manufacturer’s instructions (any spin column based RNA purification kit may be used).
2. The RNA was quantified using a NanoDrop Spectrophotometer.
3. As per the manufacturer’s instructions, RNA sample quality was assessed using the Agilent RNA 6000 Nano Kit and Agilent 2100 Bioanalyzer or by native 1% agarose gel electrophoresis and ethidium bromide staining (see, FIG. 8).

mRNA Transfection of HeLa Cells, HEK293 Cells, HPMEC Cells, HPAEC Cells and HUVEC Cells HeLa cells, were grown in DMEM complete medium. The human embryonic kidney 293 cell line (HEK293) is grown in EMEM (EBSS)+2 mM Glutamine+1% Non Essential Amino Acids (NEAA)+10% FCS culture medium.

The human embryonic kidney 293 cell line (HEK293) is grown in EMEM (EBSS)+2 mM Glutamine+1% Non Essential Amino Acids (NEAA)+10% FCS culture medium. Subculture Routine is to split sub-confluent cultures (70-80%) 1:2 to 1:6 i.e. seeding at 2-5×10,000 cells/cm$^2$ using 0.25% trypsin or trypsin/EDTA; 5% $CO_2$; 37° C. mRNA transfection are performed with the Lipofectamine™ MessengerMAX™ Transfection Reagent (Invitrogen™) according to the manufactures protocol.

Primary Human Pulmonary Microvascular Endothelial Cells (HPMEC) and Primary Human Pulmonary Artery Endothelial Cells (HPAEC) are isolated from human pulmonary arteries are most appropriate for studying human lung diseases and are isolated from the lung from a single donor. Since lung tissue contains blood and lymphatic capillaries, HPMEC comprise Blood and Lymphatic Microvascular Endothelial Cells.

The cell type of HPMEC's are characterized by immunofluorescent staining. They stain positive for CD31 and von Willebrand factor and negative for smooth muscle alpha-actin.

HUVEC, HPAEC and HPMEC cells were grown in Endothelial Cell Growth Medium as recommended from PromoCell (Heidelberg Germany,) respectively. The Endothelial Cell Growth Medium is basal Medium supplemented with Fetal Calf Serum (0.05 ml/ml), Endothelial Cell Growth Supplement (bovine hypothalamic extract; 0.004 ml ml), Heparin 90 μg/ml and Hydrocortisone 1 μg/ml. The experiments with HUVEC, HPAEC and HPMEC cells are performed on cells with passage numbers below 8.

RNA transfections and more mRNA transfections were carried out using Lipofectamin MessengerMAX (Invitrogen, Carlsbad, CA; Thermo Fisher Scientific). For mRNA transfection in 24-well plate format $1\times10^5$ cells/well were seeded 24 h before transfection to reach 70-90 confluence immediately before transfection. For one single well 1.5 μl Lipofectamine MessengerMAX Reagent was added to 25 μl OptMEM (Invitrogen, Carlsbad, CA; Thermo Fisher Scientific), vortexed and incubated for 10 min at RT. In a second well 500 ng or 1 μg mRNA were added to 25 μl OptiMEM, and vortexed. After incubation diluted mRNA was added to diluted Lipofectamin, mixed well, incubated for 5 min at RT and added dropwise to cells in the presence of 0.5 ml of complete medium for Hela and HEK293. For HUVEC, HPAEC and HPMEC the Endothelial Cell Growth medium was replaced and the cells washed with OptiMEM and then the Lipofectamin MessengerMAXX mRNA complex solution added to the well with 0.5 ml OptiMEM prewarmed to 37° C. Cells were incubated at 37° C. for 2 h and the OptiMEM medium replaced with complete Endothelial Cell Growth Medium (PromoCell, Heidelberg Germany).

Cell Lysates from Transfected cells or serum were analyzed at the indicated time points. Alternatively, mRNA-LNPs based on the cationic lipids L-Arginyl-β-alanine-N-palmityl-N-oleyl-amide or β-(L-Arginyl)-L-2,3-diamino propionic acid-N-palmityl-N-oleyl-amide in combination with neutral and PEGylated co-lipids were used for in vitro transfection. The co-lipids were Diphytanoyl-PE and the PEGylated lipid is methoxyPEG2000-DSPE Successful introduction of mRNA into host cells was monitored using various known methods, such as a fluorescent marker, such as Green Fluorescent Protein (GFP), such as reporter enzymes (e.g. luciferase derivatives). Alternatively, transfection of a modified mRNA could also be determined by measuring the protein expression level of the target polypeptide by e.g., Western Blotting or immunocytochemistry or ELISA.

Fully modified mRNAs with 5-methylcytidine and/or pseudouridine (or 5-methoxyuridine or N1-methylpseudouridine) are transfected into HUVEC or HPMEC (Human Pulmonary Microvascular Endothelial Cells, PromoCell, Heidelberg) using Lipofectamin MessengerMAX (Invitrogen, Carlsbad, CA; Thermo Fisher Scientific). The cell lysates are harvested and run by ELISA (or on immunoblot assays (western) at different time points (30", 1 h, 2 h, 4 h, 6 h hours) after transfection to determine the protein expression.

Nano-Luc Luciferase Activity Reporter Measurement

A time dependent quantitative detection of Nano-Glo-Luciferase expression (Promega) was performed for secreted versions by analyzing samples from the tissue culture supernatant according to the reporter assay technical manual Nano-Glo Luciferase Assay System (Promega). In brief, 5-20 μl of serum or lysate were diluted in 100 μl $H_2O$ final volume and equal volume of reconstituted Nano-Glo luciferase assay reagent was combined in a 96 well GloMax 96 Microplate. After at least 3 min incubation at RT luminescence were measured in an appropriate luminometer.

Immunoblot Detection of Tie-2 and Derivates

For immunoblot detection of Tie-2 and derivatives protein lysates are loaded on NuPage SDS-PAGE system (chambers and power supply) with 1.5 mm ready-to-use Bis-Tris gels and 4-12% acrylamide gradient with MOPS-buffer as running aid (all Life Technologies, Grand Island, NY). Each lysate sample is prepared to 40 μl final volume. This sample contains 25 μg protein lysate in variable volume, RIPA buffer to make up volume to 26 μl, 4 μl of 10× reducing agent and 10 μl 4×SDS loading buffer (both from Life Technologies, Grand Island, NY). Samples are heated at 95° C. for 5 min and loaded on the gel. Standard settings are chosen by the manufacturer, 200V, 120 mA and max. 25 W. Run time is 60 min, but no longer than running dye reaching the lower end of the gel.

After the run is terminated, the plastic case is cracked and the encased gel transferred to a ready-to-use nitrocellulose membrane kit and power supply (iBLOT; LifeTechnologies, Grand Island, NY). Using default settings, the protein lysate is transferred by high Ampere electricity from the gel to the membrane.

After the transfer, the membranes are incubated in 5% BSA in IX TBS for 15 minutes then in 5% BSA in IX TBS+0.1% Tween for another 15 minutes. Primary antibodies against human Tie-2 proteins or Phospho-specific Antibodies (P-Tie-2, P-Akt, see below) are applied in 3 ml of 5% BSA in IX TBS solution at a 1:500 to 1:2000 dilution for 3 hours at room temperature and gentle agitation on an orbital shaker. Membranes are washed 3 times with IX TBS/0.1% Tween, 5 minutes each time with gentle agitation. The secondary antibody (Goat anti-rabbit HRP conjugate; Abeam, Cambridge, MA) is conjugated to horse radish peroxidase and binds to the primary antibody antibodies. The secondary antibody is diluted from 1:1000 to 1:5000 in 5% BSA in IX TBS and incubated for 3 hrs at RT. At the end of incubation time, the membranes are washed 3 times with IX TBS/0.1% Tween, 5 minutes each time with gentle agitation. The membranes are developed in 5 ml Pierce WestPico Chemiluminescent Subtrate (Thermo Fisher, Rockford, IL) as directed.

Example 2: Expression of Luciferase, Ang-1 or Ang-1-Derivatives Expressing Recombinant Nucleic Acid Constructs in HPMEC, HUVEC, HPAEC and HeLa Cells mRNA Transfection of HeLa, HUVEC, HPAEC and HPMEC Cells Primary Human Pulmonary Microvascular Endothelial Cells (HPMEC) are most appropriate for studying human lung diseases and are isolated from the lung from a single donor. Since lung tissue contains blood and lymphatic capillaries, HPMEC comprise Blood and Lymphatic Microvascular Endothelial Cells. The cells were routinely analyzed by immunofluorescent staining: they stain positive for CD31 and von Willebrand factor and negative for smooth muscle alpha-actin. HeLa cells, HUVEC, HPMEC and HPAEC (human pulmonary artery endothelial cells) cells, respectively, were grown in DMEM complete medium or Endothelial Cell Growth Medium (PromoCell, Heidelberg Germany, CatNo.: C-22020) respectively. The Endothelial Cell Growth Medium was basal Medium supplemented with Fetal Calf Serum (0.05 ml/ml), Endothelial Cell Growth Supplement (bovine hypothalamic extract; 0.004 ml ml), Heparin 90 μg/ml and Hydrocortisone 1 μg/ml. The experiments with HUVEC and HPMEC cells were performed on cells with passage numbers below 8.

mRNA transfections were carried out using Lipofectamin MessengerMAX (Invitrogen, Carlsbad, CA; Thermo Fisher Scientific). For mRNA transfection in 24-well plate format $1\times10^5$ cells/well were seeded 24 h before transfection to reach 70-90 confluence immediate before transfection. For one single well 1.5 μl Lipofectamine MessengerMAX Reagent was added to 25 μl OptiMEM, vortex and incubated for 10 min at RT. In a second well add 500 ng or 1 μg mRNA were added to 25 μl OptiMEM, vortex. After incubation diluted mRNA was added to diluted Lipofectamin, mixed well, incubated for 5 min at RT and added dropwise to cells in the presence of 0.5 ml of DMEM complete medium for HeLa. For HUVEC, HPMEC and HPAEC the Endothelial Cell Growth medium was replaced and the cells washed with OptiMEM and then added the Lipofectamin MessengerMAX mRNA complex solution to the well with 0.5 ml OptiMEM prewarmed to 37° C. Cells were incubated at 37° C. for 2 h and the OptiMEM medium was replaced with complete Endothelial Cell Growth Medium (PromoCell, Heidelberg Germany) and transfected cells or serum were analyzed at the indicated time points. Alternatively, mRNA-LNPs based on the cationic lipids L-Arginyl-β-alanine-N-palmityl-N-oleyl-amide or β-(L-Arginyl)-L-2,3-diamino propionic acid-N-palmityl-N-oleyl-amide in combination with neutral and PEGylated co-lipids can be used for in vitro transfection.

Successful introduction of mRNA into host cells can be monitored using various known methods, such as a fluorescent marker, such as Green Fluorescent Protein (GFP), such as reporter enzymes (e.g. luciferase derivatives) or transfection of a modified mRNA can also be determined by measuring the protein expression level of the target polypeptide by e.g., Western Blotting or immunocytochemistry or ELISA.

Nano-Luc Luciferase Activity Reporter Measurement

A time dependent quantitative detection of Nano-Glo-Luciferase expression (Promega) was performed for secreted versions by analyzing samples from the tissue culture supernatant according to the reporter assay technical manual Nano-Glo Luciferase Assay System (Promega). In brief, 5-20 μl of serum or lysate were diluted in 100 μl $H_2O$ final volume and equal volume of reconstituted Nano-Glo luciferase assay reagent was combined in a 96 well GloMax 96 Microplate. After at least 3 min incubation at RT luminescence could be measured in an appropriate luminometer.

Detection of Ang-1, COM-Ang-1, CMP-Ang-1 Protein in Cell Lysates and Supernatant A time dependent quantitative detection of secreted Ang-1 and secreted COMP-Ang-1 or COMP-Ang-2 expression is performed by analyzing samples from the supernatant tissue culture by ELISA (Human Angiopoietin-1 Quantikine ELISA Kit (DANG10, R&D systems) or by Western blot according to the technical manual.

500 ng of COMP-Ang-1 (mRNA sequence shown in SEQ ID NO: PAN05) with poly A tail of approximately 120 nucleotides not shown in sequence; 5' cap,) fully modified with 5-methylcytidine and pseudouridine (COMP-Ang-1, 5mC/pU), fully modified with 5-methylcytidine and N1-methyl-pseudouridine (COMP-Ang-1,5mC/NlmpU) or unmodified (COMP-Ang-, unmod) is transfected into HUVEC or HPMEC (Human Pulmonary Microvascular Endothelial Cells, PromoCell, Heidelberg) using Lipofectamin MessengerMAX (Invitrogen, Carlsbad, CA; Thermo Fisher Scientific). The supernatant is harvested and run by ELISA 4 hours after transfection to determine the protein expression and cytokine induction.

For immunoblot detection of Ang-1 and derivatives protein lysates were loaded on NuPage SDS-PAGE system (chambers and power supply) with 1.5 mm ready-to-use Bis-Tris gels and 4-12% acrylamide gradient with MOPS-buffer as running aid (all Life Technologies, Grand Island, NY). Each lysate sample was prepared to 40 ul final volume. This sample contained 25 ug protein lysate in variable volume, RIPA buffer to make up volume to 26 ul, 4 ul of 10× reducing agent and 10 μl 4×SDS loading buffer (both from Life Technologies, Grand Island, NY). Samples were heated at 95° C. for 5 min and loaded on the gel. Standard settings were chosen by the manufacturer, 200V, 120 mA and max. 25 W. Run time was 60 min, but no longer than running dye reaching the lower end of the gel.

After the run is terminated, the plastic case is cracked and the encased gel transferred to a ready-to-use nitrocellulose membrane kit and power supply (iBLOT; LifeTechnologies, Grand Island, NY). Using default settings, the protein lysate is transferred by high Ampere electricity from the gel to the membrane.

After the transfer, the membranes were incubated in 5% BSA in IX TBS for 15 minutes then in 5% BSA in IX TBS+0.1% Tween for another 15 minutes. Primary antibodies (Ang-1 ab183701 Abcam, Cambridge, UK) against human Ang-1 proteins are applied in 3 ml of 5% BSA in IX TBS solution at a 1:5000 dilution overnight at 4° C. and gentle agitation on an orbital shaker. Membranes are washed 3 times with 1×TBS/0.1% Tween, 5 minutes each time with gentle agitation. The secondary antibody (Goat anti-rabbit HRP conjugate; Abeam, Cambridge, MA) is conjugated to horse radish peroxidase and binds to the primary antibody antibodies. The secondary antibody is diluted of 1:10000 in 5% BSA in IX TBS and incubated for 1 hr at RT. At the end of incubation time, the membranes are washed 3 times with IX TBS/0.1% Tween, 5 minutes each time with gentle agitation. The membranes are developed in 5 ml Pierce WestPico Chemiluminescent Subtrate (Thermo Fisher, Rockford, IL) as directed. The Western Blot detects protein around the expected size of 70 kd for human Ang-1, and of 37 kDa for COMP-Ang-1 and CMP-Ang1. For reference, recombinant human Ang-1 protein was purchased from R&D Systems (biotechne).

Results

Protein expression data presented in the FIGS. 10 to 14, 72 to 85 and 92 to 94 underline that combinations of different regulatory nucleotide sequences flanking a coding region can significantly change the protein expression levels. Such change is further impacted by modification of the nucleotides forming the constructs as exemplified by replacing 100% of uridine and 100% cytidine nucleotides by pseudo-uridine and 5-methyl-cytidine (the constructs marked with "*" in FIG. 74 and FIGS. 77 to 85. Changes are not only observed in a particular cell type but also across different cell types. For example, PAN02 (wild-type Ang-1 mRNA) shows the lowest Luciferase activity in all cell lines (FIGS. 10 to 14). All other constructs show enhanced protein expressions throughout all cell types. Therefore, the approach of using regulatory sequences from different genes can increase protein expression activity. To this end, replacing the endogenous Ang-1 sequences have shown superior effects on the protein expression of the reporter.

Worth noting, even the same regulatory sequences showed distinct protein expression activity in different cell types (FIGS. 75 to 81. These data further support our approach that the use of specific regulatory sequences can influence the activity of protein expression in a context-specific, i.e. cell-type specific cellular environment.

Figure 92:
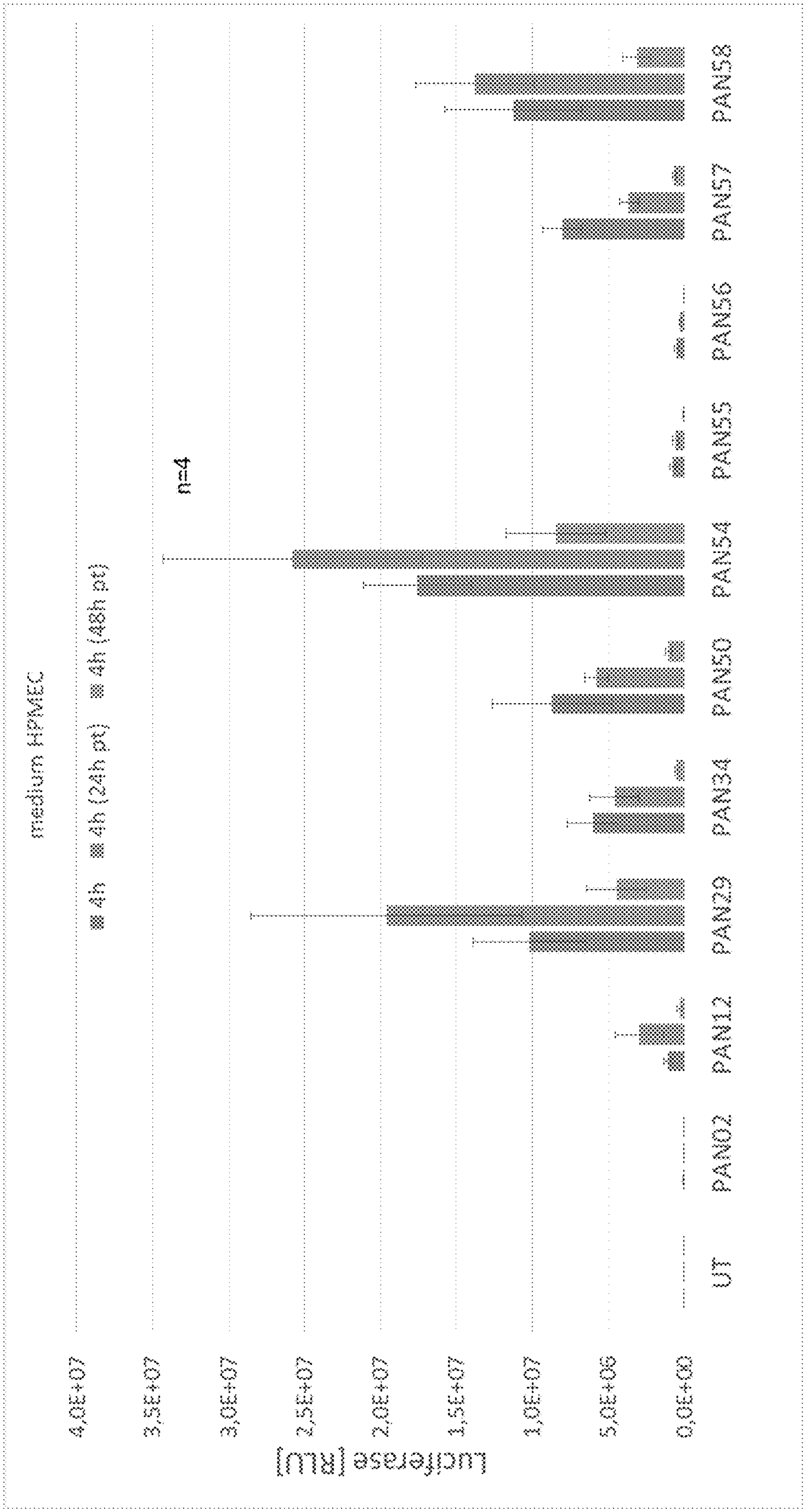
FIG. 92 is a bar diagram showing expression of luciferase, indicated as RLU (relative light units) of luciferase in medium, by the indicated recombinant nucleic acid constructs in HPMEC, where luciferase is used as the effector molecule after 4 hours (left column). Additional 4-hours luciferase activity values are assessed 24 hours (middle column) and 48 hours (right column) post transfection, after washing of the cells and supplementing the cells with fresh medium.
Figure 93:
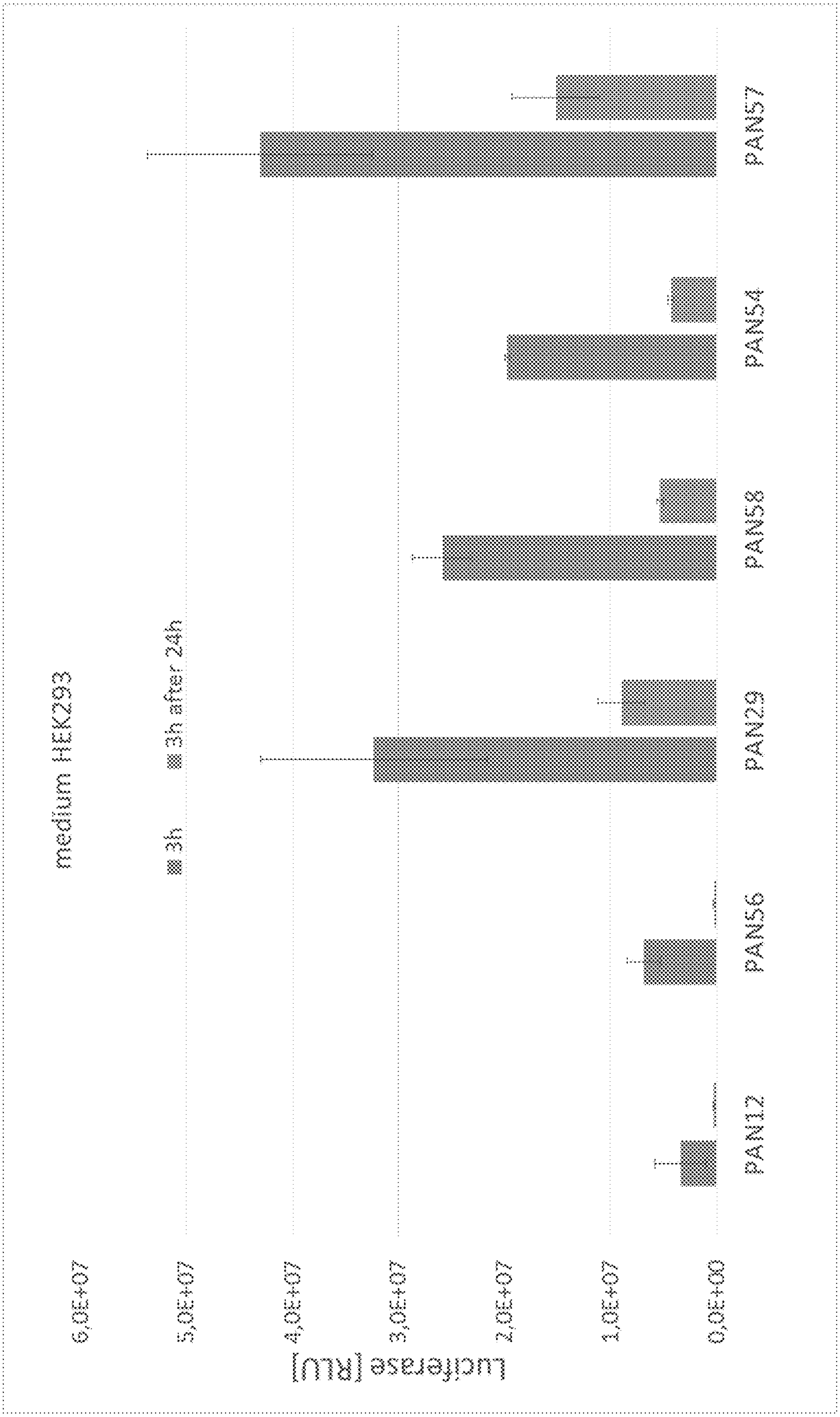
FIG. 93 is a bar diagram showing expression of luciferase, indicated as RLU (relative light units) of luciferase in medium, by the indicated recombinant nucleic acid constructs in HEK293 cells, where luciferase is used as the effector molecule after 3 hours (left column). An additional 3-hours luciferase activity value is assessed 24 hours (right column) post transfection, after washing of the cells and supplementing the cells with fresh medium.

Furthermore, we have shown that our data are also concerning a different aspect i.e. secretion. For example, the regulatory sequences used in construct PAN12 show cell-type specific (HPMEC) expression in whole cell lysates but also in medium (supernatant) (FIGS. 10-14). This indicated that these sequences are not only optimal for protein expression (translation) but also secretion. In contrast, construct PAN28 shows expression in all cell types more or less equally. The regulatory sequences used in construct PAN29 (and PAN58), namely the 5'-UTR and the signal peptide sequence of MCP-1 in combination with the 3'-UTR of vWF, were found to be particularly useful for highly efficient protein expression in human (microvascular) pulmonary endothelial cells (see e.g. FIGS. 72 and 75). The regulatory sequences used in construct PAN54, namely the 5'-UTR of spinach chloroplast RPL12, the signal peptide sequence of MCP-1 and the 3'-UTR of vWF, were found to be equally efficient for protein expression and secretion as shown in FIG. 92. As shown in FIG. 98 the regulatory sequences of PAN29 are also functional using three different ORFs, namely wt Ang-1 in PAN52; hCOMP-Ang-1 in PAN53 and CMP-Ang-1 in PAN59 in directing expression in primary human pulmonary microendothelial cells (HPMEC). In contrast the mRNA construct containing the endogenous 5'- and 3'-UTRs of human Ang-1 (PAN01) is not translated (FIG. 98). FIG. 99 shows that all four mRNA constructs display comparable quality (integrity and purity).

Example 3: Tie-2 Pathway Activation after Transfection of Modified mRNAs Encoding the Wildtype Tie-2 (PAN60) or the Activating Tie-2 Mutations (e.g. R849W (PAN61))

Modified mRNAs containing heterologous 5' and 3' UTRs are generated by in vitro transcription of PCR templates as described previously in example 1 above. Different concentration of this mRNA encoding the activating Tie-2 mutations (e.g. R849W) are transfected in different cell lines (HeLa, primary endothelial cells such as HUVECs or HPMEC or HPAEC) next to mRNAs encoding the wild-type Tie-2 using Lipofectamin MessengerMAX (Invitrogen, Carlsbad, CA; Thermo Fisher Scientific.). For qualitative Western blot cell lysates at different time points post transfection of mRNAs (1-24 h) are probed with anti-phosphotyrosine antibody (R&D systems) to evaluate Tie-2 phosphorylation (pTyr, 140 kD,). Blots are stripped and re-probed with anti-Tie-2 antibody (R&D systems) to detect total Tie-2. For quantitative measurement two different ELISAs are performed measuring human Tie-2 or Phospho-Tie-2 using the human Tie-2 DuoSet ELISA kit or human-Phospho-Tie-2 DuoSet IC ELISA according to the manufactures (e.g. both ELISA-Kits from R&D systems) protocol.

Transfection of Tie-2 mutation (PAN61, R849W) encoding mRNAs increase the presence of Phospho-Tie-2 in comparison to cell lysates derived from cells transfected with mRNAs encoding wildtype Tie-2 mRNA or in comparison to non-transfected cells. This increase in Tie-2 phosphorylation is observed in the presence or absence of co-stimulation with recombinant human Ang-1 ligand and can be observed in different cell lines. To confirm the activation of the Tie-2 signaling pathway and to demonstrate a biological relevant functional downstream signal transduction by expressing the Tie-2 (R849W) derivate a phosphorylation of Akt is demonstrated in a time course experiment. These experiments indicate that mRNAs encoding for the Tie-2 activating mutation (R849W) are functional and stronger in activating the Tie-2 signalling pathway than wt Tie-2 encoding mRNAs. These hyperactivation of the pathway can be demonstrated in the absence or presence of Tie-2 ligands (e.g. Ang-1) in human endothelial and/or non-endothelial cells.

Example 4: MRNA Formulation in Cationic LNPs for In Vivo Applications by Intravenous Administration For in vivo experiments mRNA-LNPs are prepared in a formulation process with β-(L-Arginyl)-L-2,3-diamino propionic acid-N-palmityl-N-oleyl-amide as cationic lipid. Alternatively, the cationic lipid L-Arginyl-β-alanine-N-palmityl-N-oleyl-amide can be used in an identical procedure to prepare mRNA-LNPs.

mRNA-LNP formulations are prepared using a modified procedure of a method described for siRNA (Chen, S., Tam, Y. Y., Lin, P. J., Sung, M. M., Tam, Y. K., and Cullis, P. R. (2016), Influence of particle size on the in vivo potency of lipid nanoparticle formulations of siRNA. J. Control. Release 235, 236-244. & (ii) patent application US20170121712).

Briefly, lipids are dissolved in ethanol at appropriate molar ratios (e.g. 50:49:1 β-(L-arginyl)-L-2,3-diamino propionic acid-N-palmityl-N-oleyl-amide:DPyPE:mPEG2000-DSPE). The lipid mixture is combined with an isotonic Sucrose solution of mRNA at a volume ratio of 2:1 (aqueous:ethanol) using a microfluidic mixer (NanoAssemblr®; Precision Nanosystems, Vancouver, BC) and flow rates of 18 ml/min. Similarly, LNP formulations can be obtained using citrate or acetate buffered mRNA solutions (pH 3-4) and a slightly differing mixing ratio of 3:1 (v/v; aqueous:ethanol) and flow rates of 12 ml/min.

After the mixing process, the formulations are dialyzed against 10 mM HEPES or TRIS buffered isotonic Sucrose solution using 3.5 K MWCO Slide-A-Lyzer Dialysis Cassettes (Thermo Fisher Scientific) for at least 18 hours at 4° C. Instead of Sucrose, other sugars like Trehalose or Glucose can be equally used within the formulation process.

Subsequently, the formulations are tested for particle size (Zetasizer Nano ZS instrument (Malvern Instruments Ltd, Malvern, UK), RNA encapsulation (Quant-iT RiboGreen RNA Assay Kit following manufacturer's (Thermo Fisher Scientific) protocol), and endotoxin and are found to be between 30 to 100 nm in size with a Zeta-potential of >25 mV, display greater than 90% mRNA encapsulation and <1 EU/ml of endotoxin.

mRNA-LNP formulations are stored at −80° C. at a concentration of RNA of ~0.3 μg/μl and an RNA to total lipid ratio of ~0.03-0.05 (wt/wt) until further in vitro or in vivo use.

The features of the present invention disclosed in the specification, the claims and/or the drawings may both separately and in any combination thereof be material for realizing the invention in various forms thereof.

The invention claimed is:

1. A recombinant nucleic acid construct comprising in 5'→3' direction
   a 5' UTR,
   a coding region coding for an effector molecule, and
   a 3' UTR,
   wherein the 5' UTR is a 5' UTR of a gene coding for MCP-1,
   wherein the 3' UTR is a 3' UTR of a gene coding for vWF,
   wherein the effector molecule is effective in restoring a cellular function of a cell or is effective in exercising a therapeutic effect in or on a cell, and
   wherein the recombinant nucleic acid construct is different from a wild type mRNA coding for the effector molecule.

2. The recombinant nucleic acid construct of claim 1, wherein the 5' UTR and the 3' UTR of the recombinant construct are from different species.

3. The recombinant nucleic acid construct of claim 1, wherein the 5' UTR and the 3' UTR of the recombinant construct are from the same species.

4. The recombinant nucleic acid construct of claim 1, wherein the construct comprises a poly-A tail.

5. The recombinant nucleic acid construct of claim 1, wherein the construct comprises a CAP structure.

6. The recombinant nucleic acid construct of claim 1, wherein the construct comprises a IRES (internal ribosomal entry site) sequence.

7. The recombinant nucleic acid construct of claim 1, wherein the construct comprises a nucleic acid sequence coding for a signal peptide, wherein the nucleic acid sequence coding for the signal peptide is in-frame with said nucleic acid sequence coding for the effector molecule and wherein said nucleic acid sequence coding for the signal peptide is arranged between the 5' UTR and said nucleic acid sequence coding for the effector molecule.

8. The recombinant nucleic acid construct of claim 7, wherein the nucleotide sequence coding for a signal peptide is selected from the group comprising a nucleotide sequence coding for a signal peptide of MCP-1 or a derivative thereof having a nucleotide identity of at least 85%, a nucleotide sequence coding for a signal peptide of IL-6 or a derivative thereof having a nucleotide identity of at least 85%, a nucleotide sequence coding for a signal peptide of Ang-2 or a derivative thereof having a nucleotide identity of at least 85%, and a nucleotide sequence coding for a signal peptide of Ang-1 or a derivative thereof having a nucleotide identity of at least 85%.

9. The recombinant nucleic acid construct of claim 1, wherein the cell a cellular function of which is restored and/or the cell in or on which a therapeutic effect is exercised is an endothelial cell.

10. The recombinant nucleic acid construct of claim 1, wherein the cellular function is one which can be restored by an effector molecule having anti-permeability effect of endothelial cells, an anti-vascular leakage effect, an anti-apoptotic effect of endothelial cells or an anti-inflammatory effect of endothelial cells or an anti-stress response effect, wherein optionally the effect is linked to or associated with the TIE-2 signalling pathway, VEGF-receptor pathway, NOTCH signalling pathway, PI3-kinase pathway, eNOS signalling pathway, sirtuin-dependent metabolic and energy homeostasis pathway, oxidative stress pathway, shear stress response pathway, ET-1 signal transduction pathway, NO-mediated signal transduction pathway, and mechanochemical transduction pathway.

11. A vector comprising a nucleic acid construct of claim 1.

12. A cell comprising a nucleic acid construct of claim 1.

13. A delivery vehicle comprising a nucleic acid construct of claim 1, wherein the delivery vehicle is a cationic lipid delivery particle, wherein optionally the particle is a nanoparticle, and wherein said nanoparticle optionally the average size of the nanoparticle is from about 30 nm to about 200 nm.

14. A pharmaceutical composition comprising a nucleic acid construct of claim 1, and a pharmaceutically acceptable diluent.

15. A method of expressing an effector molecule in an endothelial cell, comprising delivering a recombinant nucleic acid construct according to claim 1 to said endothelial cell.

16. The method according to claim 15, wherein said endothelial cell is a vascular endothelial cell.

17. The method according to claim 15, wherein said effector molecule is selected from the group consisting of Ang-1, Ang-4, COMP-Ang-1, hCOMP-Ang-1, COMP-ANG-2, Tie-2 receptor, Tie-1 receptor, PI3-kinase, hyperactive Tie-2 receptor R849W, VE-cadherin, GRB2, GRB7, GRB14, IQGAP1, RAC1, RAP1, DOK2, ABIN1, ABIN2, KLF2, alpha5 beta1 integrin, CD73, Akt 1, Akt 2, Akt 3, VEGF, VEGF-A, VEGF-B, PDGF, bFGF, Sirtuin, eNOS, RAS,c-MYC, PPAR-gamma, AMPK, eNOS, FOXO3,adenosine A1 receptor, adenosine A2A receptor, adenosine A2B receptor, telomerase, Oct4, sox2, klf4, c-My, PTEN, survivin, IAP, cIAP2 and XIAP, neuroglobin, prosurvival proteins Bcl-2, Bcl-x1, Bcl-w, mcl-1 A1, NR-13, BHRF1, LMW5-HL, ORF16, KS-Bcl-2, E1b-19K and P53, TNF-alpha, Fas-L, Apo2L/TRAIL, IL-12, IL-13, IL-10, IL-8, IL-2, SFRP1, 2, 3, 4, or 5, ELTD1, TGF-β, IL-6, p53, thrombospondin C, TIMP-1, TIMP-2, interferon-alpha, interferon-beta, interferon-gamma, Ang-1, cytochrome c, BH3-only proteins, Bad, Bid, Bax, Bak and Bim, Apaf1, procaspase-8, -9 -10, caspases 2, 3, 6, 7, 8, 9 and 10, IkappaB and IkappaB derivatives with mutated phosphorylation sites, Akt kinase, erythropoietin, factor VII, factor VIII, factor IX and heparan-N-sulfatase.

* * * * *

SEQUENCE LISTING

<160> NUMBER OF SEQ ID NOS: 125

<210> SEQ ID NO 1
<211> LENGTH: 38
<212> TYPE: DNA
<213> ORGANISM: Artificial Sequence
<220> FEATURE:
<223> OTHER INFORMATION: Synthetic

<400> SEQUENCE: 1
taatacgact cactataggg ccctaagcca tcagcaat 38

<210> SEQ ID NO 2
<211> LENGTH: 38
<212> TYPE: DNA
<213> ORGANISM: Artificial Sequence
<220> FEATURE:
<223> OTHER INFORMATION: Synthetic

<400> SEQUENCE: 2
taatacgact cactatagga aagtgattga ttcggata 38

<210> SEQ ID NO 3
<211> LENGTH: 38
<212> TYPE: DNA
<213> ORGANISM: Artificial Sequence
<220> FEATURE:
<223> OTHER INFORMATION: Synthetic

<400> SEQUENCE: 3
taatacgact cactataggt ccccattgaa taacagcc 38

<210> SEQ ID NO 4
<211> LENGTH: 38
<212> TYPE: DNA
<213> ORGANISM: Artificial Sequence
<220> FEATURE:
<223> OTHER INFORMATION: Synthetic

<400> SEQUENCE: 4
taatacgact cactatagga taaaagccca ggggcaag 38

<210> SEQ ID NO 5
<211> LENGTH: 38
<212> TYPE: DNA
<213> ORGANISM: Artificial Sequence
<220> FEATURE:
<223> OTHER INFORMATION: Synthetic

<400> SEQUENCE: 5
taatacgact cactataggg tcagccatct ttcaattg 38

<210> SEQ ID NO 6
<211> LENGTH: 38
<212> TYPE: DNA
<213> ORGANISM: Artificial Sequence
<220> FEATURE:
<223> OTHER INFORMATION: Synthetic

<400> SEQUENCE: 6
taatacgact cactataggc atatcttcat tcttcact 38

<210> SEQ ID NO 7

<211> LENGTH: 38
<212> TYPE: DNA
<213> ORGANISM: Artificial Sequence
<220> FEATURE:
<223> OTHER INFORMATION: Synthetic

<400> SEQUENCE: 7
taatacgact cactatagga taaaagccta gtggccat 38

<210> SEQ ID NO 8
<211> LENGTH: 38
<212> TYPE: DNA
<213> ORGANISM: Artificial Sequence
<220> FEATURE:
<223> OTHER INFORMATION: Synthetic

<400> SEQUENCE: 8
taatacgact cactataggg aggaaccgag aggctgag 38

<210> SEQ ID NO 9
<211> LENGTH: 38
<212> TYPE: DNA
<213> ORGANISM: Artificial Sequence
<220> FEATURE:
<223> OTHER INFORMATION: Synthetic

<400> SEQUENCE: 9
taatacgact cactataggg gagctgttta cccccact 38

<210> SEQ ID NO 10
<211> LENGTH: 38
<212> TYPE: DNA
<213> ORGANISM: Artificial Sequence
<220> FEATURE:
<223> OTHER INFORMATION: Synthetic

<400> SEQUENCE: 10
taatacgact cactatagga aagtgattga ttcggata 38

<210> SEQ ID NO 11
<211> LENGTH: 139
<212> TYPE: DNA
<213> ORGANISM: Artificial Sequence
<220> FEATURE:
<223> OTHER INFORMATION: Synthetic

<400> SEQUENCE: 11
tttttttttt tttttttttt tttttttttt tttttttttt tttttttttt tttttttttt 60
tttttttttt tttttttttt tttttttttt tttttttttt tttttttttt tttttttttt 120
gccttttgca agataagag 139

<210> SEQ ID NO 12
<211> LENGTH: 139
<212> TYPE: DNA
<213> ORGANISM: Artificial Sequence
<220> FEATURE:
<223> OTHER INFORMATION: Synthetic

<400> SEQUENCE: 12
tttttttttt tttttttttt tttttttttt tttttttttt tttttttttt tttttttttt 60
tttttttttt tttttttttt tttttttttt tttttttttt tttttttttt tttttttttt 120
gccttttgca agataagag 139

<210> SEQ ID NO 13
<211> LENGTH: 139
<212> TYPE: DNA
<213> ORGANISM: Artificial Sequence
<220> FEATURE:
<223> OTHER INFORMATION: Synthetic

<400> SEQUENCE: 13
tttttttttt tttttttttt tttttttttt tttttttttt tttttttttt tttttttttt 60
tttttttttt tttttttttt tttttttttt tttttttttt tttttttttt tttttttttt 120
gaattttaaa gtttattta 139

<210> SEQ ID NO 14
<211> LENGTH: 139
<212> TYPE: DNA
<213> ORGANISM: Artificial Sequence
<220> FEATURE:
<223> OTHER INFORMATION: Synthetic

<400> SEQUENCE: 14
tttttttttt tttttttttt tttttttttt tttttttttt tttttttttt tttttttttt 60
tttttttttt tttttttttt tttttttttt tttttttttt tttttttttt tttttttttt 120
atagtttaat gtattttaa 139

<210> SEQ ID NO 15
<211> LENGTH: 139
<212> TYPE: DNA
<213> ORGANISM: Artificial Sequence
<220> FEATURE:
<223> OTHER INFORMATION: Synthetic

<400> SEQUENCE: 15
tttttttttt tttttttttt tttttttttt tttttttttt tttttttttt tttttttttt 60
tttttttttt tttttttttt tttttttttt tttttttttt tttttttttt tttttttttt 120
ttaactacat ctaaaccca 139

<210> SEQ ID NO 16
<211> LENGTH: 139
<212> TYPE: DNA
<213> ORGANISM: Artificial Sequence
<220> FEATURE:
<223> OTHER INFORMATION: Synthetic

<400> SEQUENCE: 16
tttttttttt tttttttttt tttttttttt tttttttttt tttttttttt tttttttttt 60
tttttttttt tttttttttt tttttttttt tttttttttt tttttttttt tttttttttt 120
tcgctacaaa tcaaaaggc 139

<210> SEQ ID NO 17
<211> LENGTH: 139
<212> TYPE: DNA
<213> ORGANISM: Artificial Sequence
<220> FEATURE:
<223> OTHER INFORMATION: Synthetic

<400> SEQUENCE: 17
tttttttttt tttttttttt tttttttttt tttttttttt tttttttttt tttttttttt 60
tttttttttt tttttttttt tttttttttt tttttttttt tttttttttt tttttttttt 120
tgtacaaaaa tatatttat 139

<210> SEQ ID NO 18
<211> LENGTH: 144
<212> TYPE: DNA
<213> ORGANISM: Artificial Sequence
<220> FEATURE:
<223> OTHER INFORMATION: Synthetic

<400> SEQUENCE: 18
tttttttttt tttttttttt tttttttttt tttttttttt tttttttttt tttttttttt 60
tttttttttt tttttttttt tttttttttt tttttttttt tttttttttt tttttttttt 120
tttacagtaa ggaaaaaaat attt 144

<210> SEQ ID NO 19
<211> LENGTH: 139
<212> TYPE: DNA
<213> ORGANISM: Artificial Sequence
<220> FEATURE:
<223> OTHER INFORMATION: Synthetic

<400> SEQUENCE: 19
tttttttttt tttttttttt tttttttttt tttttttttt tttttttttt tttttttttt 60
tttttttttt tttttttttt tttttttttt tttttttttt tttttttttt tttttttttt 120
gccttttgca agataagag 139

<210> SEQ ID NO 20
<211> LENGTH: 73
<212> TYPE: DNA
<213> ORGANISM: Homo sapiens
<220> FEATURE:
<221> NAME/KEY: 5'UTR
<222> LOCATION: (1)..(73)

<400> SEQUENCE: 20
gaggaaccga gaggctgaga ctaacccaga aacatccaat tctcaaactg aagctcgcac 60
tctcgcctcc agc 73

<210> SEQ ID NO 21
<211> LENGTH: 69
<212> TYPE: DNA
<213> ORGANISM: Homo sapiens
<220> FEATURE:
<221> NAME/KEY: sig_peptide
<222> LOCATION: (1)..(69)

<400> SEQUENCE: 21
atgaaagtct ctgccgccct tctgtgcctg ctgctcatag cagccacctt cattccccaa 60
gggctcgct 69

<210> SEQ ID NO 22
<211> LENGTH: 23
<212> TYPE: PRT
<213> ORGANISM: Homo sapiens
<220> FEATURE:
<221> NAME/KEY: SIGNAL
<222> LOCATION: (1)..(23)

<400> SEQUENCE: 22

Met Lys Val Ser Ala Ala Leu Leu Cys Leu Leu Leu Ile Ala Ala Thr
1 5 10 15

Phe Ile Pro Gln Gly Leu Ala
20

<210> SEQ ID NO 23
<211> LENGTH: 373
<212> TYPE: DNA
<213> ORGANISM: Homo sapiens
<220> FEATURE:
<221> NAME/KEY: 3'UTR
<222> LOCATION: (1)..(373)

<400> SEQUENCE: 23
acactcactc cacaacccaa gaatctgcag ctaacttatt ttcccctagc tttccccaga 60
caccctgttt tattttatta taatgaattt tgtttgttga tgtgaaacat tatgccttaa 120
gtaatgttaa ttcttattta agttattgat gttttaagtt tatctttcat ggtactagtg 180 tttttagat acagagactt ggggaaattg cttttcctct tgaaccacag ttctacccct 240
gggatgtttt gagggtcttt gcaagaatca ttaatacaaa gaattttttt taacattcca 300
atgcattgct aaaatattat tgtggaaatg aatattttgt aactattaca ccaaataaat 360
atatttttgt aca 373

<210> SEQ ID NO 24
<211> LENGTH: 94
<212> TYPE: DNA
<213> ORGANISM: Spinacia oleracea
<220> FEATURE:
<221> NAME/KEY: 5'UTR
<222> LOCATION: (1)..(94)

<400> SEQUENCE: 24
catatcttca ttcttcactc tttccccccc ccccttatc ctcctatcta atcctctcat 60
ctctctcctc ctcttcctcc aacaacaact aaca 94

<210> SEQ ID NO 25
<211> LENGTH: 148
<212> TYPE: DNA
<213> ORGANISM: Spinacia oleracea
<220> FEATURE:
<221> NAME/KEY: 3'UTR
<222> LOCATION: (1)..(148)

<400> SEQUENCE: 25
ttttgagtaa ttttcaattt tgtttttgtt tttgtttttg ttgttgggag ttgttgtaat 60
ttggtaaatg ttggggtcac taaaatcttt tgttgcaatt ttagcacctt tttattagat 120
atataaaatt gggtttagat gtagttaa 148

<210> SEQ ID NO 26
<211> LENGTH: 329
<212> TYPE: DNA
<213> ORGANISM: Homo sapiens
<220> FEATURE:
<221> NAME/KEY: 5'UTR
<222> LOCATION: (1)..(329)

<400> SEQUENCE: 26
aaagtgattg attcggatac tgacactgta ggatctgggg agagaggaac aaaggaccgt 60
gaaagctgct ctgtaaaagc tgacacagcc ctcccaagtg agcaggactg ttcttcccac 120
tgcaatctga cagtttactg catgcctgga gagaacacag cagtaaaaac caggtttgct 180
actggaaaaa gaggaaagag aagactttca ttgacggacc cagccatggc agcgtagcag 240
ccctgcgttt tagacggcag cagctcggga ctctggacgt gtgtttgccc tcaagtttgc 300
taagctgctg gtttattact gaagaaaga 329

<210> SEQ ID NO 27
<211> LENGTH: 54
<212> TYPE: DNA
<213> ORGANISM: Homo sapiens
<220> FEATURE:
<221> NAME/KEY: sig_peptide
<222> LOCATION: (1)..(54)

<400> SEQUENCE: 27
atgtggcaga ttgttttctt tactctgagc tgtgatcttg tcttggccgc agcc 54

<210> SEQ ID NO 28
<211> LENGTH: 18
<212> TYPE: PRT
<213> ORGANISM: Homo sapiens
<220> FEATURE:
<221> NAME/KEY: SIGNAL
<222> LOCATION: (1)..(18)

<400> SEQUENCE: 28

Met Trp Gln Ile Val Phe Phe Thr Leu Ser Cys Asp Leu Val Leu Ala
1 5 10 15

Ala Ala

<210> SEQ ID NO 29
<211> LENGTH: 3450
<212> TYPE: DNA
<213> ORGANISM: Homo sapiens
<220> FEATURE:
<221> NAME/KEY: 3'UTR
<222> LOCATION: (1)..(3450)

<400> SEQUENCE: 29
acatcccagt ccacctgagg aactgtctcg aactattttc aaagacttaa gcccagtgca 60
ctgaaagtca cggctgcgca ctgtgtcctc ttccaccaca gagggcgtgt gctcggtgct 120
gacgggaccc acatgctcca gattagagcc tgtaaacttt atcacttaaa cttgcatcac 180
ttaacggacc aaagcaagac cctaaacatc cataattgtg attagacaga acacctatgc 240
aaagatgaac ccgaggctga gaatcagact gacagtttac agacgctgct gtcacaacca 300
agaatgttat gtgcaagttt atcagtaaat aactggaaaa cagaacactt atgttataca 360
atacagatca tcttggaact gcattcttct gagcactgtt tatacactgt gtaaataccc 420
atatgtcctg aattcaccat cactatcaca attaaaagga agaaaaaaac tctctaagcc 480
ataaaaagac atattcaggg atattctgag aaggggttac tagaagttta atatttggaa 540
aaacagttag tgcattttta ctccatctct taggtgcttt aaatttttat ttcaaaaaca 600
gcgtatttac atttatgttg acagcttagt tataagttaa tgctcaaata cgtatttcaa 660
atttatatgg tagaaacttc cagaatctct gaaattatca acagaaacgt gccattttag 720
tttatatgca gaccgtacta tttttttctg cctgattgtt aaatatgaag gtatttttag 780
taattaaata taacttatta ggggatatgc ctatgtttaa cttttatgat aatatttaca 840
attttataat ttgtttccaa aagacctaat tgtgccttgt gataaggaaa cttcttactt 900
ttaatgatga ggaaaattat acatttcatt ctatgacaaa gaaactttac tatcttctca 960
ctattctaaa acagaggtct gttttctttc ctagtaagat atatttttat agaactagac 1020
tacaatttaa tttctggttg agaaaagcct tctatttaag aaatttacaa agctatatgt 1080
ctcaagattc acccttaaat ttacttaagg aaaaaaataa ttgacactag taagtttttt 1140

-continued

```
tatgtcaatc agcaaactga aaaaaaaaaa agggtttcaa agtgcaaaaa caaaatctga   1200
tgttcataat atatttaaat atttaccaaa aatttgagaa cacagggctg ggcgcagtgg   1260
ctcacaccta taatcccagt acattggtag gcaaggtggg cagatcacct gaggtcagga   1320
gttcaagacc agcctggaca acatggtgaa accctgtctc tactaaataa tacaaaaatt   1380
agccaggcgt gctggcgggc acctgtaatc ccagctactc gggaggctga ggcagggaga   1440
attgcttgca ccagggaggt agaggttgca gtgagccaag atcgcaccac tgcactccag   1500
ccggggcaac agagcaagac tccatctcaa aaaaaaaaaa aaaaaaagaa agaaaagaaa   1560
atttgagaac acagctttat actcgggact acaaaaccat aaactcctgg agttttaact   1620
ccttttgaaa ttttcatagt acaattaata ctaatgaaca tttgtgtaaa gctttataat   1680
ttaaaggcaa tttctcatat attcttttct gaatcatttg caaggaagtt cagagtccag   1740
tctgtaacta gcatctacta tatgtctgtc ttcaccttac agtgttctac cattattttt   1800
tctttattcc atttcaaaat ctaatttatt ttaccccaac ttctccccac cacttgacgt   1860
agttttagaa cacacaggtg ttgctacata tttggagtca atgatggact ctggcaaagt   1920
caaggctctg ttttatttcc accaaggtgc acttttccaa caactattta actagttaag   1980
aacctcccta tcttagaact gtatctactt tatatttaag aaggttttat gaattcaaca   2040
acggtatcat ggccttgtat caagttgaaa aacaactgaa aataagaaaa tttcacagcc   2100
tcgaaagaca acaacaagtt tctaggatat ctcaatgaca agagtgatgg atacttaggt   2160
agggaaacgc taatgcagga aaaactggca acaacacaat ttatatcaat tctctttgta   2220
ggcaggtgat aaaaaattca aggacaaatc tcattatgtc attgtgcatc atatataatc   2280
tcttatgagc gagaatgggg ggaatttgtg tttttacttt acacttcaat tccttacacg   2340
gtatttcaaa caaacagttt tgctgagagg agcttttgtc tctccttaag aaaatgttta   2400
taaagctgaa aggaaatcaa acagtaatct taaaaatgaa aacaaaacaa cccaacaacc   2460
tagataacta cagtgatcag ggagcacagt tcaactcctt gttatgtttt agtcatatgg   2520
cctactcaaa cagctaaata acaacaccag tggcagataa aaatcaccat ttatctttca   2580
gctattaatc ttttgaatga ataaactgtg acaaacaaat taacattttt gaacatgaaa   2640
ggcaacttct gcacaatcct gtatccaagc aaactttaaa ttatccactt aattattact   2700
taatcttaaa aaaaattaga acccagaact tttcaatgaa gcatttgaaa gttgaagtgg   2760
aatttaggaa agccataaaa atataaatac tgttatcaca gcaccagcaa gccataatct   2820
ttatacctat cagttctatt tctattaaca gtaaaaacat taagcaagat ataagactac   2880
ctgcccaaga attcagtctt ttttcatttt tgtttttctc agttctgagg atgttaatcg   2940
tcaaattttc tttggactgc attcctcact actttttgca caatggtctc acgttctcac   3000
atttgttctc gcgaataaat tgataaaagg tgttaagttc tgtgaatgtc tttttaatta   3060
tgggcataat tgtgcttgac tggataaaaa cttaagtcca cccttatgtt tataataatt   3120
tcttgagaac agcaaactgc atttaccatc gtaaaacaac atctgactta cgggagctgc   3180
agggaagtgg tgagacagtt cgaacggctc ctcagaaatc cagtgaccca attctaaaga   3240
ccatagcacc tgcaagtgac acaacaagca gatttattat acatttatta gccttagcag   3300
gcaataaacc aagaatcact ttgaagacac agcaaaaagt gatacactcc gcagatctga   3360
aatagatgtg ttctcagaca acaaagtccc ttcagaatct tcatgttgca taaatgttat   3420
gaatattaat aaaaagttga ttgagaaaaa                                     3450
```

<210> SEQ ID NO 30
<211> LENGTH: 121
<212> TYPE: DNA
<213> ORGANISM: Homo sapiens
<220> FEATURE:
<221> NAME/KEY: 5'UTR
<222> LOCATION: (1)..(121)

<400> SEQUENCE: 30
gtctcaatat tagagtctca acccccaata aatataggac tggagatgtc tgaggctcat 60
tctgccctcg agcccaccgg gaacgaaaga gaagctctat ctcccctcca ggagcccagc 120
t 121

<210> SEQ ID NO 31
<211> LENGTH: 87
<212> TYPE: DNA
<213> ORGANISM: Homo sapiens
<220> FEATURE:
<221> NAME/KEY: sig_peptide
<222> LOCATION: (1)..(87)

<400> SEQUENCE: 31
atgaactcct tctccacaag cgccttcggt ccagttgcct tctccctggg gctgctcctg 60
gtgttgcctg ctgccttccc tgcccca 87

<210> SEQ ID NO 32
<211> LENGTH: 29
<212> TYPE: PRT
<213> ORGANISM: Homo sapiens
<220> FEATURE:
<221> NAME/KEY: SIGNAL
<222> LOCATION: (1)..(29)

<400> SEQUENCE: 32

Met Asn Ser Phe Ser Thr Ser Ala Phe Gly Pro Val Ala Phe Ser Leu
1 5 10 15

Gly Leu Leu Leu Val Leu Pro Ala Ala Phe Pro Ala Pro
20 25

<210> SEQ ID NO 33
<211> LENGTH: 429
<212> TYPE: DNA
<213> ORGANISM: Homo sapiens
<220> FEATURE:
<221> NAME/KEY: 3'UTR
<222> LOCATION: (1)..(429)

<400> SEQUENCE: 33
catgggcacc tcagattgtt gttgttaatg ggcattcctt cttctggtca gaaacctgtc 60
cactgggcac agaacttatg ttgttctcta tggagaacta aaagtatgag cgttaggaca 120
ctattttaat tatttttaat ttattaatat ttaaatatgt gaagctgagt taatttatgt 180
aagtcatatt tatattttta agaagtacca cttgaaacat tttatgtatt agttttgaaa 240
taataatgga aagtggctat gcagtttgaa tatcctttgt ttcagagcca gatcatttct 300
tggaaagtgt aggcttacct caaataaatg gctaacttat acatattttt aaagaaatat 360
ttatattgta tttatataat gtataaatgg tttttatacc aataaatggc attttaaaaa 420
attcagcaa 429

<210> SEQ ID NO 34
<211> LENGTH: 255
<212> TYPE: DNA

<213> ORGANISM: Homo sapiens
<220> FEATURE:
<221> NAME/KEY: 5'UTR
<222> LOCATION: (1)..(255)

<400> SEQUENCE: 34
gtggcagctc acagctattg tggtgggaaa gggagggtgg ttggtggatg tcacagcttg 60
ggctttatct cccccagcag tggggactcc acagcccctg ggctacataa cagcaagaca 120
gtccggagct gtagcagacc tgattgagcc tttgcagcag ctgagagcat ggcctagggt 180
gggcggcacc attgtccagc agctgagttt cccagggacc ttggagatag ccgcagccct 240
catttgcagg ggaag 255

<210> SEQ ID NO 35
<211> LENGTH: 66
<212> TYPE: DNA
<213> ORGANISM: Homo sapiens
<220> FEATURE:
<221> NAME/KEY: sig_peptide
<222> LOCATION: (1)..(66)

<400> SEQUENCE: 35
atgattcctg ccagatttgc cggggtgctg cttgctctgg ccctcatttt gccagggacc 60
ctttgt 66

<210> SEQ ID NO 36
<211> LENGTH: 22
<212> TYPE: PRT
<213> ORGANISM: Homo sapiens
<220> FEATURE:
<221> NAME/KEY: SIGNAL
<222> LOCATION: (1)..(22)

<400> SEQUENCE: 36

Met Ile Pro Ala Arg Phe Ala Gly Val Leu Leu Ala Leu Ala Leu Ile
1 5 10 15

Leu Pro Gly Thr Leu Cys
20

<210> SEQ ID NO 37
<211> LENGTH: 141
<212> TYPE: DNA
<213> ORGANISM: Homo sapiens
<220> FEATURE:
<221> NAME/KEY: 3'UTR
<222> LOCATION: (1)..(141)

<400> SEQUENCE: 37
ggctgctgca gctgcatggg tgcctgctgc tgcctgcctt ggcctgatgg ccaggccaga 60
gtgctgccag tcctctgcat gttctgctct tgtgcccttc tgagcccaca ataaaggctg 120
agctcttatc ttgcaaaagg c 141

<210> SEQ ID NO 38
<211> LENGTH: 243
<212> TYPE: DNA
<213> ORGANISM: Homo sapiens
<220> FEATURE:
<221> NAME/KEY: 5'UTR
<222> LOCATION: (1)..(243)

<400> SEQUENCE: 38
ataaaagccc aggggcaagc ggtccggata acggctagcc tgaggagctg ctgcgacagt 60
ccactacctt tttcgagagt gactcccgtt gtcccaaggc ttcccagagc gaacctgtgc 120
ggctgcaggc accggcgcgt cgagtttccg gcgtccggaa ggaccgagct cttctcgcgg 180
atccagtgtt ccgtttccag cccccaatct cagagcggag ccgacagaga gcagggaacc 240
ggc 243

<210> SEQ ID NO 39
<211> LENGTH: 258
<212> TYPE: DNA
<213> ORGANISM: Homo sapiens
<220> FEATURE:
<221> NAME/KEY: 3'UTR
<222> LOCATION: (1)..(258)

<400> SEQUENCE: 39
gggcctttcc aagattgctg tttttgtttt ggagcttcaa gactttgcat ttcctagtat 60
ttctgtttgt cagttctcaa tttcctgtgt ttgcaatgtt gaaatttttt ggtgaagtac 120
tgaacttgct ttttttccgg tttctacatg cagagatgaa tttatactgc catcttacga 180
ctatttcttc tttttaatac acttaactca ggccattttt taagttggtt acttcaaagt 240
aaataaactt taaaattc 258

<210> SEQ ID NO 40
<211> LENGTH: 261
<212> TYPE: DNA
<213> ORGANISM: Homo sapiens
<220> FEATURE:
<221> NAME/KEY: 5'UTR
<222> LOCATION: (1)..(261)

<400> SEQUENCE: 40
gggctggggg agggtatata agccgagtag gcgacggtga ggtcgacgcc ggccaagaca 60
gcacagacag attgacctat tggggtgttt cgcgagtgtg agagggaagc gccgcggcct 120
gtatttctag acctgccctt cgcctggttc gtggcgcctt gtgaccccgg gcccctgccg 180
cctgcaagtc ggaaattgcg ctgtgctcct gtgctacggc ctgtggctgg actgcctgct 240
gctgcccaac tggctggcaa g 261

<210> SEQ ID NO 41
<211> LENGTH: 54
<212> TYPE: DNA
<213> ORGANISM: Homo sapiens
<220> FEATURE:
<221> NAME/KEY: sig_peptide
<222> LOCATION: (1)..(54)

<400> SEQUENCE: 41
atgaagctct ccctggtggc cgcgatgctg ctgctgctca gcgcggcgcg ggcc 54

<210> SEQ ID NO 42
<211> LENGTH: 18
<212> TYPE: PRT
<213> ORGANISM: Homo sapiens
<220> FEATURE:
<221> NAME/KEY: SIGNAL
<222> LOCATION: (1)..(18)

<400> SEQUENCE: 42

Met Lys Leu Ser Leu Val Ala Ala Met Leu Leu Leu Leu Ser Ala Ala
1               5                   10                  15

Arg Ala

<210> SEQ ID NO 43
<211> LENGTH: 1744
<212> TYPE: DNA
<213> ORGANISM: Homo sapiens
<220> FEATURE:
<221> NAME/KEY: 3'UTR
<222> LOCATION: (1)..(1744)

<400> SEQUENCE: 43
acactgatct gctagtgctg taatattgta aatactggac tcaggaactt ttgttaggaa 60
aaaattgaaa gaacttaagt ctcgaatgta attggaatct tcacctcaga gtggagttga 120
aactgctata gcctaagcgg ctgtttactg cttttcatta gcagttgctc acatgtcttt 180
gggtgggggg gagaagaaga attggccatc ttaaaaagcg ggtaaaaaac ctgggttagg 240
gtgtgtgttc accttcaaaa tgttctattt aacaactggg tcatgtgcat ctggtgtagg 300
aagttttttc taccataagt gacaccaata aatgtttgtt atttacactg gtctaatgtt 360
tgtgagaagc ttctaattag atcaattact tattttagga aatttaagac tagatactcg 420
tgtgtggggt gaggggaggg agtatttggt atgttgggat aaggaaacac ttctatttaa 480
tgcttccagg gatttttttt tttttttta accctcctgg gcccaagtga tccttccacc 540
tcagtctccc agctaattga gaccacaggc ttgttaccac catgctcggc ttttgcatta 600
atctaagaaa aggggagaga agttaatcca catctttact caggcaaggg gcatttcaca 660
gtgcccaaga gtggggtttt cttgaacata cttggtttcc tatttcccct tatctttcta 720
aaactgcctt tctggtggct ttttttaaaa ttattactaa tgatgctttt atagctgctt 780
ggattctctg agaaatgatg gggagtgagt gatcactggt attaacttta tacacttgga 840
tttcatttgt aactttagga tgtaaaggta tattgtgaac cctagctgtg tcagaatctc 900
catccctgaa atttctcatt agtggtactg gggtgggatc ttggatggtg acattgaaac 960
tacactaaat cccctcacta tgaatgggtt gttaaaggca atggtttgtg tcaaaactgg 1020
tttaggatta cttagattgt gttcctgaag aaaagagtcc aggtaaatgg tatgatcaat 1080
aaaggacagg ctggtgctaa cataaaatcc aatattgtaa tcctagcact ttgggaggcc 1140
aaggcgggtg gatcacaagg tcaagagata gagaccatct ttgccaacat ggtgaaactc 1200
catctctact gaaaatacaa aaattagctg ggcgtggtag tgcaagctga aggctgaggc 1260
aggagaatca ctcgaacccg ggaggcagag gttgcagtga gccgagatca caccactgta 1320
ctccagcccg gcactccagc ctggcgacaa gagtgagact ccacctcaaa aaaaaaaaaa 1380
agaatccaat actgcccaag gataggtatt ttatagatgg gcaactggct gaaaggttaa 1440
ttctctaggg ctagtagaac tggatcccaa caccaaactc ttaattagac ctaggcctca 1500
gctgcactgc ccgaaaagca tttgggcaga ccctgagcag aatactggtc tcaggccaag 1560
cccaatacag ccattaaaga tgacctacag tgctgtgtac cctggggcaa tagggttaaa 1620
tggtagttag caactaggc tagtcttccc ttacctcaaa ggctctcact accgtggacc 1680
acctagtctg taactctttc tgaggagctg ttactgaata ttaaaaagat agacttcaac 1740
tatg 1744

<210> SEQ ID NO 44
<211> LENGTH: 128
<212> TYPE: DNA
<213> ORGANISM: Homo sapiens
<220> FEATURE:
<221> NAME/KEY: 5'UTR
<222> LOCATION: (1)..(128)

<400> SEQUENCE: 44
gtcagccatc tttcaattgt gttcgcagcc gccgccgcgc cgccgtcgct ctccaacgcc 60
agcgccgcct ctcgctcgcc gagctccagc cgaaggagaa gggggtaag taaggaggtc 120 tctgtacc 128

<210> SEQ ID NO 45
<211> LENGTH: 521
<212> TYPE: DNA
<213> ORGANISM: Homo sapiens
<220> FEATURE:
<221> NAME/KEY: 3'UTR
<222> LOCATION: (1)..(521)

<400> SEQUENCE: 45
gaatccacta tgatgggaaa catttcattc tcaaaaaaaa aaaaaaaaat ttctcttctt 60
cctgttattg gtagttctga acgttagata ttttttttcc atggggtcaa aaggtaccta 120
agtatatgat tgcgagtgga aaaatagggg acagaaatca ggtattggca gtttttccat 180
tttcatttgt gtgtgaattt ttaatataaa tgcggagacg taaagcatta atgcaagtta 240
aaatgtttca gtgaacaagt ttcagcggtt caactttata ataattataa ataaacctgt 300
taaatttttc tggacaatgc cagcatttgg attttttttaa aacaagtaaa tttcttattg 360
atggcaacta aatggtgttt gtagcatttt tatcatacag tagattccat ccattcacta 420
tacttttcta actgagttgt cctacatgca agtacatgtt tttaatgttg tctgtcttct 480
gtgctgttcc tgtaagtttg ctattaaaat acattaaact a 521

<210> SEQ ID NO 46
<211> LENGTH: 118
<212> TYPE: DNA
<213> ORGANISM: Homo sapiens
<220> FEATURE:
<221> NAME/KEY: 5'UTR
<222> LOCATION: (1)..(118)

<400> SEQUENCE: 46
tccccattga ataacagcca agttgctttg gtttctattt ctttgttaag tcgttccctc 60
tacaaaggac ttcctagtgg gtgtgaaagg cagcggtggc cacagaggcg gcggagag 118

<210> SEQ ID NO 47
<211> LENGTH: 578
<212> TYPE: DNA
<213> ORGANISM: Homo sapiens
<220> FEATURE:
<221> NAME/KEY: 3'UTR
<222> LOCATION: (1)..(578)

<400> SEQUENCE: 47
gcggcttcct ggccctgggg ccgggggctg gggtgtgggg cagtctgggt cctctcatca 60
tccccacttc ccaggcccag cctttccaac cctgcctggg atctgggctt taatgcagag 120
gccatgtcct tgtctggtcc tgcttctggc tacagccacc ctggaacgga gaaggcagct 180
gacggggatt gccttcctca gccgcagcag cacctggggc tccagctgct ggaatcctac 240
catcccagga ggcaggcaca gccagggaga ggggaggagt gggcagtgaa gatgaagccc 300
catgctcagt cccctcccat cccccacgca gctccacccc agtcccaagc caccagctgt 360
ctgctcctgg tgggaggtgg cctcctcagc ccctcctctc tgacctttaa cctcactctc 420
accttgcacc gtgcaccaac ccttcacccc tcctggaaag caggcctgat ggcttcccac 480
tggcctccac cacctgacca gagtgttctc ttcagaggac tggctccttt cccagtgtcc 540
ttaaaataaa gaaatgaaaa tgcttgttgg cacattca 578

<210> SEQ ID NO 48
<211> LENGTH: 4367
<212> TYPE: DNA
<213> ORGANISM: Artificial Sequence
<220> FEATURE:
<223> OTHER INFORMATION: Synthetic

<400> SEQUENCE: 48
gccctaagcc atcagcaatc cttagtatag gggcacactc atgcattcct gtcaagtcat 60
cttgtgaaag gctgcctgct tccagcttgg cttggatgtg caaccttaat aaaactcact 120
gaggtctggg agaaaatagc agatctgcag cagatagggt agaggaaagg gtctagaata 180
tgtacacgca gctgactcag gcaggctcca tgctgaacgg tcacacagag aggaaacaat 240
aaatctcagc tactatgcaa taaatatctc aagttttaac gaagaaaaac atcattgcag 300
tgaaataaaa aattttaaaa ttttagaaca aagctaacaa atggctagtt ttctatgatt 360
cttcttcaaa cgctttcttt gagggggaaa gagtcaaaca aacaagcagt tttacctgaa 420
ataaagaact agttttagag gtcagaagaa aggagcaagt tttgcgagag gcacggaagg 480
agtgtgctgg cagtacaatg acagttttcc tttcctttgc tttcctcgct gccattctga 540
ctcacatagg gtgcagcaat cagcgccgaa gtccagaaaa cagtgggaga agatataacc 600
ggattcaaca tgggcaatgt gcctacactt tcattcttcc agaacacgat ggcaactgtc 660
gtgagagtac gacagaccag tacaacacaa acgctctgca gagagatgct ccacacgtgg 720
aaccggattt ctcttcccag aaacttcaac atctggaaca tgtgatggaa aattatactc 780
agtggctgca aaaacttgag aattacattg tggaaaacat gaagtcggag atggcccaga 840
tacagcagaa tgcagttcag aaccacacgg ctaccatgct ggagatagga accagcctcc 900
tctctcagac tgcagagcag accagaaagc tgacagatgt tgagacccag gtactaaatc 960
aaacttctcg acttgagata cagctgctgg agaattcatt atccacctac aagctagaga 1020
agcaacttct tcaacagaca aatgaaatct tgaagatcca tgaaaaaaac agtttattag 1080
aacataaaat cttagaaatg gaaggaaaac acaaggaaga gttggacacc ttaaaggaag 1140
agaaagagaa ccttcaaggc ttggttactc gtcaaacata tataatccag gagctggaaa 1200
agcaattaaa cagagctacc accaacaaca gtgtccttca gaagcagcaa ctggagctga 1260
tggacacagt ccacaacctt gtcaatcttt gcactaaaga aggtgtttta ctaaagggag 1320
gaaaaagaga ggaagagaaa ccatttagag actgtgcaga tgtatatcaa gctggtttta 1380
ataaaagtgg aatctacact atttatatta ataatatgcc agaacccaaa aaggtgtttt 1440
gcaatatgga tgtcaatggg ggaggttgga ctgtaataca acatcgtgaa gatggaagtc 1500
tagatttcca aagaggctgg aaggaatata aaatgggttt tggaaatccc tccggtgaat 1560
attggctggg gaatgagttt atttttgcca ttaccagtca gaggcagtac atgctaagaa 1620
ttgagttaat ggactgggaa gggaaccgag cctattcaca gtatgacaga ttccacatag 1680
gaaatgaaaa gcaaaactat aggttgtatt taaaaggtca cactgggaca gcaggaaaac 1740
agagcagcct gatcttacac ggtgctgatt tcagcactaa agatgctgat aatgacaact 1800
gtatgtgcaa atgtgccctc atgttaacag gaggatggtg gtttgatgct tgtggcccct 1860
ccaatctaaa tggaatgttc tatactgcgg gacaaaacca tggaaaactg aatgggataa 1920
agtggcacta cttcaaaggg cccagttact ccttacgttc cacaactatg atgattcgac 1980
ctttagattt ttgaaagcgc aatgtcagaa gcgattatga aagcaacaaa gaaatccgga 2040
gaagctgcca ggtgagaaac tgtttgaaaa cttcagaagc aaacaatatt gtctcccttc 2100
cagcaataag tggtagttat gtgaagtcac caaggttctt gaccgtgaat ctggagccgt 2160
ttgagttcac aagagtctct acttggggtg acagtgctca cgtggctcga ctatagaaaa 2220
ctccactgac tgtcgggctt taaaaaggga agaaactgct gagcttgctg tgcttcaaac 2280
tactactgga ccttattttg gaactatggt agccagatga taaatatggt taatttcatg 2340
taaaacagaa aaaaagagtg aaaaagagaa tatacatgaa gaatagaaac aagcctgcca 2400
taatcctttg gaaaagatgt attataccag tgaaaaggtg ttatatctat gcaaacctac 2460
taacaaatta tactgttgca caattttgat aaaaatttag aacagcattg tcctctgagt 2520
tggttaaatg ttaatggatt tcagaagcct aattccagta tcatacttac tagttgattt 2580
ctgcttaccc atcttcaaat gaaaattcca tttttgtaag ccataatgaa ctgtagtaca 2640
tggacaataa gtgtgtggta gaaacaaact ccattactct gatttttgat acagttttca 2700
gaaaaagaaa tgaacataat caagtaagga tgtatgtggt gaaaacttac caccccccata 2760 ctatggtttt catttactct aaaaactgat tgaatgatat ataaatatat ttatagcctg 2820
agtaaagtta aaagaatgta aaatatatca tcaagttctt aaaataatat acatgcattt 2880
aatatttcct ttgatattat acaggaaagc aatattttgg agtatgttaa gttgaagtaa 2940
aagcaagtac tctggagcag ttcattttac agtatctact tgcatgtgta tacatacatg 3000
taacttcatt attttaaaaa tatttttaga actccaatac tcaccctgtt atgtcttgct 3060
aatttaaatt ttgctaatta actgaaacat gcttaccaga ttcacactgt tccagtgtct 3120
ataaaagaaa cactttgaag tctataaaaa ataaaataat tataaatatc attgtacata 3180
gcatgtttat atctgcaaaa aacctaatag ctaattaatc tggaatatgc aacattgtcc 3240
ttaattgatg caaataacac aaatgctcaa agaaatctac tatatccctt aatgaaatac 3300
atcattcttc atatatttct ccttcagtcc attcccttag gcaattttta atttttaaaa 3360
attattatca ggggagaaaa attggcaaaa ctattatatg taagggaaat atatacaaaa 3420
agaaaattaa tcatagtcac ctgactaaga aattctgact gctagttgcc ataaataact 3480
caatggaaat attcctatgg gataatgtat tttaagtgaa tttttggggt gcttgaagtt 3540
actgcattat tttatcaaga agtcttctct gcctgtaagt gtccaaggtt atgacagtaa 3600
acagttttta ttaaaacatg agtcactatg ggatgagaaa attgaaataa agctactggg 3660
cctcctctca taaaagagac agttgttggc aaggtagcaa taccagtttc aaacttggtg 3720
acttgatcca ctatgcctta atggtttcct ccatttgaga aaataaagct attcacattg 3780
ttaagaaaaa tactttttaa agtttaccat caagtctttt ttatatttat gtgtctgtat 3840
tctacccctt tttgccttac aagtgatatt tgcaggtatt ataccatttt tctattcttg 3900
gtggcttctt catagcaggt aagcctctcc ttctaaaaac ttctcaactg ttttcattta 3960
agggaaagaa aatgagtatt ttgtcctttt gtgttcctac agacactttc ttaaaccagt 4020
ttttggataa agaatactat ttccaaactc atattacaaa aacaaaataa aataataaaa 4080
aaagaaagca tgatatttac tgttttgttg tctgggtttg agaaatgaaa tattgtttcc 4140
aattatttat aataaatcag tataaaatgt tttatgattg ttatgtgtat tatgtaatac 4200
gtacatgttt atggcaattt aacatgtgta ttcttttaat tgtttcagaa taggataatt 4260
aggtattcga attttgtctt taaaattcat gtggtttcta tgcaaagttc ttcatatcat 4320
cacaacatta tttgatttaa ataaaattga aagtaatatt tgtgcaa 4367

<210> SEQ ID NO 49
<211> LENGTH: 3782
<212> TYPE: DNA
<213> ORGANISM: Artificial Sequence
<220> FEATURE:
<223> OTHER INFORMATION: Synthetic

<400> SEQUENCE: 49
gccctaagcc atcagcaatc cttagtatag gggcacactc atgcattcct gtcaagtcat 60
cttgtgaaag gctgcctgct tccagcttgg cttggatgtg caaccttaat aaaactcact 120
gaggtctggg agaaaatagc agatctgcag cagatagggt agaggaaagg gtctagaata 180
tgtacacgca gctgactcag gcaggctcca tgctgaacgg tcacacagag aggaaacaat 240
aaatctcagc tactatgcaa taaatatctc aagttttaac gaagaaaaac atcattgcag 300
tgaaataaaa aattttaaaa ttttagaaca aagctaacaa atggctagtt ttctatgatt 360
cttcttcaaa cgctttcttt gagggggaaa gagtcaaaca aacaagcagt tttacctgaa 420
ataaagaact agttttagag gtcagaagaa aggagcaagt tttgcgagag gcacggaagg 480
agtgtgctgg cagtacaatg acagttttcc tttcctttgc tttcctcgct gccattctga 540
ctgggatctt agacctagcc ccacagatgc ttcgagaact ccaggagact aatgcggcgc 600
tgcaagacgt gagagagctc ttgcgacagc aggtcaagga gatcaccttc ctgaagaata 660
cggtgatgga atgtgacgct tgcggaggct cccttgtcaa tctttgcact aaagaaggtg 720
ttttactaaa gggaggaaaa agagaggaag agaaaccatt tagagactgt gcagatgtat 780
atcaagctgg ttttaataaa agtggaatct acactattta tattaataat atgccagaac 840
ccaaaaaggt gttttgcaat atggatgtca atgggggagg ttggactgta atacaacatc 900
gtgaagatgg aagtctagat ttccaaagag gctggaagga atataaaatg ggttttggaa 960
atccctccgg tgaatattgg ctggggaatg agtttatttt tgccattacc agtcagaggc 1020
agtacatgct aagaattgag ttaatggact gggaagggaa ccgagcctat tcacagtatg 1080
acagattcca cataggaaat gaaaagcaaa actataggtt gtatttaaaa ggtcacactg 1140
ggacagcagg aaaacagagc agcctgatct tacacggtgc tgatttcagc actaaagatg 1200
ctgataatga caactgtatg tgcaaatgtg ccctcatgtt aacaggagga tggtggtttg 1260
atgcttgtgg cccctccaat ctaaatggaa tgttctatac tgcgggacaa aaccatggaa 1320
aactgaatgg gataaagtgg cactacttca aagggcccag ttactcctta cgttccacaa 1380
ctatgatgat tcgaccttta gatttttgaa agcgcaatgt cagaagcgat tatgaaagca 1440
acaaagaaat ccggagaagc tgccaggtga gaaactgttt gaaaacttca gaagcaaaca 1500
atattgtctc ccttccagca ataagtggta gttatgtgaa gtcaccaagg ttcttgaccg 1560
tgaatctgga gccgtttgag ttcacaagag tctctacttg ggtgacagt gctcacgtgg 1620 ctcgactata gaaaactcca ctgactgtcg ggctttaaaa agggaagaaa ctgctgagct 1680
tgctgtgctt caaactacta ctggacctta ttttggaact atggtagcca gatgataaat 1740
atggttaatt tcatgtaaaa cagaaaaaaa gagtgaaaaa gagaatatac atgaagaata 1800
gaaacaagcc tgccataatc ctttggaaaa gatgtattat accagtgaaa aggtgttata 1860
tctatgcaaa cctactaaca aattatactg ttgcacaatt ttgataaaaa tttagaacag 1920
cattgtcctc tgagttggtt aaatgttaat ggatttcaga agcctaattc cagtatcata 1980
cttactagtt gatttctgct tacccatctt caaatgaaaa ttccattttt gtaagccata 2040
atgaactgta gtacatggac aataagtgtg tggtagaaac aaactccatt actctgattt 2100
ttgatacagt tttcagaaaa agaaatgaac ataatcaagt aaggatgtat gtggtgaaaa 2160
cttaccaccc ccatactatg gttttcattt actctaaaaa ctgattgaat gatatataaa 2220
tatatttata gcctgagtaa agttaaaaga atgtaaaata tatcatcaag ttcttaaaat 2280
aatatacatg catttaatat ttcctttgat attatacagg aaagcaatat tttggagtat 2340
gttaagttga agtaaaagca agtactctgg agcagttcat tttacagtat ctacttgcat 2400
gtgtatacat acatgtaact tcattatttt aaaaatattt ttagaactcc aatactcacc 2460
ctgttatgtc ttgctaattt aaattttgct aattaactga aacatgctta ccagattcac 2520
actgttccag tgtctataaa agaaacactt tgaagtctat aaaaaataaa ataattataa 2580
atatcattgt acatagcatg tttatatctg caaaaaacct aatagctaat taatctggaa 2640
tatgcaacat tgtccttaat tgatgcaaat aacacaaatg ctcaaagaaa tctactatat 2700
cccttaatga aatacatcat tcttcatata tttctccttc agtccattcc cttaggcaat 2760
ttttaatttt taaaaattat tatcagggga gaaaaattgg caaaactatt atatgtaagg 2820
gaaatatata caaaaagaaa attaatcata gtcacctgac taagaaattc tgactgctag 2880
ttgccataaa taactcaatg gaaatattcc tatgggataa tgtattttaa gtgaattttt 2940
ggggtgcttg aagttactgc attattttat caagaagtct tctctgcctg taagtgtcca 3000
aggttatgac agtaaacagt ttttattaaa acatgagtca ctatgggatg agaaaattga 3060
aataaagcta ctgggcctcc tctcataaaa gagacagttg ttggcaaggt agcaatacca 3120
gtttcaaact tggtgacttg atccactatg ccttaatggt ttcctccatt tgagaaaata 3180
aagctattca cattgttaag aaaaatactt tttaaagttt accatcaagt ctttttttata 3240 tttatgtgtc tgtattctac cccttttttgc cttacaagtg atatttgcag gtattatacc 3300
atttttctat tcttggtggc ttcttcatag caggtaagcc tctccttcta aaaacttctc 3360
aactgttttc atttaaggga aagaaaatga gtattttgtc cttttgtgtt cctacagaca 3420
ctttcttaaa ccagtttttg gataaagaat actatttcca aactcatatt acaaaaacaa 3480
aataaaataa taaaaaaaga aagcatgata tttactgttt tgttgtctgg gtttgagaaa 3540
tgaaatattg tttccaatta tttataataa atcagtataa aatgttttat gattgttatg 3600
tgtattatgt aatacgtaca tgtttatggc aatttaacat gtgtattctt ttaattgttt 3660
cagaatagga taattaggta ttcgaatttt gtctttaaaa ttcatgtggt ttctatgcaa 3720
agttcttcat atcatcacaa cattatttga tttaaataaa attgaaagta atatttgtgc 3780
aa 3782

<210> SEQ ID NO 50
<211> LENGTH: 1976
<212> TYPE: DNA
<213> ORGANISM: Artificial Sequence
<220> FEATURE:
<223> OTHER INFORMATION: Synthetic

<400> SEQUENCE: 50
aaagtgattg attcggatac tgacactgta ggatctgggg agagaggaac aaaggaccgt 60
gaaagctgct ctgtaaaagc tgacacagcc ctcccaagtg agcaggactg ttcttcccac 120
tgcaatctga cagtttactg catgcctgga gagaacacag cagtaaaaac caggtttgct 180
actggaaaaa gaggaaagag aagactttca ttgacggacc cagccatggc agcgtagcag 240

```
ccctgcgttt tagacggcag cagctcggga ctctggacgt gtgtttgccc tcaagtttgc    300

taagctgctg gtttattact gaagaaagaa tgtggcagat tgttttcttt actctgagct    360

gtgatcttgt cttggccgca gcccacatag ggtgcagcaa tcagcgccga agtccagaaa    420

acagtgggag aagatataac cggattcaac atgggcaatg tgcctacact ttcattcttc    480

cagaacacga tggcaactgt cgtgagagta cgacagacca gtacaacaca aacgctctgc    540

agagagatgc tccacacgtg gaaccggatt tctcttccca gaaacttcaa catctggaac    600

atgtgatgga aaattatact cagtggctgc aaaaacttga gaattacatt gtggaaaaca    660

tgaagtcgga gatggcccag atacagcaga atgcagttca gaaccacacg gctaccatgc    720

tggagatagg aaccagcctc ctctctcaga ctgcagagca gaccagaaag ctgacagatg    780

ttgagaccca ggtactaaat caaacttctc gacttgagat acagctgctg gagaattcat    840

tatccaccta caagctagag aagcaacttc ttcaacagac aaatgaaatc ttgaagatcc    900

atgaaaaaaa cagtttatta gaacataaaa tcttagaaat ggaaggaaaa cacaaggaag    960

agttggacac cttaaaggaa gagaaagaga accttcaagg cttggttact cgtcaaacat   1020

atataatcca ggagctggaa aagcaattaa acagagctac caccaacaac agtgtccttc   1080

agaagcagca actggagctg atggacacag tccacaacct tgtcaatctt tgcactaaag   1140

aaggtgtttt actaaaggga ggaaaaagag aggaagagaa accatttaga gactgtgcag   1200

atgtatatca agctggtttt aataaaagtg gaatctacac tatttatatt aataatatgc   1260

cagaacccaa aaaggtgttt tgcaatatgg atgtcaatgg gggaggttgg actgtaatac   1320

aacatcgtga agatggaagt ctagatttcc aaagaggctg gaaggaatat aaaatgggtt   1380

ttggaaatcc ctccggtgaa tattggctgg ggaatgagtt tatttttgcc attaccagtc   1440

agaggcagta catgctaaga attgagttaa tggactggga agggaaccga gcctattcac   1500

agtatgacag attccacata ggaaatgaaa agcaaaacta taggttgtat ttaaaaggtc   1560

acactgggac agcaggaaaa cagagcagcc tgatcttaca cggtgctgat ttcagcacta   1620

aagatgctga taatgacaac tgtatgtgca aatgtgccct catgttaaca ggaggatggt   1680

ggtttgatgc ttgtggcccc tccaatctaa atggaatgtt ctatactgcg ggacaaaacc   1740

atggaaaact gaatgggata aagtggcact acttcaaagg gcccagttac tccttacgtt   1800

ccacaactat gatgattcga cctttagatt tttgaggctg ctgcagctgc atgggtgcct   1860

gctgctgcct gccttggcct gatggccagg ccagagtgct gccagtcctc tgcatgttct   1920

gctcttgtgc ccttctgagc ccacaataaa ggctgagctc ttatcttgca aaaggc        1976
```

<210> SEQ ID NO 51
<211> LENGTH: 1391
<212> TYPE: DNA
<213> ORGANISM: Artificial Sequence
<220> FEATURE:
<223> OTHER INFORMATION: Synthetic

<400> SEQUENCE: 51

```
aaagtgattg attcggatac tgacactgta ggatctgggg agagaggaac aaaggaccgt     60

gaaagctgct ctgtaaaagc tgacacagcc ctcccaagtg agcaggactg ttcttcccac    120

tgcaatctga cagtttactg catgcctgga gagaacacag cagtaaaaac caggtttgct    180

actggaaaaa gaggaaagag aagactttca ttgacggacc cagccatggc agcgtagcag    240

ccctgcgttt tagacggcag cagctcggga ctctggacgt gtgtttgccc tcaagtttgc    300
```

taagctgctg gtttattact gaagaaagaa tgtggcagat tgttttcttt actctgagct 360
gtgatcttgt cttggccgca gccgggatct tagacctagc cccacagatg cttcgagaac 420
tccaggagac taatgcggcg ctgcaagacg tgagagagct cttgcgacag caggtcaagg 480
agatcacctt cctgaagaat acggtgatgg aatgtgacgc ttgcggaggc tcccttgtca 540
atctttgcac taaagaaggt gttttactaa agggaggaaa aagagaggaa gagaaaccat 600
ttagagactg tgcagatgta tatcaagctg gttttaataa aagtggaatc tacactattt 660
atattaataa tatgccagaa cccaaaaagg tgttttgcaa tatggatgtc aatgggggag 720
gttggactgt aatacaacat cgtgaagatg gaagtctaga tttccaaaga ggctggaagg 780
aatataaaat gggttttgga aatccctccg gtgaatattg gctggggaat gagtttattt 840
ttgccattac cagtcagagg cagtacatgc taagaattga gttaatggac tgggaaggga 900
accgagccta ttcacagtat gacagattcc acataggaaa tgaaaagcaa aactataggt 960
tgtatttaaa aggtcacact gggacagcag gaaaacagag cagcctgatc ttacacggtg 1020
ctgatttcag cactaaagat gctgataatg acaactgtat gtgcaaatgt gccctcatgt 1080
taacaggagg atggtggttt gatgcttgtg gcccctccaa tctaaatgga atgttctata 1140
ctgcgggaca aaaccatgga aaactgaatg ggataaagtg gcactacttc aaagggccca 1200
gttactcctt acgttccaca actatgatga ttcgaccttt agatttttga ggctgctgca 1260
gctgcatggg tgcctgctgc tgcctgcctt ggcctgatgg ccaggccaga gtgctgccag 1320
tcctctgcat gttctgctct tgtgcccttc tgagcccaca ataaaggctg agctcttatc 1380
ttgcaaaagg c 1391

<210> SEQ ID NO 52
<211> LENGTH: 1967
<212> TYPE: DNA
<213> ORGANISM: Artificial Sequence
<220> FEATURE:
<223> OTHER INFORMATION: Synthetic

<400> SEQUENCE: 52
gaggaaccga gaggctgaga ctaacccaga aacatccaat tctcaaactg aagctcgcac 60
tctcgcctcc agcatgaaag tctctgccgc ccttctgtgc ctgctgctca tagcagccac 120
cttcattccc caagggctcg ctcacatagg gtgcagcaat cagcgccgaa gtccagaaaa 180
cagtgggaga agatataacc ggattcaaca tgggcaatgt gcctacactt tcattcttcc 240
agaacacgat ggcaactgtc gtgagagtac gacagaccag tacaacacaa acgctctgca 300
gagagatgct ccacacgtgg aaccggattt ctcttcccag aaacttcaac atctggaaca 360
tgtgatggaa aattatactc agtggctgca aaaacttgag aattacattg tggaaaacat 420
gaagtcggag atggcccaga tacagcagaa tgcagttcag aaccacacgg ctaccatgct 480
ggagatagga accagcctcc tctctcagac tgcagagcag accagaaagc tgacagatgt 540
tgagacccag gtactaaatc aaacttctcg acttgagata cagctgctgg agaattcatt 600
atccacctac aagctagaga agcaacttct tcaacagaca aatgaaatct tgaagatcca 660
tgaaaaaaac agtttattag aacataaaat cttagaaatg gaaggaaaac acaaggaaga 720
gttggacacc ttaaaggaag agaaagagaa ccttcaaggc ttggttactc gtcaaacata 780
tataatccag gagctggaaa agcaattaaa cagagctacc accaacaaca gtgtccttca 840
gaagcagcaa ctggagctga tggacacagt ccacaacctt gtcaatcttt gcactaaaga 900
aggtgtttta ctaaagggag gaaaaagaga ggaagagaaa ccatttagag actgtgcaga 960
tgtatatcaa gctggtttta ataaaagtgg aatctacact atttatatta ataatatgcc 1020
agaacccaaa aaggtgtttt gcaatatgga tgtcaatggg ggaggttgga ctgtaataca 1080
acatcgtgaa gatggaagtc tagatttcca aagaggctgg aaggaatata aaatgggttt 1140
tggaaatccc tccggtgaat attggctggg gaatgagttt atttttgcca ttaccagtca 1200
gaggcagtac atgctaagaa ttgagttaat ggactgggaa gggaaccgag cctattcaca 1260
gtatgacaga ttccacatag gaaatgaaaa gcaaaactat aggttgtatt taaaaggtca 1320
cactgggaca gcaggaaaac agagcagcct gatcttacac ggtgctgatt tcagcactaa 1380
agatgctgat aatgacaact gtatgtgcaa atgtgccctc atgttaacag gaggatggtg 1440
gtttgatgct tgtggcccct ccaatctaaa tggaatgttc tatactgcgg gacaaaacca 1500
tggaaaactg aatgggataa agtggcacta cttcaaaggg cccagttact ccttacgttc 1560
cacaactatg atgattcgac ctttagattt ttgaacactc actccacaac ccaagaatct 1620
gcagctaact tattttcccc tagctttccc cagacaccct gttttatttt attataatga 1680
attttgtttg ttgatgtgaa acattatgcc ttaagtaatg ttaattctta tttaagttat 1740
tgatgtttta agtttatctt tcatggtact agtgtttttt agatacagag acttggggaa 1800
attgcttttc ctcttgaacc acagttctac ccctgggatg ttttgagggt ctttgcaaga 1860
atcattaata caaagaattt tttttaacat tccaatgcat tgctaaaata ttattgtgga 1920
aatgaatatt ttgtaactat tacaccaaat aaatatattt ttgtaca 1967

<210> SEQ ID NO 53
<211> LENGTH: 1382
<212> TYPE: DNA
<213> ORGANISM: Artificial Sequence
<220> FEATURE:
<223> OTHER INFORMATION: Synthetic

<400> SEQUENCE: 53
gaggaaccga gaggctgaga ctaacccaga aacatccaat tctcaaactg aagctcgcac 60
tctcgcctcc agcatgaaag tctctgccgc ccttctgtgc ctgctgctca tagcagccac 120
cttcattccc caagggctcg ctgggatctt agacttgggc ccgcagatgc ttcgggaact 180
gcaggaaacc aacgcggcgc tgcaggacgt gcgggagctg ctgcggcagc aggtcaggga 240
gatcacgttc ctgaaaaaca cggtgatgga gtgtgacgcg tgcggaggct cccttgtcaa 300
tctttgcact aaagaaggtg ttttactaaa gggaggaaaa agagaggaag agaaaccatt 360
tagagactgt gcagatgtat atcaagctgg ttttaataaa agtggaatct acactattta 420
tattaataat atgccagaac ccaaaaaggt gttttgcaat atggatgtca atgggggagg 480
ttggactgta atacaacatc gtgaagatgg aagtctagat ttccaaagag gctggaagga 540
atataaaatg ggttttggaa atccctccgg tgaatattgg ctggggaatg agtttatttt 600
tgccattacc agtcagaggc agtacatgct aagaattgag ttaatggact gggaagggaa 660
ccgagcctat tcacagtatg acagattcca cataggaaat gaaaagcaaa actataggtt 720
gtatttaaaa ggtcacactg ggacagcagg aaaacagagc agcctgatct tacacggtgc 780
tgatttcagc actaaagatg ctgataatga caactgtatg tgcaaatgtg ccctcatgtt 840
aacaggagga tggtggtttg atgcttgtgg cccctccaat ctaaatggaa tgttctatac 900
tgcgggacaa aaccatggaa aactgaatgg gataaagtgg cactacttca aagggcccag 960
ttactcctta cgttccacaa ctatgatgat tcgaccttta gatttttgaa cactcactcc 1020
acaacccaag aatctgcagc taacttattt tcccctagct ttccccagac accctgtttt 1080
attttattat aatgaatttt gtttgttgat gtgaaacatt atgccttaag taatgttaat 1140
tcttatttaa gttattgatg ttttaagttt atctttcatg gtactagtgt tttttagata 1200
cagagacttg ggaaattgc ttttcctctt gaaccacagt tctacccctg ggatgttttg 1260
agggtctttg caagaatcat taatacaaag aattttttt aacattccaa tgcattgcta 1320
aaatattatt gtggaaatga atattttgta actattacac caaataaata tatttttgta 1380
ca 1382

<210> SEQ ID NO 54
<211> LENGTH: 3428
<212> TYPE: DNA
<213> ORGANISM: Artificial Sequence
<220> FEATURE:
<223> OTHER INFORMATION: Synthetic

<400> SEQUENCE: 54
gccctaagcc atcagcaatc cttagtatag gggcacactc atgcattcct gtcaagtcat 60
cttgtgaaag gctgcctgct tccagcttgg cttggatgtg caaccttaat aaaactcact 120
gaggtctggg agaaaatagc agatctgcag cagatagggt agaggaaagg gtctagaata 180
tgtacacgca gctgactcag gcaggctcca tgctgaacgg tcacacagag aggaaacaat 240
aaatctcagc tactatgcaa taaatatctc aagttttaac gaagaaaaac atcattgcag 300
tgaaataaaa aattttaaaa ttttagaaca aagctaacaa atggctagtt ttctatgatt 360
cttcttcaaa cgctttcttt gagggggaaa gagtcaaaca aacaagcagt tttacctgaa 420
ataaagaact agttttagag gtcagaagaa aggagcaagt tttgcgagag gcacggaagg 480
agtgtgctgg cagtacaatg acagttttcc tttcctttgc tttcctcgct gccattctga 540
ctgtcttcac actcgaagat ttcgttgggg actggcgaca gacagccggc tacaacctgg 600
accaagtcct tgaacaggga ggtgtgtcca gtttgtttca gaatctcggg gtgtccgtaa 660
ctccgatcca aaggattgtc ctgagcggtg aaaatgggct gaagatcgac atccatgtca 720
tcatcccgta tgaaggtctg agcggcgacc aaatgggcca gatcgaaaaa atttttaagg 780
tggtgtaccc tgtggatgat catcacttta aggtgatcct gcactatggc acactggtaa 840
tcgacggggt tacgccgaac atgatcgact atttcggacg gccgtatgaa ggcatcgccg 900
tgttcgacgg caaaaagatc actgtaacag ggaccctgtg gaacggcaac aaaattatcg 960
acgagcgcct gatcaacccc gacggctccc tgctgttccg agtaaccatc aacggagtga 1020
ccggctggcg gctgtgcgaa cgcattctgg cgtaaaagcg caatgtcaga agcgattatg 1080
aaagcaacaa agaaatccgg agaagctgcc aggtgagaaa ctgtttgaaa acttcagaag 1140
caaacaatat tgtctccctt ccagcaataa gtggtagtta tgtgaagtca ccaaggttct 1200
tgaccgtgaa tctggagccg tttgagttca caagagtctc tacttggggt gacagtgctc 1260
acgtggctcg actatagaaa actccactga ctgtcgggct ttaaaaaggg aagaaactgc 1320
tgagcttgct gtgcttcaaa ctactactgg accttatttt ggaactatgg tagccagatg 1380
ataaatatgg ttaatttcat gtaaaacaga aaaaaagagt gaaaaagaga atatacatga 1440
agaatagaaa caagcctgcc ataatccttt ggaaaagatg tattatacca gtgaaaaggt 1500
gttatatcta tgcaaaccta ctaacaaatt atactgttgc acaattttga taaaaattta 1560
gaacagcatt gtcctctgag ttggttaaat gttaatggat ttcagaagcc taattccagt 1620
atcatactta ctagttgatt tctgcttacc catcttcaaa tgaaaattcc atttttgtaa 1680

```
gccataatga actgtagtac atggacaata agtgtgtggt agaaacaaac tccattactc   1740

tgatttttga tacagttttc agaaaaagaa atgaacataa tcaagtaagg atgtatgtgg   1800

tgaaaactta ccaccccccat actatggttt tcatttactc taaaaactga ttgaatgata   1860

tataaatata tttatagcct gagtaaagtt aaaagaatgt aaaatatatc atcaagttct   1920

taaaataata tacatgcatt taatatttcc tttgatatta tacaggaaag caatattttg   1980

gagtatgtta agttgaagta aaagcaagta ctctggagca gttcatttta cagtatctac   2040

ttgcatgtgt atacatacat gtaacttcat tattttaaaa atatttttag aactccaata   2100

ctcaccctgt tatgtcttgc taatttaaat tttgctaatt aactgaaaca tgcttaccag   2160

attcacactg ttccagtgtc tataaaagaa acactttgaa gtctataaaa aataaaataa   2220

ttataaatat cattgtacat agcatgttta tatctgcaaa aaacctaata gctaattaat   2280

ctggaatatg caacattgtc cttaattgat gcaaataaca caaatgctca aagaaatcta   2340

ctatatccct taatgaaata catcattctt catatatttc tccttcagtc cattccctta   2400

ggcaattttt aatttttaaa aattattatc aggggagaaa aattggcaaa actattatat   2460

gtaagggaaa tatatacaaa aagaaaatta atcatagtca cctgactaag aaattctgac   2520

tgctagttgc cataaataac tcaatggaaa tattcctatg ggataatgta ttttaagtga   2580

atttttgggg tgcttgaagt tactgcatta ttttatcaag aagtcttctc tgcctgtaag   2640

tgtccaaggt tatgacagta aacagttttt attaaaacat gagtcactat gggatgagaa   2700

aattgaaata aagctactgg gcctcctctc ataaaagaga cagttgttgg caaggtagca   2760

ataccagttt caaacttggt gacttgatcc actatgcctt aatggtttcc tccatttgag   2820

aaaataaagc tattcacatt gttaagaaaa atacttttta aagtttacca tcaagtcttt   2880

tttatattta tgtgtctgta ttctacccct ttttgcctta caagtgatat ttgcaggtat   2940

tataccattt ttctattctt ggtggcttct tcatagcagg taagcctctc cttctaaaaa   3000

cttctcaact gttttcattt aagggaaaga aaatgagtat tttgtccttt tgtgttccta   3060

cagacacttt cttaaaccag tttttggata aagaatacta tttccaaact catattacaa   3120

aaacaaaata aaataataaa aaaagaaagc atgatattta ctgttttgtt gtctgggttt   3180

gagaaatgaa atattgtttc caattattta taataaatca gtataaaatg ttttatgatt   3240

gttatgtgta ttatgtaata cgtacatgtt tatggcaatt taacatgtgt attcttttaa   3300

ttgtttcaga ataggataat taggtattcg aattttgtct ttaaaattca tgtggtttct   3360

atgcaaagtt cttcatatca tcacaacatt atttgattta aataaaattg aaagtaatat   3420

ttgtgcaa                                                             3428
```

<210> SEQ ID NO 55
<211> LENGTH: 1037
<212> TYPE: DNA
<213> ORGANISM: Artificial Sequence
<220> FEATURE:
<223> OTHER INFORMATION: Synthetic

<400> SEQUENCE: 55

```
aaagtgattg attcggatac tgacactgta ggatctgggg agagaggaac aaaggaccgt     60

gaaagctgct ctgtaaaagc tgacacagcc ctcccaagtg agcaggactg ttcttcccac    120

tgcaatctga cagtttactg catgcctgga gagaacacag cagtaaaaac caggtttgct    180

actggaaaaa gaggaaagag aagactttca ttgacggacc cagccatggc agcgtagcag    240
```

ccctgcgttt tagacggcag cagctcggga ctctggacgt gtgtttgccc tcaagtttgc 300
taagctgctg gtttattact gaagaaagaa tgtggcagat tgttttcttt actctgagct 360
gtgatcttgt cttggccgca gccgtcttca cactcgaaga tttcgttggg gactggcgac 420
agacagccgg ctacaacctg gaccaagtcc ttgaacaggg aggtgtgtcc agtttgtttc 480
agaatctcgg ggtgtccgta actccgatcc aaaggattgt cctgagcggt gaaaatgggc 540
tgaagatcga catccatgtc atcatcccgt atgaaggtct gagcggcgac caaatgggcc 600
agatcgaaaa aatttttaag gtggtgtacc ctgtggatga tcatcacttt aaggtgatcc 660
tgcactatgg cacactggta atcgacgggg ttacgccgaa catgatcgac tatttcggac 720
ggccgtatga aggcatcgcc gtgttcgacg gcaaaaagat cactgtaaca gggaccctgt 780
ggaacggcaa caaaattatc gacgagcgcc tgatcaaccc cgacggctcc ctgctgttcc 840
gagtaaccat caacggagtg accggctggc ggctgtgcga acgcattctg gcgtaaggct 900
gctgcagctg catgggtgcc tgctgctgcc tgccttggcc tgatggccag gccagagtgc 960
tgccagtcct ctgcatgttc tgctcttgtg cccttctgag cccacaataa aggctgagct 1020
cttatcttgc aaaaggc 1037

<210> SEQ ID NO 56
<211> LENGTH: 826
<212> TYPE: DNA
<213> ORGANISM: Artificial Sequence
<220> FEATURE:
<223> OTHER INFORMATION: Synthetic

<400> SEQUENCE: 56
tccccattga ataacagcca agttgctttg gtttctattt ctttgttaag tcgttccctc 60
tacaaaggac ttcctagtgg gtgtgaaagg cagcggtggc cacagaggcg gcggagagat 120
gtggcagatt gttttcttta ctctgagctg tgatcttgtc ttggccgcag ccgtcttcac 180
actcgaagat ttcgttgggg actggcgaca gacagccggc tacaacctgg accaagtcct 240
tgaacaggga ggtgtgtcca gtttgtttca gaatctcggg gtgtccgtaa ctccgatcca 300
aaggattgtc ctgagcggtg aaaatgggct gaagatcgac atccatgtca tcatcccgta 360
tgaaggtctg agcggcgacc aaatgggcca gatcgaaaaa atttttaagg tggtgtaccc 420
tgtggatgat catcacttta aggtgatcct gcactatggc acactggtaa tcgacggggt 480
tacgccgaac atgatcgact atttcggacg gccgtatgaa ggcatcgccg tgttcgacgg 540
caaaaagatc actgtaacag ggaccctgtg gaacggcaac aaaattatcg acgagcgcct 600
gatcaacccc gacggctccc tgctgttccg agtaaccatc aacggagtga ccggctggcg 660
gctgtgcgaa cgcattctgg cgtaaggctg ctgcagctgc atgggtgcct gctgctgcct 720
gccttggcct gatggccagg ccagagtgct gccagtcctc tgcatgttct gctcttgtgc 780
ccttctgagc ccacaataaa ggctgagctc ttatcttgca aaaggc 826

<210> SEQ ID NO 57
<211> LENGTH: 1068
<212> TYPE: DNA
<213> ORGANISM: Artificial Sequence
<220> FEATURE:
<223> OTHER INFORMATION: Synthetic

<400> SEQUENCE: 57
ataaaagccc aggggcaagc ggtccggata acggctagcc tgaggagctg ctgcgacagt 60
ccactacctt tttcgagagt gactcccgtt gtcccaaggc ttcccagagc gaacctgtgc 120

```
ggctgcaggc accggcgcgt cgagtttccg gcgtccggaa ggaccgagct cttctcgcga    180

atccagtgtt ccgtttccag cccccaatct cagagcggag ccgacagaga gcagggaacc    240

ggcatgtggc agattgtttt ctttactctg agctgtgatc ttgtcttggc cgcagccgtc    300

ttcacactcg aagatttcgt tggggactgg cgacagacag ccggctacaa cctggaccaa    360

gtccttgaac agggaggtgt gtccagtttg tttcagaatc tcggggtgtc cgtaactccg    420

atccaaagga ttgtcctgag cggtgaaaat gggctgaaga tcgacatcca tgtcatcatc    480

ccgtatgaag gtctgagcgg cgaccaaatg ggccagatcg aaaaaatttt taaggtggtg    540

taccctgtgg atgatcatca ctttaaggtg atcctgcact atggcacact ggtaatcgac    600

ggggttacgc cgaacatgat cgactatttc ggacggccgt atgaaggcat cgccgtgttc    660

gacggcaaaa agatcactgt aacagggacc ctgtggaacg gcaacaaaat tatcgacgag    720

cgcctgatca accccgacgg ctccctgctg ttccgagtaa ccatcaacgg agtgaccggc    780

tggcggctgt gcgaacgcat tctggcgtaa gggcctttcc aagattgctg tttttgtttt    840

ggagcttcaa gactttgcat ttcctagtat ttctgtttgt cagttctcaa tttcctgtgt    900

ttgcaatgtt gaaatttttt ggtgaagtac tgaacttgct ttttttccgg tttctacatg    960

cagagatgaa tttatactgc catcttacga ctatttcttc tttttaatac acttaactca   1020

ggccattttt taagttggtt acttcaaagt aaataaactt taaaattc                1068
```

<210> SEQ ID NO 58
<211> LENGTH: 1217
<212> TYPE: DNA
<213> ORGANISM: Artificial Sequence
<220> FEATURE:
<223> OTHER INFORMATION: Synthetic

<400> SEQUENCE: 58

```
gtcagccatc tttcaattgt gttcgcagcc gccgccgcgc cgccgtcgct ctccaacgcc     60

agcgccgcct ctcgctcgcc gagctccagc cgaaggagaa ggggggtaag taaggaggtc    120

tctgtaccat gtggcagatt gttttcttta ctctgagctg tgatcttgtc ttggccgcag    180

ccgtcttcac actcgaagat ttcgttgggg actggcgaca gacagccggc tacaacctgg    240

accaagtcct tgaacaggga ggtgtgtcca gtttgtttca gaatctcggg gtgtccgtaa    300

ctccgatcca aaggattgtc ctgagcggtg aaaatgggct gaagatcgac atccatgtca    360

tcatcccgta tgaaggtctg agcggcgacc aaatgggcca gatcgaaaaa atttttaagg    420

tggtgtaccc tgtggatgat catcacttta aggtgatcct gcactatggc acactggtaa    480

tcgacggggt tacgccgaac atgatcgact atttcggacg gccgtatgaa ggcatcgccg    540

tgttcgacgg caaaaagatc actgtaacag ggaccctgtg gaacggcaac aaaattatcg    600

acgagcgcct gatcaacccc gacggctccc tgctgttccg agtaaccatc aacggagtga    660

ccggctggcg gctgtgcgaa cgcattctgg cgtaagaatc cactatgatg ggaaacattt    720

cattctcaaa aaaaaaaaaa aaaatttctc ttcttcctgt tattggtagt tctgaacgtt    780

agatattttt tttccatggg gtcaaaaggt acctaagtat atgattgcga gtggaaaaat    840

aggggacaga aatcaggtat tggcagtttt tccattttca tttgtgtgtg aatttttaat    900

ataaatgcgg agacgtaaag cattaatgca agttaaaatg tttcagtgaa caagtttcag    960

cggttcaact ttataataat tataaataaa cctgttaaat ttttctggac aatgccagca   1020

tttggatttt tttaaaacaa gtaaatttct tattgatggc aactaaatgg tgtttgtagc   1080
```

atttttatca tacagtagat tccatccatt cactatactt ttctaactga gttgtcctac 1140
atgcaagtac atgtttttaa tgttgtctgt cttctgtgct gttcctgtaa gtttgctatt 1200
aaaatacatt aaactat 1217

<210> SEQ ID NO 59
<211> LENGTH: 827
<212> TYPE: DNA
<213> ORGANISM: Artificial Sequence
<220> FEATURE:
<223> OTHER INFORMATION: Synthetic

<400> SEQUENCE: 59
catatcttca ttcttcactc tttccccccc cccccttatc ctcctatcta atcctctcat 60
ctctctcctc ctcttcctcc aacaacaact aacaatggca gcaactacaa caatggcaca 120
gattgttttc tttactctga gctgtgatct tgtcttggcc gcagccgtct tcacactcga 180
agatttcgtt ggggactggc gacagacagc cggctacaac ctggaccaag tccttgaaca 240
gggaggtgtg tccagtttgt ttcagaatct cggggtgtcc gtaactccga tccaaaggat 300
tgtcctgagc ggtgaaaatg ggctgaagat cgacatccat gtcatcatcc cgtatgaagg 360
tctgagcggc gaccaaatgg gccagatcga aaaaattttt aaggtggtgt accctgtgga 420
tgatcatcac tttaaggtga tcctgcacta tggcacactg gtaatcgacg gggttacgcc 480
gaacatgatc gactatttcg gacggccgta tgaaggcatc gccgtgttcg acggcaaaaa 540
gatcactgta acagggaccc tgtggaacgg caacaaaatt atcgacgagc gcctgatcaa 600
ccccgacggc tccctgctgt tccgagtaac catcaacgga gtgaccggct ggcggctgtg 660
cgaacgcatt ctggcgtaat tttgagtaat tttcaatttt gtttttgttt ttgtttttgt 720
tgttgggagt tgttgtaatt tggtaaatgt tggggtcact aaaatctttt gttgcaattt 780
tagcaccttt ttattagata tataaaattg ggtttagatg tagttaa 827

<210> SEQ ID NO 60
<211> LENGTH: 925
<212> TYPE: DNA
<213> ORGANISM: Artificial Sequence
<220> FEATURE:
<223> OTHER INFORMATION: Synthetic

<400> SEQUENCE: 60
ataaaagcct agtggccatt gtgttcgttg ctcttatcgg ttcccatccc agttgttgat 60
cttatgcaag acgctgcacg accccgcgcc cgcttgtcgc cacggcactt gaggcagccg 120
gagatactct gagttactcg gagcccgacg cctgagggtg agatgaacgc gctggcctcc 180
ctaaccgtcc ggacctgtga tcgcttctgg cagaccgaac cggcgctcct gcccccgggg 240
tgacgcgcag ctcccagccg cccagacaca tgtggcagat tgttttcttt actctgagct 300
gtgatcttgt cttggccgca gccgtcttca cactcgaaga tttcgttggg gactggcgac 360
agacagccgg ctacaacctg gaccaagtcc ttgaacaggg aggtgtgtcc agtttgtttc 420
agaatctcgg ggtgtccgta actccgatcc aaaggattgt cctgagcggt gaaaatgggc 480
tgaagatcga catccatgtc atcatcccgt atgaaggtct gagcggcgac caaatgggcc 540
agatcgaaaa aatttttaag gtggtgtacc ctgtggatga tcatcacttt aaggtgatcc 600
tgcactatgg cacactggta atcgacgggg ttacgccgaa catgatcgac tatttcggac 660
ggccgtatga aggcatcgcc gtgttcgacg gcaaaaagat cactgtaaca gggaccctgt 720
ggaacggcaa caaaattatc gacgagcgcc tgatcaaccc cgacggctcc ctgctgttcc 780
gagtaaccat caacggagtg accggctggc ggctgtgcga acgcattctg gcgtaagacc 840
aactggtttg cctataattt attaactatt tatttttttct aagtgtgggt ttatataagg 900
aataaagcct tttgatttgt agcga 925

<210> SEQ ID NO 61
<211> LENGTH: 1028
<212> TYPE: DNA
<213> ORGANISM: Artificial Sequence
<220> FEATURE:
<223> OTHER INFORMATION: Synthetic

<400> SEQUENCE: 61
gaggaaccga gaggctgaga ctaacccaga aacatccaat tctcaaactg aagctcgcac 60
tctcgcctcc agcatgaaag tctctgccgc ccttctgtgc ctgctgctca tagcagccac 120
cttcattccc caagggctcg ctgtcttcac actcgaagat ttcgttgggg actggcgaca 180
gacagccggc tacaacctgg accaagtcct tgaacaggga ggtgtgtcca gtttgtttca 240
gaatctcggg gtgtccgtaa ctccgatcca aaggattgtc ctgagcggtg aaaatgggct 300
gaagatcgac atccatgtca tcatcccgta tgaaggtctg agcggcgacc aaatgggcca 360
gatcgaaaaa atttttaagg tggtgtaccc tgtggatgat catcacttta aggtgatcct 420
gcactatggc acactggtaa tcgacggggt tacgccgaac atgatcgact atttcggacg 480
gccgtatgaa ggcatcgccg tgttcgacgg caaaaagatc actgtaacag ggaccctgtg 540
gaacggcaac aaaattatcg acgagcgcct gatcaacccc gacggctccc tgctgttccg 600
agtaaccatc aacggagtga ccggctggcg gctgtgcgaa cgcattctgg cgtaaacact 660
cactccacaa cccaagaatc tgcagctaac ttattttccc ctagctttcc ccagacaccc 720
tgttttattt tattataatg aattttgttt gttgatgtga aacattatgc cttaagtaat 780
gttaattctt atttaagtta ttgatgtttt aagtttatct ttcatggtac tagtgttttt 840
tagatacaga gacttgggga aattgctttt cctcttgaac cacagttcta cccctgggat 900
gttttgaggg tctttgcaag aatcattaat acaaagaatt ttttttaaca ttccaatgca 960
ttgctaaaat attattgtgg aaatgaatat tttgtaacta ttacaccaaa taaatatatt 1020
tttgtaca 1028

<210> SEQ ID NO 62
<211> LENGTH: 2027
<212> TYPE: DNA
<213> ORGANISM: Artificial Sequence
<220> FEATURE:
<223> OTHER INFORMATION: Synthetic

<400> SEQUENCE: 62
ggagctgttt acccccactc taataggggt tcaatataaa aagccggcag agagctgtcc 60
aagtcagacg cgcctctgca tctgcgccag gcgaacgggt cctgcgcctc ctgcagtccc 120
agctctccac cgccgcgtgc gcctgcagac gctccgctcg ctgccttctc tcctggcagg 180
cgctgccttt tctccccgtt aaaagggcac ttgggctgaa ggatcgcttt gagatctgag 240
gaacccgcag cgctttgagg gacctgaagc tgtttttctt cgttttcctt tgggttcagt 300
ttgaacggga ggtttttgat ccctttttt cagaatggat tatttgctca tgattttctc 360
tctgctgttt gtggcttgcc aaggagtctt cacactcgaa gatttcgttg gggactggcg 420
acagacagcc ggctacaacc tggaccaagt ccttgaacag ggaggtgtgt ccagtttgtt 480
tcagaatctc ggggtgtccg taactccgat ccaaaggatt gtcctgagcg gtgaaaatgg 540
gctgaagatc gacatccatg tcatcatccc gtatgaaggt ctgagcggcg accaaatggg 600
ccagatcgaa aaaattttta aggtggtgta ccctgtggat gatcatcact ttaaggtgat 660
cctgcactat ggcacactgg taatcgacgg ggttacgccg aacatgatcg actatttcgg 720
acggccgtat gaaggcatcg ccgtgttcga cggcaaaaag atcactgtaa cagggaccct 780
gtggaacggc aacaaaatta tcgacgagcg cctgatcaac cccgacggct ccctgctgtt 840
ccgagtaacc atcaacggag tgaccggctg gcggctgtgc gaacgcattc tggcgtaaca 900
gaccttcggg gcctgtctga agccatagcc tccacggaga gccctgtggc cgactctgca 960
ctctccaccc tggctgggat cagagcagga gcatcctctg ctggttcctg actggcaaag 1020
gaccagcgtc ctcgttcaaa acattccaag aaaggttaag gagttccccc aaccatcttc 1080
actggcttcc atcagtggta actgctttgg tctcttcttt catctgggga tgacaatgga 1140
cctctcagca gaaacacaca gtcacattcg aattcgggtg gcatcctccg gagagagaga 1200
gaggaaggag attccacaca ggggtggagt ttctgacgaa ggtcctaagg gagtgtttgt 1260
gtctgactca ggcgcctggc acatttcagg gagaaactcc aaagtccaca caaagatttt 1320
ctaaggaatg cacaaattga aaacacactc aaaagacaaa catgcaagta aagaaaaaaa 1380
aaagaaagac ttttgtttaa atttgtaaaa tgcaaaactg aatgaaactg ttactaccat 1440
aaatcaggat atgtttcatg aatatgagtc tacctcacct atattgcact ctggcagaag 1500
tatttcccac atttaattat tgcctcccca aactcttccc acccctgctg ccccttcctc 1560
catcccccat actaaatcct agcctcgtag aagtctggtc taatgtgtca gcagtagata 1620
taatattttc atggtaatct actagctctg atccataaga aaaaaaagat cattaaatca 1680
ggagattccc tgtccttgat ttttggagac acaatggtat agggttgttt atgaaatata 1740
ttgaaaagta agtgtttgtt acgctttaaa gcagtaaaat tattttcctt tatataaccg 1800
gctaatgaaa gaggttggat tgaattttga tgtacttatt tttttataga tatttatatt 1860
caaacaattt attccttata tttaccatgt taaatatctg tttgggcagg ccatattggt 1920
ctatgtattt ttaaaatatg tatttctaaa tgaaattgag aacatgcttt gttttgcctg 1980
tcaaggtaat gactttagaa aataaatatt tttttcctta ctgtaaa 2027

<210> SEQ ID NO 63
<211> LENGTH: 1070
<212> TYPE: DNA
<213> ORGANISM: Artificial Sequence
<220> FEATURE:
<223> OTHER INFORMATION: Synthetic

<400> SEQUENCE: 63
aaagtgattg attcggatac tgacactgta ggatctgggg agagaggaac aaaggaccgt 60
gaaagctgct ctgtaaaagc tgacacagcc ctcccaagtg agcaggactg ttcttcccac 120
tgcaatctga cagtttactg catgcctgga gagaacacag cagtaaaaac caggtttgct 180
actggaaaaa gaggaaagag aagactttca ttgacggacc cagccatggc agcgtagcag 240
ccctgcgttt tagacggcag cagctcggga ctctggacgt gtgtttgccc tcaagtttgc 300
taagctgctg gtttattact gaagaaagaa tgaactcctt ctccacaagc gccttcggtc 360
cagttgcctt ctccctgggc ctgctcctgg tgttgcctgc tgccttccct gccccagtct 420
tcacactcga agatttcgtt ggggactggc gacagacagc cggctacaac ctggaccaag 480
tccttgaaca gggaggtgtg tccagtttgt ttcagaatct cggggtgtcc gtaactccga 540
tccaaaggat tgtcctgagc ggtgaaaatg ggctgaagat cgacatccat gtcatcatcc 600
cgtatgaagg tctgagcggc gaccaaatgg gccagatcga aaaaattttt aaggtggtgt 660
accctgtgga tgatcatcac tttaaggtga tcctgcacta tggcacactg gtaatcgacg 720
gggttacgcc gaacatgatc gactatttcg gacggccgta tgaaggcatc gccgtgttcg 780
acggcaaaaa gatcactgta acagggaccc tgtggaacgg caacaaaatt atcgacgagc 840
gcctgatcaa ccccgacggc tccctgctgt tccgagtaac catcaacgga gtgaccggct 900
ggcggctgtg cgaacgcatt ctggcgtaag gctgctgcag ctgcatgggt gcctgctgct 960
gcctgccttg gcctgatggc caggccagag tgctgccagt cctctgcatg ttctgctctt 1020
gtgcccttct gagcccacaa taaaggctga gctcttatct tgcaaaaggc 1070

<210> SEQ ID NO 64
<211> LENGTH: 796
<212> TYPE: DNA
<213> ORGANISM: Artificial Sequence
<220> FEATURE:
<223> OTHER INFORMATION: Synthetic

<400> SEQUENCE: 64
gaggaaccga gaggctgaga ctaacccaga aacatccaat tctcaaactg aagctcgcac 60
tctcgcctcc agcatgaaag tctctgccgc ccttctgtgc ctgctgctca tagcagccac 120
cttcattccc caagggctcg ctgtcttcac actcgaagat ttcgttgggg actggcgaca 180
gacagccggc tacaacctgg accaagtcct tgaacaggga ggtgtgtcca gtttgtttca 240
gaatctcggg gtgtccgtaa ctccgatcca aaggattgtc ctgagcggtg aaaatgggct 300
gaagatcgac atccatgtca tcatcccgta tgaaggtctg agcggcgacc aaatgggcca 360
gatcgaaaaa atttttaagg tggtgtaccc tgtggatgat catcacttta aggtgatcct 420
gcactatggc acactggtaa tcgacggggt tacgccgaac atgatcgact atttcggacg 480
gccgtatgaa ggcatcgccg tgttcgacgg caaaaagatc actgtaacag ggaccctgtg 540
gaacggcaac aaaattatcg acgagcgcct gatcaacccc gacggctccc tgctgttccg 600
agtaaccatc aacggagtga ccggctggcg gctgtgcgaa cgcattctgg cgtaaggctg 660
ctgcagctgc atgggtgcct gctgctgcct gccttggcct gatggccagg ccagagtgct 720
gccagtcctc tgcatgttct gctcttgtgc ccttctgagc ccacaataaa ggctgagctc 780
ttatcttgca aaaggc 796

<210> SEQ ID NO 65
<211> LENGTH: 913
<212> TYPE: DNA
<213> ORGANISM: Artificial Sequence
<220> FEATURE:
<223> OTHER INFORMATION: Synthetic

<400> SEQUENCE: 65
gaggaaccga gaggctgaga ctaacccaga aacatccaat tctcaaactg aagctcgcac 60
tctcgcctcc agcatgaaag tctctgccgc ccttctgtgc ctgctgctca tagcagccac 120
cttcattccc caagggctcg ctgtcttcac actcgaagat ttcgttgggg actggcgaca 180
gacagccggc tacaacctgg accaagtcct tgaacaggga ggtgtgtcca gtttgtttca 240
gaatctcggg gtgtccgtaa ctccgatcca aaggattgtc ctgagcggtg aaaatgggct 300
gaagatcgac atccatgtca tcatcccgta tgaaggtctg agcggcgacc aaatgggcca 360
gatcgaaaaa atttttaagg tggtgtaccc tgtggatgat catcacttta aggtgatcct 420
gcactatggc acactggtaa tcgacggggt tacgccgaac atgatcgact atttcggacg 480
gccgtatgaa ggcatcgccg tgttcgacgg caaaaagatc actgtaacag ggaccctgtg 540
gaacggcaac aaaattatcg acgagcgcct gatcaacccc gacggctccc tgctgttccg 600
agtaaccatc aacggagtga ccggctggcg gctgtgcgaa cgcattctgg cgtaagggcc 660
tttccaagat tgctgttttt gttttggagc ttcaagactt tgcatttcct agtatttctg 720
tttgtcagtt ctcaatttcc tgtgtttgca atgttgaaat tttttggtga agtactgaac 780
ttgctttttt tccggtttct acatgcagag atgaatttat actgccatct tacgactatt 840
tcttcttttt aatacactta actcaggcca ttttttaagt tggttacttc aaagtaaata 900
aactttaaaa ttc 913

<210> SEQ ID NO 66
<211> LENGTH: 1046
<212> TYPE: DNA
<213> ORGANISM: Artificial Sequence
<220> FEATURE:
<223> OTHER INFORMATION: Synthetic

<400> SEQUENCE: 66
gaggaaccga gaggctgaga ctaacccaga aacatccaat tctcaaactg aagctcgcac 60
tctcgcctcc agcatgaact ccttctccac aagcgccttc ggtccagttg ccttctccct 120
gggcctgctc ctggtgttgc ctgctgcctt ccctgcccca gtcttcacac tcgaagattt 180
cgttggggac tggcgacaga cagccggcta caacctggac caagtccttg aacagggagg 240
tgtgtccagt ttgtttcaga atctcggggt gtccgtaact ccgatccaaa ggattgtcct 300
gagcggtgaa aatgggctga agatcgacat ccatgtcatc atcccgtatg aaggtctgag 360
cggcgaccaa atgggccaga tcgaaaaaat ttttaaggtg gtgtaccctg tggatgatca 420
tcactttaag gtgatcctgc actatggcac actggtaatc gacggggtta cgccgaacat 480
gatcgactat ttcggacggc cgtatgaagg catcgccgtg ttcgacggca aaaagatcac 540
tgtaacaggg accctgtgga acggcaacaa aattatcgac gagcgcctga tcaaccccga 600
cggctccctg ctgttccgag taaccatcaa cggagtgacc ggctggcggc tgtgcgaacg 660
cattctggcg taaacactca ctccacaacc caagaatctg cagctaactt attttcccct 720
agctttcccc agacaccctg ttttatttta ttataatgaa ttttgtttgt tgatgtgaaa 780
cattatgcct taagtaatgt taattcttat ttaagttatt gatgttttaa gtttatcttt 840
catggtacta gtgtttttta gatacagaga cttggggaaa ttgcttttcc tcttgaacca 900
cagttctacc cctgggatgt tttgagggtc tttgcaagaa tcattaatac aaagaatttt 960
ttttaacatt ccaatgcatt gctaaaatat tattgtggaa atgaatattt tgtaactatt 1020
acaccaaata aatatatttt tgtaca 1046

<210> SEQ ID NO 67
<211> LENGTH: 1013
<212> TYPE: DNA
<213> ORGANISM: Artificial Sequence
<220> FEATURE:
<223> OTHER INFORMATION: Synthetic

<400> SEQUENCE: 67
gaggaaccga gaggctgaga ctaacccaga aacatccaat tctcaaactg aagctcgcac 60
tctcgcctcc agcatgtggc agattgtttt ctttactctg agctgtgatc ttgtcttggc 120

```
cgcagccgtc ttcacactcg aagatttcgt tggggactgg cgacagacag ccggctacaa    180

cctggaccaa gtccttgaac agggaggtgt gtccagtttg tttcagaatc tcggggtgtc    240

cgtaactccg atccaaagga ttgtcctgag cggtgaaaat gggctgaaga tcgacatcca    300

tgtcatcatc ccgtatgaag gtctgagcgg cgaccaaatg ggccagatcg aaaaaatttt    360

taaggtggtg taccctgtgg atgatcatca ctttaaggtg atcctgcact atggcacact    420

ggtaatcgac ggggttacgc cgaacatgat cgactatttc ggacggccgt atgaaggcat    480

cgccgtgttc gacggcaaaa agatcactgt aacagggacc ctgtggaacg gcaacaaaat    540

tatcgacgag cgcctgatca accccgacgg ctccctgctg ttccgagtaa ccatcaacgg    600

agtgaccggc tggcggctgt gcgaacgcat tctggcgtaa acactcactc cacaacccaa    660

gaatctgcag ctaacttatt ttcccctagc tttccccaga caccctgttt tattttatta    720

taatgaattt tgtttgttga tgtgaaacat tatgccttaa gtaatgttaa ttcttattta    780

agttattgat gttttaagtt tatctttcat ggtactagtg tttttagat acagagactt    840

ggggaaattg cttttcctct tgaaccacag ttctacccct gggatgtttt gagggtcttt    900

gcaagaatca ttaatacaaa gaattttttt taacattcca atgcattgct aaaatattat    960

tgtggaaatg aatattttgt aactattaca ccaaataaat atatttttgt aca          1013
```

<210> SEQ ID NO 68
<211> LENGTH: 962
<212> TYPE: DNA
<213> ORGANISM: Artificial Sequence
<220> FEATURE:
<223> OTHER INFORMATION: Synthetic

<400> SEQUENCE: 68

```
gaggaaccga gaggctgaga ctaacccaga aacatccaat tctcaaactg aagctcgcac     60

tctcgcctcc agcatggtct tcacactcga agatttcgtt ggggactggc gacagacagc    120

cggctacaac ctggaccaag tccttgaaca gggaggtgtg tccagtttgt ttcagaatct    180

cggggtgtcc gtaactccga tccaaaggat tgtcctgagc ggtgaaaatg ggctgaagat    240

cgacatccat gtcatcatcc cgtatgaagg tctgagcggc gaccaaatgg gccagatcga    300

aaaaattttt aaggtggtgt accctgtgga tgatcatcac tttaaggtga tcctgcacta    360

tggcacactg gtaatcgacg gggttacgcc gaacatgatc gactatttcg gacggccgta    420

tgaaggcatc gccgtgttcg acggcaaaaa gatcactgta acagggaccc tgtggaacgg    480

caacaaaatt atcgacgagc gcctgatcaa ccccgacggc tccctgctgt tccgagtaac    540

catcaacgga gtgaccggct ggcggctgtg cgaacgcatt ctggcgtaaa cactcactcc    600

acaacccaag aatctgcagc taacttattt tcccctagct ttccccagac accctgtttt    660

attttattat aatgaatttt gtttgttgat gtgaaacatt atgccttaag taatgttaat    720

tcttatttaa gttattgatg ttttaagttt atctttcatg gtactagtgt tttttagata    780

cagagacttg gggaaattgc ttttcctctt gaaccacagt tctacccctg ggatgttttg    840

agggtctttg caagaatcat taatacaaag aatttttttt aacattccaa tgcattgcta    900

aaatattatt gtggaaatga atattttgta actattacac caaataaata tatttttgta    960

ca                                                                   962
```

<210> SEQ ID NO 69
<211> LENGTH: 1198
<212> TYPE: DNA

<213> ORGANISM: Artificial Sequence
<220> FEATURE:
<223> OTHER INFORMATION: Synthetic

<400> SEQUENCE: 69
ataaaagccc aggggcaagc ggtccggata acggctagcc tgaggagctg ctgcgacagt 60
ccactacctt tttcgagagt gactcccgtt gtcccaaggc ttcccagagc gaacctgtgc 120
ggctgcaggc accggcgcgt cgagtttccg gcgtccggaa ggaccgagct cttctcgcga 180
atccagtgtt ccgtttccag cccccaatct cagagcggag ccgacagaga gcagggaacc 240
ggcatgaaag tctctgccgc ccttctgtgc ctgctgctca tagcagccac cttcattccc 300
caagggctcg ctgtcttcac actcgaagat ttcgttgggg actggcgaca gacagccggc 360
tacaacctgg accaagtcct tgaacaggga ggtgtgtcca gtttgtttca gaatctcggg 420
gtgtccgtaa ctccgatcca aaggattgtc ctgagcggtg aaaatgggct gaagatcgac 480
atccatgtca tcatcccgta tgaaggtctg agcggcgacc aaatgggcca gatcgaaaaa 540
atttttaagg tggtgtaccc tgtggatgat catcacttta aggtgatcct gcactatggc 600
acactggtaa tcgacggggt tacgccgaac atgatcgact atttcggacg gccgtatgaa 660
ggcatcgccg tgttcgacgg caaaaagatc actgtaacag ggaccctgtg gaacggcaac 720
aaaattatcg acgagcgcct gatcaacccc gacggctccc tgctgttccg agtaaccatc 780
aacggagtga ccggctggcg gctgtgcgaa cgcattctgg cgtaaacact cactccacaa 840
cccaagaatc tgcagctaac ttattttccc ctagctttcc ccagacaccc tgttttattt 900
tattataatg aattttgttt gttgatgtga aacattatgc cttaagtaat gttaattctt 960
atttaagtta ttgatgtttt aagtttatct ttcatggtac tagtgttttt tagatacaga 1020
gacttgggga aattgctttt cctcttgaac cacagttcta cccctgggat gttttgaggg 1080
tctttgcaag aatcattaat acaaagaatt ttttttaaca ttccaatgca ttgctaaaat 1140
attattgtgg aaatgaatat tttgtaacta ttacaccaaa taaatatatt tttgtaca 1198

<210> SEQ ID NO 70
<211> LENGTH: 1067
<212> TYPE: DNA
<213> ORGANISM: Artificial Sequence
<220> FEATURE:
<223> OTHER INFORMATION: Synthetic

<400> SEQUENCE: 70
catatcttca ttcttcactc tttccccccc cccccttatc ctcctatcta atcctctcat 60
ctctctcctc ctcttcctcc aacaacaact aacaatggca gcaactacaa caatgaaagt 120
ctctgccgcc cttctgtgcc tgctgctcat agcagccacc ttcattcccc aagggctcgc 180
tgtcttcaca ctcgaagatt tcgttgggga ctggcgacag acagccggct acaacctgga 240
ccaagtcctt gaacagggag gtgtgtccag tttgtttcag aatctcgggg tgtccgtaac 300
tccgatccaa aggattgtcc tgagcggtga aaatgggctg aagatcgaca tccatgtcat 360
catcccgtat gaaggtctga gcggcgacca aatgggccag atcgaaaaaa tttttaaggt 420
ggtgtaccct gtggatgatc atcactttaa ggtgatcctg cactatggca cactggtaat 480
cgacggggtt acgccgaaca tgatcgacta tttcggacgg ccgtatgaag gcatcgccgt 540
gttcgacggc aaaaagatca ctgtaacagg gaccctgtgg aacggcaaca aaattatcga 600
cgagcgcctg atcaaccccg acggctccct gctgttccga gtaaccatca acggagtgac 660
cggctggcgg ctgtgcgaac gcattctggc gtaaacactc actccacaac ccaagaatct 720
gcagctaact tattttcccc tagctttccc cagacaccct gttttatttt attataatga 780
attttgtttg ttgatgtgaa acattatgcc ttaagtaatg ttaattctta tttaagttat 840
tgatgtttta agtttatctt tcatggtact agtgtttttt agatacagag acttggggaa 900
attgcttttc ctcttgaacc acagttctac ccctgggatg ttttgagggt ctttgcaaga 960
atcattaata caaagaattt tttttaacat tccaatgcat tgctaaaata ttattgtgga 1020
aatgaatatt ttgtaactat tacaccaaat aaatatattt ttgtaca 1067

<210> SEQ ID NO 71
<211> LENGTH: 1052
<212> TYPE: DNA
<213> ORGANISM: Artificial Sequence
<220> FEATURE:
<223> OTHER INFORMATION: Synthetic

<400> SEQUENCE: 71
aaagtgattg attcggatac tgacactgta ggatctgggg agagaggaac aaaggaccgt 60
gaaagctgct ctgtaaaagc tgacacagcc ctcccaagtg agcaggactg ttcttcccac 120
tgcaatctga cagtttactg catgcctgga gagaacacag cagtaaaaac caggtttgct 180
actggaaaaa gaggaaagag aagactttca ttgacggacc cagccatggc agcgtagcag 240
ccctgcgttt tagacggcag cagctcggga ctctggacgt gtgtttgccc tcaagtttgc 300
taagctgctg gtttattact gaagaaagaa tgaaagtctc tgccgccctt ctgtgcctgc 360
tgctcatagc agccaccttc attccccaag ggctcgctgt cttcacactc gaagatttcg 420
ttggggactg gcgacagaca gccggctaca acctggacca agtccttgaa cagggaggtg 480
tgtccagttt gtttcagaat ctcggggtgt ccgtaactcc gatccaaagg attgtcctga 540
gcggtgaaaa tgggctgaag atcgacatcc atgtcatcat cccgtatgaa ggtctgagcg 600
gcgaccaaat gggccagatc gaaaaaattt ttaaggtggt gtaccctgtg gatgatcatc 660
actttaaggt gatcctgcac tatggcacac tggtaatcga cggggttacg ccgaacatga 720
tcgactattt cggacggccg tatgaaggca tcgccgtgtt cgacggcaaa aagatcactg 780
taacagggac cctgtggaac ggcaacaaaa ttatcgacga gcgcctgatc aaccccgacg 840
gctccctgct gttccgagta accatcaacg gagtgaccgg ctggcggctg tgcgaacgca 900
ttctggcgta aggctgctgc agctgcatgg gtgcctgctg ctgcctgcct tggcctgatg 960
gccaggccag agtgctgcca gtcctctgca tgttctgctc ttgtgccctt ctgagcccac 1020
aataaaggct gagctcttat cttgcaaaag gc 1052

<210> SEQ ID NO 72
<211> LENGTH: 1064
<212> TYPE: DNA
<213> ORGANISM: Artificial Sequence
<220> FEATURE:
<223> OTHER INFORMATION: Synthetic

<400> SEQUENCE: 72
aaagtgattg attcggatac tgacactgta ggatctgggg agagaggaac aaaggaccgt 60
gaaagctgct ctgtaaaagc tgacacagcc ctcccaagtg agcaggactg ttcttcccac 120
tgcaatctga cagtttactg ccctggagag aacacagcag taaaaaccag gtttgctact 180
ggaaaaagag gaaagagaag actttcattg acggacccag ccgcagcgta gcagccctgc 240
gttttagacg gcagcagctc gggactctgg acgtgtgttt gccctcaagt ttgctaagct 300
gctggtttat tactgaagaa agaatgaact ccttctccac aagcgccttc ggtccagttg 360
ccttctccct gggcctgctc ctggtgttgc ctgctgcctt ccctgcccca gtcttcacac 420
tcgaagattt cgttggggac tggcgacaga cagccggcta caacctggac caagtccttg 480
aacagggagg tgtgtccagt ttgtttcaga atctcggggt gtccgtaact ccgatccaaa 540
ggattgtcct gagcggtgaa aatgggctga agatcgacat ccatgtcatc atcccgtatg 600
aaggtctgag cggcgaccaa atgggccaga tcgaaaaaat ttttaaggtg gtgtaccctg 660
tggatgatca tcactttaag gtgatcctgc actatggcac actggtaatc gacggggtta 720
cgccgaacat gatcgactat ttcggacggc cgtatgaagg catcgccgtg ttcgacggca 780
aaaagatcac tgtaacaggg accctgtgga acggcaacaa aattatcgac gagcgcctga 840
tcaaccccga cggctccctg ctgttccgag taaccatcaa cggagtgacc ggctggcggc 900
tgtgcgaacg cattctggcg taaggctgct gcagctgcat gggtgcctgc tgctgcctgc 960
cttggcctga tggccaggcc agagtgctgc cagtcctctg catgttctgc tcttgtgccc 1020
ttctgagccc acaataaagg ctgagctctt atcttgcaaa aggc 1064

<210> SEQ ID NO 73
<211> LENGTH: 1034
<212> TYPE: DNA
<213> ORGANISM: Artificial Sequence
<220> FEATURE:
<223> OTHER INFORMATION: Synthetic

<400> SEQUENCE: 73
aaagtgattg attcggatac tgacactgta ggatctgggg agagaggaac aaaggaccgt 60
gaaagctgct ctgtaaaagc tgacacagcc ctcccaagtg agcaggactg ttcttcccac 120
tgcaatctga cagtttactg catgcctgga gagaacacag cagtaaaaac caggtttgct 180
actggaaaaa gaggaaagag aagactttca ttgacggacc cagccatggc agcgtagcag 240
ccctgcgttt tagacggcag cagctcggga ctctggacgt gtgtttgccc tcaagtttgc 300
taagctgctg gtttattact gaagaaagaa tgggagtgaa agttcttttt gcccttattt 360
gtattgctgt ggccgaggcc gtcttcacac tcgaagattt cgttggggac tggcgacaga 420
cagccggcta caacctggac caagtccttg aacagggagg tgtgtccagt ttgtttcaga 480
atctcggggt gtccgtaact ccgatccaaa ggattgtcct gagcggtgaa aatgggctga 540
agatcgacat ccatgtcatc atcccgtatg aaggtctgag cggcgaccaa atgggccaga 600
tcgaaaaaat ttttaaggtg gtgtaccctg tggatgatca tcactttaag gtgatcctgc 660
actatggcac actggtaatc gacggggtta cgccgaacat gatcgactat ttcggacggc 720
cgtatgaagg catcgccgtg ttcgacggca aaaagatcac tgtaacaggg accctgtgga 780
acggcaacaa aattatcgac gagcgcctga tcaaccccga cggctccctg ctgttccgag 840
taaccatcaa cggagtgacc ggctggcggc tgtgcgaacg cattctggcg taaggctgct 900
gcagctgcat gggtgcctgc tgctgcctgc cttggcctga tggccaggcc agagtgctgc 960
cagtcctctg catgttctgc tcttgtgccc ttctgagccc acaataaagg ctgagctctt 1020
atcttgcaaa aggc 1034

<210> SEQ ID NO 74
<211> LENGTH: 842
<212> TYPE: DNA
<213> ORGANISM: Artificial Sequence
<220> FEATURE:
<223> OTHER INFORMATION: Synthetic

<400> SEQUENCE: 74
catatcttca ttcttcactc tttccccccc cccccttatc ctcctatcta atcctctcat 60
ctctctcctc ctcttcctcc aacaacaact aacaatggca gcaactacaa caatgaaagt 120
ctctgccgcc cttctgtgcc tgctgctcat agcagccacc ttcattcccc aagggctcgc 180
tgtcttcaca ctcgaagatt tcgttgggga ctggcgacag acagccggct acaacctgga 240
ccaagtcctt gaacagggag gtgtgtccag tttgtttcag aatctcgggg tgtccgtaac 300
tccgatccaa aggattgtcc tgagcggtga aaatgggctg aagatcgaca tccatgtcat 360
catcccgtat gaaggtctga gcggcgacca aatgggccag atcgaaaaaa tttttaaggt 420
ggtgtaccct gtggatgatc atcactttaa ggtgatcctg cactatggca cactggtaat 480
cgacggggtt acgccgaaca tgatcgacta tttcggacgg ccgtatgaag gcatcgccgt 540
gttcgacggc aaaaagatca ctgtaacagg gaccctgtgg aacggcaaca aaattatcga 600
cgagcgcctg atcaaccccg acggctccct gctgttccga gtaaccatca acggagtgac 660
cggctggcgg ctgtgcgaac gcattctggc gtaattttga gtaattttca attttgtttt 720
tgtttttgtt tttgttgttg ggagttgttg taatttggta aatgttgggg tcactaaaat 780
cttttgttgc aattttagca ccttttttatt agatatataa aattgggttt agatgtagtt 840
aa 842

<210> SEQ ID NO 75
<211> LENGTH: 824
<212> TYPE: DNA
<213> ORGANISM: Artificial Sequence
<220> FEATURE:
<223> OTHER INFORMATION: Synthetic

<400> SEQUENCE: 75
catatcttca ttcttcactc tttccccccc cccccttatc ctcctatcta atcctctcat 60
ctctctcctc ctcttcctcc aacaacaact aacaatgaaa gtctctgccg cccttctgtg 120
cctgctgctc atagcagcca ccttcattcc ccaagggctc gctgtcttca cactcgaaga 180
tttcgttggg gactggcgac agacagccgg ctacaacctg gaccaagtcc ttgaacaggg 240
aggtgtgtcc agtttgtttc agaatctcgg ggtgtccgta actccgatcc aaaggattgt 300
cctgagcggt gaaaatgggc tgaagatcga catccatgtc atcatcccgt atgaaggtct 360
gagcggcgac caaatgggcc agatcgaaaa aatttttaag gtggtgtacc ctgtggatga 420
tcatcacttt aaggtgatcc tgcactatgg cacactggta atcgacgggg ttacgccgaa 480
catgatcgac tatttcggac ggccgtatga aggcatcgcc gtgttcgacg gcaaaaagat 540
cactgtaaca gggaccctgt ggaacggcaa caaaattatc gacgagcgcc tgatcaaccc 600
cgacggctcc ctgctgttcc gagtaaccat caacggagtg accggctggc ggctgtgcga 660
acgcattctg gcgtaatttt gagtaatttt caattttgtt tttgtttttg tttttgttgt 720
tgggagttgt tgtaatttgg taaatgttgg ggtcactaaa atcttttgtt gcaattttag 780
caccttttta ttagatatat aaaattgggt ttagatgtag ttaa 824

<210> SEQ ID NO 76
<211> LENGTH: 809
<212> TYPE: DNA
<213> ORGANISM: Artificial Sequence
<220> FEATURE:
<223> OTHER INFORMATION: Synthetic

<400> SEQUENCE: 76

```
catatcttca ttcttcactc tttccccccc ccccccttatc ctcctatcta atcctctcat     60
ctctctcctc ctcttcctcc aacaacaact aacaatgtgg cagattgttt tctttactct    120
gagctgtgat cttgtcttgg ccgcagccgt cttcacactc gaagatttcg ttggggactg    180
gcgacagaca gccggctaca acctggacca agtccttgaa cagggaggtg tgtccagttt    240
gtttcagaat ctcggggtgt ccgtaactcc gatccaaagg attgtcctga gcggtgaaaa    300
tgggctgaag atcgacatcc atgtcatcat cccgtatgaa ggtctgagcg gcgaccaaat    360
gggccagatc gaaaaaattt ttaaggtggt gtaccctgtg gatgatcatc actttaaggt    420
gatcctgcac tatggcacac tggtaatcga cggggttacg ccgaacatga tcgactattt    480
cggacggccg tatgaaggca tcgccgtgtt cgacggcaaa aagatcactg taacagggac    540
cctgtggaac ggcaacaaaa ttatcgacga gcgcctgatc aaccccgacg gctccctgct    600
gttccgagta accatcaacg gagtgaccgg ctggcggctg tgcgaacgca ttctggcgta    660
attttgagta attttcaatt ttgtttttgt ttttgttttt gttgttggga gttgttgtaa    720
tttggtaaat gttggggtca ctaaaatctt ttgttgcaat tttagcacct ttttattaga    780
tatataaaat tgggtttaga tgtagttaa                                      809
```

<210> SEQ ID NO 77
<211> LENGTH: 1083
<212> TYPE: DNA
<213> ORGANISM: Artificial Sequence
<220> FEATURE:
<223> OTHER INFORMATION: Synthetic

<400> SEQUENCE: 77

```
ataaaagccc aggggcaagc ggtccggata acggctagcc tgaggagctg ctgcgacagt     60
ccactacctt tttcgagagt gactcccgtt gtcccaaggc ttcccagagc gaacctgtgc    120
ggctgcaggc accggcgcgt cgagtttccg gcgtccggaa ggaccgagct cttctcgcga    180
atccagtgtt ccgtttccag cccccaatct cagagcggag ccgacagaga gcagggaacc    240
ggcatgaaag tctctgccgc ccttctgtgc ctgctgctca tagcagccac cttcattccc    300
caagggctcg ctgtcttcac actcgaagat ttcgttgggg actggcgaca gacagccggc    360
tacaacctgg accaagtcct tgaacaggga ggtgtgtcca gtttgtttca gaatctcggg    420
gtgtccgtaa ctccgatcca aaggattgtc ctgagcggtg aaaatgggct gaagatcgac    480
atccatgtca tcatcccgta tgaaggtctg agcggcgacc aaatgggcca gatcgaaaaa    540
atttttaagg tggtgtaccc tgtggatgat catcacttta aggtgatcct gcactatggc    600
acactggtaa tcgacggggt tacgccgaac atgatcgact atttcggacg gccgtatgaa    660
ggcatcgccg tgttcgacgg caaaaagatc actgtaacag ggaccctgtg gaacggcaac    720
aaaattatcg acgagcgcct gatcaacccc gacggctccc tgctgttccg agtaaccatc    780
aacggagtga ccggctggcg gctgtgcgaa cgcattctgg cgtaagggcc tttccaagat    840
tgctgttttt gttttggagc ttcaagactt tgcatttcct agtatttctg tttgtcagtt    900
ctcaatttcc tgtgtttgca atgttgaaat tttttggtga agtactgaac ttgctttttt    960
tccggtttct acatgcagag atgaatttat actgccatct tacgactatt tcttcttttt   1020
aatacactta actcaggcca ttttttaagt tggttacttc aaagtaaata aactttaaaa   1080
ttc                                                                 1083
```

<210> SEQ ID NO 78
<211> LENGTH: 984
<212> TYPE: DNA
<213> ORGANISM: Artificial Sequence
<220> FEATURE:
<223> OTHER INFORMATION: Synthetic

<400> SEQUENCE: 78
gggctggggg agggtatata agccgagtag gcgacggtga ggtcgacgcc ggccaagaca 60
gcacagacag attgacctat tggggtgttt cgcgagtgtg agagggaagc gccgcggcct 120
gtatttctag acctgccctt cgcctggttc gtggcgcctt gtgaccccgg gcccctgccg 180
cctgcaagtc ggaaattgcg ctgtgctcct gtgctacggc ctgtggctgg actgcctgct 240
gctgcccaac tggctggcaa gatgaaagtc tctgccgccc ttctgtgcct gctgctcata 300
gcagccacct tcattcccca agggctcgct gtcttcacac tcgaagattt cgttggggac 360
tggcgacaga cagccggcta caacctggac caagtccttg aacagggagg tgtgtccagt 420
ttgtttcaga atctcggggt gtccgtaact ccgatccaaa ggattgtcct gagcggtgaa 480
aatgggctga agatcgacat ccatgtcatc atcccgtatg aaggtctgag cggcgaccaa 540
atgggccaga tcgaaaaaat ttttaaggtg gtgtaccctg tggatgatca tcactttaag 600
gtgatcctgc actatggcac actggtaatc gacggggtta cgccgaacat gatcgactat 660
ttcggacggc cgtatgaagg catcgccgtg ttcgacggca aaaagatcac tgtaacaggg 720
accctgtgga acggcaacaa aattatcgac gagcgcctga tcaaccccga cggctccctg 780
ctgttccgag taaccatcaa cggagtgacc ggctggcggc tgtgcgaacg cattctggcg 840
taaggctgct gcagctgcat gggtgcctgc tgctgcctgc cttggcctga tggccaggcc 900
agagtgctgc cagtcctctg catgttctgc tcttgtgccc ttctgagccc acaataaagg 960
ctgagctctt atcttgcaaa aggc 984

<210> SEQ ID NO 79
<211> LENGTH: 898
<212> TYPE: DNA
<213> ORGANISM: Artificial Sequence
<220> FEATURE:
<223> OTHER INFORMATION: Synthetic

<400> SEQUENCE: 79
agctgttctt ggctgacttc acatcaaaac tcctatactg acctgagaca gaggcagcag 60
tgatacccac ctgagagatc ctgtgtttga acaactgctt cccaaaacgg aaagtatttc 120
aagcctaaac ctttgggtga aaagaactct tgaagtcatg aactccttct ccacaagcgc 180
cttcggtcca gttgccttct ccctgggcct gctcctggtg ttgcctgctg ccttccctgc 240
cccagtcttc acactcgaag atttcgttgg ggactggcga cagacagccg gctacaacct 300
ggaccaagtc cttgaacagg gaggtgtgtc cagtttgttt cagaatctcg gggtgtccgt 360
aactccgatc caaaggattg tcctgagcgg tgaaaatggg ctgaagatcg acatccatgt 420
catcatcccg tatgaaggtc tgagcggcga ccaaatgggc cagatcgaaa aaatttttaa 480
ggtggtgtac cctgtggatg atcatcactt taaggtgatc ctgcactatg gcacactggt 540
aatcgacggg gttacgccga acatgatcga ctatttcgga cggccgtatg aaggcatcgc 600
cgtgttcgac ggcaaaaaga tcactgtaac agggaccctg tggaacggca acaaaattat 660
cgacgagcgc ctgatcaacc ccgacggctc cctgctgttc cgagtaacca tcaacggagt 720
gaccggctgg cggctgtgcg aacgcattct ggcgtaaggc tgctgcagct gcatgggtgc 780
ctgctgctgc ctgccttggc ctgatggcca ggccagagtg ctgccagtcc tctgcatgtt 840
ctgctcttgt gcccttctga gcccacaata aaggctgagc tcttatcttg caaaaggc 898

<210> SEQ ID NO 80
<211> LENGTH: 1060
<212> TYPE: DNA
<213> ORGANISM: Artificial Sequence
<220> FEATURE:
<223> OTHER INFORMATION: Synthetic

<400> SEQUENCE: 80
caagcttagc ctggccggga aacgggaggc gtggaggccg ggagcagccc ccggggtcat 60
cgccctgcca ccgccgcccg attgctttag cttggaaatt ccggagctga agcggccagc 120
gagggaggat gaccctctcg gcccgggcac cctgtcagtc cggaaataac tgcagcattt 180
gttccggagg ggaaggcgcg aggtttccgg gaaagcagca ccgccccttg gcccccaggt 240
ggctagcgct ataaaggatc acgcgcccca gtcgacgctg agctcctctg ctactcagag 300
ttgcaacctc agcctcgcta tgaactcctt ctccacaagc gccttcggtc cagttgcctt 360
ctccctgggc ctgctcctgg tgttgcctgc tgccttccct gccccagtct tcacactcga 420
agatttcgtt ggggactggc gacagacagc cggctacaac ctggaccaag tccttgaaca 480
gggaggtgtg tccagtttgt ttcagaatct cggggtgtcc gtaactccga tccaaaggat 540
tgtcctgagc ggtgaaaatg ggctgaagat cgacatccat gtcatcatcc cgtatgaagg 600
tctgagcggc gaccaaatgg gccagatcga aaaaattttt aaggtggtgt accctgtgga 660
tgatcatcac tttaaggtga tcctgcacta tggcacactg gtaatcgacg gggttacgcc 720
gaacatgatc gactatttcg gacggccgta tgaaggcatc gccgtgttcg acggcaaaaa 780
gatcactgta acagggaccc tgtggaacgg caacaaaatt atcgacgagc gcctgatcaa 840
ccccgacggc tccctgctgt tccgagtaac catcaacgga gtgaccggct ggcggctgtg 900
cgaacgcatt ctggcgtaag gctgctgcag ctgcatgggt gcctgctgct gcctgccttg 960
gcctgatggc caggccagag tgctgccagt cctctgcatg ttctgctctt gtgcccttct 1020
gagcccacaa taaaggctga gctcttatct tgcaaaaggc 1060

<210> SEQ ID NO 81
<211> LENGTH: 1150
<212> TYPE: DNA
<213> ORGANISM: Artificial Sequence
<220> FEATURE:
<223> OTHER INFORMATION: Synthetic

<400> SEQUENCE: 81
gtctcaatat tagagtctca acccccaata aatataggac tggagatgtc tgaggctcat 60
tctgccctgg agcccaccgg gaacgaaaga gaagctctat ctcccctcca ggagcccagc 120
tatgaactcc ttctccacaa gcgccttcgg tccagttgcc ttctccctgg gctgctcct 180 ggtgttgcct gctgccttcc ctgccccagt cttcacactc gaagatttcg ttggggactg 240
gcgacagaca gccggctaca acctggacca agtccttgaa cagggaggtg tgtccagttt 300
gtttcagaat ctcggggtgt ccgtaactcc gatccaaagg attgtcctga gcggtgaaaa 360
tgggctgaag atcgacatcc atgtcatcat cccgtatgaa ggtctgagcg gcgaccaaat 420
gggccagatc gaaaaaattt ttaaggtggt gtaccctgtg gatgatcatc actttaaggt 480
gatcctgcac tatggcacac tggtaatcga cggggttacg ccgaacatga tcgactattt 540
cggacggccg tatgaaggca tcgccgtgtt cgacggcaaa aagatcactg taacagggac 600
cctgtggaac ggcaacaaaa ttatcgacga gcgcctgatc aaccccgacg gctccctgct 660
gttccgagta accatcaacg gagtgaccgg ctggcggctg tgcgaacgca ttctggcgta 720
acatgggcac ctcagattgt tgttgttaat gggcattcct tcttctggtc agaaacctgt 780
ccactgggca cagaacttat gttgttctct atggagaact aaaagtatga gcgttaggac 840
actattttaa ttatttttaa tttattaata tttaaatatg tgaagctgag ttaatttatg 900
taagtcatat ttatattttt aagaagtacc acttgaaaca ttttatgtat tagttttgaa 960
ataataatgg aaagtggcta tgcagtttga atatcctttg tttcagagcc agatcatttc 1020
ttggaaagtg taggcttacc tcaaataaat ggctaactta tacatatttt taaagaaata 1080
tttatattgt atttatataa tgtataaatg gtttttatac caataaatgg cattttaaaa 1140
aattcagcaa 1150

<210> SEQ ID NO 82
<211> LENGTH: 975
<212> TYPE: DNA
<213> ORGANISM: Artificial Sequence
<220> FEATURE:
<223> OTHER INFORMATION: Synthetic

<400> SEQUENCE: 82
gtggcagctc acagctattg tggtgggaaa gggagggtgg ttggtggatg tcacagcttg 60
ggctttatct cccccagcag tggggactcc acagcccctg ggctacataa cagcaagaca 120
gtccggagct gtagcagacc tgattgagcc tttgcagcag ctgagagcat ggcctagggt 180
gggcggcacc attgtccagc agctgagttt cccagggacc ttggagatag ccgcagccct 240
catttgcagg ggaagatgat tcctgccaga tttgccgggg tgctgcttgc tctggccctc 300
attttgccag ggaccctttg tgtcttcaca ctcgaagatt tcgttgggga ctggcgacag 360
acagccggct acaacctgga ccaagtcctt gaacagggag gtgtgtccag tttgtttcag 420
aatctcgggg tgtccgtaac tccgatccaa aggattgtcc tgagcggtga aaatgggctg 480
aagatcgaca tccatgtcat catcccgtat gaaggtctga gcggcgacca aatgggccag 540
atcgaaaaaa tttttaaggt ggtgtaccct gtggatgatc atcactttaa ggtgatcctg 600
cactatggca cactggtaat cgacggggtt acgccgaaca tgatcgacta tttcggacgg 660
ccgtatgaag gcatcgccgt gttcgacggc aaaaagatca ctgtaacagg gaccctgtgg 720
aacggcaaca aaattatcga cgagcgcctg atcaaccccg acggctccct gctgttccga 780
gtaaccatca acggagtgac cggctggcgg ctgtgcgaac gcattctggc gtaaggctgc 840
tgcagctgca tgggtgcctg ctgctgcctg ccttggcctg atggccaggc cagagtgctg 900
ccagtcctct gcatgttctg ctcttgtgcc cttctgagcc cacaataaag gctgagctct 960
tatcttgcaa aaggc 975

<210> SEQ ID NO 83
<211> LENGTH: 497
<212> TYPE: DNA
<213> ORGANISM: Homo sapiens
<220> FEATURE:
<221> NAME/KEY: 5'UTR
<222> LOCATION: (1)..(497)

<400> SEQUENCE: 83
gccctaagcc atcagcaatc cttagtatag gggcacactc atgcattcct gtcaagtcat 60
cttgtgaaag gctgcctgct tccagcttgg cttggatgtg caaccttaat aaaactcact 120

```
gaggtctggg agaaaatagc agatctgcag cagatagggt agaggaaagg gtctagaata    180

tgtacacgca gctgactcag gcaggctcca tgctgaacgg tcacacagag aggaaacaat    240

aaatctcagc tactatgcaa taaatatctc aagttttaac gaagaaaaac atcattgcag    300

tgaaataaaa aattttaaaa ttttagaaca aagctaacaa atggctagtt ttctatgatt    360

cttcttcaaa cgctttcttt gagggggaaa gagtcaaaca aacaagcagt tttacctgaa    420

ataaagaact agttttagag gtcagaagaa aggagcaagt tttgcgagag gcacggaagg    480

agtgtgctgg cagtaca                                                   497


<210> SEQ ID NO 84
<211> LENGTH: 45
<212> TYPE: DNA
<213> ORGANISM: Homo sapiens
<220> FEATURE:
<221> NAME/KEY: sig_peptide
<222> LOCATION: (1)..(45)

<400> SEQUENCE: 84

atgacagttt tcctttcctt tgctttcctc gctgccattc tgact                     45


<210> SEQ ID NO 85
<211> LENGTH: 15
<212> TYPE: PRT
<213> ORGANISM: Homo sapiens
<220> FEATURE:
<221> NAME/KEY: SIGNAL
<222> LOCATION: (1)..(15)

<400> SEQUENCE: 85

Met Thr Val Phe Leu Ser Phe Ala Phe Leu Ala Ala Ile Leu Thr
1               5                   10                  15


<210> SEQ ID NO 86
<211> LENGTH: 1452
<212> TYPE: DNA
<213> ORGANISM: Homo sapiens
<220> FEATURE:
<221> NAME/KEY: CDS
<222> LOCATION: (1)..(1452)

<400> SEQUENCE: 86

cac ata ggg tgc agc aat cag cgc cga agt cca gaa aac agt ggg aga       48
His Ile Gly Cys Ser Asn Gln Arg Arg Ser Pro Glu Asn Ser Gly Arg
1               5                   10                  15

aga tat aac cgg att caa cat ggg caa tgt gcc tac act ttc att ctt       96
Arg Tyr Asn Arg Ile Gln His Gly Gln Cys Ala Tyr Thr Phe Ile Leu
            20                  25                  30

cca gaa cac gat ggc aac tgt cgt gag agt acg aca gac cag tac aac      144
Pro Glu His Asp Gly Asn Cys Arg Glu Ser Thr Thr Asp Gln Tyr Asn
        35                  40                  45

aca aac gct ctg cag aga gat gct cca cac gtg gaa ccg gat ttc tct      192
Thr Asn Ala Leu Gln Arg Asp Ala Pro His Val Glu Pro Asp Phe Ser
    50                  55                  60

tcc cag aaa ctt caa cat ctg gaa cat gtg atg gaa aat tat act cag      240
Ser Gln Lys Leu Gln His Leu Glu His Val Met Glu Asn Tyr Thr Gln
65                  70                  75                  80

tgg ctg caa aaa ctt gag aat tac att gtg gaa aac atg aag tcg gag      288
Trp Leu Gln Lys Leu Glu Asn Tyr Ile Val Glu Asn Met Lys Ser Glu
                85                  90                  95

atg gcc cag ata cag cag aat gca gtt cag aac cac acg gct acc atg      336
Met Ala Gln Ile Gln Gln Asn Ala Val Gln Asn His Thr Ala Thr Met
```

```
            100                 105                 110

ctg gag ata gga acc agc ctc ctc tct cag act gca gag cag acc aga      384
Leu Glu Ile Gly Thr Ser Leu Leu Ser Gln Thr Ala Glu Gln Thr Arg
        115                 120                 125

aag ctg aca gat gtt gag acc cag gta cta aat caa act tct cga ctt      432
Lys Leu Thr Asp Val Glu Thr Gln Val Leu Asn Gln Thr Ser Arg Leu
    130                 135                 140

gag ata cag ctg ctg gag aat tca tta tcc acc tac aag cta gag aag      480
Glu Ile Gln Leu Leu Glu Asn Ser Leu Ser Thr Tyr Lys Leu Glu Lys
145                 150                 155                 160

caa ctt ctt caa cag aca aat gaa atc ttg aag atc cat gaa aaa aac      528
Gln Leu Leu Gln Gln Thr Asn Glu Ile Leu Lys Ile His Glu Lys Asn
                165                 170                 175

agt tta tta gaa cat aaa atc tta gaa atg gaa gga aaa cac aag gaa      576
Ser Leu Leu Glu His Lys Ile Leu Glu Met Glu Gly Lys His Lys Glu
            180                 185                 190

gag ttg gac acc tta aag gaa gag aaa gag aac ctt caa ggc ttg gtt      624
Glu Leu Asp Thr Leu Lys Glu Glu Lys Glu Asn Leu Gln Gly Leu Val
        195                 200                 205

act cgt caa aca tat ata atc cag gag ctg gaa aag caa tta aac aga      672
Thr Arg Gln Thr Tyr Ile Ile Gln Glu Leu Glu Lys Gln Leu Asn Arg
    210                 215                 220

gct acc acc aac aac agt gtc ctt cag aag cag caa ctg gag ctg atg      720
Ala Thr Thr Asn Asn Ser Val Leu Gln Lys Gln Gln Leu Glu Leu Met
225                 230                 235                 240

gac aca gtc cac aac ctt gtc aat ctt tgc act aaa gaa ggt gtt tta      768
Asp Thr Val His Asn Leu Val Asn Leu Cys Thr Lys Glu Gly Val Leu
                245                 250                 255

cta aag gga gga aaa aga gag gaa gag aaa cca ttt aga gac tgt gca      816
Leu Lys Gly Gly Lys Arg Glu Glu Glu Lys Pro Phe Arg Asp Cys Ala
            260                 265                 270

gat gta tat caa gct ggt ttt aat aaa agt gga atc tac act att tat      864
Asp Val Tyr Gln Ala Gly Phe Asn Lys Ser Gly Ile Tyr Thr Ile Tyr
        275                 280                 285

att aat aat atg cca gaa ccc aaa aag gtg ttt tgc aat atg gat gtc      912
Ile Asn Asn Met Pro Glu Pro Lys Lys Val Phe Cys Asn Met Asp Val
    290                 295                 300

aat ggg gga ggt tgg act gta ata caa cat cgt gaa gat gga agt cta      960
Asn Gly Gly Gly Trp Thr Val Ile Gln His Arg Glu Asp Gly Ser Leu
305                 310                 315                 320

gat ttc caa aga ggc tgg aag gaa tat aaa atg ggt ttt gga aat ccc     1008
Asp Phe Gln Arg Gly Trp Lys Glu Tyr Lys Met Gly Phe Gly Asn Pro
                325                 330                 335

tcc ggt gaa tat tgg ctg ggg aat gag ttt att ttt gcc att acc agt     1056
Ser Gly Glu Tyr Trp Leu Gly Asn Glu Phe Ile Phe Ala Ile Thr Ser
            340                 345                 350

cag agg cag tac atg cta aga att gag tta atg gac tgg gaa ggg aac     1104
Gln Arg Gln Tyr Met Leu Arg Ile Glu Leu Met Asp Trp Glu Gly Asn
        355                 360                 365

cga gcc tat tca cag tat gac aga ttc cac ata gga aat gaa aag caa     1152
Arg Ala Tyr Ser Gln Tyr Asp Arg Phe His Ile Gly Asn Glu Lys Gln
    370                 375                 380

aac tat agg ttg tat tta aaa ggt cac act ggg aca gca gga aaa cag     1200
Asn Tyr Arg Leu Tyr Leu Lys Gly His Thr Gly Thr Ala Gly Lys Gln
385                 390                 395                 400

agc agc ctg atc tta cac ggt gct gat ttc agc act aaa gat gct gat     1248
Ser Ser Leu Ile Leu His Gly Ala Asp Phe Ser Thr Lys Asp Ala Asp
                405                 410                 415

aat gac aac tgt atg tgc aaa tgt gcc ctc atg tta aca gga gga tgg     1296
```

```
Asn Asp Asn Cys Met Cys Lys Cys Ala Leu Met Leu Thr Gly Gly Trp
            420                 425                 430

tgg ttt gat gct tgt ggc ccc tcc aat cta aat gga atg ttc tat act      1344
Trp Phe Asp Ala Cys Gly Pro Ser Asn Leu Asn Gly Met Phe Tyr Thr
        435                 440                 445

gcg gga caa aac cat gga aaa ctg aat ggg ata aag tgg cac tac ttc      1392
Ala Gly Gln Asn His Gly Lys Leu Asn Gly Ile Lys Trp His Tyr Phe
    450                 455                 460

aaa ggg ccc agt tac tcc tta cgt tcc aca act atg atg att cga cct      1440
Lys Gly Pro Ser Tyr Ser Leu Arg Ser Thr Thr Met Met Ile Arg Pro
465                 470                 475                 480

tta gat ttt tga                                                      1452
Leu Asp Phe


<210> SEQ ID NO 87
<211> LENGTH: 483
<212> TYPE: PRT
<213> ORGANISM: Homo sapiens

<400> SEQUENCE: 87

His Ile Gly Cys Ser Asn Gln Arg Arg Ser Pro Glu Asn Ser Gly Arg
1               5                   10                  15

Arg Tyr Asn Arg Ile Gln His Gly Gln Cys Ala Tyr Thr Phe Ile Leu
            20                  25                  30

Pro Glu His Asp Gly Asn Cys Arg Glu Ser Thr Thr Asp Gln Tyr Asn
        35                  40                  45

Thr Asn Ala Leu Gln Arg Asp Ala Pro His Val Glu Pro Asp Phe Ser
    50                  55                  60

Ser Gln Lys Leu Gln His Leu Glu His Val Met Glu Asn Tyr Thr Gln
65                  70                  75                  80

Trp Leu Gln Lys Leu Glu Asn Tyr Ile Val Glu Asn Met Lys Ser Glu
                85                  90                  95

Met Ala Gln Ile Gln Gln Asn Ala Val Gln Asn His Thr Ala Thr Met
            100                 105                 110

Leu Glu Ile Gly Thr Ser Leu Leu Ser Gln Thr Ala Glu Gln Thr Arg
        115                 120                 125

Lys Leu Thr Asp Val Glu Thr Gln Val Leu Asn Gln Thr Ser Arg Leu
    130                 135                 140

Glu Ile Gln Leu Leu Glu Asn Ser Leu Ser Thr Tyr Lys Leu Glu Lys
145                 150                 155                 160

Gln Leu Leu Gln Gln Thr Asn Glu Ile Leu Lys Ile His Glu Lys Asn
                165                 170                 175

Ser Leu Leu Glu His Lys Ile Leu Glu Met Glu Gly Lys His Lys Glu
            180                 185                 190

Glu Leu Asp Thr Leu Lys Glu Glu Lys Glu Asn Leu Gln Gly Leu Val
        195                 200                 205

Thr Arg Gln Thr Tyr Ile Ile Gln Glu Leu Glu Lys Gln Leu Asn Arg
    210                 215                 220

Ala Thr Thr Asn Asn Ser Val Leu Gln Lys Gln Gln Leu Glu Leu Met
225                 230                 235                 240

Asp Thr Val His Asn Leu Val Asn Leu Cys Thr Lys Glu Gly Val Leu
                245                 250                 255

Leu Lys Gly Gly Lys Arg Glu Glu Glu Lys Pro Phe Arg Asp Cys Ala
            260                 265                 270

Asp Val Tyr Gln Ala Gly Phe Asn Lys Ser Gly Ile Tyr Thr Ile Tyr
        275                 280                 285
```

```
Ile Asn Asn Met Pro Glu Pro Lys Lys Val Phe Cys Asn Met Asp Val
    290                 295                 300

Asn Gly Gly Gly Trp Thr Val Ile Gln His Arg Glu Asp Gly Ser Leu
305                 310                 315                 320

Asp Phe Gln Arg Gly Trp Lys Glu Tyr Lys Met Gly Phe Gly Asn Pro
                325                 330                 335

Ser Gly Glu Tyr Trp Leu Gly Asn Glu Phe Ile Phe Ala Ile Thr Ser
            340                 345                 350

Gln Arg Gln Tyr Met Leu Arg Ile Glu Leu Met Asp Trp Glu Gly Asn
        355                 360                 365

Arg Ala Tyr Ser Gln Tyr Asp Arg Phe His Ile Gly Asn Glu Lys Gln
    370                 375                 380

Asn Tyr Arg Leu Tyr Leu Lys Gly His Thr Gly Thr Ala Gly Lys Gln
385                 390                 395                 400

Ser Ser Leu Ile Leu His Gly Ala Asp Phe Ser Thr Lys Asp Ala Asp
                405                 410                 415

Asn Asp Asn Cys Met Cys Lys Cys Ala Leu Met Leu Thr Gly Gly Trp
            420                 425                 430

Trp Phe Asp Ala Cys Gly Pro Ser Asn Leu Asn Gly Met Phe Tyr Thr
        435                 440                 445

Ala Gly Gln Asn His Gly Lys Leu Asn Gly Ile Lys Trp His Tyr Phe
    450                 455                 460

Lys Gly Pro Ser Tyr Ser Leu Arg Ser Thr Thr Met Met Ile Arg Pro
465                 470                 475                 480

Leu Asp Phe
```

<210> SEQ ID NO 88
<211> LENGTH: 2373
<212> TYPE: DNA
<213> ORGANISM: Homo sapiens
<220> FEATURE:
<221> NAME/KEY: 5'UTR
<222> LOCATION: (1)..(2373)

<400> SEQUENCE: 88

```
aagcgcaatg tcagaagcga ttatgaaagc aacaaagaaa tccggagaag ctgccaggtg     60

agaaactgtt tgaaaacttc agaagcaaac aatattgtct cccttccagc aataagtggt    120

agttatgtga agtcaccaag gttcttgacc gtgaatctgg agccgtttga gttcacaaga    180

gtctctactt ggggtgacag tgctcacgtg gctcgactat agaaaactcc actgactgtc    240

gggctttaaa aagggaagaa actgctgagc ttgctgtgct tcaaactact actggacctt    300

attttggaac tatggtagcc agatgataaa tatggttaat ttcatgtaaa acagaaaaaa    360

agagtgaaaa agagaatata catgaagaat agaaacaagc ctgccataat cctttggaaa    420

agatgtatta taccagtgaa aaggtgttat atctatgcaa acctactaac aaattatact    480

gttgcacaat tttgataaaa atttagaaca gcattgtcct ctgagttggt taaatgttaa    540

tggatttcag aagcctaatt ccagtatcat acttactagt tgatttctgc ttacccatct    600

tcaaatgaaa attccatttt tgtaagccat aatgaactgt agtacatgga caataagtgt    660

gtggtagaaa caaactccat tactctgatt tttgatacag ttttcagaaa aagaaatgaa    720

cataatcaag taaggatgta tgtggtgaaa acttaccacc cccatactat ggttttcatt    780

tactctaaaa actgattgaa tgatatataa atatatttat agcctgagta aagttaaaag    840

aatgtaaaat atatcatcaa gttcttaaaa taatatacat gcatttaata tttcctttga    900
```

tattatacag gaaagcaata ttttggagta tgttaagttg aagtaaaagc aagtactctg 960
gagcagttca ttttacagta tctacttgca tgtgtataca tacatgtaac ttcattattt 1020
taaaaatatt tttagaactc caatactcac cctgttatgt cttgctaatt taaattttgc 1080
taattaactg aaacatgctt accagattca cactgttcca gtgtctataa aagaaacact 1140
ttgaagtcta taaaaaataa aataattata aatatcattg tacatagcat gtttatatct 1200
gcaaaaaacc taatagctaa ttaatctgga atatgcaaca ttgtccttaa ttgatgcaaa 1260
taacacaaat gctcaaagaa atctactata tcccttaatg aaatacatca ttcttcatat 1320
atttctcctt cagtccattc ccttaggcaa tttttaattt ttaaaaatta ttatcagggg 1380
agaaaaattg gcaaaactat tatatgtaag ggaaatatat acaaaaagaa aattaatcat 1440
agtcacctga ctaagaaatt ctgactgcta gttgccataa ataactcaat ggaaatattc 1500
ctatgggata atgtatttta agtgaatttt tggggtgctt gaagttactg cattatttta 1560
tcaagaagtc ttctctgcct gtaagtgtcc aaggttatga cagtaaacag tttttattaa 1620
aacatgagtc actatgggat gagaaaattg aaataaagct actgggcctc ctctcataaa 1680
agagacagtt gttggcaagg tagcaatacc agtttcaaac ttggtgactt gatccactat 1740
gccttaatgg tttcctccat ttgagaaaat aaagctattc acattgttaa gaaaaatact 1800
ttttaaagtt taccatcaag tctttttat atttatgtgt ctgtattcta ccccttttg 1860 ccttacaagt gatatttgca ggtattatac catttttcta ttcttggtgg cttcttcata 1920
gcaggtaagc ctctccttct aaaaacttct caactgtttt catttaaggg aaagaaaatg 1980
agtattttgt ccttttgtgt tcctacagac actttcttaa accagttttt ggataaagaa 2040
tactatttcc aaactcatat tacaaaaaca aaataaaata ataaaaaaag aaagcatgat 2100
atttactgtt ttgttgtctg ggtttgagaa atgaaatatt gtttccaatt atttataata 2160
aatcagtata aaatgtttta tgattgttat gtgtattatg taatacgtac atgtttatgg 2220
caatttaaca tgtgtattct tttaattgtt tcagaatagg ataattaggt attcgaattt 2280
tgtctttaaa attcatgtgg tttctatgca aagttcttca tatcatcaca acattatttg 2340
atttaaataa aattgaaagt aatatttgtg caa 2373

<210> SEQ ID NO 89
<211> LENGTH: 120
<212> TYPE: DNA
<213> ORGANISM: Homo sapiens
<220> FEATURE:
<221> NAME/KEY: 5'UTR
<222> LOCATION: (1)..(120)

<400> SEQUENCE: 89
agacagaggt ttgtagctgc agctgcaggc aagcctggcc actgttggct gcagcaggac 60
atcccaggca cagcccctag ggctctgagc agacatccct cgccattgac acatcttcag 120

<210> SEQ ID NO 90
<211> LENGTH: 66
<212> TYPE: DNA
<213> ORGANISM: Homo sapiens
<220> FEATURE:
<221> NAME/KEY: sig_peptide
<222> LOCATION: (1)..(66)

<400> SEQUENCE: 90
atgctctccc agctagccat gctgcagggc agcctcctcc ttgtggttgc caccatgtct 60

```
gtggct                                                                  66


<210> SEQ ID NO 91
<211> LENGTH: 22
<212> TYPE: PRT
<213> ORGANISM: Homo sapiens
<220> FEATURE:
<221> NAME/KEY: SIGNAL
<222> LOCATION: (1)..(22)

<400> SEQUENCE: 91

Met Leu Ser Gln Leu Ala Met Leu Gln Gly Ser Leu Leu Leu Val Val
1               5                   10                  15

Ala Thr Met Ser Val Ala
            20


<210> SEQ ID NO 92
<211> LENGTH: 1446
<212> TYPE: DNA
<213> ORGANISM: Homo sapiens
<220> FEATURE:
<221> NAME/KEY: CDS
<222> LOCATION: (1)..(1446)

<400> SEQUENCE: 92

caa cag aca agg cag gag gcg gat agg ggc tgc gag aca ctt gta gtc       48
Gln Gln Thr Arg Gln Glu Ala Asp Arg Gly Cys Glu Thr Leu Val Val
1               5                   10                  15

cag cac ggc cac tgt agc tac acc ttc ttg ctg ccc aag tct gag ccc       96
Gln His Gly His Cys Ser Tyr Thr Phe Leu Leu Pro Lys Ser Glu Pro
            20                  25                  30

tgc cct ccg ggg cct gag gtc tcc agg gac tcc aac acc ctc cag aga      144
Cys Pro Pro Gly Pro Glu Val Ser Arg Asp Ser Asn Thr Leu Gln Arg
        35                  40                  45

gaa tca ctg gcc aac cca ctg cac ctg ggg aag ttg ccc acc cag cag      192
Glu Ser Leu Ala Asn Pro Leu His Leu Gly Lys Leu Pro Thr Gln Gln
    50                  55                  60

gtg aaa cag ctg gag cag gca ctg cag aac aac acg cag tgg ctg aag      240
Val Lys Gln Leu Glu Gln Ala Leu Gln Asn Asn Thr Gln Trp Leu Lys
65                  70                  75                  80

aag cta gag agg gcc atc aag acg atc ttg agg tcg aag ctg gag cag      288
Lys Leu Glu Arg Ala Ile Lys Thr Ile Leu Arg Ser Lys Leu Glu Gln
                85                  90                  95

gtc cag cag caa atg gcc cag aat cag acg gcc ccc atg cta gag ctg      336
Val Gln Gln Gln Met Ala Gln Asn Gln Thr Ala Pro Met Leu Glu Leu
            100                 105                 110

ggc acc agc ctc ctg aac cag acc act gcc cag atc cgc aag ctg acc      384
Gly Thr Ser Leu Leu Asn Gln Thr Thr Ala Gln Ile Arg Lys Leu Thr
        115                 120                 125

gac atg gag gct cag ctc ctg aac cag aca tca aga atg gat gcc cag      432
Asp Met Glu Ala Gln Leu Leu Asn Gln Thr Ser Arg Met Asp Ala Gln
    130                 135                 140

atg cca gag acc ttt ctg tcc acc aac aag ctg gag aac cag ctg ctg      480
Met Pro Glu Thr Phe Leu Ser Thr Asn Lys Leu Glu Asn Gln Leu Leu
145                 150                 155                 160

cta cag agg cag aag ctc cag cag ctt cag ggc caa aac agc gcg ctc      528
Leu Gln Arg Gln Lys Leu Gln Gln Leu Gln Gly Gln Asn Ser Ala Leu
                165                 170                 175

gag aag cgg ttg cag gcc ctg gag acc aag cag cag gag gag ctg gcc      576
Glu Lys Arg Leu Gln Ala Leu Glu Thr Lys Gln Gln Glu Glu Leu Ala
            180                 185                 190

agc atc ctc agc aag aag gcg aag ctg ctg aac acg ctg agc cgc cag      624
```

```
Ser Ile Leu Ser Lys Lys Ala Lys Leu Leu Asn Thr Leu Ser Arg Gln
        195                 200                 205

agc gcc gcc ctc acc aac atc gag cgc ggc ctg cgc ggt gtc agg cac      672
Ser Ala Ala Leu Thr Asn Ile Glu Arg Gly Leu Arg Gly Val Arg His
    210                 215                 220

aac tcc agc ctc ctg cag gac cag cag cac agc ctg cgc cag ctg ctg      720
Asn Ser Ser Leu Leu Gln Asp Gln Gln His Ser Leu Arg Gln Leu Leu
225                 230                 235                 240

gtg ttg ttg cgg cac ctg gtg caa gaa agg gct aac gcc tcg gcc ccg      768
Val Leu Leu Arg His Leu Val Gln Glu Arg Ala Asn Ala Ser Ala Pro
                245                 250                 255

gcc ttc ata atg gca ggt gag cag gtg ttc cag gac tgt gca gag atc      816
Ala Phe Ile Met Ala Gly Glu Gln Val Phe Gln Asp Cys Ala Glu Ile
            260                 265                 270

cag cgc tct ggg gcc agt gcc agt ggt gtc tac acc atc cag gtg tcc      864
Gln Arg Ser Gly Ala Ser Ala Ser Gly Val Tyr Thr Ile Gln Val Ser
        275                 280                 285

aat gca acg aag ccc agg aag gtg ttc tgt gac ctg cag agc agt gga      912
Asn Ala Thr Lys Pro Arg Lys Val Phe Cys Asp Leu Gln Ser Ser Gly
    290                 295                 300

ggc agg tgg acc ctc atc cag cgc cgt gag aat ggc acc gtg aat ttt      960
Gly Arg Trp Thr Leu Ile Gln Arg Arg Glu Asn Gly Thr Val Asn Phe
305                 310                 315                 320

cag cgg aac tgg aag gat tac aaa cag ggc ttc gga gac cca gct ggg     1008
Gln Arg Asn Trp Lys Asp Tyr Lys Gln Gly Phe Gly Asp Pro Ala Gly
                325                 330                 335

gag cac tgg ctg ggc aat gaa gtg gtg cac cag ctc acc aga agg gca     1056
Glu His Trp Leu Gly Asn Glu Val Val His Gln Leu Thr Arg Arg Ala
            340                 345                 350

gcc tac tct ctg cgt gtg gag ctg caa gac tgg gaa ggc cac gag gcc     1104
Ala Tyr Ser Leu Arg Val Glu Leu Gln Asp Trp Glu Gly His Glu Ala
        355                 360                 365

tat gcc cag tac gaa cat ttc cac ctg ggc agt gag aac cag cta tac     1152
Tyr Ala Gln Tyr Glu His Phe His Leu Gly Ser Glu Asn Gln Leu Tyr
    370                 375                 380

agg ctt tct gtg gtc ggg tac agc ggc tca gca ggg cgc cag agc agc     1200
Arg Leu Ser Val Val Gly Tyr Ser Gly Ser Ala Gly Arg Gln Ser Ser
385                 390                 395                 400

ctg gtc ctg cag aac acc agc ttt agc acc ctt gac tca gac aac gac     1248
Leu Val Leu Gln Asn Thr Ser Phe Ser Thr Leu Asp Ser Asp Asn Asp
                405                 410                 415

cac tgt ctc tgc aag tgt gcc caa gtg atg tct gga ggg tgg tgg ttt     1296
His Cys Leu Cys Lys Cys Ala Gln Val Met Ser Gly Gly Trp Trp Phe
            420                 425                 430

gac gcc tgt ggc ctg tca aac ctc aac ggc gtc tac tac cac gct ccc     1344
Asp Ala Cys Gly Leu Ser Asn Leu Asn Gly Val Tyr Tyr His Ala Pro
        435                 440                 445

gac aac aag tac aag atg gac ggc atc cgc tgg cac tac ttc aag ggc     1392
Asp Asn Lys Tyr Lys Met Asp Gly Ile Arg Trp His Tyr Phe Lys Gly
    450                 455                 460

ccc agc tac tca ctg cgt gcc tct cgc atg atg ata cgg cct ttg gac     1440
Pro Ser Tyr Ser Leu Arg Ala Ser Arg Met Met Ile Arg Pro Leu Asp
465                 470                 475                 480

atc taa                                                             1446
Ile
```

<210> SEQ ID NO 93
<211> LENGTH: 481
<212> TYPE: PRT
<213> ORGANISM: Homo sapiens

<400> SEQUENCE: 93

Gln Gln Thr Arg Gln Glu Ala Asp Arg Gly Cys Glu Thr Leu Val Val
1               5                   10                  15

Gln His Gly His Cys Ser Tyr Thr Phe Leu Leu Pro Lys Ser Glu Pro
            20                  25                  30

Cys Pro Pro Gly Pro Glu Val Ser Arg Asp Ser Asn Thr Leu Gln Arg
        35                  40                  45

Glu Ser Leu Ala Asn Pro Leu His Leu Gly Lys Leu Pro Thr Gln Gln
    50                  55                  60

Val Lys Gln Leu Glu Gln Ala Leu Gln Asn Asn Thr Gln Trp Leu Lys
65                  70                  75                  80

Lys Leu Glu Arg Ala Ile Lys Thr Ile Leu Arg Ser Lys Leu Glu Gln
                85                  90                  95

Val Gln Gln Gln Met Ala Gln Asn Gln Thr Ala Pro Met Leu Glu Leu
            100                 105                 110

Gly Thr Ser Leu Leu Asn Gln Thr Thr Ala Gln Ile Arg Lys Leu Thr
        115                 120                 125

Asp Met Glu Ala Gln Leu Leu Asn Gln Thr Ser Arg Met Asp Ala Gln
    130                 135                 140

Met Pro Glu Thr Phe Leu Ser Thr Asn Lys Leu Glu Asn Gln Leu Leu
145                 150                 155                 160

Leu Gln Arg Gln Lys Leu Gln Gln Leu Gln Gly Gln Asn Ser Ala Leu
                165                 170                 175

Glu Lys Arg Leu Gln Ala Leu Glu Thr Lys Gln Gln Glu Glu Leu Ala
            180                 185                 190

Ser Ile Leu Ser Lys Lys Ala Lys Leu Leu Asn Thr Leu Ser Arg Gln
        195                 200                 205

Ser Ala Ala Leu Thr Asn Ile Glu Arg Gly Leu Arg Gly Val Arg His
    210                 215                 220

Asn Ser Ser Leu Leu Gln Asp Gln Gln His Ser Leu Arg Gln Leu Leu
225                 230                 235                 240

Val Leu Leu Arg His Leu Val Gln Glu Arg Ala Asn Ala Ser Ala Pro
                245                 250                 255

Ala Phe Ile Met Ala Gly Glu Gln Val Phe Gln Asp Cys Ala Glu Ile
            260                 265                 270

Gln Arg Ser Gly Ala Ser Ala Ser Gly Val Tyr Thr Ile Gln Val Ser
        275                 280                 285

Asn Ala Thr Lys Pro Arg Lys Val Phe Cys Asp Leu Gln Ser Ser Gly
    290                 295                 300

Gly Arg Trp Thr Leu Ile Gln Arg Arg Glu Asn Gly Thr Val Asn Phe
305                 310                 315                 320

Gln Arg Asn Trp Lys Asp Tyr Lys Gln Gly Phe Gly Asp Pro Ala Gly
                325                 330                 335

Glu His Trp Leu Gly Asn Glu Val Val His Gln Leu Thr Arg Arg Ala
            340                 345                 350

Ala Tyr Ser Leu Arg Val Glu Leu Gln Asp Trp Glu Gly His Glu Ala
        355                 360                 365

Tyr Ala Gln Tyr Glu His Phe His Leu Gly Ser Glu Asn Gln Leu Tyr
    370                 375                 380

Arg Leu Ser Val Val Gly Tyr Ser Gly Ser Ala Gly Arg Gln Ser Ser
385                 390                 395                 400

Leu Val Leu Gln Asn Thr Ser Phe Ser Thr Leu Asp Ser Asp Asn Asp

```
                405                 410                 415

His Cys Leu Cys Lys Cys Ala Gln Val Met Ser Gly Gly Trp Trp Phe
            420                 425                 430

Asp Ala Cys Gly Leu Ser Asn Leu Asn Gly Val Tyr Tyr His Ala Pro
        435                 440                 445

Asp Asn Lys Tyr Lys Met Asp Gly Ile Arg Trp His Tyr Phe Lys Gly
    450                 455                 460

Pro Ser Tyr Ser Leu Arg Ala Ser Arg Met Met Ile Arg Pro Leu Asp
465                 470                 475                 480

Ile


<210> SEQ ID NO 94
<211> LENGTH: 3061
<212> TYPE: DNA
<213> ORGANISM: Homo sapiens
<220> FEATURE:
<221> NAME/KEY: 3'UTR
<222> LOCATION: (1)..(3061)

<400> SEQUENCE: 94

cgagcagctg tgccagaggc tggaccacac aggagaagct cggacttggc actcctggac     60

aacctggacc cagatgcaag acactgtgcc accgccttcc ctgacaccct gggcttcctg    120

agccagccct ccttgaccca gaagtccaga agggtcatct gcccccccaac tcccctccgt    180

ctgtgacatg gagggtgttc ggggcccatc cctctgatgt agtcctcgcc cctcttctct    240

ccctccccct tcaggggctc cctgcctgag ggtcacagta ccttgaatgg gctgagaaca    300

gaccaaactt gattcccatg accaatggtg gggttgcagg caggtgggaa tgtatttgca    360

catcggaagc tgcccagatg gcccaggttc tctcccttgg attggcaaga aggccatctc    420

ccattctaag ctcctgttcc aagattttct agtcttgaga tgtccttgaa ctttcttttc    480

aagtctgaag gggctgcatc cacccccttag tgggtgggtt aatcattatt tccccttcac    540

acttcaccac ttctaggttc taatgaccct agatctcagg gtctttagac ttcaccactt    600

ctaggcttta ccacttcacc acttctaggc tccaatgttt ggagctcagg gtctttagga    660

gacccaaaag gacatgctcc ttcacctcca gcatgtccta gaggatgtgt cacagggaat    720

aactatggct tgtctctaaa agtacctatg agcaatgaga aaaggaaaca gcaggttaag    780

tcaaagtgaa caggcactct tcactgcagg actgatcaga gcctttaata tggccaagtg    840

ccttgtgact acccatgaag gggctagagt gggcagcttt ctccaaattt acttatttga    900

aaatgggctc ggtttgtccc agagcatctc acaggactgt agatgctctt ggacaaagct    960

agtgctcccc tggcataagg aggagcccta cgaccccatc cccaccccag ctatactcac   1020

ccttttttggc tacaagggcc acagtgacag cctcaaacaa cctctaaaaa caactggaaa   1080

taacctttca gttaaaacag ataccatccc tgaagaaggg tctagaacta ggtccctgtc   1140

tgtgttatag gctcatgtcc tccaaggctc cttcaagtcc caggaagctg atctctacct   1200

gggtggcttc ccttaggact ccctgtaacc tcaactcccc caggctcaat tacagggact   1260

gttaggcagg acatctgtct ccaagtccag atcctctctg cctccaagcc ctaaccccta   1320

gcctccctcc cttccccatc cagcagtgat gctgcctctg tggtggtagg tggggagctg   1380

caggggagga gataaggcct ctgcctgagt ttgggagacc agggccctca tagcttcttt   1440

cagaggatgg agtcagaaag gatccacagc tactctgtca cctgccccca tcactgtgtc   1500

atgctgtctg ccctgttgtc atcagccaac acccaggcat agccaggagc ccacctgccc   1560
```

```
taccgccagg atacacctct gtcctcagaa ggttttctcc tggatgagac tgagccaatg   1620
ggaatgggac cccttcatcc ccctggctcg ccccagccct gagtcccact ctcagccgat   1680
ccctgagtaa acccagcaca gactgacttt gatctcattc ctgggaatta gcactcttcc   1740
ccttcaagac tcaaaggaca tggttgctaa tggtggcatt tcaggcatga tgggaaatct   1800
ttaggggcag attgctgccc agagagctca aatcgcctta agcagcattt gcccagcaga   1860
cctttattta gcctctactg tgtgcagtgt ggtgtggtgg gcagggcttt ggagtcggac   1920
aaacctgctc cagctctgac actttggtcc agtggctcag cctctcaagg caccagttat   1980
cttcacatca tcaaagcctc agttttccca tctgtaaaat ggagatgata atattccttc   2040
ctggctgggc tatggcaagg aggaaatgag accatgtatg tcatcttctt aatagagcct   2100
ggcatgaagc aggtgcctaa taaatgtttg tcctcaaaga ggagaatggg gtgaggaagg   2160
cattccccag cacatgccgc cccttctcct gcactcaggt gaggaaaagg cattttattt   2220
ttgtatccac atcatttatt tttctattgt agtttctagg ctgactgcaa gctagagagg   2280
agacagggca aagctgtgag gcccagggac agaactcctc tgggtgggtt gaaggcccaa   2340
gtccctctct actcccattt tataaggggg caggaagctg atttgagtta tcctcagaca   2400
cctgttcttt atgtaatttt attttatttt tttgagacag agtctcactc tgtcacccag   2460
gctggagtgc agtggcatga tctcagatca ctgcaatctc tgcctcctgg ttcaagtgat   2520
tctcctacct cagcctcctg agtaatggga ttacagacgc ctaccaccac gcccggaaaa   2580
cttttgtatt tttagtagaa acgggttttc accatgttgg ccaggctggt ctcaaactcc   2640
tggcctcatg tgatccacct gcctcagcct cccaaagtgc tgggattaca ggcatgagcc   2700
accataccca gcctcagaca cctgttctta aatattcatc cttctttctt accttccttc   2760
ctcttccatg ccaggactca ggtataaggg atagaaattc tagccctaag gaataaattg   2820
actcacataa ctggaaagtc taagggtaaa ggcaagtgag gttagatcca gaggctcaaa   2880
tgatgtcagc tccacctctc agcccctcca tctgccccgt tgacttcatt ctcagccagg   2940
atctttcctc acaagaaggc tctggcagcc ccaggctcat gtcctcccag ctcagcatcc   3000
ctgacccggg gagctccctc gtctccatga ttccagtaaa ggaatgattt tctgcagcca   3060
g                                                                   3061
```

<210> SEQ ID NO 95
<211> LENGTH: 867
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(867)

<400> SEQUENCE: 95

```
ggg atc tta gac cta gcc cca cag atg ctt cga gaa ctc cag gag act       48
Gly Ile Leu Asp Leu Ala Pro Gln Met Leu Arg Glu Leu Gln Glu Thr
1               5                   10                  15

aat gcg gcg ctg caa gac gtg aga gag ctc ttg cga cag cag gtc aag       96
Asn Ala Ala Leu Gln Asp Val Arg Glu Leu Leu Arg Gln Gln Val Lys
            20                  25                  30

gag atc acc ttc ctg aag aat acg gtg atg gaa tgt gac gct tgc gga      144
Glu Ile Thr Phe Leu Lys Asn Thr Val Met Glu Cys Asp Ala Cys Gly
        35                  40                  45

ggc tcc ctt gtc aat ctt tgc act aaa gaa ggt gtt tta cta aag gga      192
Gly Ser Leu Val Asn Leu Cys Thr Lys Glu Gly Val Leu Leu Lys Gly
```

```
    50                  55                  60

gga aaa aga gag gaa gag aaa cca ttt aga gac tgt gca gat gta tat      240
Gly Lys Arg Glu Glu Glu Lys Pro Phe Arg Asp Cys Ala Asp Val Tyr
65                  70                  75                  80

caa gct ggt ttt aat aaa agt gga atc tac act att tat att aat aat      288
Gln Ala Gly Phe Asn Lys Ser Gly Ile Tyr Thr Ile Tyr Ile Asn Asn
                85                  90                  95

atg cca gaa ccc aaa aag gtg ttt tgc aat atg gat gtc aat ggg gga      336
Met Pro Glu Pro Lys Lys Val Phe Cys Asn Met Asp Val Asn Gly Gly
            100                 105                 110

ggt tgg act gta ata caa cat cgt gaa gat gga agt cta gat ttc caa      384
Gly Trp Thr Val Ile Gln His Arg Glu Asp Gly Ser Leu Asp Phe Gln
        115                 120                 125

aga ggc tgg aag gaa tat aaa atg ggt ttt gga aat ccc tcc ggt gaa      432
Arg Gly Trp Lys Glu Tyr Lys Met Gly Phe Gly Asn Pro Ser Gly Glu
    130                 135                 140

tat tgg ctg ggg aat gag ttt att ttt gcc att acc agt cag agg cag      480
Tyr Trp Leu Gly Asn Glu Phe Ile Phe Ala Ile Thr Ser Gln Arg Gln
145                 150                 155                 160

tac atg cta aga att gag tta atg gac tgg gaa ggg aac cga gcc tat      528
Tyr Met Leu Arg Ile Glu Leu Met Asp Trp Glu Gly Asn Arg Ala Tyr
                165                 170                 175

tca cag tat gac aga ttc cac ata gga aat gaa aag caa aac tat agg      576
Ser Gln Tyr Asp Arg Phe His Ile Gly Asn Glu Lys Gln Asn Tyr Arg
            180                 185                 190

ttg tat tta aaa ggt cac act ggg aca gca gga aaa cag agc agc ctg      624
Leu Tyr Leu Lys Gly His Thr Gly Thr Ala Gly Lys Gln Ser Ser Leu
        195                 200                 205

atc tta cac ggt gct gat ttc agc act aaa gat gct gat aat gac aac      672
Ile Leu His Gly Ala Asp Phe Ser Thr Lys Asp Ala Asp Asn Asp Asn
    210                 215                 220

tgt atg tgc aaa tgt gcc ctc atg tta aca gga gga tgg tgg ttt gat      720
Cys Met Cys Lys Cys Ala Leu Met Leu Thr Gly Gly Trp Trp Phe Asp
225                 230                 235                 240

gct tgt ggc ccc tcc aat cta aat gga atg ttc tat act gcg gga caa      768
Ala Cys Gly Pro Ser Asn Leu Asn Gly Met Phe Tyr Thr Ala Gly Gln
                245                 250                 255

aac cat gga aaa ctg aat ggg ata aag tgg cac tac ttc aaa ggg ccc      816
Asn His Gly Lys Leu Asn Gly Ile Lys Trp His Tyr Phe Lys Gly Pro
            260                 265                 270

agt tac tcc tta cgt tcc aca act atg atg att cga cct tta gat ttt      864
Ser Tyr Ser Leu Arg Ser Thr Thr Met Met Ile Arg Pro Leu Asp Phe
        275                 280                 285

tga                                                                  867


<210> SEQ ID NO 96
<211> LENGTH: 288
<212> TYPE: PRT
<213> ORGANISM: Artificial Sequence
<220> FEATURE:
<223> OTHER INFORMATION: Synthetic Construct

<400> SEQUENCE: 96

Gly Ile Leu Asp Leu Ala Pro Gln Met Leu Arg Glu Leu Gln Glu Thr
1               5                   10                  15

Asn Ala Ala Leu Gln Asp Val Arg Glu Leu Leu Arg Gln Gln Val Lys
            20                  25                  30

Glu Ile Thr Phe Leu Lys Asn Thr Val Met Glu Cys Asp Ala Cys Gly
        35                  40                  45
```

```
Gly Ser Leu Val Asn Leu Cys Thr Lys Glu Gly Val Leu Leu Lys Gly
    50                  55                  60

Gly Lys Arg Glu Glu Glu Lys Pro Phe Arg Asp Cys Ala Asp Val Tyr
65                  70                  75                  80

Gln Ala Gly Phe Asn Lys Ser Gly Ile Tyr Thr Ile Tyr Ile Asn Asn
                85                  90                  95

Met Pro Glu Pro Lys Lys Val Phe Cys Asn Met Asp Val Asn Gly Gly
            100                 105                 110

Gly Trp Thr Val Ile Gln His Arg Glu Asp Gly Ser Leu Asp Phe Gln
        115                 120                 125

Arg Gly Trp Lys Glu Tyr Lys Met Gly Phe Gly Asn Pro Ser Gly Glu
    130                 135                 140

Tyr Trp Leu Gly Asn Glu Phe Ile Phe Ala Ile Thr Ser Gln Arg Gln
145                 150                 155                 160

Tyr Met Leu Arg Ile Glu Leu Met Asp Trp Glu Gly Asn Arg Ala Tyr
                165                 170                 175

Ser Gln Tyr Asp Arg Phe His Ile Gly Asn Glu Lys Gln Asn Tyr Arg
            180                 185                 190

Leu Tyr Leu Lys Gly His Thr Gly Thr Ala Gly Lys Gln Ser Ser Leu
        195                 200                 205

Ile Leu His Gly Ala Asp Phe Ser Thr Lys Asp Ala Asp Asn Asp Asn
    210                 215                 220

Cys Met Cys Lys Cys Ala Leu Met Leu Thr Gly Gly Trp Trp Phe Asp
225                 230                 235                 240

Ala Cys Gly Pro Ser Asn Leu Asn Gly Met Phe Tyr Thr Ala Gly Gln
                245                 250                 255

Asn His Gly Lys Leu Asn Gly Ile Lys Trp His Tyr Phe Lys Gly Pro
            260                 265                 270

Ser Tyr Ser Leu Arg Ser Thr Thr Met Met Ile Arg Pro Leu Asp Phe
        275                 280                 285


<210> SEQ ID NO 97
<211> LENGTH: 867
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(867)

<400> SEQUENCE: 97

ggg atc tta gac ttg ggc ccg cag atg ctt cgg gaa ctg cag gaa acc       48
Gly Ile Leu Asp Leu Gly Pro Gln Met Leu Arg Glu Leu Gln Glu Thr
1               5                   10                  15

aac gcg gcg ctg cag gac gtg cgg gag ctg ctg cgg cag cag gtc agg       96
Asn Ala Ala Leu Gln Asp Val Arg Glu Leu Leu Arg Gln Gln Val Arg
            20                  25                  30

gag atc acg ttc ctg aaa aac acg gtg atg gag tgt gac gcg tgc gga      144
Glu Ile Thr Phe Leu Lys Asn Thr Val Met Glu Cys Asp Ala Cys Gly
        35                  40                  45

ggc tcc ctt gtc aat ctt tgc act aaa gaa ggt gtt tta cta aag gga      192
Gly Ser Leu Val Asn Leu Cys Thr Lys Glu Gly Val Leu Leu Lys Gly
    50                  55                  60

gga aaa aga gag gaa gag aaa cca ttt aga gac tgt gca gat gta tat      240
Gly Lys Arg Glu Glu Glu Lys Pro Phe Arg Asp Cys Ala Asp Val Tyr
65                  70                  75                  80

caa gct ggt ttt aat aaa agt gga atc tac act att tat att aat aat      288
```

```
Gln Ala Gly Phe Asn Lys Ser Gly Ile Tyr Thr Ile Tyr Ile Asn Asn
                85                  90                  95

atg cca gaa ccc aaa aag gtg ttt tgc aat atg gat gtc aat ggg gga      336
Met Pro Glu Pro Lys Lys Val Phe Cys Asn Met Asp Val Asn Gly Gly
            100                 105                 110

ggt tgg act gta ata caa cat cgt gaa gat gga agt cta gat ttc caa      384
Gly Trp Thr Val Ile Gln His Arg Glu Asp Gly Ser Leu Asp Phe Gln
        115                 120                 125

aga ggc tgg aag gaa tat aaa atg ggt ttt gga aat ccc tcc ggt gaa      432
Arg Gly Trp Lys Glu Tyr Lys Met Gly Phe Gly Asn Pro Ser Gly Glu
    130                 135                 140

tat tgg ctg ggg aat gag ttt att ttt gcc att acc agt cag agg cag      480
Tyr Trp Leu Gly Asn Glu Phe Ile Phe Ala Ile Thr Ser Gln Arg Gln
145                 150                 155                 160

tac atg cta aga att gag tta atg gac tgg gaa ggg aac cga gcc tat      528
Tyr Met Leu Arg Ile Glu Leu Met Asp Trp Glu Gly Asn Arg Ala Tyr
                165                 170                 175

tca cag tat gac aga ttc cac ata gga aat gaa aag caa aac tat agg      576
Ser Gln Tyr Asp Arg Phe His Ile Gly Asn Glu Lys Gln Asn Tyr Arg
            180                 185                 190

ttg tat tta aaa ggt cac act ggg aca gca gga aaa cag agc agc ctg      624
Leu Tyr Leu Lys Gly His Thr Gly Thr Ala Gly Lys Gln Ser Ser Leu
        195                 200                 205

atc tta cac ggt gct gat ttc agc act aaa gat gct gat aat gac aac      672
Ile Leu His Gly Ala Asp Phe Ser Thr Lys Asp Ala Asp Asn Asp Asn
    210                 215                 220

tgt atg tgc aaa tgt gcc ctc atg tta aca gga gga tgg tgg ttt gat      720
Cys Met Cys Lys Cys Ala Leu Met Leu Thr Gly Gly Trp Trp Phe Asp
225                 230                 235                 240

gct tgt ggc ccc tcc aat cta aat gga atg ttc tat act gcg gga caa      768
Ala Cys Gly Pro Ser Asn Leu Asn Gly Met Phe Tyr Thr Ala Gly Gln
                245                 250                 255

aac cat gga aaa ctg aat ggg ata aag tgg cac tac ttc aaa ggg ccc      816
Asn His Gly Lys Leu Asn Gly Ile Lys Trp His Tyr Phe Lys Gly Pro
            260                 265                 270

agt tac tcc tta cgt tcc aca act atg atg att cga cct tta gat ttt      864
Ser Tyr Ser Leu Arg Ser Thr Thr Met Met Ile Arg Pro Leu Asp Phe
        275                 280                 285

tga                                                                  867


<210> SEQ ID NO 98
<211> LENGTH: 288
<212> TYPE: PRT
<213> ORGANISM: Artificial Sequence
<220> FEATURE:
<223> OTHER INFORMATION: Synthetic Construct

<400> SEQUENCE: 98

Gly Ile Leu Asp Leu Gly Pro Gln Met Leu Arg Glu Leu Gln Glu Thr
1               5                   10                  15

Asn Ala Ala Leu Gln Asp Val Arg Glu Leu Leu Arg Gln Gln Val Arg
            20                  25                  30

Glu Ile Thr Phe Leu Lys Asn Thr Val Met Glu Cys Asp Ala Cys Gly
        35                  40                  45

Gly Ser Leu Val Asn Leu Cys Thr Lys Glu Gly Val Leu Leu Lys Gly
    50                  55                  60

Gly Lys Arg Glu Glu Glu Lys Pro Phe Arg Asp Cys Ala Asp Val Tyr
65                  70                  75                  80

Gln Ala Gly Phe Asn Lys Ser Gly Ile Tyr Thr Ile Tyr Ile Asn Asn
```

```
                85                  90                  95

Met Pro Glu Pro Lys Lys Val Phe Cys Asn Met Asp Val Asn Gly Gly
            100                 105                 110

Gly Trp Thr Val Ile Gln His Arg Glu Asp Gly Ser Leu Asp Phe Gln
        115                 120                 125

Arg Gly Trp Lys Glu Tyr Lys Met Gly Phe Gly Asn Pro Ser Gly Glu
    130                 135                 140

Tyr Trp Leu Gly Asn Glu Phe Ile Phe Ala Ile Thr Ser Gln Arg Gln
145                 150                 155                 160

Tyr Met Leu Arg Ile Glu Leu Met Asp Trp Glu Gly Asn Arg Ala Tyr
                165                 170                 175

Ser Gln Tyr Asp Arg Phe His Ile Gly Asn Glu Lys Gln Asn Tyr Arg
            180                 185                 190

Leu Tyr Leu Lys Gly His Thr Gly Thr Ala Gly Lys Gln Ser Ser Leu
        195                 200                 205

Ile Leu His Gly Ala Asp Phe Ser Thr Lys Asp Ala Asp Asn Asp Asn
    210                 215                 220

Cys Met Cys Lys Cys Ala Leu Met Leu Thr Gly Gly Trp Trp Phe Asp
225                 230                 235                 240

Ala Cys Gly Pro Ser Asn Leu Asn Gly Met Phe Tyr Thr Ala Gly Gln
                245                 250                 255

Asn His Gly Lys Leu Asn Gly Ile Lys Trp His Tyr Phe Lys Gly Pro
            260                 265                 270

Ser Tyr Ser Leu Arg Ser Thr Thr Met Met Ile Arg Pro Leu Asp Phe
        275                 280                 285


<210> SEQ ID NO 99
<211> LENGTH: 861
<212> TYPE: DNA
<213> ORGANISM: Artificial Sequence
<220> FEATURE:
<223> OTHER INFORMATION: Synthetic

<400> SEQUENCE: 99

gggatcttag aggaagaccc ggccgcctgc gagtccctgg tgaaattcca agccaaagtg     60

gaggggctgc tgcaggccct gaccaggaaa ctggaagctg tgagtaagcg gctggccatc    120

ctggagaaca cagttgtcgg atcccttgtc aatcttgcca ctaaagaagg tgttttacta    180

aagggaggaa aaagagagga agagaaacca tttagagact gtgcagatgt atatcaagct    240

ggttttaata aaagtggaat ctacactatt tatattaata atatgccaga acccaaaaag    300

gtgttttgca atatggatgt caatgggggga ggttggactg taatacaaca tcgtgaagat    360

ggaagtctag atttccaaag aggctggaag gaatataaaa tgggttttgg aaatccctcc    420

ggtgaatatt ggctggggaa tgagtttatt tttgccatta ccagtcagag gcagtacatg    480

ctaagaattg agttaatgga ctgggaaggg aaccgagcct attcacagta tgacagattc    540

cacataggaa atgaaaagca aaactatagg ttgtatttaa aaggtcacac tgggacagca    600

ggaaaacaga gcagcctgat cttacacggt gctgatttca gcactaaaga tgctgataat    660

gacaactgta tgtgcaaatg tgccctcatg ttaacaggag gatggtggtt tgatgcttgt    720

ggcccctcca atctaaatgg aatgttctat actgcgggac aaaaccatgg aaaactgaat    780

gggataaagt ggcactactt caaagggccc agttactcct tacgttccac aactatgatg    840

attcgacctt tagatttttg a                                               861
```

<210> SEQ ID NO 100
<211> LENGTH: 870
<212> TYPE: DNA
<213> ORGANISM: Artificial Sequence
<220> FEATURE:
<223> OTHER INFORMATION: Synthetic

<400> SEQUENCE: 100

```
gggatcttag acctagcccc acagatgctt cgagaactcc aggagactaa tgcggcgctg      60

caagacgtga gagagctctt gcgacagcag gtcaaggaga tcaccttcct gaagaatacg     120

gtgatggaat gtgacgcttg cggaggctcc ttactgacta tgatgtccac atcaaactca     180

gctaaggacc ccactgttgc taaagaagaa caaatcagct tcagagactg tgctgaagta     240

ttcaaatcag gacacaccac gaatggcatc tacacgttaa cattccctaa ttctacagaa     300

gagatcaagg cctactgtga catggaagct ggaggaggcg ggtggacaat tattcagcga     360

cgtgaggatg gcagcgttga ttttcagagg acttggaaag aatataaagt gggatttggt     420

aacccttcag gagaatattg gctgggaaat gagtttgttt cgcaactgac taatcagcaa     480

cgctatgtgc ttaaaataca ccttaaagac tgggaaggga atgaggctta ctcattgtat     540

gaacatttct atctctcaag tgaagaactc aattatagga ttcaccttaa aggacttaca     600

gggacagccg gcaaaataag cagcatcagc caaccaggaa atgattttag cacaaaggat     660

ggagacaacg acaaatgtat ttgcaaatgt tcacaaatgc taacaggagg ctggtggttt     720

gatgcatgtg gtccttccaa cttgaacgga atgtactatc cacagaggca gaacacaaat     780

aagttcaacg gcattaaatg gtactactgg aaaggctcag gctattcgct caaggccaca     840

accatgatga tccgaccagc agatttctaa                                      870
```

<210> SEQ ID NO 101
<211> LENGTH: 3375
<212> TYPE: DNA
<213> ORGANISM: Homo sapiens
<220> FEATURE:
<221> NAME/KEY: CDS
<222> LOCATION: (1)..(3375)

<400> SEQUENCE: 101

```
atg gac tct tta gcc agc tta gtt ctc tgt gga gtc agc ttg ctc ctt       48
Met Asp Ser Leu Ala Ser Leu Val Leu Cys Gly Val Ser Leu Leu Leu
1               5                   10                  15

tct gga act gtg gaa ggt gcc atg gac ttg atc ttg atc aat tcc cta       96
Ser Gly Thr Val Glu Gly Ala Met Asp Leu Ile Leu Ile Asn Ser Leu
            20                  25                  30

cct ctt gta tct gat gct gaa aca tct ctc acc tgc att gcc tct ggg      144
Pro Leu Val Ser Asp Ala Glu Thr Ser Leu Thr Cys Ile Ala Ser Gly
        35                  40                  45

tgg cgc ccc cat gag ccc atc acc ata gga agg gac ttt gaa gcc tta      192
Trp Arg Pro His Glu Pro Ile Thr Ile Gly Arg Asp Phe Glu Ala Leu
    50                  55                  60

atg aac cag cac cag gat ccg ctg gaa gtt act caa gat gtg acc aga      240
Met Asn Gln His Gln Asp Pro Leu Glu Val Thr Gln Asp Val Thr Arg
65                  70                  75                  80

gaa tgg gct aaa aaa gtt gtt tgg aag aga gaa aag gct agt aag atc      288
Glu Trp Ala Lys Lys Val Val Trp Lys Arg Glu Lys Ala Ser Lys Ile
                85                  90                  95

aat ggt gct tat ttc tgt gaa ggg cga gtt cga gga gag gca atc agg      336
Asn Gly Ala Tyr Phe Cys Glu Gly Arg Val Arg Gly Glu Ala Ile Arg
            100                 105                 110

ata cga acc atg aag atg cgt caa caa gct tcc ttc cta cca gct act      384
```

```
Ile Arg Thr Met Lys Met Arg Gln Gln Ala Ser Phe Leu Pro Ala Thr
        115                 120                 125

tta act atg act gtg gac aag gga gat aac gtg aac ata tct ttc aaa      432
Leu Thr Met Thr Val Asp Lys Gly Asp Asn Val Asn Ile Ser Phe Lys
    130                 135                 140

aag gta ttg att aaa gaa gaa gat gca gtg att tac aaa aat ggt tcc      480
Lys Val Leu Ile Lys Glu Glu Asp Ala Val Ile Tyr Lys Asn Gly Ser
145                 150                 155                 160

ttc atc cat tca gtg ccc cgg cat gaa gta cct gat att cta gaa gta      528
Phe Ile His Ser Val Pro Arg His Glu Val Pro Asp Ile Leu Glu Val
                165                 170                 175

cac ctg cct cat gct cag ccc cag gat gct gga gtg tac tcg gcc agg      576
His Leu Pro His Ala Gln Pro Gln Asp Ala Gly Val Tyr Ser Ala Arg
            180                 185                 190

tat ata gga gga aac ctc ttc acc tcg gcc ttc acc agg ctg ata gtc      624
Tyr Ile Gly Gly Asn Leu Phe Thr Ser Ala Phe Thr Arg Leu Ile Val
        195                 200                 205

cgg aga tgt gaa gcc cag aag tgg gga cct gaa tgc aac cat ctc tgt      672
Arg Arg Cys Glu Ala Gln Lys Trp Gly Pro Glu Cys Asn His Leu Cys
    210                 215                 220

act gct tgt atg aac aat ggt gtc tgc cat gaa gat act gga gaa tgc      720
Thr Ala Cys Met Asn Asn Gly Val Cys His Glu Asp Thr Gly Glu Cys
225                 230                 235                 240

att tgc cct cct ggg ttt atg gga agg acg tgt gag aag gct tgt gaa      768
Ile Cys Pro Pro Gly Phe Met Gly Arg Thr Cys Glu Lys Ala Cys Glu
                245                 250                 255

ctg cac acg ttt ggc aga act tgt aaa gaa agg tgc agt gga caa gag      816
Leu His Thr Phe Gly Arg Thr Cys Lys Glu Arg Cys Ser Gly Gln Glu
            260                 265                 270

gga tgc aag tct tat gtg ttc tgt ctc cct gac ccc tat ggg tgt tcc      864
Gly Cys Lys Ser Tyr Val Phe Cys Leu Pro Asp Pro Tyr Gly Cys Ser
        275                 280                 285

tgt gcc aca ggc tgg aag ggt ctg cag tgc aat gaa gca tgc cac cct      912
Cys Ala Thr Gly Trp Lys Gly Leu Gln Cys Asn Glu Ala Cys His Pro
    290                 295                 300

ggt ttt tac ggg cca gat tgt aag ctt agg tgc agc tgc aac aat ggg      960
Gly Phe Tyr Gly Pro Asp Cys Lys Leu Arg Cys Ser Cys Asn Asn Gly
305                 310                 315                 320

gag atg tgt gat cgc ttc caa gga tgt ctc tgc tct cca gga tgg cag     1008
Glu Met Cys Asp Arg Phe Gln Gly Cys Leu Cys Ser Pro Gly Trp Gln
                325                 330                 335

ggg ctc cag tgt gag aga gaa ggc ata ccg agg atg acc cca aag ata     1056
Gly Leu Gln Cys Glu Arg Glu Gly Ile Pro Arg Met Thr Pro Lys Ile
            340                 345                 350

gtg gat ttg cca gat cat ata gaa gta aac agt ggt aaa ttt aat ccc     1104
Val Asp Leu Pro Asp His Ile Glu Val Asn Ser Gly Lys Phe Asn Pro
        355                 360                 365

att tgc aaa gct tct ggc tgg ccg cta cct act aat gaa gaa atg acc     1152
Ile Cys Lys Ala Ser Gly Trp Pro Leu Pro Thr Asn Glu Glu Met Thr
    370                 375                 380

ctg gtg aag ccg gat ggg aca gtg ctc cat cca aaa gac ttt aac cat     1200
Leu Val Lys Pro Asp Gly Thr Val Leu His Pro Lys Asp Phe Asn His
385                 390                 395                 400

acg gat cat ttc tca gta gcc ata ttc acc atc cac cgg atc ctc ccc     1248
Thr Asp His Phe Ser Val Ala Ile Phe Thr Ile His Arg Ile Leu Pro
                405                 410                 415

cct gac tca gga gtt tgg gtc tgc agt gtg aac aca gtg gct ggg atg     1296
Pro Asp Ser Gly Val Trp Val Cys Ser Val Asn Thr Val Ala Gly Met
            420                 425                 430
```

```
gtg gaa aag ccc ttc aac att tct gtt aaa gtt ctt cca aag ccc ctg     1344
Val Glu Lys Pro Phe Asn Ile Ser Val Lys Val Leu Pro Lys Pro Leu
        435                 440                 445

aat gcc cca aac gtg att gac act gga cat aac ttt gct gtc atc aac     1392
Asn Ala Pro Asn Val Ile Asp Thr Gly His Asn Phe Ala Val Ile Asn
    450                 455                 460

atc agc tct gag cct tac ttt ggg gat gga cca atc aaa tcc aag aag     1440
Ile Ser Ser Glu Pro Tyr Phe Gly Asp Gly Pro Ile Lys Ser Lys Lys
465                 470                 475                 480

ctt cta tac aaa ccc gtt aat cac tat gag gct tgg caa cat att caa     1488
Leu Leu Tyr Lys Pro Val Asn His Tyr Glu Ala Trp Gln His Ile Gln
                485                 490                 495

gtg aca aat gag att gtt aca ctc aac tat ttg gaa cct cgg aca gaa     1536
Val Thr Asn Glu Ile Val Thr Leu Asn Tyr Leu Glu Pro Arg Thr Glu
            500                 505                 510

tat gaa ctc tgt gtg caa ctg gtc cgt cgt gga gag ggt ggg gaa ggg     1584
Tyr Glu Leu Cys Val Gln Leu Val Arg Arg Gly Glu Gly Gly Glu Gly
        515                 520                 525

cat cct gga cct gtg aga cgc ttc aca aca gct tct atc gga ctc cct     1632
His Pro Gly Pro Val Arg Arg Phe Thr Thr Ala Ser Ile Gly Leu Pro
    530                 535                 540

cct cca aga ggt cta aat ctc ctg cct aaa agt cag acc act cta aat     1680
Pro Pro Arg Gly Leu Asn Leu Leu Pro Lys Ser Gln Thr Thr Leu Asn
545                 550                 555                 560

ttg acc tgg caa cca ata ttt cca agc tcg gaa gat gac ttt tat gtt     1728
Leu Thr Trp Gln Pro Ile Phe Pro Ser Ser Glu Asp Asp Phe Tyr Val
                565                 570                 575

gaa gtg gag aga agg tct gtg caa aaa agt gat cag cag aat att aaa     1776
Glu Val Glu Arg Arg Ser Val Gln Lys Ser Asp Gln Gln Asn Ile Lys
            580                 585                 590

gtt cca ggc aac ttg act tcg gtg cta ctt aac aac tta cat ccc agg     1824
Val Pro Gly Asn Leu Thr Ser Val Leu Leu Asn Asn Leu His Pro Arg
        595                 600                 605

gag cag tac gtg gtc cga gct aga gtc aac acc aag gcc cag ggg gaa     1872
Glu Gln Tyr Val Val Arg Ala Arg Val Asn Thr Lys Ala Gln Gly Glu
    610                 615                 620

tgg agt gaa gat ctc act gct tgg acc ctt agt gac att ctt cct cct     1920
Trp Ser Glu Asp Leu Thr Ala Trp Thr Leu Ser Asp Ile Leu Pro Pro
625                 630                 635                 640

caa cca gaa aac atc aag att tcc aac att aca cac tcc tca gct gtg     1968
Gln Pro Glu Asn Ile Lys Ile Ser Asn Ile Thr His Ser Ser Ala Val
                645                 650                 655

att tct tgg aca ata ttg gat ggc tat tct att tct tct att act atc     2016
Ile Ser Trp Thr Ile Leu Asp Gly Tyr Ser Ile Ser Ser Ile Thr Ile
            660                 665                 670

cgt tac aag gtt caa ggc aag aat gaa gac cag cac gtt gat gtg aag     2064
Arg Tyr Lys Val Gln Gly Lys Asn Glu Asp Gln His Val Asp Val Lys
        675                 680                 685

ata aag aat gcc acc atc act cag tat cag ctc aag ggc cta gag cct     2112
Ile Lys Asn Ala Thr Ile Thr Gln Tyr Gln Leu Lys Gly Leu Glu Pro
    690                 695                 700

gaa aca gca tac cag gtg gac att ttt gca gag aac aac ata ggg tca     2160
Glu Thr Ala Tyr Gln Val Asp Ile Phe Ala Glu Asn Asn Ile Gly Ser
705                 710                 715                 720

agc aac cca gcc ttt tct cat gaa ctg gtg acc ctc cca gaa tct caa     2208
Ser Asn Pro Ala Phe Ser His Glu Leu Val Thr Leu Pro Glu Ser Gln
                725                 730                 735

gca cca gcg gac ctc gga ggg ggg aag atg ctg ctt ata gcc atc ctt     2256
Ala Pro Ala Asp Leu Gly Gly Gly Lys Met Leu Leu Ile Ala Ile Leu
            740                 745                 750
```

-continued

```
ggc tct gct gga atg acc tgc ctg act gtg ctg ttg gcc ttt ctg atc     2304
Gly Ser Ala Gly Met Thr Cys Leu Thr Val Leu Leu Ala Phe Leu Ile
        755                 760                 765

ata ttg caa ttg aag agg gca aat gtg caa agg aga atg gcc caa gcc     2352
Ile Leu Gln Leu Lys Arg Ala Asn Val Gln Arg Arg Met Ala Gln Ala
    770                 775                 780

ttc caa aac gtg agg gaa gaa cca gct gtg cag ttc aac tca ggg act     2400
Phe Gln Asn Val Arg Glu Glu Pro Ala Val Gln Phe Asn Ser Gly Thr
785                 790                 795                 800

ctg gcc cta aac agg aag gtc aaa aac aac cca gat cct aca att tat     2448
Leu Ala Leu Asn Arg Lys Val Lys Asn Asn Pro Asp Pro Thr Ile Tyr
                805                 810                 815

cca gtg ctt gac tgg aat gac atc aaa ttt caa gat gtg att ggg gag     2496
Pro Val Leu Asp Trp Asn Asp Ile Lys Phe Gln Asp Val Ile Gly Glu
            820                 825                 830

ggc aat ttt ggc caa gtt ctt aag gcg cgc atc aag aag gat ggg tta     2544
Gly Asn Phe Gly Gln Val Leu Lys Ala Arg Ile Lys Lys Asp Gly Leu
        835                 840                 845

cgg atg gat gct gcc atc aaa aga atg aaa gaa tat gcc tcc aaa gat     2592
Arg Met Asp Ala Ala Ile Lys Arg Met Lys Glu Tyr Ala Ser Lys Asp
    850                 855                 860

gat cac agg gac ttt gca gga gaa ctg gaa gtt ctt tgt aaa ctt gga     2640
Asp His Arg Asp Phe Ala Gly Glu Leu Glu Val Leu Cys Lys Leu Gly
865                 870                 875                 880

cac cat cca aac atc atc aat ctc tta gga gca tgt gaa cat cga ggc     2688
His His Pro Asn Ile Ile Asn Leu Leu Gly Ala Cys Glu His Arg Gly
                885                 890                 895

tac ttg tac ctg gcc att gag tac gcg ccc cat gga aac ctt ctg gac     2736
Tyr Leu Tyr Leu Ala Ile Glu Tyr Ala Pro His Gly Asn Leu Leu Asp
            900                 905                 910

ttc ctt cgc aag agc cgt gtg ctg gag acg gac cca gca ttt gcc att     2784
Phe Leu Arg Lys Ser Arg Val Leu Glu Thr Asp Pro Ala Phe Ala Ile
        915                 920                 925

gcc aat agc acc gcg tcc aca ctg tcc tcc cag cag ctc ctt cac ttc     2832
Ala Asn Ser Thr Ala Ser Thr Leu Ser Ser Gln Gln Leu Leu His Phe
    930                 935                 940

gct gcc gac gtg gcc cgg ggc atg gac tac ttg agc caa aaa cag ttt     2880
Ala Ala Asp Val Ala Arg Gly Met Asp Tyr Leu Ser Gln Lys Gln Phe
945                 950                 955                 960

atc cac agg gat ctg gct gcc aga aac att tta gtt ggt gaa aac tat     2928
Ile His Arg Asp Leu Ala Ala Arg Asn Ile Leu Val Gly Glu Asn Tyr
                965                 970                 975

gtg gca aaa ata gca gat ttt gga ttg tcc cga ggt caa gag gtg tat     2976
Val Ala Lys Ile Ala Asp Phe Gly Leu Ser Arg Gly Gln Glu Val Tyr
            980                 985                 990

gtg aaa aag aca atg gga agg ctc  cca gtg cgc tgg atg  gcc atc gag   3024
Val Lys Lys Thr Met Gly Arg Leu  Pro Val Arg Trp Met  Ala Ile Glu
        995                 1000                1005

tca ctg  aat tac agt gtg tac  aca acc aac agt gat  gta tgg tcc      3069
Ser Leu  Asn Tyr Ser Val Tyr  Thr Thr Asn Ser Asp  Val Trp Ser
    1010                1015                1020

tat ggt  gtg tta cta tgg gag  att gtt agc tta gga  ggc aca ccc      3114
Tyr Gly  Val Leu Leu Trp Glu  Ile Val Ser Leu Gly  Gly Thr Pro
    1025                1030                1035

tac tgc  ggg atg act tgt gca  gaa ctc tac gag aag  ctg ccc cag      3159
Tyr Cys  Gly Met Thr Cys Ala  Glu Leu Tyr Glu Lys  Leu Pro Gln
    1040                1045                1050

ggc tac  aga ctg gag aag ccc  ctg aac tgt gat gat  gag gtg tat      3204
Gly Tyr  Arg Leu Glu Lys Pro  Leu Asn Cys Asp Asp  Glu Val Tyr
```

```
    1055                1060                1065

gat cta  atg aga caa tgc tgg  cgg gag aag cct tat  gag agg cca      3249
Asp Leu  Met Arg Gln Cys Trp  Arg Glu Lys Pro Tyr  Glu Arg Pro
    1070                1075                1080

tca ttt  gcc cag ata ttg gtg  tcc tta aac aga atg  tta gag gag      3294
Ser Phe  Ala Gln Ile Leu Val  Ser Leu Asn Arg Met  Leu Glu Glu
    1085                1090                1095

cga aag  acc tac gtg aat acc  acg ctt tat gag aag  ttt act tat      3339
Arg Lys  Thr Tyr Val Asn Thr  Thr Leu Tyr Glu Lys  Phe Thr Tyr
    1100                1105                1110

gca gga  att gac tgt tct gct  gaa gaa gcg gcc tag                   3375
Ala Gly  Ile Asp Cys Ser Ala  Glu Glu Ala Ala
    1115                1120


<210> SEQ ID NO 102
<211> LENGTH: 1124
<212> TYPE: PRT
<213> ORGANISM: Homo sapiens

<400> SEQUENCE: 102

Met Asp Ser Leu Ala Ser Leu Val Leu Cys Gly Val Ser Leu Leu Leu
1               5                   10                  15

Ser Gly Thr Val Glu Gly Ala Met Asp Leu Ile Leu Ile Asn Ser Leu
            20                  25                  30

Pro Leu Val Ser Asp Ala Glu Thr Ser Leu Thr Cys Ile Ala Ser Gly
        35                  40                  45

Trp Arg Pro His Glu Pro Ile Thr Ile Gly Arg Asp Phe Glu Ala Leu
    50                  55                  60

Met Asn Gln His Gln Asp Pro Leu Glu Val Thr Gln Asp Val Thr Arg
65                  70                  75                  80

Glu Trp Ala Lys Lys Val Val Trp Lys Arg Glu Lys Ala Ser Lys Ile
                85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
    130                 135                 140

Lys Val Leu Ile Lys Glu Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gln Lys Trp Gly Pro Glu Cys Asn His Leu Cys
    210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Leu His Thr Phe Gly Arg Thr Cys Lys Glu Arg Cys Ser Gly Gln Glu
            260                 265                 270

Gly Cys Lys Ser Tyr Val Phe Cys Leu Pro Asp Pro Tyr Gly Cys Ser
        275                 280                 285
```

```
Cys Ala Thr Gly Trp Lys Gly Leu Gln Cys Asn Glu Ala Cys His Pro
    290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
                325                 330                 335

Gly Leu Gln Cys Glu Arg Glu Gly Ile Pro Arg Met Thr Pro Lys Ile
            340                 345                 350

Val Asp Leu Pro Asp His Ile Glu Val Asn Ser Gly Lys Phe Asn Pro
        355                 360                 365

Ile Cys Lys Ala Ser Gly Trp Pro Leu Pro Thr Asn Glu Glu Met Thr
    370                 375                 380

Leu Val Lys Pro Asp Gly Thr Val Leu His Pro Lys Asp Phe Asn His
385                 390                 395                 400

Thr Asp His Phe Ser Val Ala Ile Phe Thr Ile His Arg Ile Leu Pro
                405                 410                 415

Pro Asp Ser Gly Val Trp Val Cys Ser Val Asn Thr Val Ala Gly Met
            420                 425                 430

Val Glu Lys Pro Phe Asn Ile Ser Val Lys Val Leu Pro Lys Pro Leu
        435                 440                 445

Asn Ala Pro Asn Val Ile Asp Thr Gly His Asn Phe Ala Val Ile Asn
    450                 455                 460

Ile Ser Ser Glu Pro Tyr Phe Gly Asp Gly Pro Ile Lys Ser Lys Lys
465                 470                 475                 480

Leu Leu Tyr Lys Pro Val Asn His Tyr Glu Ala Trp Gln His Ile Gln
                485                 490                 495

Val Thr Asn Glu Ile Val Thr Leu Asn Tyr Leu Glu Pro Arg Thr Glu
            500                 505                 510

Tyr Glu Leu Cys Val Gln Leu Val Arg Arg Gly Glu Gly Gly Glu Gly
        515                 520                 525

His Pro Gly Pro Val Arg Arg Phe Thr Thr Ala Ser Ile Gly Leu Pro
    530                 535                 540

Pro Pro Arg Gly Leu Asn Leu Leu Pro Lys Ser Gln Thr Thr Leu Asn
545                 550                 555                 560

Leu Thr Trp Gln Pro Ile Phe Pro Ser Ser Glu Asp Asp Phe Tyr Val
                565                 570                 575

Glu Val Glu Arg Arg Ser Val Gln Lys Ser Asp Gln Gln Asn Ile Lys
            580                 585                 590

Val Pro Gly Asn Leu Thr Ser Val Leu Leu Asn Asn Leu His Pro Arg
        595                 600                 605

Glu Gln Tyr Val Val Arg Ala Arg Val Asn Thr Lys Ala Gln Gly Glu
    610                 615                 620

Trp Ser Glu Asp Leu Thr Ala Trp Thr Leu Ser Asp Ile Leu Pro Pro
625                 630                 635                 640

Gln Pro Glu Asn Ile Lys Ile Ser Asn Ile Thr His Ser Ser Ala Val
                645                 650                 655

Ile Ser Trp Thr Ile Leu Asp Gly Tyr Ser Ile Ser Ser Ile Thr Ile
            660                 665                 670

Arg Tyr Lys Val Gln Gly Lys Asn Glu Asp Gln His Val Asp Val Lys
        675                 680                 685

Ile Lys Asn Ala Thr Ile Thr Gln Tyr Gln Leu Lys Gly Leu Glu Pro
    690                 695                 700
```

-continued

```
Glu Thr Ala Tyr Gln Val Asp Ile Phe Ala Glu Asn Asn Ile Gly Ser
705                 710                 715                 720

Ser Asn Pro Ala Phe Ser His Glu Leu Val Thr Leu Pro Glu Ser Gln
            725                 730                 735

Ala Pro Ala Asp Leu Gly Gly Gly Lys Met Leu Leu Ile Ala Ile Leu
        740                 745                 750

Gly Ser Ala Gly Met Thr Cys Leu Thr Val Leu Leu Ala Phe Leu Ile
    755                 760                 765

Ile Leu Gln Leu Lys Arg Ala Asn Val Gln Arg Arg Met Ala Gln Ala
    770                 775                 780

Phe Gln Asn Val Arg Glu Glu Pro Ala Val Gln Phe Asn Ser Gly Thr
785                 790                 795                 800

Leu Ala Leu Asn Arg Lys Val Lys Asn Asn Pro Asp Pro Thr Ile Tyr
            805                 810                 815

Pro Val Leu Asp Trp Asn Asp Ile Lys Phe Gln Asp Val Ile Gly Glu
        820                 825                 830

Gly Asn Phe Gly Gln Val Leu Lys Ala Arg Ile Lys Lys Asp Gly Leu
    835                 840                 845

Arg Met Asp Ala Ala Ile Lys Arg Met Lys Glu Tyr Ala Ser Lys Asp
    850                 855                 860

Asp His Arg Asp Phe Ala Gly Glu Leu Glu Val Leu Cys Lys Leu Gly
865                 870                 875                 880

His His Pro Asn Ile Ile Asn Leu Leu Gly Ala Cys Glu His Arg Gly
            885                 890                 895

Tyr Leu Tyr Leu Ala Ile Glu Tyr Ala Pro His Gly Asn Leu Leu Asp
        900                 905                 910

Phe Leu Arg Lys Ser Arg Val Leu Glu Thr Asp Pro Ala Phe Ala Ile
    915                 920                 925

Ala Asn Ser Thr Ala Ser Thr Leu Ser Ser Gln Gln Leu Leu His Phe
    930                 935                 940

Ala Ala Asp Val Ala Arg Gly Met Asp Tyr Leu Ser Gln Lys Gln Phe
945                 950                 955                 960

Ile His Arg Asp Leu Ala Ala Arg Asn Ile Leu Val Gly Glu Asn Tyr
            965                 970                 975

Val Ala Lys Ile Ala Asp Phe Gly Leu Ser Arg Gly Gln Glu Val Tyr
        980                 985                 990

Val Lys Lys Thr Met Gly Arg Leu  Pro Val Arg Trp Met  Ala Ile Glu
    995                 1000                1005

Ser Leu  Asn Tyr Ser Val Tyr  Thr Thr Asn Ser Asp  Val Trp Ser
    1010                1015                1020

Tyr Gly  Val Leu Leu Trp Glu  Ile Val Ser Leu Gly  Gly Thr Pro
    1025                1030                1035

Tyr Cys  Gly Met Thr Cys Ala  Glu Leu Tyr Glu Lys  Leu Pro Gln
    1040                1045                1050

Gly Tyr  Arg Leu Glu Lys Pro  Leu Asn Cys Asp Asp  Glu Val Tyr
    1055                1060                1065

Asp Leu  Met Arg Gln Cys Trp  Arg Glu Lys Pro Tyr  Glu Arg Pro
    1070                1075                1080

Ser Phe  Ala Gln Ile Leu Val  Ser Leu Asn Arg Met  Leu Glu Glu
    1085                1090                1095

Arg Lys  Thr Tyr Val Asn Thr  Thr Leu Tyr Glu Lys  Phe Thr Tyr
    1100                1105                1110

Ala Gly  Ile Asp Cys Ser Ala  Glu Glu Ala Ala
```

1115 1120

<210> SEQ ID NO 103
<211> LENGTH: 3375
<212> TYPE: DNA
<213> ORGANISM: Homo sapiens
<220> FEATURE:
<221> NAME/KEY: CDS
<222> LOCATION: (1)..(3375)

<400> SEQUENCE: 103

```
atg gac tct tta gcc agc tta gtt ctc tgt gga gtc agc ttg ctc ctt       48
Met Asp Ser Leu Ala Ser Leu Val Leu Cys Gly Val Ser Leu Leu Leu
1               5                   10                  15

tct gga act gtg gaa ggt gcc atg gac ttg atc ttg atc aat tcc cta       96
Ser Gly Thr Val Glu Gly Ala Met Asp Leu Ile Leu Ile Asn Ser Leu
            20                  25                  30

cct ctt gta tct gat gct gaa aca tct ctc acc tgc att gcc tct ggg      144
Pro Leu Val Ser Asp Ala Glu Thr Ser Leu Thr Cys Ile Ala Ser Gly
        35                  40                  45

tgg cgc ccc cat gag ccc atc acc ata gga agg gac ttt gaa gcc tta      192
Trp Arg Pro His Glu Pro Ile Thr Ile Gly Arg Asp Phe Glu Ala Leu
    50                  55                  60

atg aac cag cac cag gat ccg ctg gaa gtt act caa gat gtg acc aga      240
Met Asn Gln His Gln Asp Pro Leu Glu Val Thr Gln Asp Val Thr Arg
65                  70                  75                  80

gaa tgg gct aaa aaa gtt gtt tgg aag aga gaa aag gct agt aag atc      288
Glu Trp Ala Lys Lys Val Val Trp Lys Arg Glu Lys Ala Ser Lys Ile
                85                  90                  95

aat ggt gct tat ttc tgt gaa ggg cga gtt cga gga gag gca atc agg      336
Asn Gly Ala Tyr Phe Cys Glu Gly Arg Val Arg Gly Glu Ala Ile Arg
            100                 105                 110

ata cga acc atg aag atg cgt caa caa gct tcc ttc cta cca gct act      384
Ile Arg Thr Met Lys Met Arg Gln Gln Ala Ser Phe Leu Pro Ala Thr
        115                 120                 125

tta act atg act gtg gac aag gga gat aac gtg aac ata tct ttc aaa      432
Leu Thr Met Thr Val Asp Lys Gly Asp Asn Val Asn Ile Ser Phe Lys
    130                 135                 140

aag gta ttg att aaa gaa gaa gat gca gtg att tac aaa aat ggt tcc      480
Lys Val Leu Ile Lys Glu Glu Asp Ala Val Ile Tyr Lys Asn Gly Ser
145                 150                 155                 160

ttc atc cat tca gtg ccc cgg cat gaa gta cct gat att cta gaa gta      528
Phe Ile His Ser Val Pro Arg His Glu Val Pro Asp Ile Leu Glu Val
                165                 170                 175

cac ctg cct cat gct cag ccc cag gat gct gga gtg tac tcg gcc agg      576
His Leu Pro His Ala Gln Pro Gln Asp Ala Gly Val Tyr Ser Ala Arg
            180                 185                 190

tat ata gga gga aac ctc ttc acc tcg gcc ttc acc agg ctg ata gtc      624
Tyr Ile Gly Gly Asn Leu Phe Thr Ser Ala Phe Thr Arg Leu Ile Val
        195                 200                 205

cgg aga tgt gaa gcc cag aag tgg gga cct gaa tgc aac cat ctc tgt      672
Arg Arg Cys Glu Ala Gln Lys Trp Gly Pro Glu Cys Asn His Leu Cys
    210                 215                 220

act gct tgt atg aac aat ggt gtc tgc cat gaa gat act gga gaa tgc      720
Thr Ala Cys Met Asn Asn Gly Val Cys His Glu Asp Thr Gly Glu Cys
225                 230                 235                 240

att tgc cct cct ggg ttt atg gga agg acg tgt gag aag gct tgt gaa      768
Ile Cys Pro Pro Gly Phe Met Gly Arg Thr Cys Glu Lys Ala Cys Glu
                245                 250                 255

ctg cac acg ttt ggc aga act tgt aaa gaa agg tgc agt gga caa gag      816
Leu His Thr Phe Gly Arg Thr Cys Lys Glu Arg Cys Ser Gly Gln Glu
```

```
            260                 265                 270

gga tgc aag tct tat gtg ttc tgt ctc cct gac ccc tat ggg tgt tcc      864
Gly Cys Lys Ser Tyr Val Phe Cys Leu Pro Asp Pro Tyr Gly Cys Ser
        275                 280                 285

tgt gcc aca ggc tgg aag ggt ctg cag tgc aat gaa gca tgc cac cct      912
Cys Ala Thr Gly Trp Lys Gly Leu Gln Cys Asn Glu Ala Cys His Pro
    290                 295                 300

ggt ttt tac ggg cca gat tgt aag ctt agg tgc agc tgc aac aat ggg      960
Gly Phe Tyr Gly Pro Asp Cys Lys Leu Arg Cys Ser Cys Asn Asn Gly
305                 310                 315                 320

gag atg tgt gat cgc ttc caa gga tgt ctc tgc tct cca gga tgg cag     1008
Glu Met Cys Asp Arg Phe Gln Gly Cys Leu Cys Ser Pro Gly Trp Gln
                325                 330                 335

ggg ctc cag tgt gag aga gaa ggc ata ccg agg atg acc cca aag ata     1056
Gly Leu Gln Cys Glu Arg Glu Gly Ile Pro Arg Met Thr Pro Lys Ile
            340                 345                 350

gtg gat ttg cca gat cat ata gaa gta aac agt ggt aaa ttt aat ccc     1104
Val Asp Leu Pro Asp His Ile Glu Val Asn Ser Gly Lys Phe Asn Pro
        355                 360                 365

att tgc aaa gct tct ggc tgg ccg cta cct act aat gaa gaa atg acc     1152
Ile Cys Lys Ala Ser Gly Trp Pro Leu Pro Thr Asn Glu Glu Met Thr
    370                 375                 380

ctg gtg aag ccg gat ggg aca gtg ctc cat cca aaa gac ttt aac cat     1200
Leu Val Lys Pro Asp Gly Thr Val Leu His Pro Lys Asp Phe Asn His
385                 390                 395                 400

acg gat cat ttc tca gta gcc ata ttc acc atc cac cgg atc ctc ccc     1248
Thr Asp His Phe Ser Val Ala Ile Phe Thr Ile His Arg Ile Leu Pro
                405                 410                 415

cct gac tca gga gtt tgg gtc tgc agt gtg aac aca gtg gct ggg atg     1296
Pro Asp Ser Gly Val Trp Val Cys Ser Val Asn Thr Val Ala Gly Met
            420                 425                 430

gtg gaa aag ccc ttc aac att tct gtt aaa gtt ctt cca aag ccc ctg     1344
Val Glu Lys Pro Phe Asn Ile Ser Val Lys Val Leu Pro Lys Pro Leu
        435                 440                 445

aat gcc cca aac gtg att gac act gga cat aac ttt gct gtc atc aac     1392
Asn Ala Pro Asn Val Ile Asp Thr Gly His Asn Phe Ala Val Ile Asn
    450                 455                 460

atc agc tct gag cct tac ttt ggg gat gga cca atc aaa tcc aag aag     1440
Ile Ser Ser Glu Pro Tyr Phe Gly Asp Gly Pro Ile Lys Ser Lys Lys
465                 470                 475                 480

ctt cta tac aaa ccc gtt aat cac tat gag gct tgg caa cat att caa     1488
Leu Leu Tyr Lys Pro Val Asn His Tyr Glu Ala Trp Gln His Ile Gln
                485                 490                 495

gtg aca aat gag att gtt aca ctc aac tat ttg gaa cct cgg aca gaa     1536
Val Thr Asn Glu Ile Val Thr Leu Asn Tyr Leu Glu Pro Arg Thr Glu
            500                 505                 510

tat gaa ctc tgt gtg caa ctg gtc cgt cgt gga gag ggt ggg gaa ggg     1584
Tyr Glu Leu Cys Val Gln Leu Val Arg Arg Gly Glu Gly Gly Glu Gly
        515                 520                 525

cat cct gga cct gtg aga cgc ttc aca aca gct tct atc gga ctc cct     1632
His Pro Gly Pro Val Arg Arg Phe Thr Thr Ala Ser Ile Gly Leu Pro
    530                 535                 540

cct cca aga ggt cta aat ctc ctg cct aaa agt cag acc act cta aat     1680
Pro Pro Arg Gly Leu Asn Leu Leu Pro Lys Ser Gln Thr Thr Leu Asn
545                 550                 555                 560

ttg acc tgg caa cca ata ttt cca agc tcg gaa gat gac ttt tat gtt     1728
Leu Thr Trp Gln Pro Ile Phe Pro Ser Ser Glu Asp Asp Phe Tyr Val
                565                 570                 575

gaa gtg gag aga agg tct gtg caa aaa agt gat cag cag aat att aaa     1776
```

```
Glu Val Glu Arg Arg Ser Val Gln Lys Ser Asp Gln Gln Asn Ile Lys
            580                 585                 590

gtt cca ggc aac ttg act tcg gtg cta ctt aac aac tta cat ccc agg      1824
Val Pro Gly Asn Leu Thr Ser Val Leu Leu Asn Asn Leu His Pro Arg
        595                 600                 605

gag cag tac gtg gtc cga gct aga gtc aac acc aag gcc cag ggg gaa      1872
Glu Gln Tyr Val Val Arg Ala Arg Val Asn Thr Lys Ala Gln Gly Glu
    610                 615                 620

tgg agt gaa gat ctc act gct tgg acc ctt agt gac att ctt cct cct      1920
Trp Ser Glu Asp Leu Thr Ala Trp Thr Leu Ser Asp Ile Leu Pro Pro
625                 630                 635                 640

caa cca gaa aac atc aag att tcc aac att aca cac tcc tca gct gtg      1968
Gln Pro Glu Asn Ile Lys Ile Ser Asn Ile Thr His Ser Ser Ala Val
                645                 650                 655

att tct tgg aca ata ttg gat ggc tat tct att tct tct att act atc      2016
Ile Ser Trp Thr Ile Leu Asp Gly Tyr Ser Ile Ser Ser Ile Thr Ile
            660                 665                 670

cgt tac aag gtt caa ggc aag aat gaa gac cag cac gtt gat gtg aag      2064
Arg Tyr Lys Val Gln Gly Lys Asn Glu Asp Gln His Val Asp Val Lys
        675                 680                 685

ata aag aat gcc acc atc act cag tat cag ctc aag ggc cta gag cct      2112
Ile Lys Asn Ala Thr Ile Thr Gln Tyr Gln Leu Lys Gly Leu Glu Pro
    690                 695                 700

gaa aca gca tac cag gtg gac att ttt gca gag aac aac ata ggg tca      2160
Glu Thr Ala Tyr Gln Val Asp Ile Phe Ala Glu Asn Asn Ile Gly Ser
705                 710                 715                 720

agc aac cca gcc ttt tct cat gaa ctg gtg acc ctc cca gaa tct caa      2208
Ser Asn Pro Ala Phe Ser His Glu Leu Val Thr Leu Pro Glu Ser Gln
                725                 730                 735

gca cca gcg gac ctc gga ggg ggg aag atg ctg ctt ata gcc atc ctt      2256
Ala Pro Ala Asp Leu Gly Gly Gly Lys Met Leu Leu Ile Ala Ile Leu
            740                 745                 750

ggc tct gct gga atg acc tgc ctg act gtg ctg ttg gcc ttt ctg atc      2304
Gly Ser Ala Gly Met Thr Cys Leu Thr Val Leu Leu Ala Phe Leu Ile
        755                 760                 765

ata ttg caa ttg aag agg gca aat gtg caa agg aga atg gcc caa gcc      2352
Ile Leu Gln Leu Lys Arg Ala Asn Val Gln Arg Arg Met Ala Gln Ala
    770                 775                 780

ttc caa aac gtg agg gaa gaa cca gct gtg cag ttc aac tca ggg act      2400
Phe Gln Asn Val Arg Glu Glu Pro Ala Val Gln Phe Asn Ser Gly Thr
785                 790                 795                 800

ctg gcc cta aac agg aag gtc aaa aac aac cca gat cct aca att tat      2448
Leu Ala Leu Asn Arg Lys Val Lys Asn Asn Pro Asp Pro Thr Ile Tyr
                805                 810                 815

cca gtg ctt gac tgg aat gac atc aaa ttt caa gat gtg att ggg gag      2496
Pro Val Leu Asp Trp Asn Asp Ile Lys Phe Gln Asp Val Ile Gly Glu
            820                 825                 830

ggc aat ttt ggc caa gtt ctt aag gcg cgc atc aag aag gat ggg tta      2544
Gly Asn Phe Gly Gln Val Leu Lys Ala Arg Ile Lys Lys Asp Gly Leu
        835                 840                 845

tgg atg gat gct gcc atc aaa aga atg aaa gaa tat gcc tcc aaa gat      2592
Trp Met Asp Ala Ala Ile Lys Arg Met Lys Glu Tyr Ala Ser Lys Asp
    850                 855                 860

gat cac agg gac ttt gca gga gaa ctg gaa gtt ctt tgt aaa ctt gga      2640
Asp His Arg Asp Phe Ala Gly Glu Leu Glu Val Leu Cys Lys Leu Gly
865                 870                 875                 880

cac cat cca aac atc atc aat ctc tta gga gca tgt gaa cat cga ggc      2688
His His Pro Asn Ile Ile Asn Leu Leu Gly Ala Cys Glu His Arg Gly
                885                 890                 895
```

```
tac ttg tac ctg gcc att gag tac gcg ccc cat gga aac ctt ctg gac     2736
Tyr Leu Tyr Leu Ala Ile Glu Tyr Ala Pro His Gly Asn Leu Leu Asp
            900                 905                 910

ttc ctt cgc aag agc cgt gtg ctg gag acg gac cca gca ttt gcc att     2784
Phe Leu Arg Lys Ser Arg Val Leu Glu Thr Asp Pro Ala Phe Ala Ile
        915                 920                 925

gcc aat agc acc gcg tcc aca ctg tcc tcc cag cag ctc ctt cac ttc     2832
Ala Asn Ser Thr Ala Ser Thr Leu Ser Ser Gln Gln Leu Leu His Phe
    930                 935                 940

gct gcc gac gtg gcc cgg ggc atg gac tac ttg agc caa aaa cag ttt     2880
Ala Ala Asp Val Ala Arg Gly Met Asp Tyr Leu Ser Gln Lys Gln Phe
945                 950                 955                 960

atc cac agg gat ctg gct gcc aga aac att tta gtt ggt gaa aac tat     2928
Ile His Arg Asp Leu Ala Ala Arg Asn Ile Leu Val Gly Glu Asn Tyr
                965                 970                 975

gtg gca aaa ata gca gat ttt gga ttg tcc cga ggt caa gag gtg tat     2976
Val Ala Lys Ile Ala Asp Phe Gly Leu Ser Arg Gly Gln Glu Val Tyr
            980                 985                 990

gtg aaa aag aca atg gga agg ctc  cca gtg cgc tgg atg  gcc atc gag   3024
Val Lys Lys Thr Met Gly Arg Leu  Pro Val Arg Trp Met  Ala Ile Glu
        995                 1000                1005

tca ctg  aat tac agt gtg tac  aca acc aac agt gat  gta tgg tcc     3069
Ser Leu  Asn Tyr Ser Val Tyr  Thr Thr Asn Ser Asp  Val Trp Ser
    1010                1015                1020

tat ggt  gtg tta cta tgg gag  att gtt agc tta gga  ggc aca ccc     3114
Tyr Gly  Val Leu Leu Trp Glu  Ile Val Ser Leu Gly  Gly Thr Pro
    1025                1030                1035

tac tgc  ggg atg act tgt gca  gaa ctc tac gag aag  ctg ccc cag     3159
Tyr Cys  Gly Met Thr Cys Ala  Glu Leu Tyr Glu Lys  Leu Pro Gln
    1040                1045                1050

ggc tac  aga ctg gag aag ccc  ctg aac tgt gat gat  gag gtg tat     3204
Gly Tyr  Arg Leu Glu Lys Pro  Leu Asn Cys Asp Asp  Glu Val Tyr
    1055                1060                1065

gat cta  atg aga caa tgc tgg  cgg gag aag cct tat  gag agg cca     3249
Asp Leu  Met Arg Gln Cys Trp  Arg Glu Lys Pro Tyr  Glu Arg Pro
    1070                1075                1080

tca ttt  gcc cag ata ttg gtg  tcc tta aac aga atg  tta gag gag     3294
Ser Phe  Ala Gln Ile Leu Val  Ser Leu Asn Arg Met  Leu Glu Glu
    1085                1090                1095

cga aag  acc tac gtg aat acc  acg ctt tat gag aag  ttt act tat     3339
Arg Lys  Thr Tyr Val Asn Thr  Thr Leu Tyr Glu Lys  Phe Thr Tyr
    1100                1105                1110

gca gga  att gac tgt tct gct  gaa gaa gcg gcc tag                 3375
Ala Gly  Ile Asp Cys Ser Ala  Glu Glu Ala Ala
    1115                1120


<210> SEQ ID NO 104
<211> LENGTH: 1124
<212> TYPE: PRT
<213> ORGANISM: Homo sapiens

<400> SEQUENCE: 104

Met Asp Ser Leu Ala Ser Leu Val Leu Cys Gly Val Ser Leu Leu Leu
1               5                   10                  15

Ser Gly Thr Val Glu Gly Ala Met Asp Leu Ile Leu Ile Asn Ser Leu
            20                  25                  30

Pro Leu Val Ser Asp Ala Glu Thr Ser Leu Thr Cys Ile Ala Ser Gly
        35                  40                  45

Trp Arg Pro His Glu Pro Ile Thr Ile Gly Arg Asp Phe Glu Ala Leu
    50                  55                  60
```

```
Met Asn Gln His Gln Asp Pro Leu Glu Val Thr Gln Asp Val Thr Arg
65                  70                  75                  80

Glu Trp Ala Lys Lys Val Val Trp Lys Arg Glu Lys Ala Ser Lys Ile
                85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
    130                 135                 140

Lys Val Leu Ile Lys Glu Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gln Lys Trp Gly Pro Glu Cys Asn His Leu Cys
    210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Leu His Thr Phe Gly Arg Thr Cys Lys Glu Arg Cys Ser Gly Gln Glu
            260                 265                 270

Gly Cys Lys Ser Tyr Val Phe Cys Leu Pro Asp Pro Tyr Gly Cys Ser
        275                 280                 285

Cys Ala Thr Gly Trp Lys Gly Leu Gln Cys Asn Glu Ala Cys His Pro
    290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
                325                 330                 335

Gly Leu Gln Cys Glu Arg Glu Gly Ile Pro Arg Met Thr Pro Lys Ile
            340                 345                 350

Val Asp Leu Pro Asp His Ile Glu Val Asn Ser Gly Lys Phe Asn Pro
        355                 360                 365

Ile Cys Lys Ala Ser Gly Trp Pro Leu Pro Thr Asn Glu Glu Met Thr
    370                 375                 380

Leu Val Lys Pro Asp Gly Thr Val Leu His Pro Lys Asp Phe Asn His
385                 390                 395                 400

Thr Asp His Phe Ser Val Ala Ile Phe Thr Ile His Arg Ile Leu Pro
                405                 410                 415

Pro Asp Ser Gly Val Trp Val Cys Ser Val Asn Thr Val Ala Gly Met
            420                 425                 430

Val Glu Lys Pro Phe Asn Ile Ser Val Lys Val Leu Pro Lys Pro Leu
        435                 440                 445

Asn Ala Pro Asn Val Ile Asp Thr Gly His Asn Phe Ala Val Ile Asn
    450                 455                 460

Ile Ser Ser Glu Pro Tyr Phe Gly Asp Gly Pro Ile Lys Ser Lys Lys
465                 470                 475                 480
```

```
Leu Leu Tyr Lys Pro Val Asn His Tyr Glu Ala Trp Gln His Ile Gln
                485                 490                 495

Val Thr Asn Glu Ile Val Thr Leu Asn Tyr Leu Glu Pro Arg Thr Glu
            500                 505                 510

Tyr Glu Leu Cys Val Gln Leu Val Arg Arg Gly Glu Gly Gly Glu Gly
        515                 520                 525

His Pro Gly Pro Val Arg Arg Phe Thr Thr Ala Ser Ile Gly Leu Pro
    530                 535                 540

Pro Pro Arg Gly Leu Asn Leu Leu Pro Lys Ser Gln Thr Thr Leu Asn
545                 550                 555                 560

Leu Thr Trp Gln Pro Ile Phe Pro Ser Ser Glu Asp Asp Phe Tyr Val
                565                 570                 575

Glu Val Glu Arg Arg Ser Val Gln Lys Ser Asp Gln Gln Asn Ile Lys
            580                 585                 590

Val Pro Gly Asn Leu Thr Ser Val Leu Leu Asn Asn Leu His Pro Arg
        595                 600                 605

Glu Gln Tyr Val Val Arg Ala Arg Val Asn Thr Lys Ala Gln Gly Glu
    610                 615                 620

Trp Ser Glu Asp Leu Thr Ala Trp Thr Leu Ser Asp Ile Leu Pro Pro
625                 630                 635                 640

Gln Pro Glu Asn Ile Lys Ile Ser Asn Ile Thr His Ser Ser Ala Val
                645                 650                 655

Ile Ser Trp Thr Ile Leu Asp Gly Tyr Ser Ile Ser Ser Ile Thr Ile
            660                 665                 670

Arg Tyr Lys Val Gln Gly Lys Asn Glu Asp Gln His Val Asp Val Lys
        675                 680                 685

Ile Lys Asn Ala Thr Ile Thr Gln Tyr Gln Leu Lys Gly Leu Glu Pro
    690                 695                 700

Glu Thr Ala Tyr Gln Val Asp Ile Phe Ala Glu Asn Asn Ile Gly Ser
705                 710                 715                 720

Ser Asn Pro Ala Phe Ser His Glu Leu Val Thr Leu Pro Glu Ser Gln
                725                 730                 735

Ala Pro Ala Asp Leu Gly Gly Gly Lys Met Leu Leu Ile Ala Ile Leu
            740                 745                 750

Gly Ser Ala Gly Met Thr Cys Leu Thr Val Leu Leu Ala Phe Leu Ile
        755                 760                 765

Ile Leu Gln Leu Lys Arg Ala Asn Val Gln Arg Arg Met Ala Gln Ala
    770                 775                 780

Phe Gln Asn Val Arg Glu Glu Pro Ala Val Gln Phe Asn Ser Gly Thr
785                 790                 795                 800

Leu Ala Leu Asn Arg Lys Val Lys Asn Asn Pro Asp Pro Thr Ile Tyr
                805                 810                 815

Pro Val Leu Asp Trp Asn Asp Ile Lys Phe Gln Asp Val Ile Gly Glu
            820                 825                 830

Gly Asn Phe Gly Gln Val Leu Lys Ala Arg Ile Lys Lys Asp Gly Leu
        835                 840                 845

Trp Met Asp Ala Ala Ile Lys Arg Met Lys Glu Tyr Ala Ser Lys Asp
    850                 855                 860

Asp His Arg Asp Phe Ala Gly Glu Leu Glu Val Leu Cys Lys Leu Gly
865                 870                 875                 880

His His Pro Asn Ile Ile Asn Leu Leu Gly Ala Cys Glu His Arg Gly
                885                 890                 895

Tyr Leu Tyr Leu Ala Ile Glu Tyr Ala Pro His Gly Asn Leu Leu Asp
```

```
            900                 905                 910

Phe Leu Arg Lys Ser Arg Val Leu Glu Thr Asp Pro Ala Phe Ala Ile
        915                 920                 925

Ala Asn Ser Thr Ala Ser Thr Leu Ser Ser Gln Gln Leu Leu His Phe
    930                 935                 940

Ala Ala Asp Val Ala Arg Gly Met Asp Tyr Leu Ser Gln Lys Gln Phe
945                 950                 955                 960

Ile His Arg Asp Leu Ala Ala Arg Asn Ile Leu Val Gly Glu Asn Tyr
                965                 970                 975

Val Ala Lys Ile Ala Asp Phe Gly Leu Ser Arg Gly Gln Glu Val Tyr
            980                 985                 990

Val Lys Lys Thr Met Gly Arg Leu  Pro Val Arg Trp Met  Ala Ile Glu
        995                 1000                1005

Ser Leu  Asn Tyr Ser Val Tyr  Thr Thr Asn Ser Asp  Val Trp Ser
    1010                1015                1020

Tyr Gly  Val Leu Leu Trp Glu  Ile Val Ser Leu Gly  Gly Thr Pro
    1025                1030                1035

Tyr Cys  Gly Met Thr Cys Ala  Glu Leu Tyr Glu Lys  Leu Pro Gln
    1040                1045                1050

Gly Tyr  Arg Leu Glu Lys Pro  Leu Asn Cys Asp Asp  Glu Val Tyr
    1055                1060                1065

Asp Leu  Met Arg Gln Cys Trp  Arg Glu Lys Pro Tyr  Glu Arg Pro
    1070                1075                1080

Ser Phe  Ala Gln Ile Leu Val  Ser Leu Asn Arg Met  Leu Glu Glu
    1085                1090                1095

Arg Lys  Thr Tyr Val Asn Thr  Thr Leu Tyr Glu Lys  Phe Thr Tyr
    1100                1105                1110

Ala Gly  Ile Asp Cys Ser Ala  Glu Glu Ala Ala
    1115                1120
```

<210> SEQ ID NO 105
<211> LENGTH: 814
<212> TYPE: DNA
<213> ORGANISM: Artificial Sequence
<220> FEATURE:
<223> OTHER INFORMATION: Synthetic

<400> SEQUENCE: 105

```
gaggaaccga gaggctgaga ctaacccaga aacatccaat tctcaaactg aagctcgcac     60

tctcgcctcc agcatgaact ccttctccac aagcgccttc ggtccagttg ccttctccct    120

gggcctgctc ctggtgttgc ctgctgcctt ccctgcccca gtcttcacac tcgaagattt    180

cgttggggac tggcgacaga cagccggcta caacctggac caagtccttg aacagggagg    240

tgtgtccagt ttgtttcaga atctcggggt gtccgtaact ccgatccaaa ggattgtcct    300

gagcggtgaa aatgggctga agatcgacat ccatgtcatc atcccgtatg aaggtctgag    360

cggcgaccaa atgggccaga tcgaaaaaat ttttaaggtg gtgtaccctg tggatgatca    420

tcactttaag gtgatcctgc actatggcac actggtaatc gacggggtta cgccgaacat    480

gatcgactat ttcggacggc cgtatgaagg catcgccgtg ttcgacggca aaaagatcac    540

tgtaacaggg accctgtgga acggcaacaa aattatcgac gagcgcctga tcaaccccga    600

cggctccctg ctgttccgag taaccatcaa cggagtgacc ggctggcggc tgtgcgaacg    660

cattctggcg taaggctgct gcagctgcat gggtgcctgc tgctgcctgc cttggcctga    720

tggccaggcc agagtgctgc cagtcctctg catgttctgc tcttgtgccc ttctgagccc    780
```

acaataaagg ctgagctctt atcttgcaaa aggc 814

<210> SEQ ID NO 106
<211> LENGTH: 984
<212> TYPE: DNA
<213> ORGANISM: Artificial Sequence
<220> FEATURE:
<223> OTHER INFORMATION: Synthetic

<400> SEQUENCE: 106
ataaaagccc aggggcaagc ggtccggata acggctagcc tgaggagctg ctgcgacagt 60
ccactacctt tttcgagagt gactcccgtt gtcccaaggc ttcccagagc gaacctgtgc 120
ggctgcaggc accggcgcgt cgagtttccg gcgtccggaa ggaccgagct cttctcgcga 180
atccagtgtt ccgtttccag cccccaatct cagagcggag ccgacagaga gcagggaacc 240
ggcatgaact ccttctccac aagcgccttc ggtccagttg ccttctccct gggcctgctc 300
ctggtgttgc ctgctgcctt ccctgcccca gtcttcacac tcgaagattt cgttggggac 360
tggcgacaga cagccggcta caacctggac caagtccttg aacagggagg tgtgtccagt 420
ttgtttcaga atctcggggt gtccgtaact ccgatccaaa ggattgtcct gagcggtgaa 480
aatgggctga agatcgacat ccatgtcatc atcccgtatg aaggtctgag cggcgaccaa 540
atgggccaga tcgaaaaaat ttttaaggtg gtgtaccctg tggatgatca tcactttaag 600
gtgatcctgc actatggcac actggtaatc gacggggtta cgccgaacat gatcgactat 660
ttcggacggc cgtatgaagg catcgccgtg ttcgacggca aaaagatcac tgtaacaggg 720
accctgtgga acggcaacaa aattatcgac gagcgcctga tcaaccccga cggctccctg 780
ctgttccgag taaccatcaa cggagtgacc ggctggcggc tgtgcgaacg cattctggcg 840
taaggctgct gcagctgcat gggtgcctgc tgctgcctgc cttggcctga tggccaggcc 900
agagtgctgc cagtcctctg catgttctgc tcttgtgccc ttctgagccc acaataaagg 960
ctgagctctt atcttgcaaa aggc 984

<210> SEQ ID NO 107
<211> LENGTH: 1735
<212> TYPE: DNA
<213> ORGANISM: Artificial Sequence
<220> FEATURE:
<223> OTHER INFORMATION: Synthetic

<400> SEQUENCE: 107
gaggaaccga gaggctgaga ctaacccaga aacatccaat tctcaaactg aagctcgcac 60
tctcgcctcc agcatgaaag tctctgccgc ccttctgtgc ctgctgctca tagcagccac 120
cttcattccc caagggctcg ctcacatagg gtgcagcaat cagcgccgaa gtccagaaaa 180
cagtgggaga agatataacc ggattcaaca tgggcaatgt gcctacactt tcattcttcc 240
agaacacgat ggcaactgtc gtgagagtac gacagaccag tacaacacaa acgctctgca 300
gagagatgct ccacacgtgg aaccggattt ctcttcccag aaacttcaac atctggaaca 360
tgtgatggaa aattatactc agtggctgca aaaacttgag aattacattg tggaaaacat 420
gaagtcggag atggcccaga tacagcagaa tgcagttcag aaccacacgg ctaccatgct 480
ggagatagga accagcctcc tctctcagac tgcagagcag accagaaagc tgacagatgt 540
tgagacccag gtactaaatc aaacttctcg acttgagata cagctgctgg agaattcatt 600
atccacctac aagctagaga agcaacttct tcaacagaca aatgaaatct tgaagatcca 660
tgaaaaaaac agtttattag aacataaaat cttagaaatg gaaggaaaac acaaggaaga 720
gttggacacc ttaaaggaag agaaagagaa ccttcaaggc ttggttactc gtcaaacata 780
tataatccag gagctggaaa agcaattaaa cagagctacc accaacaaca gtgtccttca 840
gaagcagcaa ctggagctga tggacacagt ccacaacctt gtcaatcttt gcactaaaga 900
aggtgtttta ctaaagggag gaaaaagaga ggaagagaaa ccatttagag actgtgcaga 960
tgtatatcaa gctggtttta ataaaagtgg aatctacact atttatatta ataatatgcc 1020
agaacccaaa aaggtgtttt gcaatatgga tgtcaatggg ggaggttgga ctgtaataca 1080
acatcgtgaa gatggaagtc tagatttcca aagaggctgg aaggaatata aaatgggttt 1140
tggaaatccc tccggtgaat attggctggg gaatgagttt atttttgcca ttaccagtca 1200
gaggcagtac atgctaagaa ttgagttaat ggactgggaa gggaaccgag cctattcaca 1260
gtatgacaga ttccacatag gaaatgaaaa gcaaaactat aggttgtatt taaaaggtca 1320
cactgggaca gcaggaaaac agagcagcct gatcttacac ggtgctgatt tcagcactaa 1380
agatgctgat aatgacaact gtatgtgcaa atgtgccctc atgttaacag gaggatggtg 1440
gtttgatgct tgtggcccct ccaatctaaa tggaatgttc tatactgcgg gacaaaacca 1500
tggaaaactg aatgggataa agtggcacta cttcaaaggg cccagttact ccttacgttc 1560
cacaactatg atgattcgac ctttagattt ttgaggctgc tgcagctgca tgggtgcctg 1620
ctgctgcctg ccttggcctg atggccaggc cagagtgctg ccagtcctct gcatgttctg 1680
ctcttgtgcc cttctgagcc cacaataaag gctgagctct tatcttgcaa aaggc 1735

<210> SEQ ID NO 108
<211> LENGTH: 1150
<212> TYPE: DNA
<213> ORGANISM: Artificial Sequence
<220> FEATURE:
<223> OTHER INFORMATION: Synthetic

<400> SEQUENCE: 108
gaggaaccga gaggctgaga ctaacccaga aacatccaat tctcaaactg aagctcgcac 60
tctcgcctcc agcatgaaag tctctgccgc ccttctgtgc ctgctgctca tagcagccac 120
cttcattccc caagggctcg ctgggatctt agacttgggc ccgcagatgc ttcgggaact 180
gcaggaaacc aacgcggcgc tgcaggacgt gcgggagctg ctgcggcagc aggtcaggga 240
gatcacgttc ctgaaaaaca cggtgatgga gtgtgacgcg tgcggaggct cccttgtcaa 300
tctttgcact aaagaaggtg ttttactaaa gggaggaaaa agagaggaag agaaaccatt 360
tagagactgt gcagatgtat atcaagctgg ttttaataaa agtggaatct acactattta 420
tattaataat atgccagaac ccaaaaaggt gttttgcaat atggatgtca atgggggagg 480
ttggactgta atacaacatc gtgaagatgg aagtctagat ttccaaagag gctggaagga 540
atataaaatg ggttttggaa atccctccgg tgaatattgg ctggggaatg agtttatttt 600
tgccattacc agtcagaggc agtacatgct aagaattgag ttaatggact gggaagggaa 660
ccgagcctat tcacagtatg acagattcca cataggaaat gaaaagcaaa actataggtt 720
gtatttaaaa ggtcacactg ggacagcagg aaaacagagc agcctgatct tacacggtgc 780
tgatttcagc actaaagatg ctgataatga caactgtatg tgcaaatgtg ccctcatgtt 840
aacaggagga tggtggtttg atgcttgtgg cccctccaat ctaaatggaa tgttctatac 900
tgcgggacaa aaccatggaa aactgaatgg gataaagtgg cactacttca aagggcccag 960
ttactcctta cgttccacaa ctatgatgat tcgaccttta gatttttgag gctgctgcag 1020
ctgcatgggt gcctgctgct gcctgccttg gcctgatggc caggccagag tgctgccagt 1080
cctctgcatg ttctgctctt gtgcccttct gagcccacaa taaaggctga gctcttatct 1140
tgcaaaaggc 1150

<210> SEQ ID NO 109
<211> LENGTH: 817
<212> TYPE: DNA
<213> ORGANISM: Artificial Sequence
<220> FEATURE:
<223> OTHER INFORMATION: Synthetic

<400> SEQUENCE: 109
catatcttca ttcttcactc tttccccccc ccccc ttatc ctcctatcta atcctctcat 60
ctctctcctc ctcttcctcc aacaacaact aacaatgaaa gtctctgccg cccttctgtg 120
cctgctgctc atagcagcca ccttcattcc ccaagggctc gctgtcttca cactcgaaga 180
tttcgttggg gactggcgac agacagccgg ctacaacctg gaccaagtcc ttgaacaggg 240
aggtgtgtcc agtttgtttc agaatctcgg ggtgtccgta actccgatcc aaaggattgt 300
cctgagcggt gaaaatgggc tgaagatcga catccatgtc atcatcccgt atgaaggtct 360
gagcggcgac caaatgggcc agatcgaaaa aatttttaag gtggtgtacc ctgtggatga 420
tcatcacttt aaggtgatcc tgcactatgg cacactggta atcgacgggg ttacgccgaa 480
catgatcgac tatttcggac ggccgtatga aggcatcgcc gtgttcgacg gcaaaaagat 540
cactgtaaca gggaccctgt ggaacggcaa caaaattatc gacgagcgcc tgatcaaccc 600
cgacggctcc ctgctgttcc gagtaaccat caacggagtg accggctggc ggctgtgcga 660
acgcattctg gcgtaaggct gctgcagctg catgggtgcc tgctgctgcc tgccttggcc 720
tgatggccag gccagagtgc tgccagtcct ctgcatgttc tgctcttgtg cccttctgag 780
cccacaataa aggctgagct cttatcttgc aaaaggc 817

<210> SEQ ID NO 110
<211> LENGTH: 978
<212> TYPE: DNA
<213> ORGANISM: Artificial Sequence
<220> FEATURE:
<223> OTHER INFORMATION: Synthetic

<400> SEQUENCE: 110
gtggcagctc acagctattg tggtgggaaa gggagggtgg ttggtggatg tcacagcttg 60
ggctttatct cccccagcag tggggactcc acagcccctg ggctacataa cagcaagaca 120
gtccggagct gtagcagacc tgattgagcc tttgcagcag ctgagagcat ggcctagggt 180
gggcggcacc attgtccagc agctgagttt cccagggacc ttggagatag ccgcagccct 240
catttgcagg ggaagatgaa agtctctgcc gcccttctgt gcctgctgct catagcagcc 300
accttcattc cccaagggct cgctgtcttc acactcgaag atttcgttgg ggactggcga 360
cagacagccg gctacaacct ggaccaagtc cttgaacagg gaggtgtgtc cagtttgttt 420
cagaatctcg gggtgtccgt aactccgatc caaaggattg tcctgagcgg tgaaaatggg 480
ctgaagatcg acatccatgt catcatcccg tatgaaggtc tgagcggcga ccaaatgggc 540
cagatcgaaa aaatttttaa ggtggtgtac cctgtggatg atcatcactt taaggtgatc 600
ctgcactatg gcacactggt aatcgacggg gttacgccga acatgatcga ctatttcgga 660
cggccgtatg aaggcatcgc cgtgttcgac ggcaaaaaga tcactgtaac agggaccctg 720

```
tggaacggca acaaaattat cgacgagcgc ctgatcaacc ccgacggctc cctgctgttc    780

cgagtaacca tcaacggagt gaccggctgg cggctgtgcg aacgcattct ggcgtaaggc    840

tgctgcagct gcatgggtgc ctgctgctgc ctgccttggc ctgatggcca ggccagagtg    900

ctgccagtcc tctgcatgtt ctgctcttgt gcccttctga gcccacaata aaggctgagc    960

tcttatcttg caaaaggc                                                  978
```

<210> SEQ ID NO 111
<211> LENGTH: 975
<212> TYPE: DNA
<213> ORGANISM: Artificial Sequence
<220> FEATURE:
<223> OTHER INFORMATION: Synthetic

<400> SEQUENCE: 111

```
gtggcagctc acagctattg tggtgggaaa gggagggtgg ttggtggatg tcacagcttg     60

ggctttatct cccccagcag tggggactcc acagcccctg ggctacataa cagcaagaca    120

gtccggagct gtagcagacc tgattgagcc tttgcagcag ctgagagcat ggcctagggt    180

gggcggcacc attgtccagc agctgagttt cccagggacc ttggagatag ccgcagccct    240

catttgcagg ggaagatgat tcctgccaga tttgccgggg tgctgcttgc tctggccctc    300

attttgccag ggaccctttg tgtcttcaca ctcgaagatt tcgttgggga ctggcgacag    360

acagccggct acaacctgga ccaagtcctt gaacagggag gtgtgtccag tttgtttcag    420

aatctcgggg tgtccgtaac tccgatccaa aggattgtcc tgagcggtga aaatgggctg    480

aagatcgaca tccatgtcat catcccgtat gaaggtctga gcggcgacca aatgggccag    540

atcgaaaaaa tttttaaggt ggtgtaccct gtggatgatc atcactttaa ggtgatcctg    600

cactatggca cactggtaat cgacggggtt acgccgaaca tgatcgacta tttcggacgg    660

ccgtatgaag gcatcgccgt gttcgacggc aaaaagatca ctgtaacagg gaccctgtgg    720

aacggcaaca aaattatcga cgagcgcctg atcaaccccg acggctccct gctgttccga    780

gtaaccatca acggagtgac cggctggcgg ctgtgcgaac gcattctggc gtaaggctgc    840

tgcagctgca tgggtgcctg ctgctgcctg ccttggcctg atggccaggc cagagtgctg    900

ccagtcctct gcatgttctg ctcttgtgcc cttctgagcc cacaataaag gctgagctct    960

tatcttgcaa aaggc                                                     975
```

<210> SEQ ID NO 112
<211> LENGTH: 778
<212> TYPE: DNA
<213> ORGANISM: Artificial Sequence
<220> FEATURE:
<223> OTHER INFORMATION: Synthetic

<400> SEQUENCE: 112

```
gggaaataag agagaaaaga agagtaagaa gaaatataag accccggcgc cgccaccatg     60

aaagtctctg ccgcccttct gtgcctgctg ctcatagcag ccaccttcat tccccaaggg    120

ctcgctgtct tcacactcga agatttcgtt ggggactggc gacagacagc cggctacaac    180

ctggaccaag tccttgaaca gggaggtgtg tccagtttgt ttcagaatct cggggtgtcc    240

gtaactccga tccaaaggat tgtcctgagc ggtgaaaatg ggctgaagat cgacatccat    300

gtcatcatcc cgtatgaagg tctgagcggc gaccaaatgg gccagatcga aaaaattttt    360

aaggtggtgt accctgtgga tgatcatcac tttaaggtga tcctgcacta tggcacactg    420

gtaatcgacg gggttacgcc gaacatgatc gactatttcg gacggccgta tgaaggcatc    480
```

gccgtgttcg acggcaaaaa gatcactgta acagggaccc tgtggaacgg caacaaaatt 540
atcgacgagc gcctgatcaa ccccgacggc tccctgctgt tccgagtaac catcaacgga 600
gtgaccggct ggcggctgtg cgaacgcatt ctggcgtaat aataggctgg agcctcggtg 660
gcctagcttc ttgccccttg ggcctccccc cagcccctcc tccccttcct gcacccgtac 720
cccctccata aagtaggaaa cactacagtg gtctttgaat aaagtctgag tgggcggc 778

<210> SEQ ID NO 113
<211> LENGTH: 796
<212> TYPE: DNA
<213> ORGANISM: Artificial Sequence
<220> FEATURE:
<223> OTHER INFORMATION: Synthetic

<400> SEQUENCE: 113
gaggaaccga gaggctgaga ctaacccaga aacatccaat tctcaaactg aagctcgcac 60
tctcgccgcc accatgaaag tctctgccgc ccttctgtgc ctgctgctca tagcagccac 120
cttcattccc caagggctcg ctgtcttcac actcgaagat ttcgttgggg actggcgaca 180
gacagccggc tacaacctgg accaagtcct tgaacaggga ggtgtgtcca gtttgtttca 240
gaatctcggg gtgtccgtaa ctccgatcca aaggattgtc ctgagcggtg aaaatgggct 300
gaagatcgac atccatgtca tcatcccgta tgaaggtctg agcggcgacc aaatgggcca 360
gatcgaaaaa atttttaagg tggtgtaccc tgtggatgat catcacttta aggtgatcct 420
gcactatggc acactggtaa tcgacggggt tacgccgaac atgatcgact atttcggacg 480
gccgtatgaa ggcatcgccg tgttcgacgg caaaaagatc actgtaacag ggaccctgtg 540
gaacggcaac aaaattatcg acgagcgcct gatcaacccc gacggctccc tgctgttccg 600
agtaaccatc aacggagtga ccggctggcg gctgtgcgaa cgcattctgg cgtaaggctg 660
ctgcagctgc atgggtgcct gctgctgcct gccttggcct gatggccagg ccagagtgct 720
gccagtcctc tgcatgttct gctcttgtgc ccttctgagc ccacaataaa ggctgagctc 780
ttatcttgca aaaggc 796

<210> SEQ ID NO 114
<211> LENGTH: 1144
<212> TYPE: DNA
<213> ORGANISM: Artificial Sequence
<220> FEATURE:
<223> OTHER INFORMATION: Synthetic

<400> SEQUENCE: 114
gaggaaccga gaggctgaga ctaacccaga aacatccaat tctcaaactg aagctcgcac 60
tctcgcctcc agcatgaaag tctctgccgc ccttctgtgc ctgctgctca tagcagccac 120
cttcattccc caagggctcg ctgggatctt agaggaagac ccggccgcct gcgagtccct 180
ggtgaaattc caagccaaag tggaggggct gctgcaggcc ctgaccagga aactggaagc 240
tgtgagtaag cggctggcca tcctggagaa cacagttgtc ggctcccttg tcaatcttgc 300
cactaaagaa ggtgttttac taaagggagg aaaaagagag gaagagaaac catttagaga 360
ctgtgcagat gtatatcaag ctggttttaa taaaagtgga atctacacta tttatattaa 420
taatatgcca gaacccaaaa aggtgttttg caatatggat gtcaatgggg gaggttggac 480
tgtaatacaa catcgtgaag atggaagtct agatttccaa agaggctgga aggaatataa 540
aatgggtttt ggaaatccct ccggtgaata ttggctgggg aatgagttta tttttgccat 600

```
taccagtcag aggcagtaca tgctaagaat tgagttaatg gactgggaag ggaaccgagc    660

ctattcacag tatgacagat tccacatagg aaatgaaaag caaaactata ggttgtattt    720

aaaaggtcac actgggacag caggaaaaca gagcagcctg atcttacacg gtgctgattt    780

cagcactaaa gatgctgata atgacaactg tatgtgcaaa tgtgccctca tgttaacagg    840

aggatggtgg tttgatgctt gtggcccctc caatctaaat ggaatgttct atactgcggg    900

acaaaaccat ggaaaactga atgggataaa gtggcactac ttcaaagggc ccagttactc    960

cttacgttcc acaactatga tgattcgacc tttagatttt tgaggctgct gcagctgcat   1020

gggtgcctgc tgctgcctgc cttggcctga tggccaggcc agagtgctgc cagtcctctg   1080

catgttctgc tcttgtgccc ttctgagccc acaataaagg ctgagctctt atcttgcaaa   1140

aggc                                                                1144
```

<210> SEQ ID NO 115
<211> LENGTH: 3589
<212> TYPE: DNA
<213> ORGANISM: Artificial Sequence
<220> FEATURE:
<223> OTHER INFORMATION: Synthetic

<400> SEQUENCE: 115

```
gaggaaccga gaggctgaga ctaacccaga aacatccaat tctcaaactg aagctcgcac     60

tctcgcctcc agcatggact ctttagccag cttagttctc tgtggagtca gcttgctcct    120

ttctggaact gtggaaggtg ccatggactt gatcttgatc aattccctac ctcttgtatc    180

tgatgctgaa acatctctca cctgcattgc ctctgggtgg cgcccccatg agcccatcac    240

cataggaagg gactttgaag ccttaatgaa ccagcaccag gacccgctgg aagttactca    300

agatgtgacc agagaatggg ctaaaaaagt tgtttggaag agagaaaagg ctagtaagat    360

caatggtgct tatttctgtg aagggcgagt tcgaggagag gcaatcagga tacgaaccat    420

gaagatgcgt caacaagctt ccttcctacc agctacttta actatgactg tggacaaggg    480

agataacgtg aacatatctt tcaaaaaggt attgattaaa gaagaagatg cagtgattta    540

caaaaatggt tccttcatcc attcagtgcc ccggcatgaa gtacctgata ttctagaagt    600

acacctgcct catgctcagc cccaggatgc tggagtgtac tcggccaggt atataggagg    660

aaacctcttc acctcggcct tcaccaggct gatagtccgg agatgtgaag cccagaagtg    720

gggacctgaa tgcaaccatc tctgtactgc ttgtatgaac aatggtgtct gccatgaaga    780

tactggagaa tgcatttgcc ctcctgggtt tatgggaagg acgtgtgaga aggcttgtga    840

actgcacacg tttggcagaa cttgtaaaga aaggtgcagt ggacaagagg gatgcaagtc    900

ttatgtgttc tgtctccctg acccctatgg gtgttcctgt gccacaggct ggaagggtct    960

gcagtgcaat gaagcatgcc accctggttt ttacgggcca gattgtaagc ttaggtgcag   1020

ctgcaacaat ggggagatgt gtgatcgctt ccaaggatgt ctctgctctc caggatggca   1080

ggggctccag tgtgagagag aaggcatacc gaggatgacc ccaaagatag tggatttgcc   1140

agatcatata gaagtaaaca gtggtaaatt taatcccatt tgcaaagctt ctggctggcc   1200

gctacctact aatgaagaaa tgaccctggt gaagccggat gggacagtgc tccatccaaa   1260

agactttaac catacggatc atttctcagt agccatattc accatccaca gaatcctccc   1320

ccctgactca ggagtttggg tctgcagtgt gaacacagtg gctgggatgg tggaaaagcc   1380

cttcaacatt tctgttaaag ttcttccaaa gcccctgaat gccccaaacg tgattgacac   1440

tggacataac tttgctgtca tcaacatcag ctctgagcct tactttgggg atggaccaat   1500
```

```
caaatccaag aagcttctat acaaacccgt taatcactat gaggcttggc aacatattca   1560
agtgacaaat gagattgtta cactcaacta tttggaacct cggacagaat atgaactctg   1620
tgtgcaactg gtccgtcgtg gagagggtgg ggaagggcat cctggacctg tgagacgctt   1680
cacaacagct tctatcggac tccctcctcc aagaggtcta aatctcctgc ctaaaagtca   1740
gaccactcta aatttgacct ggcaaccaat atttccaagc tcggaagatg acttttatgt   1800
tgaagtggag agaaggtctg tgcaaaaaag tgatcagcag aatattaaag ttccaggcaa   1860
cttgacttcg gtgctactta acaacttaca tcccagggag cagtacgtgg tccgagctag   1920
agtcaacacc aaggcccagg gggaatggag tgaagatctc actgcttgga cccttagtga   1980
cattcttcct cctcaaccag aaaacatcaa gatttccaac attacacact cctcagctgt   2040
gatttcttgg acaatattgg atggctattc tatttcttct attactatcc gttacaaggt   2100
tcaaggcaag aatgaagacc agcacgttga tgtgaagata aagaatgcca ccatcactca   2160
gtatcagctc aagggcctag agcctgaaac agcataccag gtggacattt ttgcagagaa   2220
caacataggg tcaagcaacc cagccttttc tcatgaactg gtgaccctcc cagaatctca   2280
agcaccagcg gacctcggag gggggaagat gctgcttata gccatccttg gctctgctgg   2340
aatgacctgc ctgactgtgc tgttggcctt tctgatcata ttgcaattga agagggcaaa   2400
tgtgcaaagg agaatggccc aagccttcca aaacgtgagg gaagaaccag ctgtgcagtt   2460
caactcaggg actctggccc taaacaggaa ggtcaaaaac aacccagatc ctacaattta   2520
tccagtgctt gactggaatg acatcaaatt tcaagatgtg attggggagg gcaattttgg   2580
ccaagttctt aaggcgcgca tcaagaagga tgggttacgg atggatgctg ccatcaaaag   2640
aatgaaagaa tatgcctcca aagatgatca cagggacttt gcaggagaac tggaagttct   2700
ttgtaaactt ggacaccatc caaacatcat caatctctta ggagcatgtg aacatcgagg   2760
ctacttgtac ctggccattg agtacgcgcc ccatggaaac cttctggact tccttcgcaa   2820
gagccgtgtg ctggagacgg acccagcatt tgccattgcc aatagcaccg cgtccacact   2880
gtcctcccag cagctccttc acttcgctgc cgacgtggcc cggggcatgg actacttgag   2940
ccaaaaacag tttatccaca gggatctggc tgccagaaac attttagttg gtgaaaacta   3000
tgtggcaaaa atagcagatt ttggattgtc ccgaggtcaa gaggtgtatg tgaaaaagac   3060
aatgggaagg ctcccagtgc gctggatggc catcgagtca ctgaattaca gtgtgtacac   3120
aaccaacagt gatgtatggt cctatggtgt gttactatgg gagattgtta gcttaggagg   3180
cacaccctac tgcgggatga cttgtgcaga actctacgag aagctgcccc agggctacag   3240
actggagaag cccctgaact gtgatgatga ggtgtatgat ctaatgagac aatgctggcg   3300
ggagaagcct tatgagaggc catcatttgc ccagatattg gtgtccttaa acagaatgtt   3360
agaggagcga aagacctacg tgaataccac gctttatgag aagtttactt atgcaggaat   3420
tgactgttct gctgaagaag cggcctaggg ctgctgcagc tgcatgggtg cctgctgctg   3480
cctgccttgg cctgatggcc aggccagagt gctgccagtc ctctgcatgt tctgctcttg   3540
tgcccttctg agcccacaat aaaggctgag ctcttatctt gcaaaaggc              3589
```

<210> SEQ ID NO 116
<211> LENGTH: 3589
<212> TYPE: DNA
<213> ORGANISM: Artificial Sequence
<220> FEATURE:
<223> OTHER INFORMATION: Synthetic

<400> SEQUENCE: 116
gaggaaccga gaggctgaga ctaacccaga aacatccaat tctcaaactg aagctcgcac 60
tctcgcctcc agcatggact ctttagccag cttagttctc tgtggagtca gcttgctcct 120
ttctggaact gtggaaggtg ccatggactt gatcttgatc aattccctac ctcttgtatc 180
tgatgctgaa acatctctca cctgcattgc ctctgggtgg cgcccccatg agcccatcac 240
cataggaagg gactttgaag ccttaatgaa ccagcaccag gacccgctgg aagttactca 300
agatgtgacc agagaatggg ctaaaaaagt tgtttggaag agagaaaagg ctagtaagat 360
caatggtgct tatttctgtg aagggcgagt tcgaggagag gcaatcagga tacgaaccat 420
gaagatgcgt caacaagctt ccttcctacc agctacttta actatgactg tggacaaggg 480
agataacgtg aacatatctt tcaaaaaggt attgattaaa gaagaagatg cagtgattta 540
caaaaatggt tccttcatcc attcagtgcc ccggcatgaa gtacctgata ttctagaagt 600
acacctgcct catgctcagc cccaggatgc tggagtgtac tcggccaggt atataggagg 660
aaacctcttc acctcggcct tcaccaggct gatagtccgg agatgtgaag cccagaagtg 720
gggacctgaa tgcaaccatc tctgtactgc ttgtatgaac aatggtgtct gccatgaaga 780
tactggagaa tgcatttgcc ctcctgggtt tatgggaagg acgtgtgaga aggcttgtga 840
actgcacacg tttggcagaa cttgtaaaga aaggtgcagt ggacaagagg gatgcaagtc 900
ttatgtgttc tgtctccctg acccctatgg gtgttcctgt gccacaggct ggaagggtct 960
gcagtgcaat gaagcatgcc accctggttt ttacgggcca gattgtaagc ttaggtgcag 1020
ctgcaacaat ggggagatgt gtgatcgctt ccaaggatgt ctctgctctc caggatggca 1080
ggggctccag tgtgagagag aaggcatacc gaggatgacc ccaaagatag tggatttgcc 1140
agatcatata gaagtaaaca gtggtaaatt taatcccatt tgcaaagctt ctggctggcc 1200
gctacctact aatgaagaaa tgaccctggt gaagccggat gggacagtgc tccatccaaa 1260
agactttaac catacggatc atttctcagt agccatattc accatccaca gaatcctccc 1320
ccctgactca ggagtttggg tctgcagtgt gaacacagtg gctgggatgg tggaaaagcc 1380
cttcaacatt tctgttaaag ttcttccaaa gcccctgaat gccccaaacg tgattgacac 1440
tggacataac tttgctgtca tcaacatcag ctctgagcct tactttgggg atggaccaat 1500
caaatccaag aagcttctat acaaacccgt taatcactat gaggcttggc aacatattca 1560
agtgacaaat gagattgtta cactcaacta tttggaacct cggacagaat atgaactctg 1620
tgtgcaactg gtccgtcgtg gagagggtgg ggaagggcat cctggacctg tgagacgctt 1680
cacaacagct tctatcggac tccctcctcc aagaggtcta aatctcctgc ctaaaagtca 1740
gaccactcta aatttgacct ggcaaccaat atttccaagc tcggaagatg acttttatgt 1800
tgaagtggag agaaggtctg tgcaaaaaag tgatcagcag aatattaaag ttccaggcaa 1860
cttgacttcg gtgctactta acaacttaca tcccagggag cagtacgtgg tccgagctag 1920
agtcaacacc aaggcccagg gggaatggag tgaagatctc actgcttgga ccccttagtga 1980
cattcttcct cctcaaccag aaaacatcaa gatttccaac attacacact cctcagctgt 2040
gatttcttgg acaatattgg atggctattc tatttcttct attactatcc gttacaaggt 2100
tcaaggcaag aatgaagacc agcacgttga tgtgaagata aagaatgcca ccatcactca 2160
gtatcagctc aagggcctag agcctgaaac agcataccag gtggacattt ttgcagagaa 2220
caacataggg tcaagcaacc cagccttttc tcatgaactg gtgaccctcc cagaatctca 2280
agcaccagcg gacctcggag gggggaagat gctgcttata gccatccttg gctctgctgg 2340

```
aatgacctgc ctgactgtgc tgttggcctt tctgatcata ttgcaattga agagggcaaa   2400

tgtgcaaagg agaatggccc aagccttcca aaacgtgagg gaagaaccag ctgtgcagtt   2460

caactcaggg actctggccc taaacaggaa ggtcaaaaac aacccagatc ctacaattta   2520

tccagtgctt gactggaatg acatcaaatt tcaagatgtg attggggagg gcaattttgg   2580

ccaagttctt aaggcgcgca tcaagaagga tgggttatgg atggatgctg ccatcaaaag   2640

aatgaaagaa tatgcctcca aagatgatca cagggacttt gcaggagaac tggaagttct   2700

ttgtaaactt ggacaccatc caaacatcat caatctctta ggagcatgtg aacatcgagg   2760

ctacttgtac ctggccattg agtacgcgcc ccatggaaac cttctggact tccttcgcaa   2820

gagccgtgtg ctggagacgg acccagcatt tgccattgcc aatagcaccg cgtccacact   2880

gtcctcccag cagctccttc acttcgctgc cgacgtggcc cggggcatgg actacttgag   2940

ccaaaaacag tttatccaca gggatctggc tgccagaaac attttagttg gtgaaaacta   3000

tgtggcaaaa atagcagatt ttggattgtc ccgaggtcaa gaggtgtatg tgaaaaagac   3060

aatgggaagg ctcccagtgc gctggatggc catcgagtca ctgaattaca gtgtgtacac   3120

aaccaacagt gatgtatggt cctatggtgt gttactatgg gagattgtta gcttaggagg   3180

cacaccctac tgcgggatga cttgtgcaga actctacgag aagctgcccc agggctacag   3240

actggagaag cccctgaact gtgatgatga ggtgtatgat ctaatgagac aatgctggcg   3300

ggagaagcct tatgagaggc catcatttgc ccagatattg gtgtccttaa acagaatgtt   3360

agaggagcga aagacctacg tgaataccac gctttatgag aagtttactt atgcaggaat   3420

tgactgttct gctgaagaag cggcctaggg ctgctgcagc tgcatgggtg cctgctgctg   3480

cctgccttgg cctgatggcc aggccagagt gctgccagtc ctctgcatgt tctgctcttg   3540

tgcccttctg agcccacaat aaaggctgag ctcttatctt gcaaaaggc              3589
```

```
<210> SEQ ID NO 117
<211> LENGTH: 3207
<212> TYPE: DNA
<213> ORGANISM: Homo sapiens
<220> FEATURE:
<221> NAME/KEY: CDS
<222> LOCATION: (1)..(3207)

<400> SEQUENCE: 117

atg cct cca cga cca tca tca ggt gaa ctg tgg ggc atc cac ttg atg       48
Met Pro Pro Arg Pro Ser Ser Gly Glu Leu Trp Gly Ile His Leu Met
1               5                   10                  15

ccc cca aga atc cta gta gaa tgt tta cta cca aat gga atg ata gtg       96
Pro Pro Arg Ile Leu Val Glu Cys Leu Leu Pro Asn Gly Met Ile Val
            20                  25                  30

act tta gaa tgc ctc cgt gag gct aca tta ata acc ata aag cat gaa      144
Thr Leu Glu Cys Leu Arg Glu Ala Thr Leu Ile Thr Ile Lys His Glu
        35                  40                  45

cta ttt aaa gaa gca aga aaa tac ccc ctc cat caa ctt ctt caa gat      192
Leu Phe Lys Glu Ala Arg Lys Tyr Pro Leu His Gln Leu Leu Gln Asp
    50                  55                  60

gaa tct tct tac att ttc gta agt gtt act caa gaa gca gaa agg gaa      240
Glu Ser Ser Tyr Ile Phe Val Ser Val Thr Gln Glu Ala Glu Arg Glu
65                  70                  75                  80

gaa ttt ttt gat gaa aca aga cga ctt tgt gac ctt cgg ctt ttt caa      288
Glu Phe Phe Asp Glu Thr Arg Arg Leu Cys Asp Leu Arg Leu Phe Gln
                85                  90                  95

ccc ttt tta aaa gta att gaa cca gta ggc aac cgt gaa gaa aag atc      336
```

```
Pro Phe Leu Lys Val Ile Glu Pro Val Gly Asn Arg Glu Glu Lys Ile
            100                 105                 110

ctc aat cga gaa att ggt ttt gct atc ggc atg cca gtg tgt gaa ttt      384
Leu Asn Arg Glu Ile Gly Phe Ala Ile Gly Met Pro Val Cys Glu Phe
        115                 120                 125

gat atg gtt aaa gat cca gaa gta cag gac ttc cga aga aat att ctg      432
Asp Met Val Lys Asp Pro Glu Val Gln Asp Phe Arg Arg Asn Ile Leu
    130                 135                 140

aac gtt tgt aaa gaa gct gtg gat ctt agg gac ctc aat tca cct cat      480
Asn Val Cys Lys Glu Ala Val Asp Leu Arg Asp Leu Asn Ser Pro His
145                 150                 155                 160

agt aga gca atg tat gtc tat cct cca aat gta gaa tct tca cca gaa      528
Ser Arg Ala Met Tyr Val Tyr Pro Pro Asn Val Glu Ser Ser Pro Glu
                165                 170                 175

ttg cca aag cac ata tat aat aaa tta gat aaa ggg caa ata ata gtg      576
Leu Pro Lys His Ile Tyr Asn Lys Leu Asp Lys Gly Gln Ile Ile Val
            180                 185                 190

gtg atc tgg gta ata gtt tct cca aat aat gac aag cag aag tat act      624
Val Ile Trp Val Ile Val Ser Pro Asn Asn Asp Lys Gln Lys Tyr Thr
        195                 200                 205

ctg aaa atc aac cat gac tgt gta cca gaa caa gta att gct gaa gca      672
Leu Lys Ile Asn His Asp Cys Val Pro Glu Gln Val Ile Ala Glu Ala
    210                 215                 220

atc agg aaa aaa act cga agt atg ttg cta tcc tct gaa caa cta aaa      720
Ile Arg Lys Lys Thr Arg Ser Met Leu Leu Ser Ser Glu Gln Leu Lys
225                 230                 235                 240

ctc tgt gtt tta gaa tat cag ggc aag tat att tta aaa gtg tgt gga      768
Leu Cys Val Leu Glu Tyr Gln Gly Lys Tyr Ile Leu Lys Val Cys Gly
                245                 250                 255

tgt gat gaa tac ttc cta gaa aaa tat cct ctg agt cag tat aag tat      816
Cys Asp Glu Tyr Phe Leu Glu Lys Tyr Pro Leu Ser Gln Tyr Lys Tyr
            260                 265                 270

ata aga agc tgt ata atg ctt ggg agg atg ccc aat ttg atg ttg atg      864
Ile Arg Ser Cys Ile Met Leu Gly Arg Met Pro Asn Leu Met Leu Met
        275                 280                 285

gct aaa gaa agc ctt tat tct caa ctg cca atg gac tgt ttt aca atg      912
Ala Lys Glu Ser Leu Tyr Ser Gln Leu Pro Met Asp Cys Phe Thr Met
    290                 295                 300

cca tct tat tcc aga cgc att tcc aca gct aca cca tat atg aat gga      960
Pro Ser Tyr Ser Arg Arg Ile Ser Thr Ala Thr Pro Tyr Met Asn Gly
305                 310                 315                 320

gaa aca tct aca aaa tcc ctt tgg gtt ata aat agt gca ctc aga ata     1008
Glu Thr Ser Thr Lys Ser Leu Trp Val Ile Asn Ser Ala Leu Arg Ile
                325                 330                 335

aaa att ctt tgt gca acc tac gtg aat gta aat att cga gac att gat     1056
Lys Ile Leu Cys Ala Thr Tyr Val Asn Val Asn Ile Arg Asp Ile Asp
            340                 345                 350

aag atc tat gtt cga aca ggt atc tac cat gga gga gaa ccc tta tgt     1104
Lys Ile Tyr Val Arg Thr Gly Ile Tyr His Gly Gly Glu Pro Leu Cys
        355                 360                 365

gac aat gtg aac act caa aga gta cct tgt tcc aat ccc agg tgg aat     1152
Asp Asn Val Asn Thr Gln Arg Val Pro Cys Ser Asn Pro Arg Trp Asn
    370                 375                 380

gaa tgg ctg aat tat gat ata tac att cct gat ctt cct cgt gct gct     1200
Glu Trp Leu Asn Tyr Asp Ile Tyr Ile Pro Asp Leu Pro Arg Ala Ala
385                 390                 395                 400

cga ctt tgc ctt tcc att tgc tct gtt aaa ggc cga aag ggt gct aaa     1248
Arg Leu Cys Leu Ser Ile Cys Ser Val Lys Gly Arg Lys Gly Ala Lys
                405                 410                 415
```

```
gag gaa cac tgt cca ttg gca tgg gga aat ata aac ttg ttt gat tac      1296
Glu Glu His Cys Pro Leu Ala Trp Gly Asn Ile Asn Leu Phe Asp Tyr
            420                 425                 430

aca gac act cta gta tct gga aaa atg gct ttg aat ctt tgg cca gta      1344
Thr Asp Thr Leu Val Ser Gly Lys Met Ala Leu Asn Leu Trp Pro Val
        435                 440                 445

cct cat gga tta gaa gat ttg ctg aac cct att ggt gtt act gga tca      1392
Pro His Gly Leu Glu Asp Leu Leu Asn Pro Ile Gly Val Thr Gly Ser
    450                 455                 460

aat cca aat aaa gaa act cca tgc tta gag ttg gag ttt gac tgg ttc      1440
Asn Pro Asn Lys Glu Thr Pro Cys Leu Glu Leu Glu Phe Asp Trp Phe
465                 470                 475                 480

agc agt gtg gta aag ttc cca gat atg tca gtg att gaa gag cat gcc      1488
Ser Ser Val Val Lys Phe Pro Asp Met Ser Val Ile Glu Glu His Ala
                485                 490                 495

aat tgg tct gta tcc cga gaa gca gga ttt agc tat tcc cac gca gga      1536
Asn Trp Ser Val Ser Arg Glu Ala Gly Phe Ser Tyr Ser His Ala Gly
            500                 505                 510

ctg agt aac aga cta gct aga gac aat gaa tta agg gaa aat gac aaa      1584
Leu Ser Asn Arg Leu Ala Arg Asp Asn Glu Leu Arg Glu Asn Asp Lys
        515                 520                 525

gaa cag ctc aaa gca att tct aca cga gat cct ctc tct gaa atc act      1632
Glu Gln Leu Lys Ala Ile Ser Thr Arg Asp Pro Leu Ser Glu Ile Thr
    530                 535                 540

gag cag gag aaa gat ttt cta tgg agt cac aga cac tat tgt gta act      1680
Glu Gln Glu Lys Asp Phe Leu Trp Ser His Arg His Tyr Cys Val Thr
545                 550                 555                 560

atc ccc gaa att cta ccc aaa ttg ctt ctg tct gtt aaa tgg aat tct      1728
Ile Pro Glu Ile Leu Pro Lys Leu Leu Leu Ser Val Lys Trp Asn Ser
                565                 570                 575

aga gat gaa gta gcc cag atg tat tgc ttg gta aaa gat tgg cct cca      1776
Arg Asp Glu Val Ala Gln Met Tyr Cys Leu Val Lys Asp Trp Pro Pro
            580                 585                 590

atc aaa cct gaa cag gct atg gaa ctt ctg gac tgt aat tac cca gat      1824
Ile Lys Pro Glu Gln Ala Met Glu Leu Leu Asp Cys Asn Tyr Pro Asp
        595                 600                 605

cct atg gtt cga ggt ttt gct gtt cgg tgc ttg gaa aaa tat tta aca      1872
Pro Met Val Arg Gly Phe Ala Val Arg Cys Leu Glu Lys Tyr Leu Thr
    610                 615                 620

gat gac aaa ctt tct cag tat tta att cag cta gta cag gtc cta aaa      1920
Asp Asp Lys Leu Ser Gln Tyr Leu Ile Gln Leu Val Gln Val Leu Lys
625                 630                 635                 640

tat gaa caa tat ttg gat aac ttg ctt gtg aga ttt tta ctg aag aaa      1968
Tyr Glu Gln Tyr Leu Asp Asn Leu Leu Val Arg Phe Leu Leu Lys Lys
                645                 650                 655

gca ttg act aat caa agg att ggg cac ttt ttc ttt tgg cat tta aaa      2016
Ala Leu Thr Asn Gln Arg Ile Gly His Phe Phe Phe Trp His Leu Lys
            660                 665                 670

tct gag atg cac aat aaa aca gtt agc cag agg ttt ggc ctg ctt ttg      2064
Ser Glu Met His Asn Lys Thr Val Ser Gln Arg Phe Gly Leu Leu Leu
        675                 680                 685

gag tcc tat tgt cgt gca tgt ggg atg tat ttg aag cac ctg aat agg      2112
Glu Ser Tyr Cys Arg Ala Cys Gly Met Tyr Leu Lys His Leu Asn Arg
    690                 695                 700

caa gtc gag gca atg gaa aag ctc att aac tta act gac att ctc aaa      2160
Gln Val Glu Ala Met Glu Lys Leu Ile Asn Leu Thr Asp Ile Leu Lys
705                 710                 715                 720

cag gag aag aag gat gaa aca caa aag gta cag atg aag ttt tta gtt      2208
Gln Glu Lys Lys Asp Glu Thr Gln Lys Val Gln Met Lys Phe Leu Val
                725                 730                 735
```

```
gag caa atg agg cga cca gat ttc atg gat gct cta cag ggc ttt ctg     2256
Glu Gln Met Arg Arg Pro Asp Phe Met Asp Ala Leu Gln Gly Phe Leu
            740                 745                 750

tct cct cta aac cct gct cat caa cta gga aac ctc agg ctt gaa gag     2304
Ser Pro Leu Asn Pro Ala His Gln Leu Gly Asn Leu Arg Leu Glu Glu
        755                 760                 765

tgt cga att atg tcc tct gca aaa agg cca ctg tgg ttg aat tgg gag     2352
Cys Arg Ile Met Ser Ser Ala Lys Arg Pro Leu Trp Leu Asn Trp Glu
    770                 775                 780

aac cca gac atc atg tca gag tta ctg ttt cag aac aat gag atc atc     2400
Asn Pro Asp Ile Met Ser Glu Leu Leu Phe Gln Asn Asn Glu Ile Ile
785                 790                 795                 800

ttt aaa aat ggg gat gat tta cgg caa gat atg cta aca ctt caa att     2448
Phe Lys Asn Gly Asp Asp Leu Arg Gln Asp Met Leu Thr Leu Gln Ile
                805                 810                 815

att cgt att atg gaa aat atc tgg caa aat caa ggt ctt gat ctt cga     2496
Ile Arg Ile Met Glu Asn Ile Trp Gln Asn Gln Gly Leu Asp Leu Arg
            820                 825                 830

atg tta cct tat ggt tgt ctg tca atc ggt gac tgt gtg gga ctt att     2544
Met Leu Pro Tyr Gly Cys Leu Ser Ile Gly Asp Cys Val Gly Leu Ile
        835                 840                 845

gag gtg gtg cga aat tct cac act att atg caa att cag tgc aaa ggc     2592
Glu Val Val Arg Asn Ser His Thr Ile Met Gln Ile Gln Cys Lys Gly
    850                 855                 860

ggc ttg aaa ggt gca ctg cag ttc aac agc cac aca cta cat cag tgg     2640
Gly Leu Lys Gly Ala Leu Gln Phe Asn Ser His Thr Leu His Gln Trp
865                 870                 875                 880

ctc aaa gac aag aac aaa gga gaa ata tat gat gca gcc att gac ctg     2688
Leu Lys Asp Lys Asn Lys Gly Glu Ile Tyr Asp Ala Ala Ile Asp Leu
                885                 890                 895

ttt aca cgt tca tgt gct gga tac tgt gta gct acc ttc att ttg gga     2736
Phe Thr Arg Ser Cys Ala Gly Tyr Cys Val Ala Thr Phe Ile Leu Gly
            900                 905                 910

att gga gat cgt cac aat agt aac atc atg gtg aaa gac gat gga caa     2784
Ile Gly Asp Arg His Asn Ser Asn Ile Met Val Lys Asp Asp Gly Gln
        915                 920                 925

ctg ttt cat ata gat ttt gga cac ttt ttg gat cac aag aag aaa aaa     2832
Leu Phe His Ile Asp Phe Gly His Phe Leu Asp His Lys Lys Lys Lys
    930                 935                 940

ttt ggt tat aaa cga gaa cgt gtg cca ttt gtt ttg aca cag gat ttc     2880
Phe Gly Tyr Lys Arg Glu Arg Val Pro Phe Val Leu Thr Gln Asp Phe
945                 950                 955                 960

tta ata gtg att agt aaa gga gcc caa gaa tgc aca aag aca aga gaa     2928
Leu Ile Val Ile Ser Lys Gly Ala Gln Glu Cys Thr Lys Thr Arg Glu
                965                 970                 975

ttt gag agg ttt cag gag atg tgt tac aag gct tat cta gct att cga     2976
Phe Glu Arg Phe Gln Glu Met Cys Tyr Lys Ala Tyr Leu Ala Ile Arg
            980                 985                 990

cag cat gcc aat ctc ttc ata aat  ctt ttc tca atg atg  ctt ggc tct   3024
Gln His Ala Asn Leu Phe Ile Asn  Leu Phe Ser Met Met  Leu Gly Ser
        995                 1000                 1005

gga atg  cca gaa cta caa tct  ttt gat gac att gca  tac att cga     3069
Gly Met  Pro Glu Leu Gln Ser  Phe Asp Asp Ile Ala  Tyr Ile Arg
    1010                 1015                 1020

aag acc  cta gcc tta gat aaa  act gag caa gag gct  ttg gag tat     3114
Lys Thr  Leu Ala Leu Asp Lys  Thr Glu Gln Glu Ala  Leu Glu Tyr
    1025                 1030                 1035

ttc atg  aaa caa atg aat gat  gca cat cat ggt ggc  tgg aca aca     3159
Phe Met  Lys Gln Met Asn Asp  Ala His His Gly Gly  Trp Thr Thr
```

```
    1040                1045                1050

aaa atg  gat tgg atc ttc cac  aca att aaa cag cat  gca ttg aac      3204
Lys Met  Asp Trp Ile Phe His  Thr Ile Lys Gln His  Ala Leu Asn
    1055                1060                1065

tga                                                                 3207


<210> SEQ ID NO 118
<211> LENGTH: 1068
<212> TYPE: PRT
<213> ORGANISM: Homo sapiens

<400> SEQUENCE: 118

Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Met Asp Cys Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335
```

```
Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
    370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
        435                 440                 445

Pro His Gly Leu Glu Asp Leu Leu Asn Pro Ile Gly Val Thr Gly Ser
    450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Ala Gly
            500                 505                 510

Leu Ser Asn Arg Leu Ala Arg Asp Asn Glu Leu Arg Glu Asn Asp Lys
        515                 520                 525

Glu Gln Leu Lys Ala Ile Ser Thr Arg Asp Pro Leu Ser Glu Ile Thr
    530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
        595                 600                 605

Pro Met Val Arg Gly Phe Ala Val Arg Cys Leu Glu Lys Tyr Leu Thr
    610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
    690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Arg Pro Asp Phe Met Asp Ala Leu Gln Gly Phe Leu
            740                 745                 750

Ser Pro Leu Asn Pro Ala His Gln Leu Gly Asn Leu Arg Leu Glu Glu
```

```
        755                 760                 765

Cys Arg Ile Met Ser Ser Ala Lys Arg Pro Leu Trp Leu Asn Trp Glu
    770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
            805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
    850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
            885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
            965                 970                 975

Phe Glu Arg Phe Gln Glu Met Cys Tyr Lys Ala Tyr Leu Ala Ile Arg
            980                 985                 990

Gln His Ala Asn Leu Phe Ile Asn  Leu Phe Ser Met Met  Leu Gly Ser
        995                 1000                1005

Gly Met  Pro Glu Leu Gln Ser  Phe Asp Asp Ile Ala  Tyr Ile Arg
    1010                1015                1020

Lys Thr  Leu Ala Leu Asp Lys  Thr Glu Gln Glu Ala  Leu Glu Tyr
    1025                1030                1035

Phe Met  Lys Gln Met Asn Asp  Ala His His Gly Gly  Trp Thr Thr
    1040                1045                1050

Lys Met  Asp Trp Ile Phe His  Thr Ile Lys Gln His  Ala Leu Asn
    1055                1060                1065
```

<210> SEQ ID NO 119
<211> LENGTH: 513
<212> TYPE: DNA
<213> ORGANISM: Artificial Sequence
<220> FEATURE:
<223> OTHER INFORMATION: Synthetic

<400> SEQUENCE: 119

```
gtcttcacac tcgaagattt cgttggggac tggcgacaga cagccggcta caacctggac     60

caagtccttg aacagggagg tgtgtccagt ttgtttcaga atctcggggt gtccgtaact    120

ccgatccaaa ggattgtcct gagcggtgaa aatgggctga agatcgacat ccatgtcatc    180

atcccgtatg aaggtctgag cggcgaccaa atgggccaga tcgaaaaaat ttttaaggtg    240

gtgtaccctg tggatgatca tcactttaag gtgatcctgc actatggcac actggtaatc    300
```

gacggggtta cgccgaacat gatcgactat ttcggacggc cgtatgaagg catcgccgtg 360
ttcgacggca aaaagatcac tgtaacaggg accctgtgga acggcaacaa aattatcgac 420
gagcgcctga tcaaccccga cggctccctg ctgttccgag taaccatcaa cggagtgacc 480
ggctggcggc tgtgcgaacg cattctggcg taa 513

<210> SEQ ID NO 120
<211> LENGTH: 57
<212> TYPE: DNA
<213> ORGANISM: Artificial Sequence
<220> FEATURE:
<223> OTHER INFORMATION: Synthetic

<400> SEQUENCE: 120
gggaaataag agagaaaaga agagtaagaa gaaatataag accccggcgc cgccacc 57

<210> SEQ ID NO 121
<211> LENGTH: 139
<212> TYPE: DNA
<213> ORGANISM: Artificial Sequence
<220> FEATURE:
<223> OTHER INFORMATION: Synthetic

<400> SEQUENCE: 121
taataggctg gagcctcggt ggcctagctt cttgcccctt gggcctcccc ccagcccctc 60
ctccccttcc tgcacccgta ccccctccat aaagtaggaa acactacagt ggtctttgaa 120
taaagtctga gtgggcggc 139

<210> SEQ ID NO 122
<211> LENGTH: 139
<212> TYPE: DNA
<213> ORGANISM: Artificial Sequence
<220> FEATURE:
<223> OTHER INFORMATION: Synthetic

<400> SEQUENCE: 122
tttttttttt tttttttttt tttttttttt tttttttttt tttttttttt tttttttttt 60
tttttttttt tttttttttt tttttttttt tttttttttt tttttttttt tttttttttt 120
ttgcacaaat attactttc 139

<210> SEQ ID NO 123
<211> LENGTH: 38
<212> TYPE: DNA
<213> ORGANISM: Artificial Sequence
<220> FEATURE:
<223> OTHER INFORMATION: Synthetic

<400> SEQUENCE: 123
taatacgact cactataggg aaataagaga gaaaagaa 38

<210> SEQ ID NO 124
<211> LENGTH: 139
<212> TYPE: DNA
<213> ORGANISM: Artificial Sequence
<220> FEATURE:
<223> OTHER INFORMATION: Synthetic

<400> SEQUENCE: 124
tttttttttt tttttttttt tttttttttt tttttttttt tttttttttt tttttttttt 60
tttttttttt tttttttttt tttttttttt tttttttttt tttttttttt tttttttttt 120
gccgcccact cagacttta 139

```
<210> SEQ ID NO 125
<211> LENGTH: 38
<212> TYPE: DNA
<213> ORGANISM: Artificial Sequence
<220> FEATURE:
<223> OTHER INFORMATION: Synthetic

<400> SEQUENCE: 125

taatacgact cactataggg tggcagctca cagctatt                          38
```